United States Patent
Youngs et al.

(10) Patent No.: US 9,278,951 B2
(45) Date of Patent: Mar. 8, 2016

(54) AZOLIUM AND PURINIUM SALT ANTICANCER AND ANTIMICROBIAL AGENTS

(75) Inventors: Wiley Youngs, Akron, OH (US); Matthew Panzner, Akron, OH (US); Claire Tessier, Akron, OH (US); Michael Deblock, Akron, OH (US); Brian Wright, Akron, OH (US); Patrick Wagers, Akron, OH (US); Nikki Robishaw, Seville, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/114,324

(22) PCT Filed: Apr. 30, 2012

(86) PCT No.: PCT/US2012/035773
§ 371 (c)(1),
(2), (4) Date: Feb. 3, 2014

(87) PCT Pub. No.: WO2012/149523
PCT Pub. Date: Nov. 1, 2012

(65) Prior Publication Data
US 2014/0142307 A1   May 22, 2014

Related U.S. Application Data

(60) Provisional application No. 61/480,410, filed on Apr. 29, 2011.

(51) Int. Cl.
| | | |
|---|---|---|
| *C07D 235/02* | (2006.01) |
| *C07D 235/04* | (2006.01) |
| *C07D 233/58* | (2006.01) |
| *C07D 233/60* | (2006.01) |
| *C07D 233/68* | (2006.01) |
| *C07D 401/14* | (2006.01) |
| *C07D 403/12* | (2006.01) |
| *C07D 401/06* | (2006.01) |
| *C07D 401/12* | (2006.01) |
| *C07D 403/04* | (2006.01) |
| *C07D 405/06* | (2006.01) |
| *C07D 487/04* | (2006.01) |
| *C07D 403/14* | (2006.01) |
| *C07D 473/08* | (2006.01) |

(52) U.S. Cl.
CPC ............ *C07D 401/14* (2013.01); *C07D 233/58* (2013.01); *C07D 233/60* (2013.01); *C07D 233/68* (2013.01); *C07D 235/02* (2013.01); *C07D 235/04* (2013.01); *C07D 401/06* (2013.01); *C07D 401/12* (2013.01); *C07D 403/04* (2013.01); *C07D 403/12* (2013.01); *C07D 403/14* (2013.01); *C07D 405/06* (2013.01); *C07D 473/08* (2013.01); *C07D 487/04* (2013.01)

(58) Field of Classification Search
CPC .. C07D 233/58; C07D 233/60; C07D 233/68; C07D 235/02; C07D 235/04
See application file for complete search history.

(56) References Cited

U.S. PATENT DOCUMENTS

2005/0240025 A1   10/2005   Glorius
2007/0034698 A1   2/2007    Hautvast et al.

FOREIGN PATENT DOCUMENTS

WO    2009/096905       8/2009
WO    WO 2009/096905   *   8/2009   ........... A61K 31/439

OTHER PUBLICATIONS

Pauly, et al., Berichte der Deutschen Chemischen Gesellschaft (1909), 41, 3999-4012.*
Roechling. Zeitschrift fuer Naturforshung, Teil B: Anorganische Chemie, Organische Chemie, Biochemie, Biophysik, Biologie (1970), 25(9), 631-4.*

* cited by examiner

*Primary Examiner* — Erich A Leeser
(74) *Attorney, Agent, or Firm* — Renner Kenner; Greive Bobak; Taylor & Weber

(57) ABSTRACT

Singly and multiply charged imidazolium cations (ICs) have been identified as a class of chemical compositions that possess potent antineoplastic, antibacterial and antimicrobial properties. The imidazolium cations disclosed demonstrate greater or equivalent potency towards cancerous cells as the current clinical standard, cisplatin. These imidazolium cations, however, achieve this efficacy without any of the known toxic side effects caused by heavy metal-based antineoplastic drugs such as cisplatin.

2 Claims, No Drawings

AZOLIUM AND PURINIUM SALT ANTICANCER AND ANTIMICROBIAL AGENTS

CROSS REFERENCE TO RELATED APPLICATIONS

This application claims the benefit of U.S. Provisional Patent Application No. 61/480,410 filed Apr. 29, 2011, the disclosure of which is hereby incorporated by reference.

TECHNICAL FIELD

This invention relates to compositions of antineoplastic azolium and purinium salts for the effective treatment of human cancers and microbial infections.

BACKGROUND OF THE INVENTION

Cancer is a broad group of diseases that are characterized by an uncontrolled growth and spread of abnormal cells. These cancerous cells are caused from a malfunction in the genes that control cell growth and division; this malfunction can be caused by both internal and external factors. According to the American Cancer Society one out of every 3 people will be diagnosed with cancer in their lifetime and will cause 1 out of every 4 deaths in the United States. The survival rate of those diagnosed has increased in recent years, in large part due to new chemotherapeutic agents. Cisplatin and Carboplatin are chemotherapeutic agents that have been widely used over the past 45 years to treat a large variety of cancers. These drugs are far from ideal because of their toxic side effects and the ability of cancers to develop resistance to them. There is a need to find new anticancer drugs that that less toxic is highly desirous.

Another leading cause of human disease and mortality is microbial infection. Of particular concern are infections caused by microbes which have developed resistance to current antibiotics. According to the U.S. Food and Drug Administration, bacterial resistance to both single and multiple antibiotics are on the rise. The U.S. Center for Disease Control and Prevention reports that almost all major bacterial infections in the world are becoming resistant to the antibiotics used to treat them. This is a major health issue which is felt both economically and physically. Infection with resistant microbes such as bacteria can translate into more frequent doctor visits, longer illness and recovery times, more aggressive treatment regimes, and increased mortality rates. For example, penicillin, which was the first antibiotic, was introduced in the late 1940's, and only a few years later, penicillin resistant Staphylococcus aureus bacterial infections surfaced. The penicillin derivative methicillin was created to combat this resistance; however it too has lost its effectiveness against some strains of S. aureus, now known as methicillin resistant S. aureus (MRSA). MRSA infections are now being treated with stronger antibiotics such as Vancomycin, an antibiotic which carries a risk of toxic side effects. Even now Vancomycin resistant S. aureus strains have begun to be reported.

Accordingly, it is clear that a need exists to develop new classes of antibiotics that may help to circumvent the resistance of some microbes to conventional therapies. There is also a need for drugs that are less toxic but still effective in the treatment of cancer.

Heretofore, attempts have been made to provide new anticancer compositions. For example, WO 2009/096905 has disclosed the use of imidazolium and certain imidazolium compounds for the treatment of cancer. However, these compounds do not include halogens, and therefore, have been found to be less effective against cancer cells than those compositions that include one or more halogens. Furthermore, multi-cationic azolium and purinium salt compositions have been found to further improve the effectiveness against cancer cells and against bacterial and fungal infections than the mono-cationic compositions disclosed therein.

Thus, the need exists for azolium and perineum salt compositions that are as good as or better than anti-cancer drugs or antimicrobial drugs currently on the market.

SUMMARY OF INVENTION

The present invention, together with the advantages thereof over the known art relating to azolium and purinium salts compositions, antineoplastic agents, and antimicrobial agents, which shall become apparent from the specification that follows, are accomplished by the invention as hereinafter described and claimed.

In general, the present invention provides an azolium or purinium salt composition having one of the general formulas (I) to (VIII) set forth below:

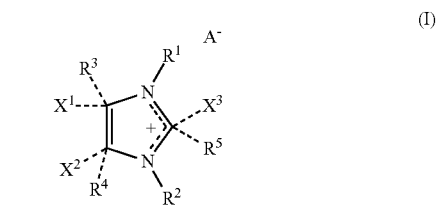
(I)

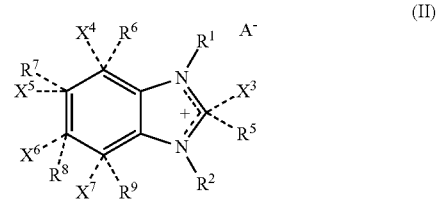
(II)

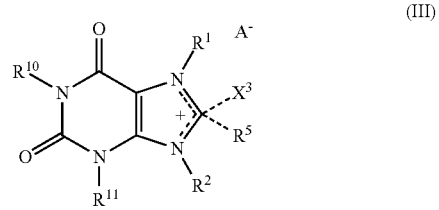
(III)

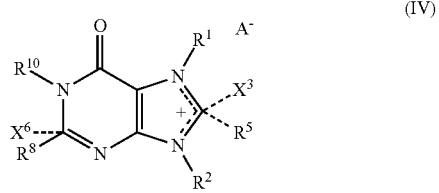
(IV)

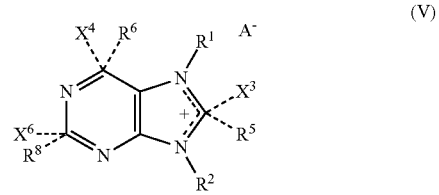
(V)

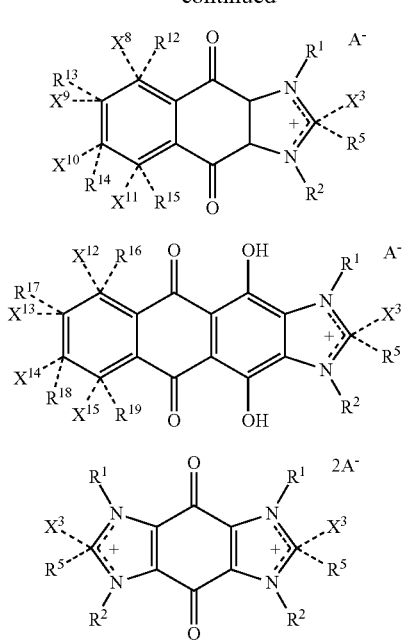

The dashed lines in formulas (I) to (VIII) represent either (i) a variable attachment of either R or X to a corresponding ring atom, where the dashed line connects the R or X to the ring atom, or (ii) a delocalized bond, where the dashed line is within a ring. At least one X is always present in each of the formulas (I) to (VIII) with the proviso that, if one or more R is a polycyclic aromatic, then X may or may not be present. When present, each X, namely $X^1, X^2, X^3, X^4, X^5, X^6, X^7, X^8, X^9, X^{10}, X^{11}, X^{12}, X^{13}, X^{14},$ and $X^{15}$, when present, may be the same or different, and is a halogen (F, Cl, Br, or I). $R^1$ and $R^2$ may be each independently selected from hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, fluoroquinolone compound and derivatives thereof, penicillin compounds and derivatives thereof, aminoglycoside compounds and derivatives thereof; cephalosporin compounds and derivatives thereof, glycopeptides or derivatives thereof, sulfonamides and derivatives thereof, tetracycline and derivatives thereof, anti-microbial compounds and derivatives thereof, steroids and derivatives thereof, anti-inflammatory compounds and derivatives thereof, anti-fungal compounds and derivatives thereof, anti-bacterial compounds and derivatives thereof, antagonist compounds and derivatives thereof, chemotherapy compounds and derivatives thereof; and tumor suppressor compounds and derivatives thereof. $R^3, R^4, R^5, R^6, R^7, R^8, R^9, R^{10}, R^{11}, R^{12}, R^{13}, R^{14}, R^{15}, R^{16}, R^{17}, R^{18},$ and $R^{19}$, where present, may be each independently selected from hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N; $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, hydroxyl, carbonyl, amino, acetyl, acetoxy, oxo, nitro, cyano, isocyano, cyanato, isocyanato, fluoroquinolone compound and derivatives thereof, penicillin compounds and derivatives thereof, aminoglycoside compounds and derivatives thereof; cephalosporin compounds and derivatives thereof, glycopeptides or derivatives thereof, sulfonamides and derivatives thereof, tetracycline and derivatives thereof, anti-microbial compounds and derivatives thereof, steroids and derivatives thereof, anti-inflammatory compounds and derivatives thereof, anti-fungal compounds and derivatives thereof, antibacterial compounds and derivatives thereof, antagonist compounds and derivatives thereof, chemotherapy compounds and derivatives thereof; and tumor suppressor compounds and derivatives thereof. When any of $R^3, R^4, R^5, R^6, R^7, R^8, R^9, R^{12}, R^{13}, R^{14}, R^{15}, R^{16}, R^{17}, R^{18},$ and $R^{19}$, is shown to be attached to a ring carbon atom in formulas (I) to (VIII), the ring carbon atom may optionally be replaced by a nitrogen, oxygen or sulfur atom. In one embodiment, all of the Rs are attached to ring carbon atoms, except as otherwise shown in the formulas (I) to (VIII) above. The above description provides the cationic structural portion of the formulas (I) to (VIII). $A^-$ is defined as an anion independently selected as a halide, hydroxide, alkoxide, aryloxide, carboxylate, sulfate, phosphate, triflate, tosylate or borate.

In another embodiment, the present invention provides a multicationic azolium or purinium salt composition having one of the formulas (IX) to (XI):

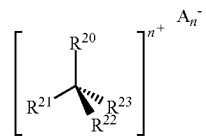

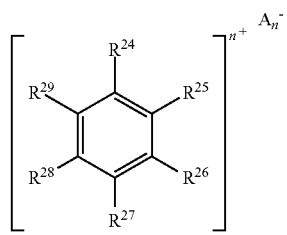

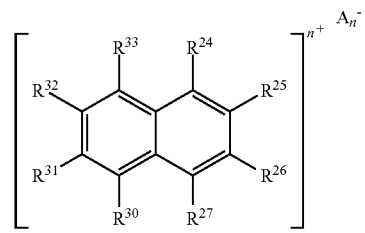

In this embodiment, at least two of the R groups present in formulas (IX) to (XI) are independently selected from one of the cationic structural portions defined in formulas (I) to (VIII)

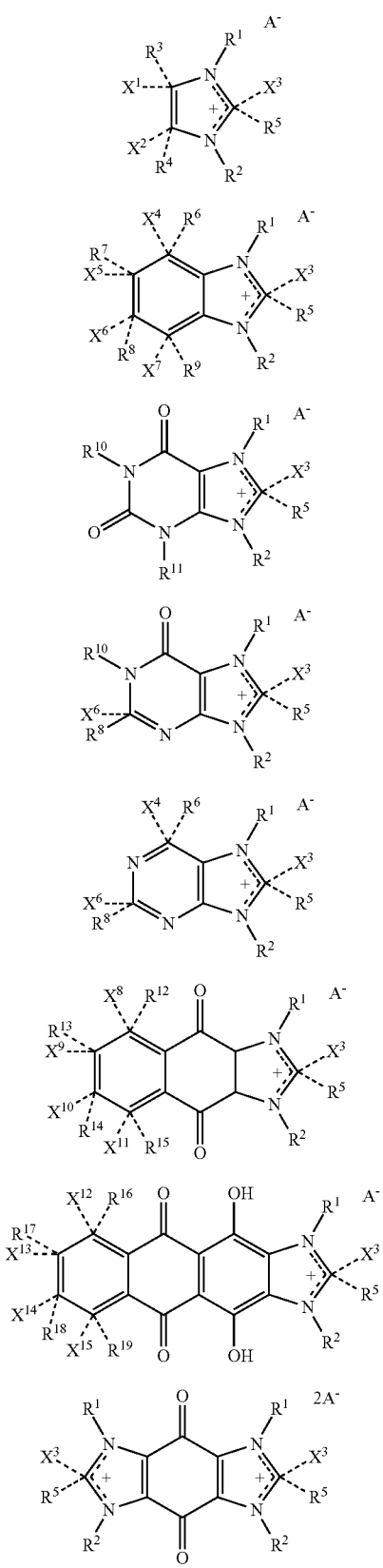

wherein any X may or may not be present, but when present, each $X^1, X^2, X^3, X^4, X^5, X^6, X^7, X^8, X^9, X^{10}, X^{11}, X^{12}, X^{13}$, $X^{14}$, and $X^{15}$ may be the same or different, and is a halogen (F, Cl, Br, or I). For formulas (I) to (VIII), $R^1$ and $R^2$ are each independently selected from hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, fluoroquinolone compound and derivatives thereof, penicillin compounds and derivatives thereof, aminoglycoside compounds and derivatives thereof; cephalosporin compounds and derivatives thereof, glycopeptides or derivatives thereof, sulfonamides and derivatives thereof, tetracycline and derivatives thereof, anti-microbial compounds and derivatives thereof, steroids and derivatives thereof, anti-inflammatory compounds and derivatives thereof, anti-fungal compounds and derivatives thereof, anti-bacterial compounds and derivatives thereof, antagonist compounds and derivatives thereof, chemotherapy compounds and derivatives thereof; and tumor suppressor compounds and derivatives thereof; and each $R^3$, $R^4, R^5, R^6, R^7, R^8, R^9, R^{10}, R^{11}, R^{12}, R^{13}, R^{14}, R^{15}, R^{16}, R^{17}$, $R^{18}$, and $R^{19}$, are independently selected from any of the cationic structural portions of formulas (I) to (VIII) above, hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, hydroxyl, carbonyl, amino, acetyl, acetoxy, oxo, nitro, cyano, isocyano, cyanato, isocyanato, fluoroquinolone compound and derivatives thereof, penicillin compounds and derivatives thereof, aminoglycoside compounds and derivatives thereof; cephalosporin compounds and derivatives thereof, glycopeptides or derivatives thereof, sulfonamides and derivatives thereof, tetracycline and derivatives thereof, anti-microbial compounds and derivatives thereof, steroids and derivatives thereof, anti-inflammatory compounds and derivatives thereof, anti-fungal compounds and derivatives thereof, anti-bacterial compounds and derivatives thereof, antagonist compounds and derivatives thereof, chemotherapy compounds and derivatives thereof; and tumor suppressor compounds and derivatives thereof. It is noted that, when any of $R^3, R^4, R^5, R^6, R^7$, $R^8, R^9, R^{12}, R^{13}, R^{14}, R^{15}, R^{16}, R^{17}, R^{18}$, and $R^{19}$, is shown to be attached to a ring carbon atom in formulas (I) to (VIII), the ring carbon atom may optionally be replaced by a nitrogen, oxygen or sulfur atom. With respect to formulas (IX) to (XI), $R^{20}, R^{21}, R^{22}, R^{23}, R^{24}, R^{25}, R^{26}, R^{27}, R^{28}, R^{29}, R^{30}, R^{31}, R^{32}$ and $R^{33}$, where present, are each independently selected from hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy, biphenyl, $C_1$ to $C_6$ alkyl biphenyl, $C_2$ to $C_6$ alkenyl biphenyl, $C_2$ to $C_6$ alkynyl biphenyl, halogen, hydroxyl, carbonyl, amino, acetyl, acetoxy, oxo, nitro, cyano, isocyano, cyanato, isocyanato, fluoroquinolone compound and derivatives thereof, penicillin compounds and derivatives thereof, aminoglycoside compounds and derivatives thereof; cephalosporin compounds and derivatives thereof, glycopeptides or derivatives thereof, sulfonamides and derivatives thereof, tetracycline and derivatives thereof, anti-microbial compounds and derivatives thereof, steroids and derivatives thereof, anti-inflammatory compounds and derivatives thereof, anti-fungal compounds and derivatives thereof, anti-bacterial compounds and derivatives thereof, antagonist compounds and derivatives thereof, chemotherapy compounds or derivatives thereof; tumor suppressor compounds or derivatives thereof. The ring carbon atoms in formulas (X) to (IX) may optionally be replaced by a nitrogen, oxygen or sulfur atom. In one embodiment none of the ring carbon atoms are replaced. In other embodiments, one carbon atom is replaced. In other embodiments two or more carbon atoms are replaced. This above description provides disclosure of the cationic portion of the structural formulas. $A^-$ is defined as an anion independently selected as a halide, hydroxide, alkoxide, aryloxide, carboxylate, sulfate, phosphate, triflate, tosylate or borate. For each formula (IX) to (XI), each n is an integer from 1 to 8 based upon the number of R groups in the formula, and is the same integer. Thus, for formula (IX), n is an integer from 1 to 4; for formula (X), n is an integer from 1 to 6; and for formula (XI), n is an integer from 1 to 8.

Advantageously, the compositions of the present invention possess potent antineoplastic, antibacterial, and antimicrobial properties. In one or more embodiments, the compositions have been synthesized and tested for such properties. Test data suggests and demonstrates the composition of the present invention may have greater than or at least as great a potency towards the killing of cancerous cells as the current clinical standard, cisplatin. However, these are believed more desirable in that they achieve this efficacy without the toxic side effects caused by heavy metal-based antineoplastic drugs, such as cisplatin.

DETAILED DESCRIPTION OF THE INVENTION

As noted hereinabove, the present invention results from the discovery that both single-charged and multiple-charged imidazolium cations (ICs) as a class of chemical compounds that possess potent antineoplastic, antibacterial, and antimicrobial properties. In several of the embodiments the ICs demonstrate greater or equivalent potency towards cancerous cells as the current clinical standard cisplatin. It is believe ICs hold the advantage in that they achieve this efficacy without the toxic side effects caused by heavy metal based antineoplastic drugs such as cisplatin.

In the present invention, novel compositions containing azolium salts or purinium salts are disclosed. These compositions are believed to be useful as pharmaceutical compositions for a variety of purposes, including use as antineoplastic agents, anti-bacterial agents, anti-fungal agents and antimicrobial agents. That is, use of these azolium salt and purinium salt compositions are believed useful in the production of drugs effective in the treatment of human cancers and microbial infections.

In one embodiment, the useful composition is a azolium or purinium salt composition having one of the following eight general formulas:

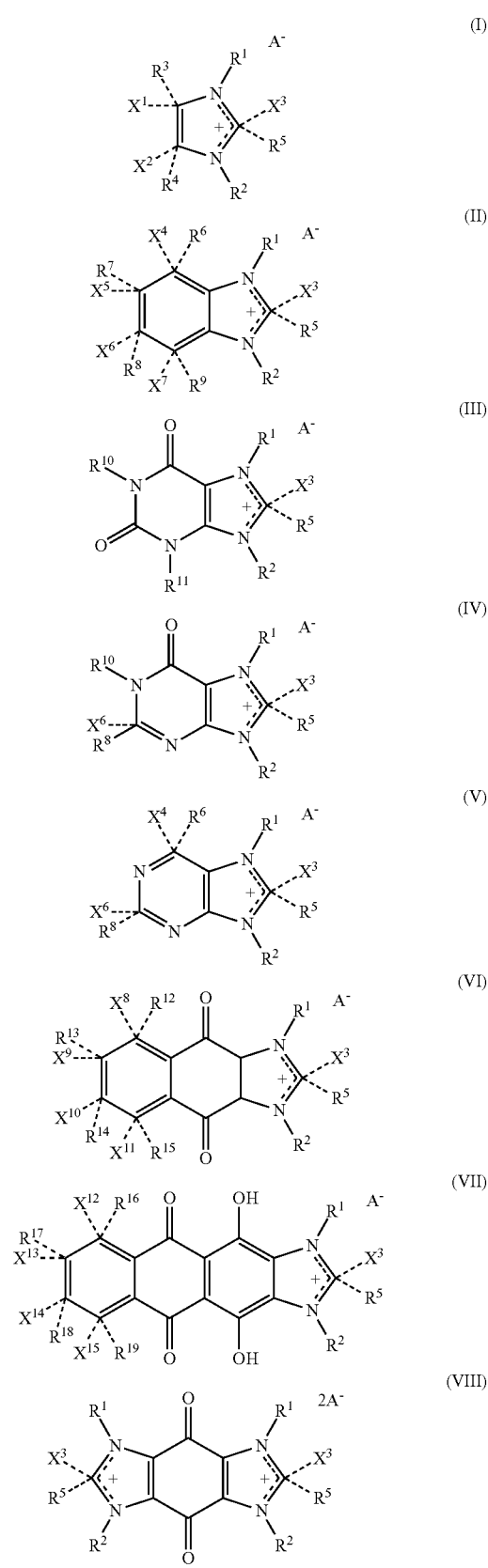

The dashed lines in formulas (I) to (VIII) represent either (i) a variable attachment of either R or X to a corresponding ring atom, where the dashed line connects the R or X to the ring atom, or (ii) a delocalized bond, where the dashed line is within a ring.

At least one X is always present in each of the formulas (I) to (VIII) unless one or more of the Rs is a polycyclic aromatic. Then X may optionally be present. When present, each X, including $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$, is a halogen (F, Cl, Br, or I). Each X in each formula can be the same or different. In one embodiment, $X^1$ and $X^2$ are Cl. In another embodiment, $X^4$, $X^5$, $X^6$, and $X^7$ are all Cl.

In each of the formulas (I) to (VIII), $R^1$ and $R^2$ may be each independently selected from hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, fluoroquinolone compound and derivatives thereof, penicillin compounds and derivatives thereof, aminoglycoside compounds and derivatives thereof; cephalosporin compounds and derivatives thereof, glycopeptides or derivatives thereof, sulfonamides and derivatives thereof, tetracycline and derivatives thereof, anti-microbial compounds and derivatives thereof, steroids and derivatives thereof, anti-inflammatory compounds and derivatives thereof, anti-fungal compounds and derivatives thereof, anti-bacterial compounds and derivatives thereof, antagonist compounds and derivatives thereof, chemotherapy compounds and derivatives thereof; and tumor suppressor compounds and derivatives thereof. In one embodiment, $R^1$ and $R^2$ are polycyclic aromatics. In a further embodiment, $R^1$ and $R^2$ are alkyl naphthalene groups. In another embodiment, $R^1$ and $R^2$ are alkyl quinoline groups.

Also in each of the formulas (I) to (VIII), $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$, where present, may be each independently selected from hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N; $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, hydroxyl, carbonyl, amino, acetyl, acetoxy, oxo, nitro, cyano, isocyano, cyanato, isocyanato, fluoroquinolone compound and derivatives thereof, penicillin compounds and derivatives thereof, aminoglycoside compounds and derivatives thereof; cephalosporin compounds and derivatives thereof, glycopeptides or derivatives thereof, sulfonamides and derivatives thereof, tetracycline and derivatives thereof, anti-microbial compounds and derivatives thereof, steroids and derivatives thereof, anti-inflammatory compounds and derivatives thereof, anti-fungal compounds and derivatives thereof, anti-bacterial compounds and derivatives thereof, antagonist compounds and derivatives thereof, chemotherapy compounds and derivatives thereof; and tumor suppressor compounds and derivatives thereof. When any of $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, and $R^{19}$, is shown to be attached to a ring carbon atom in formulas (I) to (VIII), the ring carbon atom may optionally be replaced by a nitrogen, oxygen or sulfur atom. In one embodiment, all of the Rs are attached to ring carbon atoms, except as otherwise shown in the formulas (I) to (VIII) above.

The above description provides the cationic structural portion of the formulas (I) to (VIII). $A^-$ is defined as an anion independently selected as a halide, hydroxide, alkoxide, aryloxide, carboxylate, sulfate, phosphate, triflate, tosylate or borate.

In other embodiments, the novel compositions may be multi-cationic compositions containing an azolium or purinium salt. Such compositions include one of the following three general formulas (IX) to (XI):

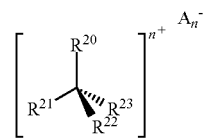
(IX)

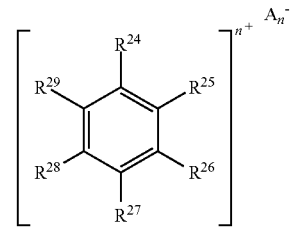
(X)

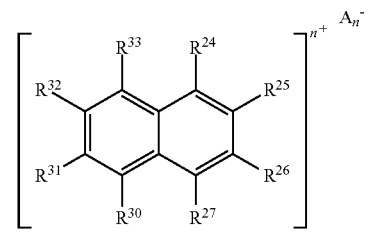
(XI)

In this embodiment, at least two of the R groups present in formulas (IX) to (XI) are independently selected from one of the cationic structural portions defined in formulas (I) to (VIII) above, it being understood that such portions do not include the $A^-$ anion. For formulas (I) to (VIII), each of the Rs may be the same as set forth above, and when any of $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, and $R^{19}$, is shown to be attached to a ring carbon atom in formulas (I) to (VIII), the ring carbon atom may optionally be replaced by a nitrogen, oxygen or sulfur atom.

The Xs in formulas (IX) to (XI) may differ from the formulas (I) to (VIII) in that the Xs may or may not be present. But when present, each $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ may be the same or different, and each X is a halogen (i.e., F, Cl, Br, or I).

For $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$ and $R^{33}$ in formulas (IX) to (XI), where present, each R may be independently selected from hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy, biphenyl, $C_1$ to $C_6$ alkyl biphenyl, $C_2$ to $C_6$ alkenyl biphenyl, $C_2$ to $C_6$ alkynyl biphenyl, halogen, hydroxyl, carbonyl, amino, acetyl, acetoxy, oxo, nitro, cyano, isocyano, cyanato, isocyanato, fluoroquinolone compound and derivatives thereof, penicillin compounds and derivatives thereof, aminoglycoside compounds and derivatives thereof; cephalosporin compounds and derivatives thereof, glycopeptides or derivatives thereof, sulfonamides and derivatives thereof, tetracycline and derivatives thereof, anti-microbial compounds and derivatives thereof, steroids and derivatives thereof, anti-inflammatory compounds and derivatives thereof, anti-fungal compounds and derivatives thereof, anti-bacterial compounds and derivatives thereof, antagonist compounds and derivatives thereof, chemotherapy compounds or derivatives thereof; tumor suppressor compounds or derivatives thereof.

The ring carbon atoms in formulas (X) to (IX) may optionally be replaced by a nitrogen, oxygen or sulfur atom. In one embodiment none of the ring carbon atoms are replaced. In other embodiments, one carbon atom is replaced. In other embodiments two or more carbon atoms are replaced.

This above description provides disclosure of the cationic portion of the structural formulas. $A^-$ is defined as an anion independently selected as a halide, hydroxide, alkoxide, aryloxide, carboxylate, sulfate, phosphate, triflate, tosylate or borate. In one embodiment, the anion is a halide. In another embodiment, the anion is any of $Cl^-$, $Br^-$, or $I^-$.

For each formula (IX) to (XI), each n is an integer from 1 to 8 based upon the number of R groups in the formula, and is the same integer. Thus, for formula (IX), n is an integer from 1 to 4; for formula (X), n is an integer from 1 to 6; and for formula (XI), n is an integer from 1 to 8.

Although none of the compositions disclosed herein are believe known in the prior art, synthesis of these compounds follow synthesis schemes generally regarded as known in the art, but for the production of other compounds. More particularly, the general synthesis scheme following a known bromination technique wherein a brominated ligand is reacted with an azolium compound having a ($H^+$) proton donor attached to one or more of the Nitrogen atoms in the ring structure. The resultant compounds have been found to be potent against various cancer cells and microbes.

In order to demonstrate practice of the invention, a more thorough analysis of the synthesis of several of the proposed novel compositions is disclosed herein below. Furthermore, test data is also provided. The below examples are for purposes of providing demonstration of practice of the invention, it being understood that other examples not disclosed but falling within the scope of the claims provided herein will also meet the parameters and requirements as antineoplastic agents, antimicrobial agents, anti-bacterial agents and anti-fungal agents.

In the following examples, the novel IC composition is provided along with the schematic representation of the synthesis of the composition. The synthesis of the composition is then recited for each example. Prophetic examples are set forth in the future tense.

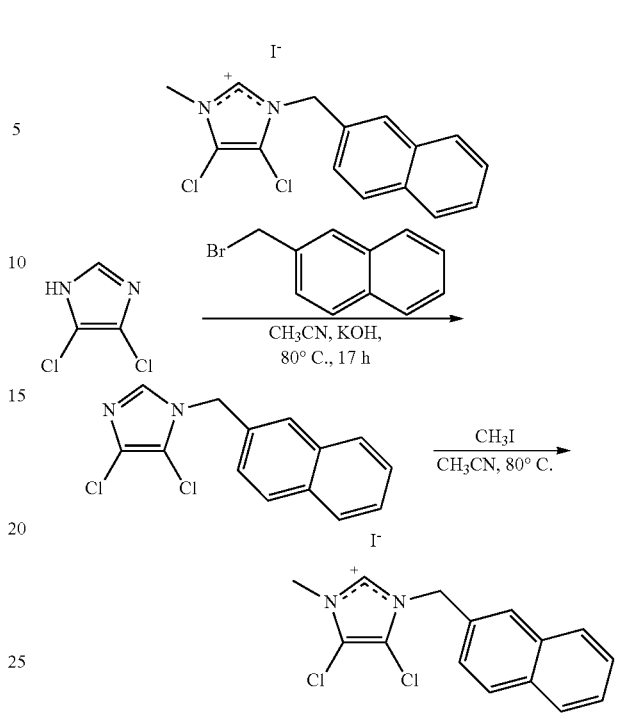

Synthesis of 4,5-dichloro-1-methyl-3-(naphthalen-2-ylmethyl)-1H-imidazolium iodide 4,5-dichloroimidazole (40.0 mmol, 5.479 g) and KOH (44.0 mmol, 2.469 g) were placed in a round bottom flask with 100 mL acetonitrile. The mixture was brought to reflux (85° C.) and stirred 1 h until KOH was consumed. 2-Bromomethylnapthalene (40.00 mmol, 8.844 g) was added and the solution was stirred at reflux for 17 hours. KBr was removed by vacuum filtration and the filtrate was collected. The volatiles were removed by rotary evaporation to give 4,5-dichloro-1-(naphthalen-2-ylmethyl)-1H-imidazole as a light brown solid. 4,5-dichloro-1-(naphthalen-2-ylmethyl)-1H-imidazole (18 mmol) was dissolved in acetonitrile (40 mL) in a round bottom flask. The solution was brought to reflux and iodomethane (5 mL) was added. The reaction was stirred at reflux for 20 h after which time it was cooled. The resulting white precipitate was collected by filtration and analyzed. Yield: 89.6% $^1$H NMR (300 MHz, $d_6$-DMSO): δ 3.86 (s), 5.68 (s), 7.53-7.59 (m), 7.93-8.03 (m), 9.51 (s) ppm.

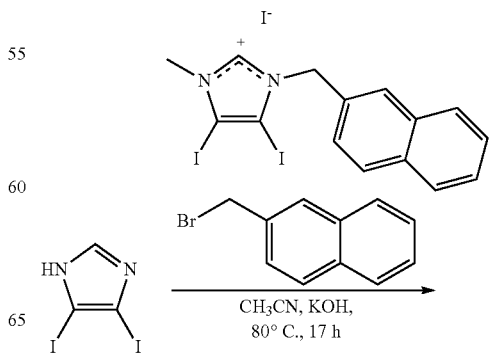

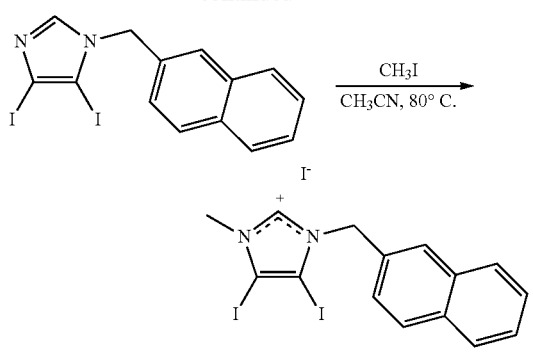

Synthesis of 4,5-diiodo-1-methyl-3-(naphthalen-2-ylmethyl)-1H-imidazolium iodide 4,5-diiodoimidazole (5.0 mmol) and KOH (5.0 mmol) were placed in a round bottom flask with 50 mL THF. The mixture was brought to reflux and stirred 0.5 h until KOH was consumed. 2-bromomethylnapthalene (5.0 mmol) was added and the solution was stirred at reflux for 17 hours. KBr was removed by vacuum filtration and the filtrate was collected. The volatiles were removed by rotary evaporation to give 4,5-diiodo-1-(naphthalen-2-ylmethyl)-1H-imidazole as a off white solid. 4,5-diiodo-1-(naphthalen-2-ylmethyl)-1H-imidazole was dissolved in acetonitrile in a round bottom flask. The solution was brought to reflux and excess iodomethane was added. The reaction was stirred at reflux for overnight after which time it was cooled. The resulting yellow precipitate was collected by filtration and analyzed. $^1$H NMR (300 MHz, $_{d6}$-DMSO): δ 3.88 (s), 5.64 (s), 7.47-7.60 (m), 7.89-8.02 (m), 9.57 (s) ppm.

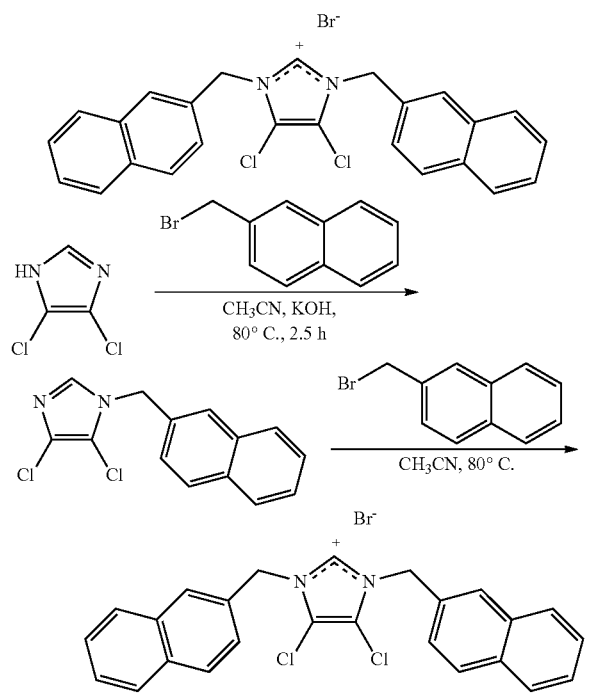

Synthesis of 4,5-dichloro-1,3-bis(naphthalen-2-ylmethyl)-1H-imidazolium bromide 4,5-dichloroimidazole (10.0 mmol, 1.370 g) and KOH (11.0 mmol, 0.617 g) were placed in a 50 mL round bottom flask with 10 mL acetonitrile. The mixture was brought to reflux (85° C.) and stirred 1 h until KOH was consumed. 2-Bromomethylnapthalene (10.00 mmol, 2.211 g) was added and the solution was stirred 2.5 hours. KBr was removed by vacuum filtration and a second equivalent of bromomethylnapthalene was added to the filtrate. The mixture was stirred at reflux for 1.5 hours. The white precipitate was collected by filtration and analyzed. Yield: 92.0% $^1$H NMR (500 MHz, $_{d6}$-DMSO): δ 5.71 (s, 4H), 7.57-7.62 (m, 6H), 7.95-8.06 (m, 8H), 9.75 (s, 1H) ppm. $^{13}$C NMR (500 MHz, d$_6$-DMSO): δ 51.8, 117.9, 119.3, 125.5, 136.7, 136.8, 127.7, 127.8, 128.8, 130.1, 132.7, 132.8, 136.9 ppm.

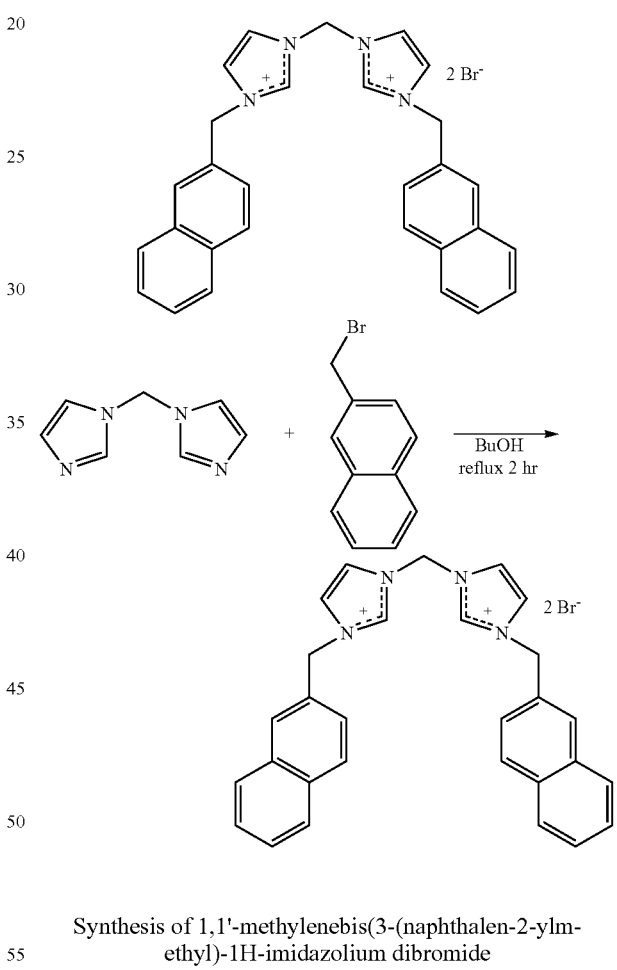

Synthesis of 1,1'-methylenebis(3-(naphthalen-2-ylmethyl)-1H-imidazolium dibromide To a 50 ml flask was added 0.74 g (5 mmol) 1,1'-Methylene bis(imidazole), 2.21 g (10 mmol) 2-(bromomethyl) naphthalene and 10 ml butyl alcohol. The solution was brought to reflux for 2 hours in which time a white precipitate formed. The solid was filtered and washed with THF to afford 2.19 g (74.2%) of 2 as a white solid. $^1$H NMR (DMSO-d$_6$): δ 5.69 (s, 4H, CH$_2$), 6.75 (s, 2H, CH$_2$), 7.55-7.60 (m, 6H, CH), 7.93-8.04 (m, 10H, CH), 7.18 (s, 2H, CH), 9.77 (s, 2H, CH). $^{13}$C NMR (DMSO-d$_6$): δ 52.5 (N—CH$_2$-nap), 58.2 (N—CH$_2$—N), 122.5 (im, CH), 123.3 (im, CH), 126.0 (nap, CH), 126.7 (nap, CH), 126.8 (nap, CH), 127.7 (nap, CH), 127.9 (nap, CH), 128.0 (nap, CH), 128.8 (nap, CH), 131.6 (nap, C), 132.7 (nap, C), 132.8 (nap, C), 137.9 (im, CH). Mz+ ESI (M-Br): calcd 511.1, found 510.9.

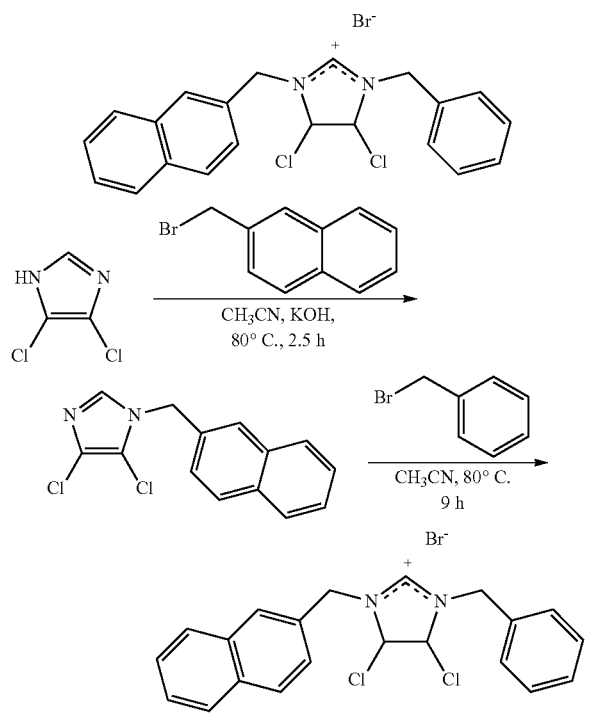

Synthesis of 1-benzyl-3-methylnaphthyl-4,5-dichloroimidazolium bromide 4,5-dichloroimidazole (10.0 mmol, 1.370 g) and KOH (11.0 mmol, 0.617 g) were placed in a 50 mL round bottom flask with 10 mL acetonitrile. The mixture was brought to reflux (85° C.) and stirred 1 h until KOH was consumed. 2-Bromomethylnapthalene (10.00 mmol, 2.211 g) was added and the solution was stirred 2.5 hours. KBr was removed by vacuum filtration and benzyl bromide (10 mmol) was added to the filtrate. The mixture was stirred at reflux for 1.5 hours. The white precipitate was collected by filtration and analyzed. $^1$H NMR (500 MHz, $d_6$-DMSO): δ 5.51 (2, 2H), 5.65 (s, 2H), 7.94-8.02 (m, 8H), 7.95-8.06 (m, 4H), 9.63 (s, 1H) ppm.

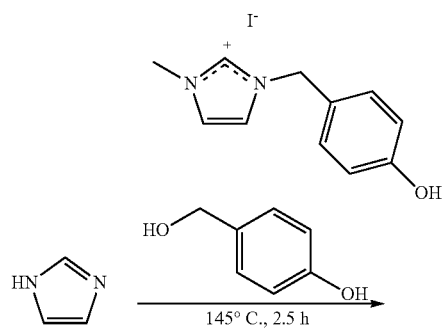

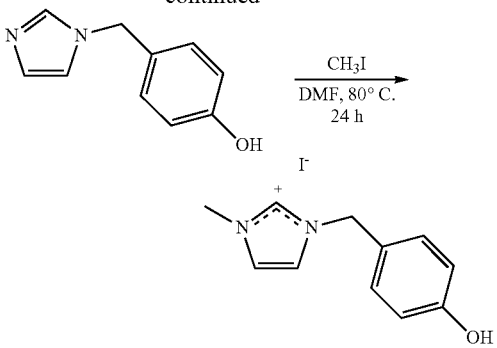

Synthesis of 3-(4-hydroxybenzyl)-1-methyl-imidazolium iodide

Imidazole (0.1 mol) and 4-hydroxybenzyl alcohol (0.1 mol) were combined and heated to 155° C. The crude product was washed with cold ethanol and recrystallized in an EtOH/DMF mixture. This powder (3-(4-hydroxybenzyl)imidazole, 2.20 mmol) was then was dissolved in DMF (3 mL). Iodomethane (3.21 mmol) was added to the reaction mixture and refluxed for 24 hours at 80° C. The solvent was evaporated and remaining oil was washed using ethyl ether to yield a brown precipitate. Yield: 0.573 g, 82.2%. Mp: 82.9-85.5° C. FTIR: (KBr, cm$^{-1}$) u(Ar) 1327.37, 1378.80, 1459.39, 1506.20, 1587.78; u(OH) 2922.97. $^1$H NMR (300 MHz, DMSO-$d_6$) 3.836 (3H, s, CH$_3$N), 5.265 (2H, s, NCH$_2$Ar), 6.796 (2H, d, NCHCHN), 7.275 (2H, d, NCAr), 7.729 (2H, d, HOAr), 9.122 (1H, s, OH), 9.627 (1H, s, NHN).

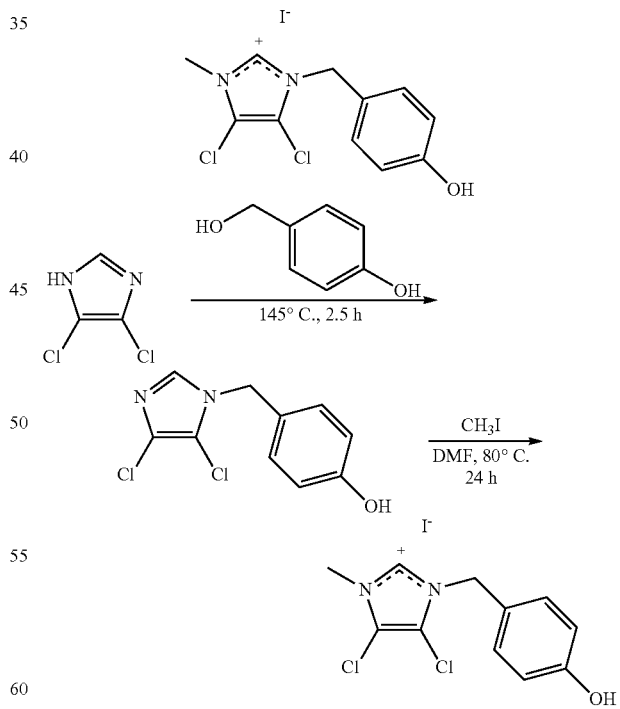

Synthesis of 3-(4-hydroxybenzyl)-1-methyl-imidazolium iodide 4,5-Dichloroimidazole (0.1 mol) and 4-hydroxybenzyl alcohol (0.1 mol) were combined and heated to 155° C. The crude product was washed with cold ethanol and recrystallized in an EtOH/DMF mixture. This powder (3-(4-hydroxybenzyl)-4,5-dichloroimidazole, 8.23 mmol) was then was dissolved in DMF (3 mL). Iodomethane (72.3 mmol) was added to the reaction mixture and refluxed for 24 hours at 80° C. The solvent was evaporated and remaining oil was washed using ethyl ether to yield a brown precipitate. Yield: 1.28 g, 61%. ¹H NMR (300 MHz, DMSO-d₆) 3.81 (3H, s, CH₃N), 5.34 (2H, CH₂), 6.82 (2H, d, Ar), 7.26 (2H, d, Ar), 9.32 (1H, s, NCHN), 9.70 (1H, s, OH).

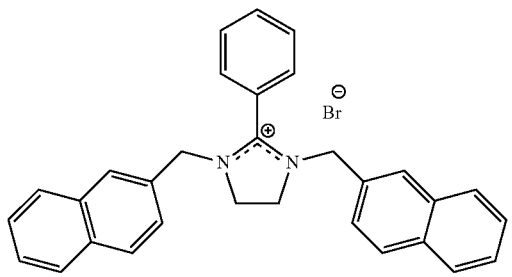

Synthesis of
1,3-methylnaphthyl-2-phenyl-2-imidazolinium bromide 2-phenyl-2-imidazoline (10.0 mmol) and KOH (11.0 mmol, 0.617 g) were placed in a 50 mL round bottom flask with 10 mL acetonitrile. The mixture was brought to reflux (85° C.) and stirred 1 h until KOH was consumed. 2-Bromomethylnapthalene (10.00 mmol, 2.211 g) was added and the solution was stirred 2.5 hours. KBr was removed by vacuum filtration and a second equivalent of bromomethylnapthalene was added to the filtrate. The mixture was stirred at reflux for 1.5 hours, and then allowed to cool to room temperature. The white precipitate was collected by filtration and analyzed.

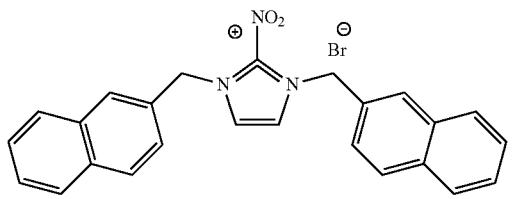

Synthesis of
1,3-methylnaphthyl-2-nitro-2-imidazolinium bromide 2-nitro-2-imidazole (1.0 mmol) and KOH (1.1 mmol, 0.617 g) were placed in a 50 mL round bottom flask with 10 mL acetonitrile. The mixture was brought to reflux (85° C.) and stirred 1 h until KOH was consumed. 2-Bromomethylnapthalene (1.00 mmol, 0.2211 g) was added and the solution was stirred 2.5 hours. KBr was removed by vacuum filtration and a second equivalent of bromomethylnapthalene was added to the filtrate. The mixture was stirred at reflux for 1.5 hours. The white precipitate was collected by filtration and analyzed.

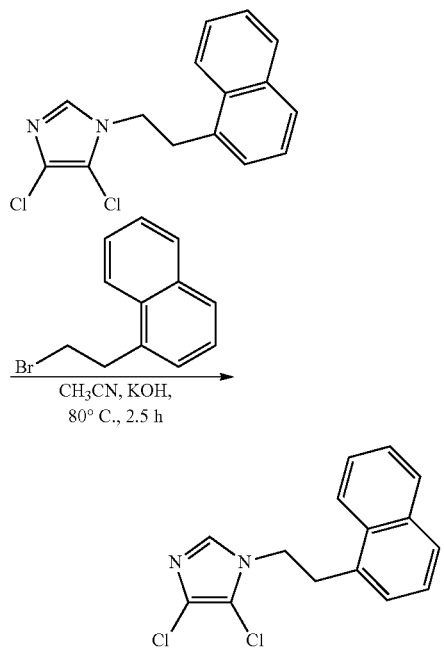

Synthesis of
1-(2-ethyl-1-naphthyl)-4,5-dichloroimidazole 4,5-Dichloroimidazole (0.137 g, 1 mmol) was dissolved into 1 mL of acetonitrile. Potassium hydroxide (0.061 g, 1.1 mmol) was added and the mixture was allowed to stir for 0.5 h. 1-(2-bromoethyl)-naphthalene (0.142 mL, 0.235 g, 1 mmol) was added and the solution was allowed to reflux for 2.5 h. The solution was filtered hot to remove a white precipitate (presumed to be KBr) and the solution was allowed to cool to room temperature to yield a tan crystalline material (0.085 g, 29% yield). ¹H NMR (500 MHz, DMSO-d₆) 8.13 (1H, d, Ar), 7.93 (1H, d, Ar), 7.84 (1H, d, Ar), 7.69 (1H, s, NCHN), 7.58 (2H, m, Ar), 7.42 (1H, t, Ar), 7.27 (1H, d, Ar), 4.31 (2H, t, NCH₂), 3.49 (2H, t, CH₂). ¹³C{1H} NMR (125 MHz, DMSO-d₆) 135.9 (NCN), 133.4 (Ar—Cl), 133.3 (Ar—Cl), 131.3 (Ar—Cl), 128.6 (Ar—Cl), 127.4 (Ar), 126.9 (Ar), 126.3 (Ar), 125.7 (Ar), 125.5 (Ar), 124.0 (Ar), 123.3 (Ar), 111.9 (Ar), 46.2 (CH₂), 32.8 (CH₃). MS: m/z=290.04 (theor for C₁₅H₁₂Cl₂N₂=291.0).

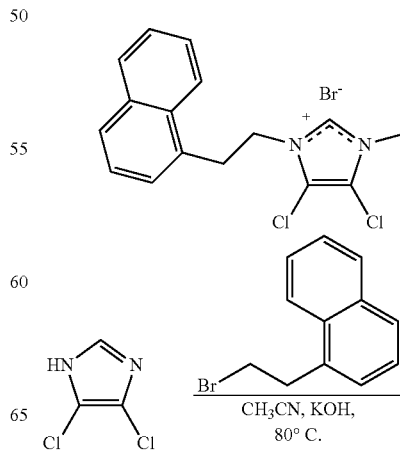

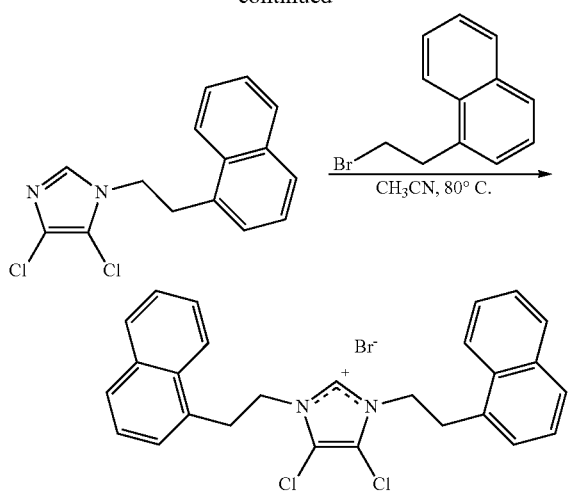

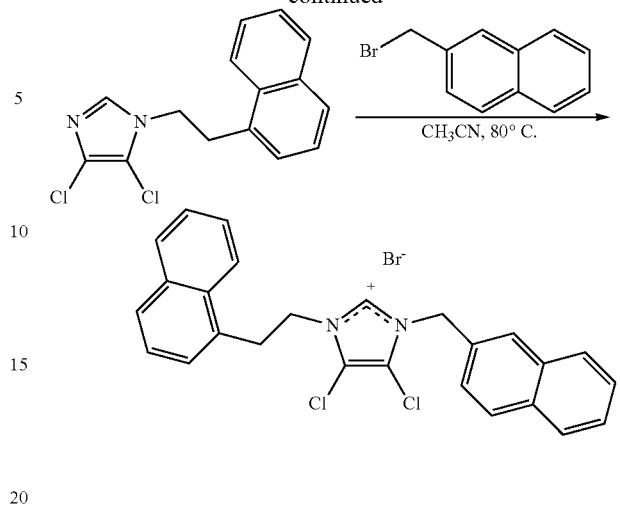

Synthesis of 1,3-bis(2-ethyl-1-naphthyl)-4,5-dichloroimidazolium bromide 4,5-Dichloroimidazole (1.23 g, 9 mmol) was dissolved into 27 mL of acetonitrile. Potassium hydroxide (0.61 g, 9.9 mmol) was added and the mixture was allowed to stir for 0.5 h. 1-(2-bromoethyl)-naphthalene (1.28 mL, 2.1 g, 9 mmol) was added and the solution was allowed to reflux overnight. The solution was filtered hot to remove a white precipitate (presumed to be KBr), the solution was concentrated down to 20 mL and was transferred to a pressure tube. A second equivalent of 1-(2-bromoethyl)-naphthalene (1.28 mL, 2.1 g, 9 mmol) was added, the pressure tube was sealed, and heated to 140° C. overnight. The resulting brown precipitate was collected and washed with ethyl ether $^1$H NMR (500 MHz, DMSO-$d_6$) 9.49 (1H, s, NCHN), 8.13 (2H, d, Ar), 7.98 (2H, d, Ar), 7.89 (2H, d, Ar), 7.64 (2H, m, Ar), 7.47 (2H, t, Ar), 7.32 (2H, d, Ar), 7.08 (2H, d, Ar), 4.54 (4H, t, NCH$_2$), 3.54 (4H, t, CH$_2$). $^{13}$C{1H} NMR (125 MHz, DMSO-$d_6$) 136.5 (NCN), 133.5 (Ar), 132.1 (Ar), 131.2 (Ar), 128.8 (Ar), 127.9 (Ar), 127.2 (Ar), 126.5 (Ar), 125.9 (Ar), 125.6 (Ar), 123.1 (Ar), 118.6 (Ar), 48.8 (CH$_2$), 31.7 (CH$_2$). MS: m/z=444.9 (theor for $C_{27}H_{23}Cl_2N_2Br_1$=526.3).

Synthesis of 1-(2-ethyl-1-naphthyl)-3-(2-methylnaphthyl)-4,5-dichloro imidazolium bromide 4,5-Dichloroimidazole (0.137 g, 1 mmol) was dissolved into 1 mL of acetonitrile. Potassium hydroxide (0.061 g, 1.1 mmol) was added and the mixture was allowed to stir for 0.5 h. 1-(2-bromoethyl)-naphthalene (0.142 mL, 0.235 g, 1 mmol) was added and the solution was allowed to reflux for 2.5 h. The solution was filtered hot to remove a white precipitate (presumed to be KBr) and the solution was allowed to cool to room temperature to yield a tan crystalline material (0.085 g, 29% yield). This solid (0.085 g, 0.3 mmol) was then dissolved into 1 mL of acetonitrile and 2-bromomethyl naphthalene (0.065 g, 0.3 mmol) was added. The mixture was refluxed at 80° C. for 3.5 h, during which a white precipitate formed. The precipitate was collected and washed with ethyl ether. $^1$H NMR (500 MHz, DMSO-$d_6$) 9.46 (1H, s, NCHN), 8.13 (1H, d, Ar), 7.96 (1H, d, Ar), 7.92 (1H, d, Ar), 7.61 (2H, m, Ar), 7.57 (4H, m, Ar), 7.39 (1H, d, Ar), 7.34 (2H, m, Ar), 5.62 (2H, s, CH$_2$), 4.60 (2H, t, NCH$_2$), 3.63 (2H, t, CH$_2$). $^{13}$C{1H} NMR (125 MHz, DMSO-$d_6$) 136.5 (NCN), 133.5 (Ar), 132.8 (Ar), 132.6 (Ar), 132.2 (Ar), 131.2 (Ar), 129.8 (Ar), 128.9 (Ar), 128.8 (Ar), 127.9 (Ar), 127.8 (Ar), 127.7 (Ar), 127.6 (Ar), 127.2 (Ar), 126.9 (Ar), 126.8 (Ar), 126.5 (Ar), 125.9 (Ar), 125.5 (Ar), 125.3 (Ar), 123.1 (Ar), 51.6 (CH$_2$), 49.0 (CH$_2$), 31.4 (CH$_2$). MS: m/z=444.9 (theor for $C_{27}H_{23}Cl_2N_2Br_1$=526.3).

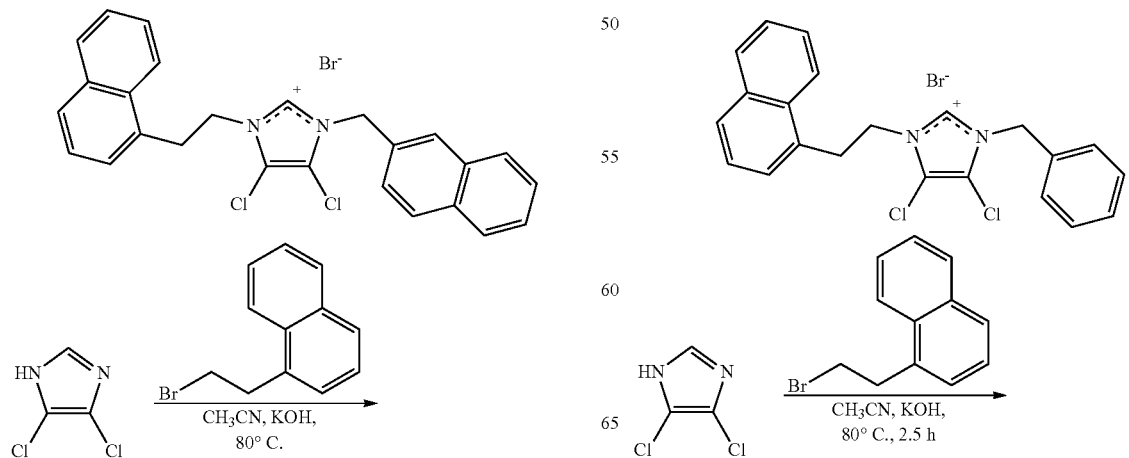

-continued

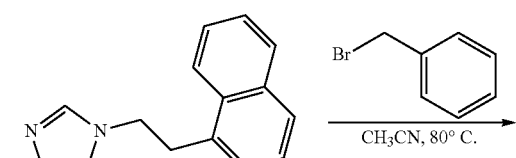

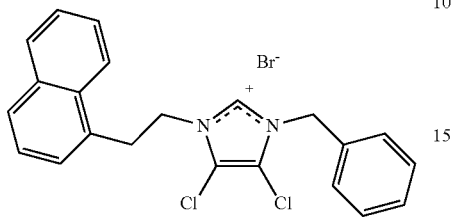

Synthesis of 1-benzyl-3-(2-ethyl-1-naphthyl)-4,5-dichloroimidazolium bromide 4,5-Dichloroimidazole (0.137 g, 1 mmol) was dissolved into 1 mL of acetonitrile. Potassium hydroxide (0.061 g, 1.1 mmol) was added and the mixture was allowed to stir for 0.5 h. 1-(2-bromoethyl)-naphthalene (0.142 mL, 0.235 g, 1 mmol) was added and the solution was allowed to reflux for 2.5 h. The solution was filtered hot to remove a white precipitate (presumed to be KBr) and the solution was allowed to cool to room temperature to yield a tan crystalline material (0.085 g, 29% yield). This solid (0.082 g, 0.28 mmol) was then dissolved into 1 mL of acetonitrile and benzyl bromide (33 μL, 0.48 g, 0.28 mmol) was added. The mixture was refluxed at 80° C. for 9 h, during which a white precipitate formed. The precipitate was collected and washed with ethyl ether (0.057 g, 44.3% yield). $^1$H NMR (500 MHz, DMSO-d$_6$) 9.52 (1H, s, NCHN), 8.15 (1H, d, Ar), 7.90 (1H, d, Ar), 7.92 (1H, d, Ar), 7.61 (1H, m, Ar), 7.57 (1H, t, Ar), 7.39 (1H, d, Ar), 7.34 (1H, d, Ar), 5.62 (2H, s, CH$_2$), 4.60 (2H, t, NCH$_2$), 3.63 (2H, t, CH$_2$). MS: m/z=380.9 (theor for C$_{22}$H$_{19}$Cl$_2$N$_2$Br$_1$=462.2).

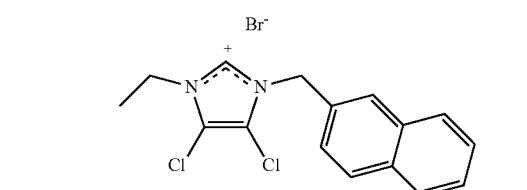

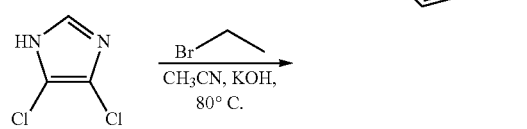

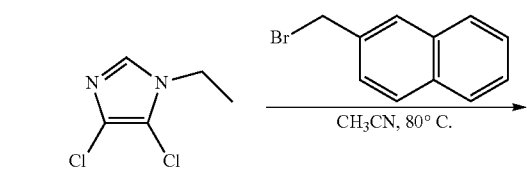

-continued

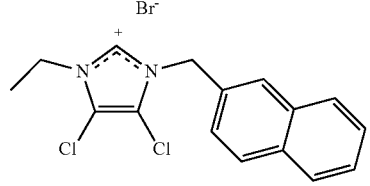

Synthesis of 1-ethyl-3-methylnaphthyl-4,5-dichloroimidazolium bromide 4,5-Dichloroimidazole (1.23 g, 9 mmol) was dissolved into 27 mL of acetonitrile. Potassium hydroxide (0.61 g, 9.9 mmol) was added and the mixture was allowed to stir for 0.5 h. Bromoethane (0.66 mL, 9 mmol) was added and the solution was allowed to reflux overnight. The solution was filtered hot to remove a white precipitate (presumed to be KBr) and 2-bromomethylnaphthalene (1.98 g, 9 mmol) was added and the mixture was returned to reflux overnight. The mixture was then allowed to cool to room temperature, resulting in a white precipitate (0.3538, 10% yield). $^1$H NMR (500 MHz, DMSO-d$_6$) 9.62 (1H, s, NCHN), 7.61 (4H, m, Ar), 7.58 (3H, m, Ar),), 5.66 (2H, s, NCH$_2$), 4.27 (2H, q, NCH$_2$), 1.47 (3H, t, CH$_3$). MS: m/z=304.8 (theor for C$_{16}$H$_{15}$Cl$_2$N$_2$Br$_1$=386.12).

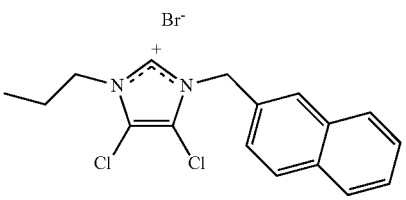

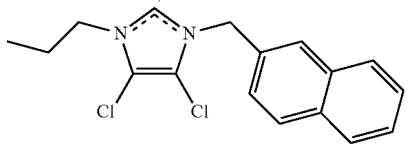

Synthesis of 1-propyl-3-methylnaphthyl-4,5-dichloroimidazolium bromide 4,5-Dichloroimidazole (1.23 g, 9 mmol) was dissolved into 27 mL of acetonitrile. Potassium hydroxide (0.61 g, 9.9 mmol) was added and the mixture was allowed to stir for 0.5 h. 1-iodopropane (0.88 mL, 9 mmol) was added and the solution was allowed to reflux overnight. The solution was filtered hot to remove a white precipitate (presumed to be KBr) and 2-bromomethylnaphthalene (1.98 g, 9 mmol) was added and the mixture was returned to reflux overnight. The mixture was then allowed to cool to room temperature, resulting in a yellow precipitate (1.125, 31% yield). $^1$H NMR (500 MHz, DMSO-$d_6$) 9.58 (1H, s, NCHN), 8.02 (4H, m, Ar), 7.57 (3H, m, Ar), 5.66 (2H, s, NCH$_2$), 4.21 (2H, t, NCH$_2$), 1.85 (2H, tq, CH$_2$), 0.94 (3H, t, CH$_3$). $^{13}$C{1H} NMR (125 MHz, DMSO-$d_6$) 136.4 (NCN), 132.8 (Ar), 132.6 (Ar), 130.0 (Ar), 128.8 (Ar), 127.8 (Ar), 127.7 (Ar), 127.6 (Ar), 126.9 (Ar), 126.8 (Ar), 125.5 (Ar), 119.1 (Ar), 118.8 (Ar), 51.6 (CH$_2$), 50.0 (CH$_2$), 21.7 (CH$_2$), 10.3 (CH$_3$). MS: m/z=318.8 (theor for $C_{17}H_{17}Cl_2N_2Br_1$=399.13).

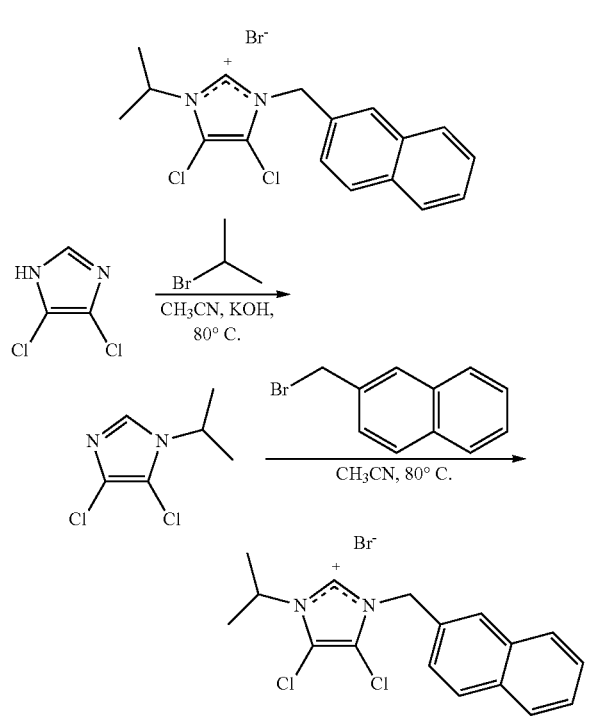

Synthesis of 2-propyl-3-methylnaphthyl-4,5-dichloroimidazolium bromide 4,5-Dichloroimidazole (1.23 g, 9 mmol) was dissolved into 27 mL of acetonitrile. Potassium hydroxide (0.61 g, 9.9 mmol) was added and the mixture was allowed to stir for 0.5 h. 2-iodopropane (0.88 mL, 9 mmol) was added and the solution was allowed to reflux overnight. The solution was filtered hot to remove a white precipitate (presumed to be KBr) and 2-bromomethylnaphthalene (1.98 g, 9 mmol) was added and the mixture was returned to reflux overnight. The mixture was then allowed to cool to room temperature, resulting in a white crystalline solid (1.33 g, 36% yield). $^1$H NMR (500 MHz, DMSO-$d_6$) 9.82 (1H, s, NCHN), 7.99 (4H, m, Ar), 7.57 (3H, m, Ar), 5.66 (2H, s, NCH$_2$), 4.71 (1H, 5, NCH), 10.94 (6H, t, CH$_3$). $^{13}$C{1H} NMR (125 MHz, DMSO-$d_6$) 136.4 (NCN), 132.8 (Ar), 132.6 (Ar), 130.0 (Ar), 128.8 (Ar), 127.8 (Ar), 127.7 (Ar), 127.6 (Ar), 126.9 (Ar), 126.8 (Ar), 125.5 (Ar), 119.1 (Ar), 118.8 (Ar), 51.6 (CH$_2$), 50.0 (CH$_2$), 21.7 (CH$_2$), 10.3 (CH$_3$). MS: m/z=318.8 (theor for $C_{17}H_{17}Cl_2N_2Br_1$=397.99).

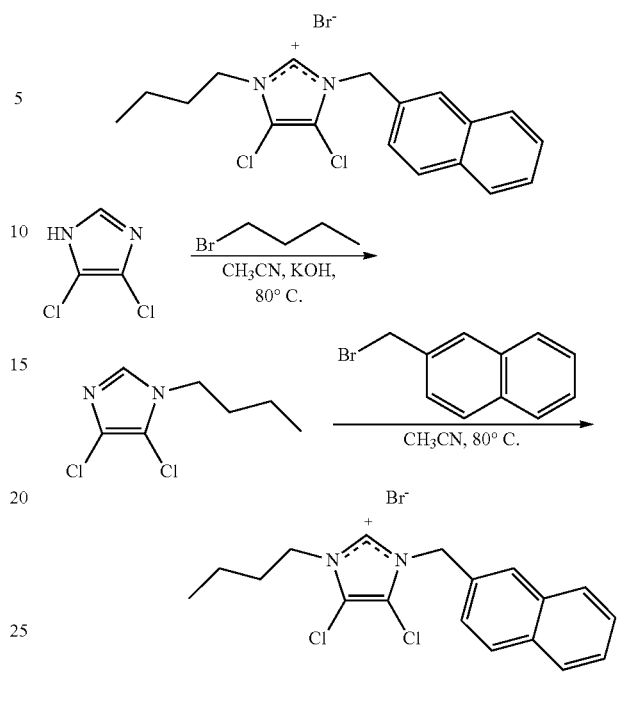

Synthesis of 1-butyl-3-methylnaphthyl-4,5-dichloroimidazolium bromide 4,5-Dichloroimidazole (1.23 g, 9 mmol) was dissolved into 27 mL of acetonitrile. Potassium hydroxide (0.61 g, 9.9 mmol) was added and the mixture was allowed to stir for 0.5 h. 1-iodobutane (1 mL, 9 mmol) was added and the solution was allowed to reflux overnight. The solution was filtered hot to remove a white precipitate (presumed to be KBr) and 2-bromomethylnaphthalene (1.98 g, 9 mmol) was added and the mixture was returned to reflux overnight. The mixture was then allowed to cool to room temperature, resulting in a yellow precipitate (1.125, 31% yield). $^1$H NMR (500 MHz, DMSO-$d_6$) 9.66 (1H, s, NCHN), 8.02 (4H, m, Ar), 7.57 (3H, m, Ar), 5.66 (2H, s, NCH$_2$), 4.24 (2H, t, NCH$_2$), 1.80 (2H, tt, CH$_2$), 1.37 (2H, tq, CH$_2$), 0.93 (3H, t, CH$_3$). $^{13}$C{1H} NMR (125 MHz, DMSO-$d_6$) 136.4 (NCN), 132.8 (Ar), 132.6 (Ar), 130.0 (Ar), 128.8 (Ar), 127.8 (Ar), 127.7 (Ar), 127.6 (Ar), 126.8 (Ar), 126.7 (Ar), 125.5 (Ar), 119.1 (Ar), 118.7 (Ar), 51.6 (CH$_2$), 48.3 (CH$_2$), 30.1 (CH$_2$), 18.7 (CH$_2$), 13.2 (CH$_3$). MS: m/z=332.9 (theor for $C_{18}H_{19}Cl_2N_2Br_1$=414.17).

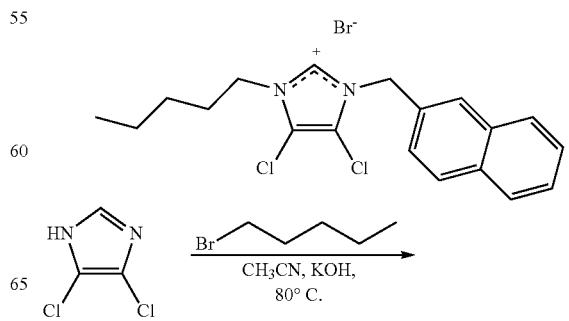

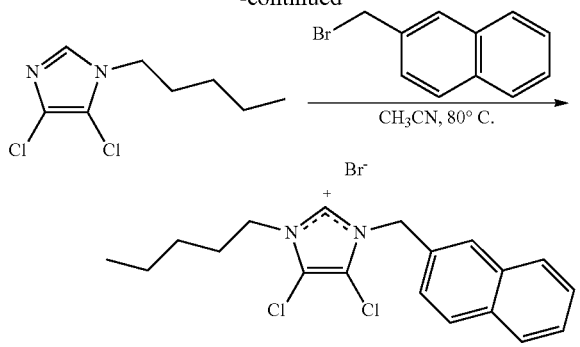

Synthesis of 1-pentyl-3-methylnaphthyl-4,5-dichloroimidazolium bromide 4,5-Dichloroimidazole (1.23 g, 9 mmol) was dissolved into 27 mL of acetonitrile. Potassium hydroxide (0.61 g, 9.9 mmol) was added and the mixture was allowed to stir for 0.5 h. 1-bromopentane (1.1 mL, 9 mmol) was added and the solution was allowed to reflux overnight. The solution was filtered hot to remove a white precipitate (presumed to be KBr) and 2-bromomethylnaphthalene (1.98 g, 9 mmol) was added and the mixture was returned to reflux overnight. The mixture was then allowed to cool to room temperature, resulting in a yellow precipitate (1.793, 49% yield). $^1$H NMR (500 MHz, DMSO-$d_6$) 9.66 (1H, s, NCHN), 8.02 (4H, m, Ar), 7.57 (3H, m, Ar), 5.66 (2H, s, NCH$_2$), 4.24 (2H, t, NCH$_2$), 1.80 (2H, tt, CH$_2$), 1.37 (2H, tq, CH$_2$), 0.93 (3H, t, CH$_3$). $^{13}$C{1H} NMR (125 MHz, DMSO-$d_6$) 136.4 (NCN), 132.8 (Ar), 132.6 (Ar), 130.0 (Ar), 128.8 (Ar), 127.8 (Ar), 127.7 (Ar), 127.6 (Ar), 126.8 (Ar), 126.7 (Ar), 125.5 (Ar), 120.9 (Ar), 114.1 (Ar), 112.9 (Ar), 51.6 (CH$_2$), 48.5 (CH$_2$), 27.8 (CH$_2$), 27.4 (CH$_2$), 21.4 (CH$_2$), 13.6 (CH$_3$).

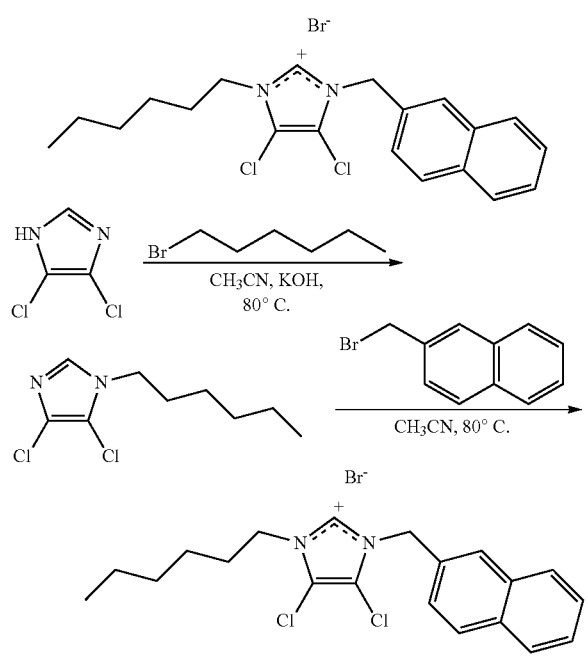

Synthesis of 1-hexyl-3-methylnaphthyl-4,5-dichloroimidazolium bromide 4,5-Dichloroimidazole (1.23 g, 9 mmol) was dissolved into 27 mL of acetonitrile. Potassium hydroxide (0.61 g, 9.9 mmol) was added and the mixture was allowed to stir for 0.5 h. 1-bromohexane (1.26 mL, 9 mmol) was added and the solution was allowed to reflux overnight. The solution was filtered hot to remove a white precipitate (presumed to be KBr) and 2-bromomethylnaphthalene (1.98 g, 9 mmol) was added and the mixture was returned to reflux overnight. The mixture was then allowed to cool to room temperature, resulting in a yellow precipitate (2.57, 65% yield). $^1$H NMR (500 MHz, DMSO-$d_6$) 9.64 (1H, s, NCHN), 8.02 (4H, m, Ar), 7.57 (3H, m, Ar), 5.66 (2H, s, NCH$_2$), 4.22 (2H, t, NCH$_2$), 1.80 (2H, tt, CH$_2$), 1.30 (6H, m, CH$_2$), 0.93 (3H, t, CH$_3$). $^{13}$C{1H} NMR (125 MHz, DMSO-$d_6$) 136.4 (NCN), 132.8 (Ar), 132.6 (Ar), 130.0 (Ar), 128.8 (Ar), 127.8 (Ar), 127.7 (Ar), 127.6 (Ar), 126.8 (Ar), 126.7 (Ar), 125.5 (Ar), 119.1 (Ar), 51.6 (CH$_2$), 48.3 (CH$_2$), 30.5 (CH$_2$), 28.0 (CH$_2$), 24.9 (CH$_2$), 21.8 (CH$_2$), 13.2 (CH$_3$). MS: m/z=332.9 (theor for $C_{20}H_{23}Cl_2N_2Br_1$=414.17).

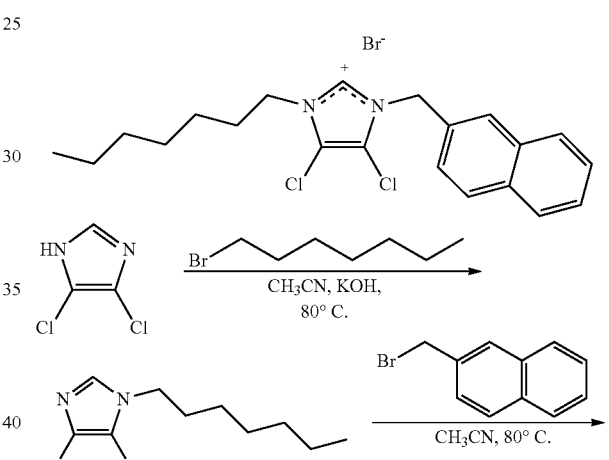

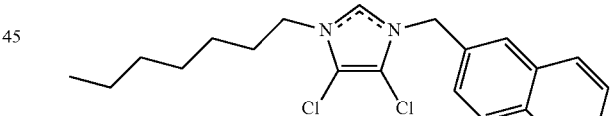

Synthesis of 1-heptyl-3-methylnaphthyl-4,5-dichloroimidazolium bromide 4,5-Dichloroimidazole (1.23 g, 9 mmol) was dissolved into 27 mL of acetonitrile. Potassium hydroxide (0.61 g, 9.9 mmol) was added and the mixture was allowed to stir for 0.5 h. 1-bromoheptane (1.41 mL, 9 mmol) was added and the solution was allowed to reflux overnight. The solution was filtered hot to remove a white precipitate (presumed to be KBr) and 2-bromomethylnaphthalene (1.98 g, 9 mmol) was added and the mixture was returned to reflux overnight. The mixture was then allowed to cool to room temperature, resulting in a yellow/white precipitate (2.73, 67% yield). $^1$H NMR (500 MHz, DMSO-$d_6$) 9.70 (1H, s, NCHN), 7.99 (4H, m, Ar), 7.57 (3H, m, Ar), 5.68 (2H, s, NCH$_2$), 4.23 (2H, t, NCH$_2$), 1.82 (2H, tt, CH$_2$), 1.30 (8H, m, CH$_2$), 0.93 (3H, t, CH$_3$). MS: m/z=374.8 (theor for C$_{21}$H$_{25}$Cl$_2$N$_2$Br$_1$=456.25).

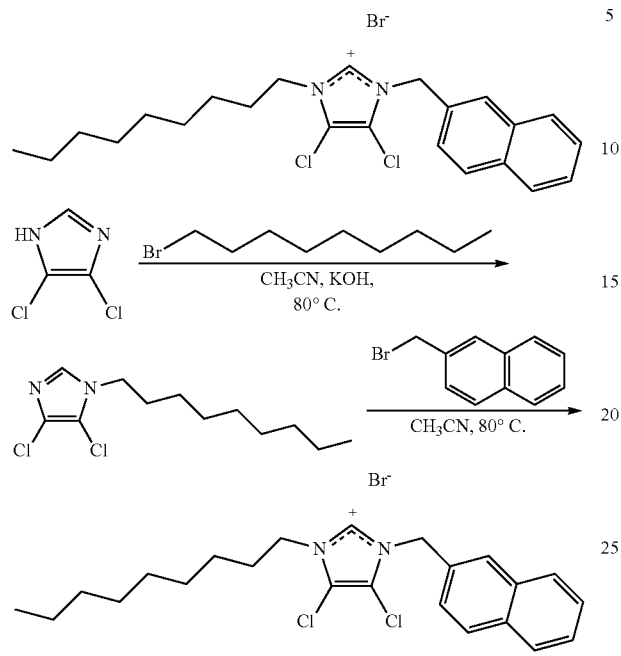

Synthesis of 1-nonyl-3-methylnaphthyl-4,5-dichloroimidazolium bromide 4,5-Dichloroimidazole (1.23 g, 9 mmol) was dissolved into 27 mL of acetonitrile. Potassium hydroxide (0.61 g, 9.9 mmol) was added and the mixture was allowed to stir for 0.5 h. 1-bromononane (1.72 mL, 9 mmol) was added and the solution was allowed to reflux overnight. The solution was filtered hot to remove a white precipitate (presumed to be KBr) and 2-bromomethylnaphthalene (1.98 g, 9 mmol) was added and the mixture was returned to reflux overnight. The mixture was then allowed to cool to room temperature, resulting in a yellow/white precipitate (2.73, 56% yield). $^1$H NMR (500 MHz, DMSO-d$_6$) 9.63 (1H, s, NCHN), 7.99 (4H, m, Ar), 7.58 (3H, m, Ar), 5.66 (2H, s, NCH$_2$), 4.22 (2H, t, NCH$_2$), 1.82 (2H, tt, CH$_2$), 1.25 (12H, m, CH$_2$), 0.93 (3H, t, CH$_3$). MS: m/z=402.8 (theor for C$_{23}$H$_{29}$Cl$_2$N$_2$Br$_1$=484.31).

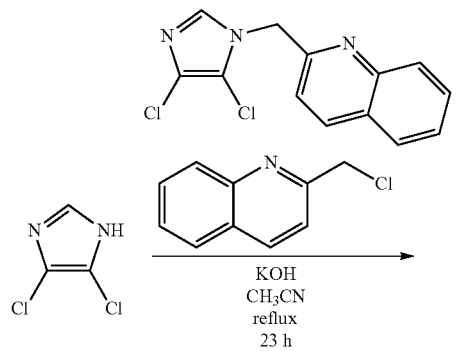

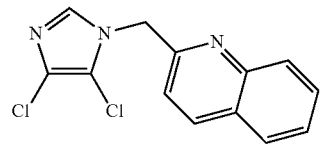

Synthesis of 1-(quinolin-2-ylmethyl)-4,5-dichloroimidazole 4,5-Dichloroimidazole (2.00 g, 14.6 mmol) was dissolved in 15 mL acetonitrile in a round bottom flask. Potassium hydroxide (0.90 g, 16.0 mmol) was added and the mixture was refluxed for 15 min. Concurrently, 2-chloromethylquinoline hydrochloride (3.13 g, 14.6 mmol) and potassium hydroxide (0.82 g, 14.6 mmol) were added to a second round bottom flask and stirred in 60 mL acetonitrile at reflux for 10 min. The contents of the second flask were added to the first, and the combined mixture was refluxed overnight, during which time a white precipitate formed. The reaction mixture was filtered hot, yielding a clear, tan filtrate. Slow evaporation and cooling of the filtrate yielded tan crystals, which were collected by a second filtration (2.28 g, 56% yield). $^1$H NMR (300 MHz, DMSO-d$_6$) 8.42 (1H, d, Ar), 8.04 (1H, s, NCHN), 8.00 (1H, d, Ar), 7.93 (1H, d, Ar), 7.76 (1H, t, Ar), 7.61 (1H, t, Ar), 7.38 (1H, d, Ar), 5.57 (2H, s, CH$_2$).

Crystals suitable for single crystal X-ray diffraction were grown from acetonitrile. Crystal data for 1-(quinolin-2-ylmethyl)-4,5-dichloroimidazole: C$_{13}$H$_9$Cl$_2$N$_3$, M$_r$=278.13, monoclinic, a=11.4028(5) Å, b=5.6309(3) Å, c=18.5920(9) Å, β=99.935(2)°, V=1175.85(10) Å$^3$, T=100(2) K, space group P2(1)/n, Z=4, μ(Mo Kα)=0.534 mm$^{-1}$, 19272 reflections measured, 2717 independent reflections (R$_{int}$=0.0226). The final R$_1$ values were 0.0247 (I>2σ(I)). The final wR(F$^2$) values were 0.0690 (I>2σ(I)). The final R$_1$ values were 0.0263 (all data). The goodness of fit on F$^2$ was 0.997.

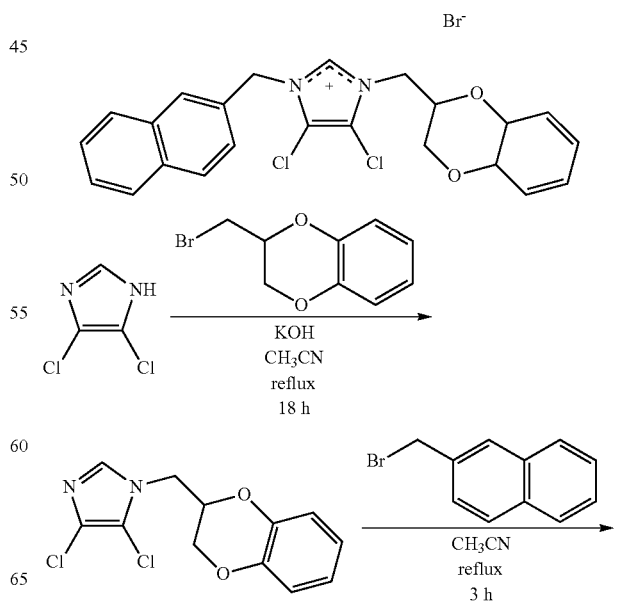

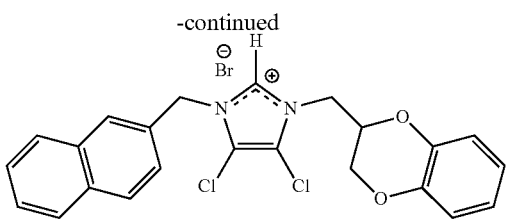

Synthesis of 1-(benzo[1,4]dioxan-2-ylmethyl)-4,5-dichloroimidazole 4,5-Dichloroimidazole (0.68 g, 5 mmol) and potassium hydroxide (0.28 g, 5 mmol) were added to a round bottom flask. Acetonitrile (2 mL) was added and the mixture was brought to reflux and stirred 30 min until all KOH was consumed. 2-(Bromomethyl)-1,4-benzodioxane (1.5 mL, 10 mmol) was added and the solution was returned to reflux overnight, during which time a white precipitate formed. The mixture was cooled to ambient temperature and filtered to remove the precipitate. The filtrate was concentrated via rotary evaporation at 75° C. until a yellow liquid remained. Upon cooling, the solution yielded a yellow solid. The solid was stirred in diethyl ether and filtered to yield a pale yellow solid (0.73 g, 52% yield).

Synthesis of 1-(benzo[1,4]dioxan-2-ylmethyl)-4,5-dichloro-3-(napthalen-2-ylmethyl)imidazolium bromide 1-(Benzo[1,4]dioxan-2-ylmethyl)-4,5-dichloroimidazole (0.28 g, 1 mmol) was combined with acetonitrile (2 mL) and heated until all solid dissolved. 2-(Bromomethyl)naphthalene (0.22 g, 1 mmol) was added and the solution was refluxed for 3 h, during which time a white precipitate formed. The precipitate was collected by filtration and washed with diethyl ether to yield a white solid (0.29 g, 57% yield). $^1$H NMR (300 MHz, DMSO-$d_6$) 9.65 (1H, s, NCHN), 8.00 (4H, m, Ar), 7.57 (3H, m, Ar), 6.87 (4H, m, Ar), 5.72 (2H, s, CH$_2$), 4.11-4.88 (5H, m, CH$_2$CHCH$_2$O).

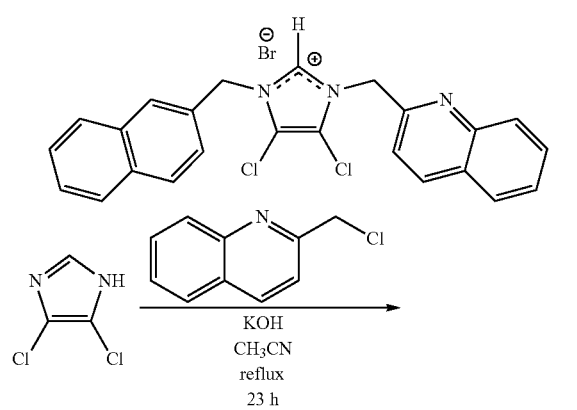

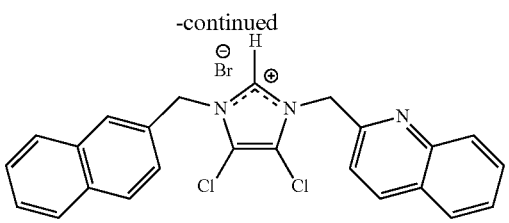

Synthesis of 3-(naphthalen-2-ylmethyl)-1-(quinolin-2-ylmethyl)-4,5-dichloroimidazolium bromide 4,5-Dichloroimidazole (2.00 g, 14.6 mmol) was dissolved in 15 mL acetonitrile in a round bottom flask. Potassium hydroxide (0.90 g, 16.0 mmol) was added and the mixture was refluxed for 15 min. Concurrently, 2-chloromethylquinoline hydrochloride (3.13 g, 14.6 mmol) and potassium hydroxide (0.82 g, 14.6 mmol) were added to a second round bottom flask and stirred in 60 mL acetonitrile at reflux for 10 min. The contents of the second flask were added to the first, and the combined mixture was refluxed overnight, during which time a white precipitate formed. The reaction mixture was filtered hot, yielding a clear, tan filtrate. Slow evaporation and cooling of the filtrate yielded tan crystals of 1-(quinolin-2-ylmethyl)-4,5-dichloroimidazole, which were collected by a second filtration. The crystals (0.66 g, 2.4 mmol) and 2-(bromomethyl)naphthalene (0.58 g, 2.6 mmol) were dissolved in 2 mL acetonitrile and refluxed for 3.5 h, during which time a white precipitate formed. The precipitate was collected via filtration of the reaction mixture and washed with acetonitrile to yield a white powder (1.02 g, 86% yield).). $^1$H NMR (300 MHz, DMSO-$d_6$) 9.84 (1H, s, NCHN), 8.52 (1H, d, Ar), 7.8 (12H, m, Ar), 5.95 (2H, s, CH$_2$), 5.83 (2H, s, CH$_2$).

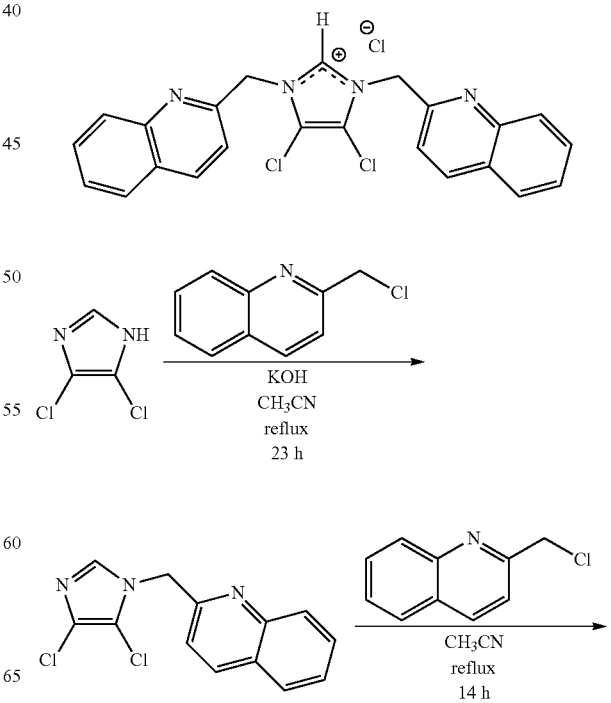

-continued

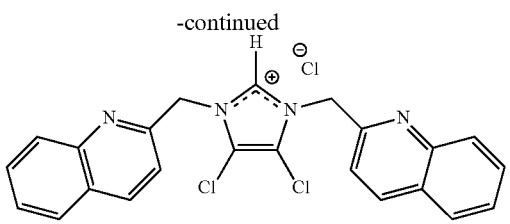

Synthesis of 1,3-bis(quinolin-2-ylmethyl)-4,5-dichloroimidazolium chloride 4,5-Dichloroimidazole (2.00 g, 14.6 mmol) was dissolved in 15 mL acetonitrile in a round bottom flask. Potassium hydroxide (0.90 g, 16.0 mmol) was added and the mixture was refluxed for 15 min. Concurrently, 2-chloromethylquinoline hydrochloride (3.13 g, 14.6 mmol) and potassium hydroxide (0.82 g, 14.6 mmol) were added to a second round bottom flask and stirred in 60 mL acetonitrile at reflux for 10 min. The contents of the second flask were added to the first, and the combined mixture was refluxed overnight, during which time a white precipitate formed. The reaction mixture was filtered hot, yielding a clear, tan filtrate. Slow evaporation and cooling of the filtrate yielded tan crystals of 1-(quinolin-2-ylmethyl)-4,5-dichloroimidazole, which were collected by a second filtration. 2-Chloromethylquinoline hydrochloride (0.19 g, 0.88 mmol) and potassium hydroxide (0.05 g, 0.90 mmol) were added to 5 mL acetonitrile and refluxed for 30 min. Crystals of 1-(quinolin-2-ylmethyl)-4,5-dichloroimidazole (0.1087 g, 0.39 mmol) were added, and the mixture was refluxed overnight, during which time it became red in color and viscous. The residue was extracted with dichloromethane (2×10 mL) and the combined organic layers were dried with $Mg_2SO_4$. The volatile components were removed under reduced pressure yielding an oil. The oil was dissolved in water, and the solution was extracted with toluene (2×). The combined aqueous layer was collected and the solvent allowed to evaporate in air. A sticky brown solid was collected in low yield. $^1$H NMR (300 MHz, DMSO-$d_6$) 10.03 (1H, s, NCHN), 8.55 (2H, d, Ar), 8.07 (2H, d, Ar), 7.89 (2H, d, Ar), 7.79 (2H, t, Ar), 7.74 (2H, d, Ar), 7.67 (2H, t, Ar), 6.07 (4H, s, $CH_2$).

-continued

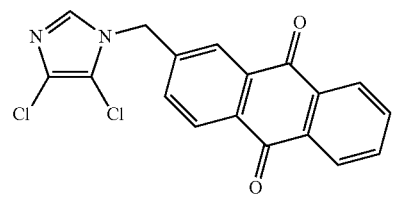

Synthesis of 1-(2-methylanthraquinonyl)-4,5-dichloroimidazole 4,5-Dichloroimidazole (0.18 g, 1.33 mmol) and potassium hydroxide (0.08 g, 1.46 mmol) were combined in a round bottom flask. Acetonitrile (2 mL) was added and the mixture was stirred at reflux for 30 min, dissolving the remaining solid. Concurrently, 2-(Bromomethyl)anthraquinone (0.4 g, 1.33 mmol) was added to 30 mL acetonitrile and stirred at reflux for 30 min, partially dissolving the solid. The solution in the initial flask was added to the 2-(bromomethyl)anthraquinone mixture, and the solution was returned to reflux for 3 h. The mixture was filtered hot, and a precipitate quickly formed in the tan filtrate. The precipitate was collected by a second filtration and washed with cold acetonitrile to yield a yellow powder (0.19 g, 40% yield). $^1$H NMR (300 MHz, DMSO-$d_6$) 8.20 (3H, m, Ar), 8.10 (1H, s, NCHN), 8.01 (1H, d, Ar), 7.89-7.95 (2H, m, Ar), 7.74 (1H, dd, Ar), 5.51 (2H, s, $CH_2$).

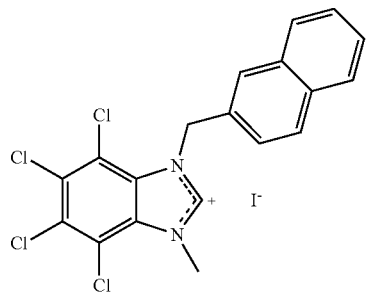

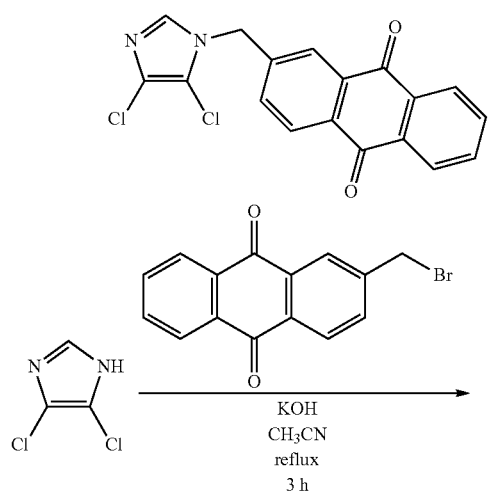

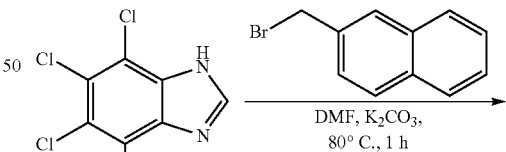

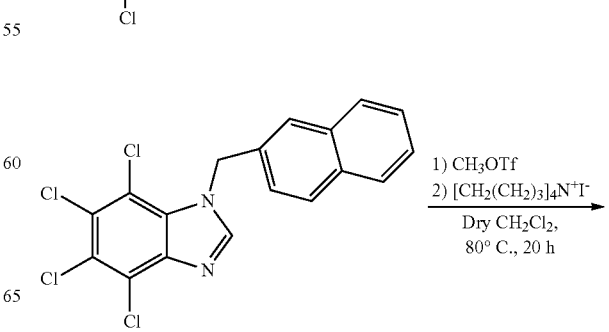

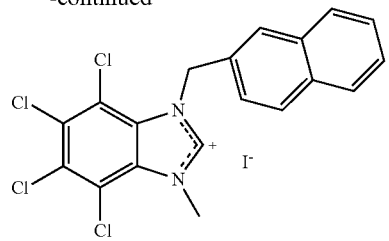

Synthesis of 4,5,6,7-tetrachloro-3-methyl-1-(naphthalen-2-ylmethyl)-1H-benzo[d]imidazolium iodide Synthesis was conducted under anaerobic conditions. 1-methylnaphthyl-4,5,6,7-tetrachlorobenzimidazole (0.77 g, 2.0 mmol) was dissolved into 30 mL of dry methylene chloride combined with methyl trifluoromethanesulfonate (0.25 mL, 2.3 mmol). The resulting mixture was refluxed for 20 h, during which time a precipitate formed. The precipitate was collected, washed with benzene, and redissolved in methanol that contained tetra-n-butylammonium iodide (0.59 g, 1.5 mmol). A white solid that precipitated out was then collected and washed with cold ethanol to yield a white powder (0.54 g, 50% yield). Mp: 187-189° C. Found: C, 42.4; H, 2.2; N, 5.0 Calc. for $C_{19}H_{13}Cl_4N_2I_1$: C, 42.4; H, 2.4; N, 5.2%. FTIR (KBr, cm-1) u(CN) 1305 and 1104, u(CCl) 669. $^1$H NMR (500 MHz, DMSO-$d_6$) 9.46 (1H, s, NCHN), 7.98 (4H, m, Ar), 7.57 (3H, m, Ar), 5.66 (2H, s, NCH$_2$), 3.84 (3H, s, NCH$_3$). $^{13}$C{1H} NMR (125 MHz, DMSO-$d_6$) 148.3 (NCN), 132.7 (Ar—Cl), 132.6 (Ar—Cl), 131.8 (Ar—Cl), 130.8 (Ar—Cl), 129.8 (Ar), 128.6 (Ar), 128.5 (Ar), 127.7 (Ar), 127.6 (Ar), 126.6 (Ar), 125.9 (Ar), 124.7 (Ar), 52.2 (CH$_2$), 37.7 (CH$_3$). MS: m/z=408.8 (theor for $C_{19}H_{13}Cl_4N_2^+$=408.98).

Crystals suitable for single crystal X-ray diffraction were grown from a concentrated solution of chloroform. Crystal data for 6: $C_{19}H_{13}Cl_4N_2I_1$, M=538.01, monoclinic, a=24.500 (3) Å, b=12.9443(12) Å, c=14.1288(13) Å, β=117.003(2)°, V=3992.3(7) Å$^3$, T=100(2) K, space group C2/c, Z=8, μ(Mo Kα)=2.146 mm$^{-1}$, 17009 reflections measured, 4569 independent reflections (Rint=0.0396). The final R1 values were 0.0330 (I>2σ(I)). The final wR(F$^2$) values were 0.0798 (I>2σ (I)). The final R1 values were 0.0404 (all data). The final wR(F$^2$) values were 0.0850 (all data). The goodness of fit on F$^2$ was 1.048.

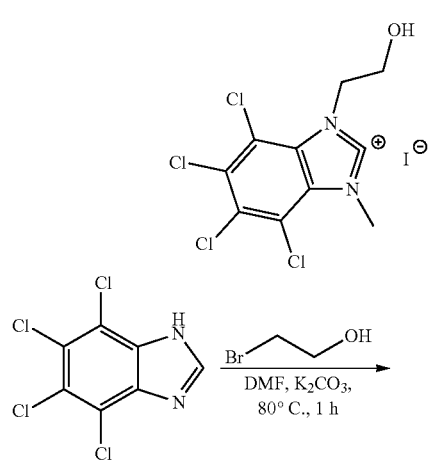

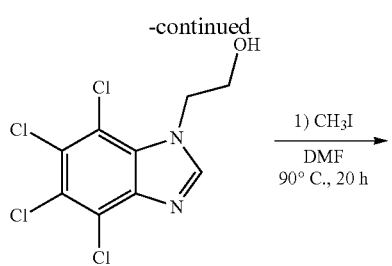

Synthesis of 1-hydroxyethyl-3-methyl-4,5,6,7-tetrachlorobenzimidazole 1-hydroxyethyl-4,5,6,7-tetrachlorobenzimidazole (1.0 g, 3.6 mmol) was dissolved in 17 mL of DMF. Iodomethane (1.00 mL, 10.8 mmol) was added and the solution was heated at 90° C. for 20 h. The solution was then cooled and a light yellow precipitate was collected via filtration and then immediately washed with cold ethanol to give a light yellow powder (1.59 g, 62% yield). Mp: 218-220° C. Found: C, 27.1; H, 1.9; N, 6.1 Calc. for $C_{10}H_9Cl_4N_2O_1I_1$: C, 27.2; H, 2.05; N, 6.3%. FTIR (KBr, cm-1) u(OH) 3304, u(CN) 1305 and 1075, u(CCl) 673. $^1$H NMR (500 MHz, DMSO-$d_6$) 9.94 (1H, s, NCHN), 5.17 (1H, t, OH), 4.79 (2H, t, CH$_2$), 4.33 (3H, s, CH$_3$), 3.85 (2H, t, CH$_2$). $^{13}$C{1H} NMR (125 MHz, DMSO-$d_6$) 148.1 (NCN), 130.7 (Ar—Cl), 130.5 (Ar—Cl), 129.5 (Ar—Cl), 128.5 (Ar—Cl), 118.7 (Ar), 118.2 (Ar), 58.9 (CH$_2$), 52.1 (CH$_2$), 37.3 (CH$_3$). MS: m/z=312.9 (theor. for $C_7H_3Cl_4N_2^+$=312.9).

Crystals suitable for X-ray diffraction were grown from a concentrated chloroform solution. Crystal data for 4: $C_{10}H_9Cl_4N_2O_1I_1$, M=441.89, monoclinic, a=9.2405(9) Å, b=6.9153(7) Å, c=22.244(2) Å, β=99.331(2)°, V=1402.6(2) Å$^3$, T=100(2) K, space group P2(1)/c, Z=4, μ(Mo Kα)=3.033 mm$^{-1}$, 11737 reflections measured, 3346 independent reflections (Rint=0.0311). The final R1 values were 0.0257 (I>2σ (I)). The final wR(F$^2$) values were 0.0630 (I>2σ(I)). The final R1 values were 0.0276 (all data). The final wR(F$^2$) values were 0.0639 (all data). The goodness of fit on F$^2$ was 1.087.

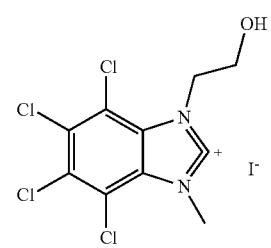

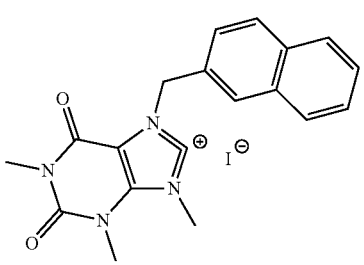

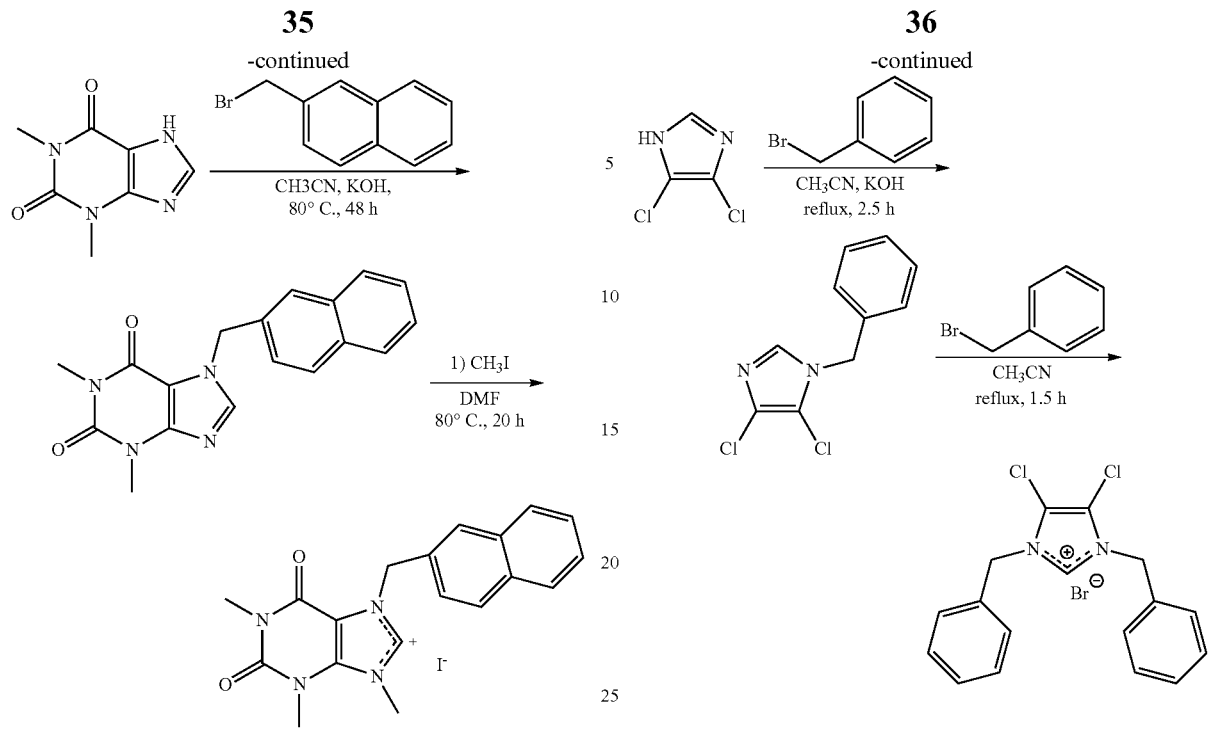

Synthesis of 1,3,9-trimethyl-7-methylnaphthylxanthinium iodide (8)

2.90 g (9.05 mmol) of 1,2-dimethyl-7-methylnaphthylxanthine was dissolved in 15 mL of DMF. 10 mL (160 mmol) of Iodomethane was added and the mixture was heated to 80° C. for 20 h. Volatiles were removed via rotary evaporation to produce a dark brown oil. The oil was washed with cold acetone to precipitate a light yellow powder. The precipitate was collected and washed with 50 mL of chloroform and 50 mL of water to yield 2.44 g of pure product (58% yield). Anal. Calcd for $C_{19}H_{19}N_4O_2I$: C, 49.36; H, 4.19; N, 12.12. Found C, 48.82; H, 3.86; N, 11.78. Mass Spectrometry gave m/z (M-I)=335.1 (Theor for $C_{19}H_{19}N_4O_2+$=335.3). 1H NMR (500 MHz, DMSO-$d_6$) 9.54 (s, 1H, NCHN), 7.95 (m, 4H, Ar), 7.56 (m, 3H, Ar), 5.89 (s, 2H, $CH_2$), 4.18 (s, 3H, $CH_3$), 3.74 (s, 3H, $CH_3$), 3.24 (s, 3H, $CH_3$). 13C NMR (500 MHz, DMSO-$d_6$) 153.04 (s, NCO), 150.04 (s, NCON), 139.7 (s, NCN), 139.49 (s, NC+N), 132.49 (s, Ar), 132.69 (s, Ar), 132.63 (s, Ar), 131.44 (s, Ar), 128.56 (s, Ar), 127.85 (s, Ar), 127.57 (s, Ar), 127.22 (s, Ar), 126.70 (s, Ar), 126.61 (s, Ar), 125.56 (s, Ar), 107.10 (s, NCCO), 51.33 (s, $CH_2$), 37.39 (s, $CH_3$), 31.46 (s, $CH_3$), 28.46 (s, $CH_3$)

Synthesis of 1,3-dibenzyl-4,5-dichloro-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of benzyl bromide (1.26 g, 7.36 mmol) was added to the solution and refluxed for 2.5 h. Solution was filtered hot to remove the KBr precipitate and placed back onto reflux. The second equivalent of benzyl bromide (1.38 g, 8.10 mmol) was added to solution and refluxed for 1.5 h. The solution was cooled and the white precipitate was collected and analyzed. Yield: 93%. $^1$H NMR (500 MHz, DMSO-$d_6$): δ 5.55 (s, 4H, $CH_2$), 7.43-7.46 (m, 10H, aryl), 9.86 (s, 1H, NCHN); $^{13}$C NMR (125 MHz, DMSO-$d_6$): δ 51.50, 119.11, 128.27, 128.84, 128.93, 132.61, 136.68

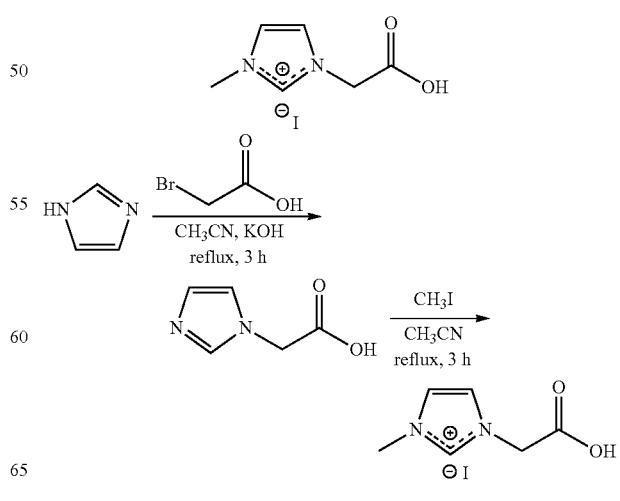

Synthesis of 1-(carboxymethyl)-3-methyl-1H-imidazol-3-ium

1H-Imidazole (1.00 g, 14.69 mmol) was dissolved in acetonitrile. Potassium hydroxide (1.65 g, 29.33 mmol) was added to the solution and allowed to reflux for 30 min. 1 equivalent of 2-bromoacetic acid (2.04 g, 14.69 mmol) was added to the solution and refluxed for 3 h. KBr was removed by vacuum filtration and the filtrate placed back onto reflux. Methyl iodide (1.8 mL, 4.17 g, 29.38 mmol) was added to solution and refluxed for 3 h. The solution was cooled and the white precipitate was collected and analyzed. $^1$H NMR (300 MHz, DMSO-$d_6$): δ 3.91, 5.20, 7.77, 7.78, 9.20, 13.63; $^{13}$C NMR (125 MHz, DMSO-$d_6$): δ 35.9, 49.7, 123.2, 123.7, 137.6, 168.2

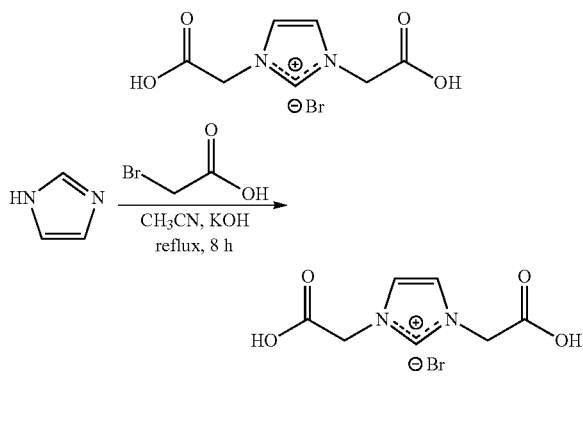

Synthesis of 1,3-bis(carboxymethyl)-1H-imidazol-3-ium

1H-Imidazole (1.00 g, 14.69 mmol) was dissolved in acetonitrile. Potassium hydroxide (1.65 g, 29.33 mmol) was added to the solution and allowed to reflux for 30 min. 2.1 equivalents of 2-bromoacetic acid (4.29 g, 30.85 mmol) was added to the solution and refluxed for 6 h. KBr was removed by vacuum filtration and the filtrate placed into a round bottom flask. The solution was neutralized with 6M HBr. The volatiles were removed in vacuo and the product washed with ethyl ether. The resulting white precipitate was collected and analyzed. $^1$H NMR (300 MHz, DMSO-$d_6$): δ 4.71, 7.71, 7.78, 9.20, 13.96.

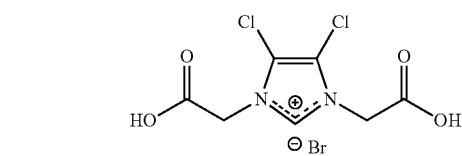

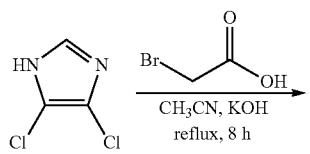

Synthesis of 1,3-bis(carboxymethyl)-4,5-dichloro-1H-imidazol-3-ium 4,5-dichloroimidazole (1.00 g, 7.36 mmol) was dissolved in acetonitrile. Potassium hydroxide (0.828 g, 14.72 mmol) was added to the solution and allowed to reflux for 30 min. 2.1 equivalents of 2-bromoacetic acid (2.15 g, 15.46 mmol) was added to the solution and refluxed for 6 h. KBr was removed by vacuum filtration and the filtrate placed into a round bottom flask. The solution was neutralized with 6M HBr. The volatiles were removed in vacuo and the product washed with ethyl ether. The resulting white precipitate was collected and analyzed. $^1$H NMR (300 MHz, DMSO-$d_6$): δ 4.89, 9.57, 12.71.

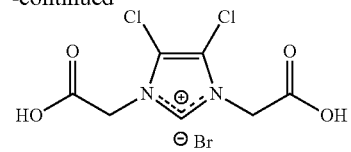

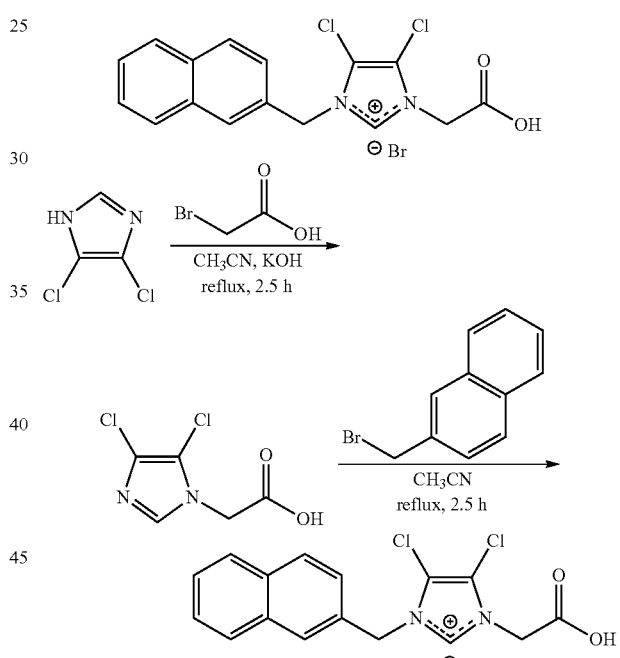

Synthesis of 1-(carboxymethyl)-4,5-dichloro-3-(naphthalen-2-ylmethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 2-bromoacetic acid (2.15 g, 15.46 mmol) was added to the solution and refluxed for 2.5 h. Solution was filtered to remove the KBr precipitate and placed back onto reflux. An equivalent of 2-(bromomethyl)naphthalene (1.63 g, 7.36 mmol) was added to solution and refluxed for 2.5 h. The solution was neutralized with 6M HBr, volatiles removed in vacuo, and the resulting white precipitate was collected and analyzed. $^1$H NMR (300 MHz, DMSO-$d_6$): δ 4.71, 5.75, 7.59, 8.02, 9.81, 12.71.

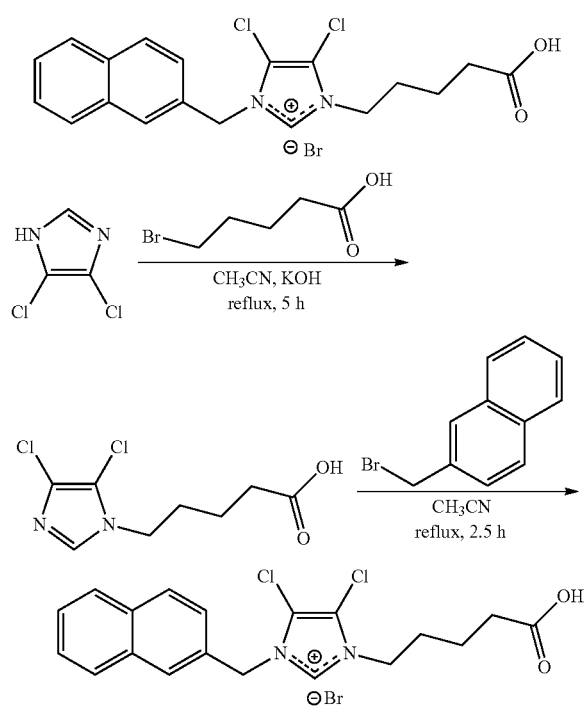

Synthesis of 1-(4-carboxybutyl)-4,5-dichloro-3-(naphthalen-2-ylmethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 5-bromopentanoic acid (1.33 g, 7.36 mmol) was added to the solution and refluxed for 5 h. Solution was filtered to remove the KBr precipitate and placed back onto reflux. An equivalent of 2-(bromomethyl)naphthalene (1.63 g, 7.36 mmol) was added to solution and refluxed for 2.5 h. The solution was neutralized with 6M HBr, volatiles removed in vacuo, and the resulting white precipitate was collected and analyzed. $^1$H NMR (300 MHz, DMSO-$d_6$): δ 1.61, 1.80, 2.25, 3.51, 5.76, 7.61, 8.05, 9.74, 12.07.

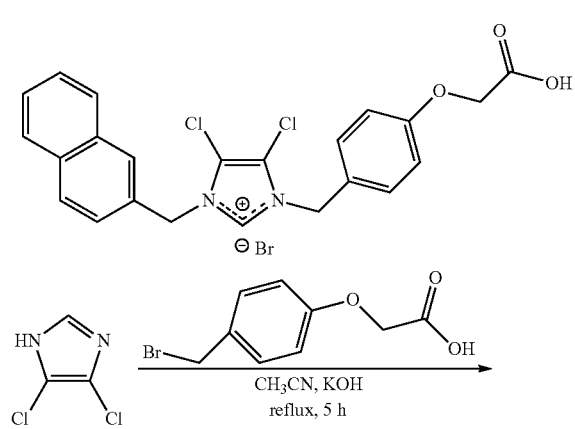

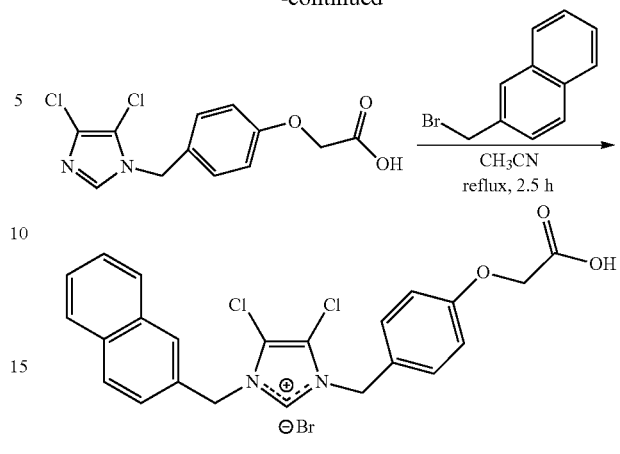

Synthesis of 1-(4-(carboxymethoxy)benzyl)-4,5-dichloro-3-(naphthalen-2-ylmethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 2-(4-(bromomethyl)phenoxy)acetic acid (1.80 g, 7.36 mmol) was added to the solution and refluxed for 5 h. Solution was filtered to remove the KBr precipitate and placed back onto reflux. An equivalent of 2-(bromomethyl)naphthalene (1.63 g, 7.36 mmol) was added to solution and refluxed for 2.5 h. The solution was neutralized with 6M HBr, volatiles removed in vacuo, and the resulting white precipitate was collected and analyzed. $^1$H NMR (300 MHz, DMSO-$d_6$): δ 4.70, 5.45, 5.76, 7.12, 7.61, 8.05, 9.74, 12.32.

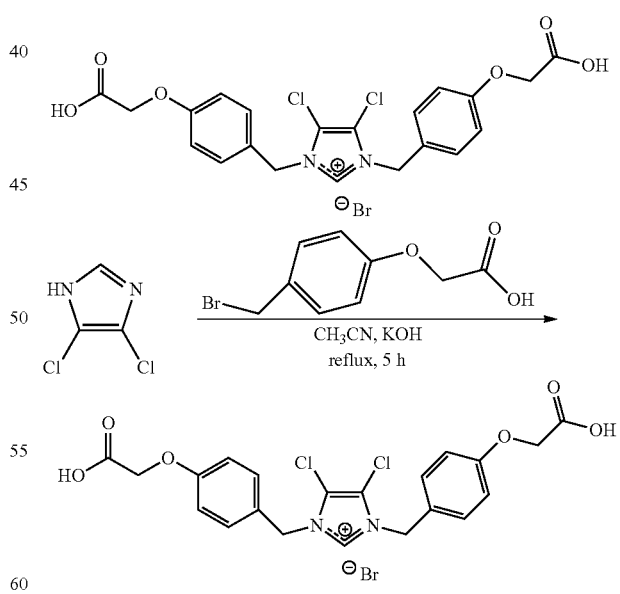

Synthesis of 1,3-bis(4-(carboxymethoxy)benzyl)-4,5-dichloro-1H-imidazol-3-ium bromide 4,5-dichloroimidazole (1.00 g, 7.36 mmol) was dissolved in acetonitrile. Potassium hydroxide (0.828 g, 14.72 mmol)

was added to the solution and allowed to reflux for 30 min. 2 equivalents of 2-(4-(bromomethyl)phenoxy)acetic acid (3.61 g, 14.72 mmol) was added to the solution and refluxed for 5 h. Solution was filtered to remove the KBr precipitate and neutralized with 6M HBr. Volatiles were removed in vacuo and the resulting white precipitate was collected and analyzed. $^1$H NMR (300 MHz, DMSO-$d_6$): δ 4.67, 5.51, 7.12, 7.61, 9.23, 12.17.

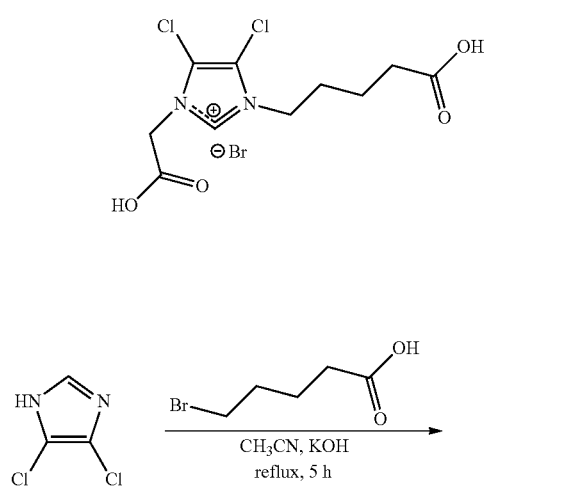

Synthesis of 1-(4-carboxybutyl)-3-(carboxymethyl)-4,5-dichloro-1H-imidazol-3-iumbromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 5-bromopentanoic acid (1.33 g, 7.36 mmol) was added to the solution and refluxed for 5 h. Solution was filtered to remove the KBr precipitate and placed back onto reflux. 2-bromoacetic acid (2.15 g, 15.46 mmol) was added to the solution and refluxed for 2.5 h. The solution was neutralized with 6M HBr, volatiles removed in vacuo, and the resulting white precipitate was collected and analyzed. $^1$H NMR (300 MHz, DMSO-$d_6$): δ 3.11, 3.56, 4.68, 4.91, 5.24, 8.24, 10.06, 12.04.

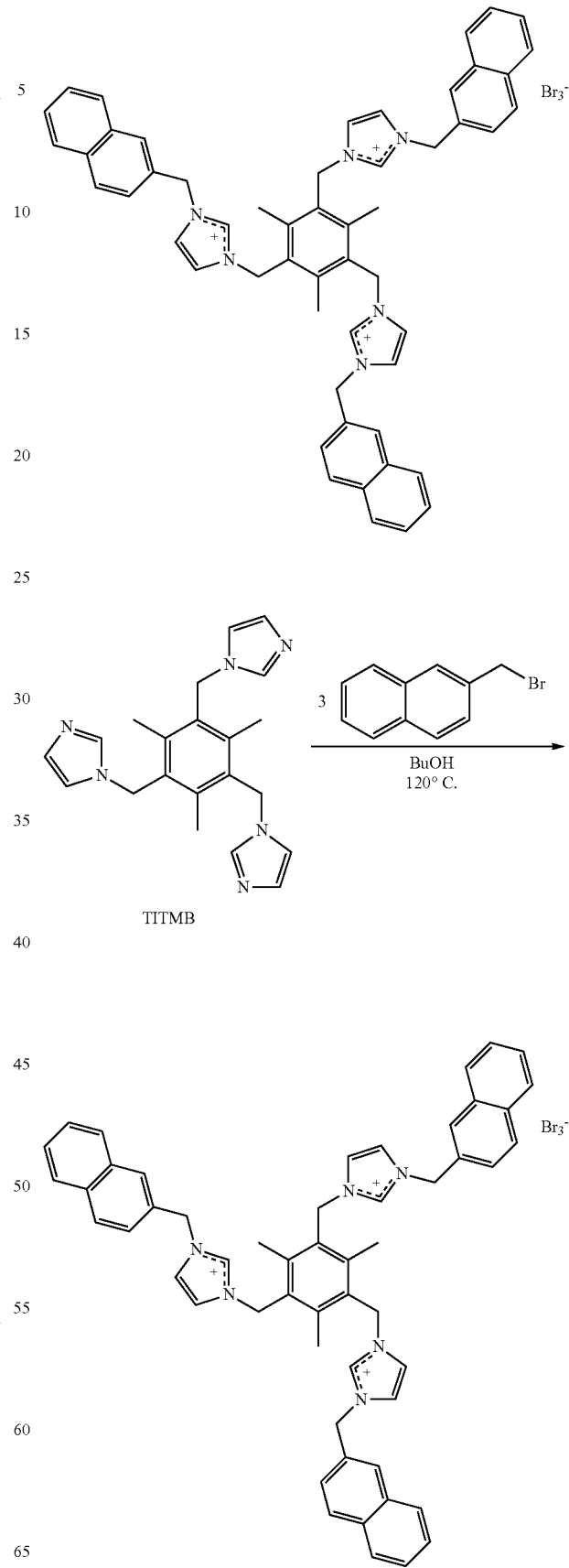

Synthesis of 1,1',1"-((2,4,6-trimethylbenzene-1,3,5-triyl)tris(methylene))tris(3-(naphthalen-2-ylmethyl)-1H-imidazolium)tribromide To a round bottom flask was added 0.72 g (2 mmol) TITMB, 1.32 g (6 mmol) 2-(bromomethyl) naphthalene and 10 ml butyl alcohol. The solution was refluxed overnight during which time a precipitate formed. The solid was filtered and washed with THF to afford 1.32 g of 1,1',1"-((2,4,6-trimethylbenzene-1,3,5-triyl)tris(methylene))tris(3-(naphthalen-2-ylmethyl)-1H-imidazolium)tribromide as a yellowish-white solid. $^1$H NMR (DMSO-d$_6$): δ 2.35, 5.63, 5.67, 7.53, 7.54, 7.72, 7.79, 7.86, 7.89, 7.96, 9.66.

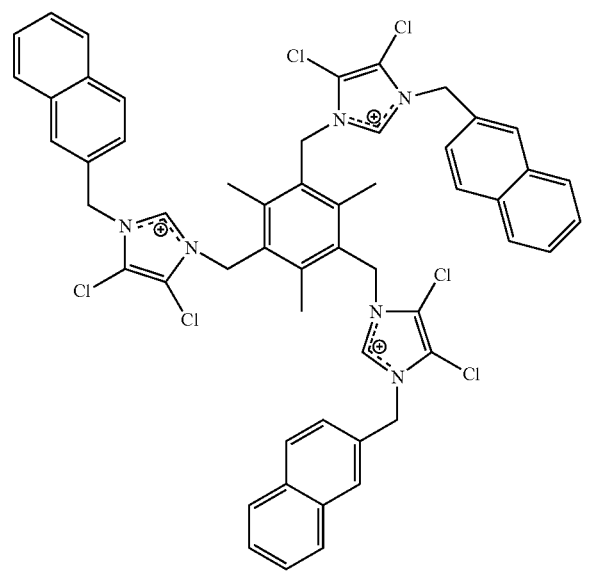

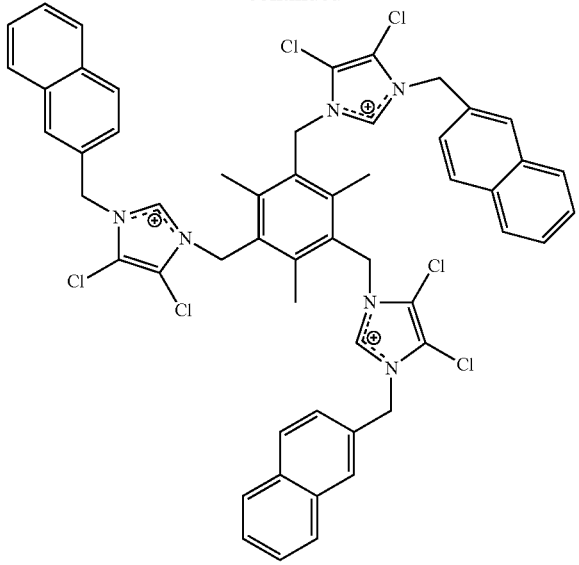

Synthesis of 3,3',3"-(2,4,6-trimethylbenzene-1,3,5-triyl)tris(methylene)tris(4,5-dichloro-1-(naphthalen-2-ylmethyl)-1H-imidazol-3-ium) bromide)

4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)-2,4,6-trimethylbenzene (2.91 g, 7.30 mmol) was added to the solution and refluxed overnight. Solution was filtered while hot to remove the KBr precipitate and the filtrate returned to reflux. 2-(bromomethyl)naphthalene (4.84 g, 21.90 mmol) was added to the solution and refluxed for 3 h. The volatiles were removed in vacuo and the resulting waxy yellow solid was washed in ethyl ether. A white precipitate was collected and analyzed. $^1$H NMR (300 MHz, DMSO-d$_6$): δ 2.18, 4.86, 5.16, 7.33, 7.54, 7.92, 10.28.

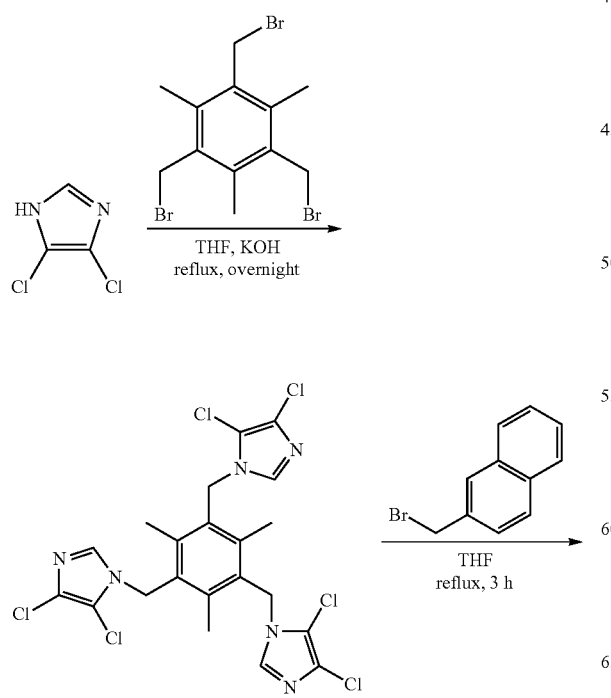

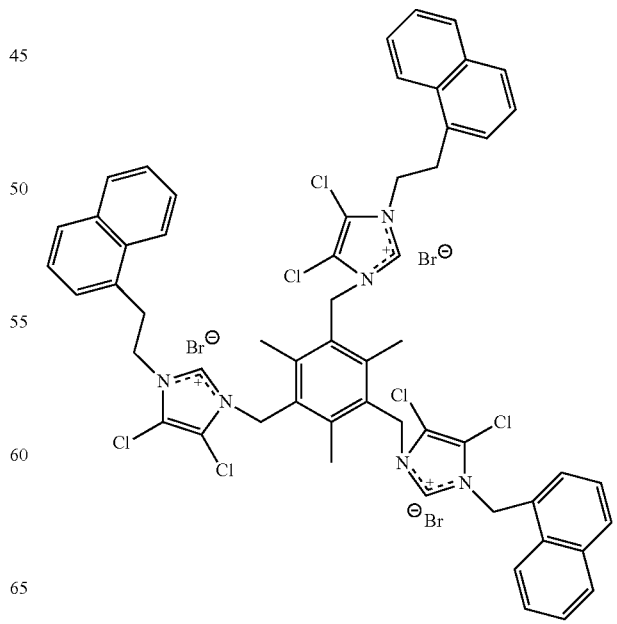

filtered while hot to remove the KBr precipitate and the filtrate was returned to reflux. 1,3,5-tris(bromomethyl)-2,4,6-trimethylbenzene (2.91 g, 7.30 mmol) was added to the solution and refluxed overnight. The volatiles were removed in vacuo and the resulting waxy yellow solid was washed in ethyl ether. A white precipitate was collected and analyzed. $^1$H NMR (300 MHz, DMSO-$d_6$): δ 2.36, 3.59, 4.66, 5.48, 7.14, 7.42, 7.76, 7.95, 8.10, 10.12.

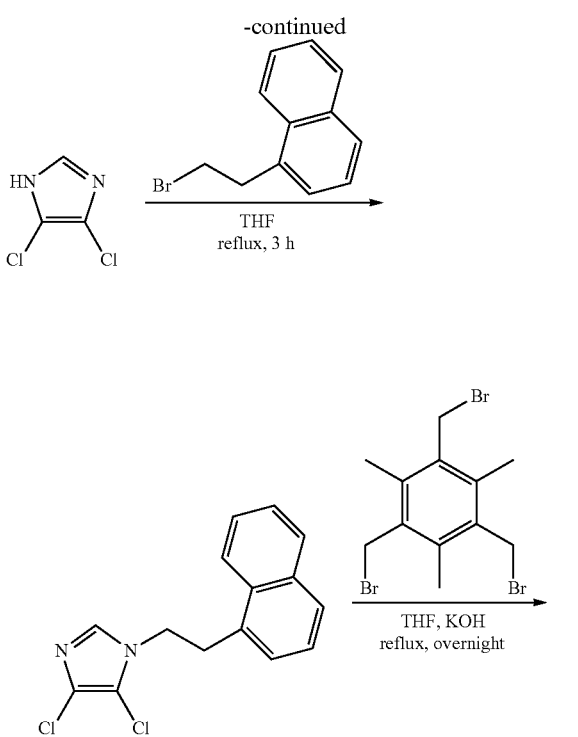

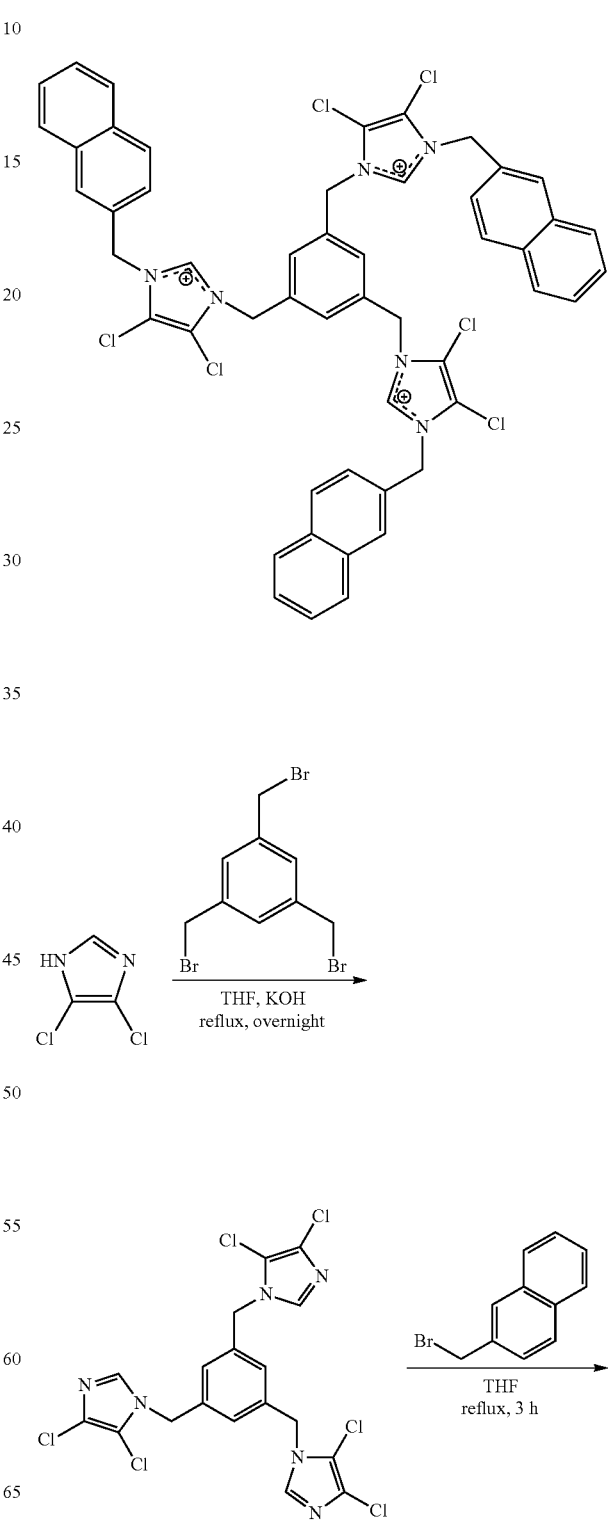

Synthesis of 3,3',3''-(5-(((4,5-dichloro-1-(naphthalen-1-ylmethyl)-1H-imidazol-3-ium-3-yl)methyl)-2,4,6-trimethyl-1,3-phenylene)bis(methylene)bis(4,5-dichloro-1-(2-(naphthalen-1-yl)ethyl)-1H-imidazol-3-ium) bromide)

4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1-(bromoethyl)naphthalene (5.15 g, 21.90 mmol) was added to the solution and refluxed for 3 h. Solution was 47
-continued

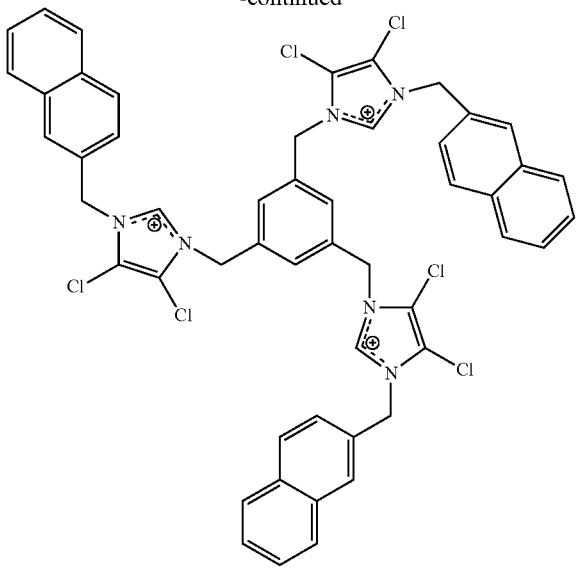

Synthesis of 3,3',3"-(benzene-1,3,5-triyltris(methylene))tris(4,5-dichloro-1-(naphthalen-2-ylmethyl)-1H-imidazol-3-ium) bromide)

4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)benzene (2.61, 7.30 mmol) was added to the solution and refluxed overnight. Solution was filtered while hot to remove the KBr precipitate and the filtrate returned to reflux. 2-(bromomethyl)naphthalene (4.84 g, 21.90 mmol) was added to the solution and refluxed for 3 h. The volatiles were removed in vacuo and the resulting waxy yellow solid was washed in ethyl ether. A white precipitate was collected and analyzed. $^1$H NMR (300 MHz, DMSO-$d_6$): δ 4.87, 5.18, 7.32, 7.57, 7.95, 10.30.

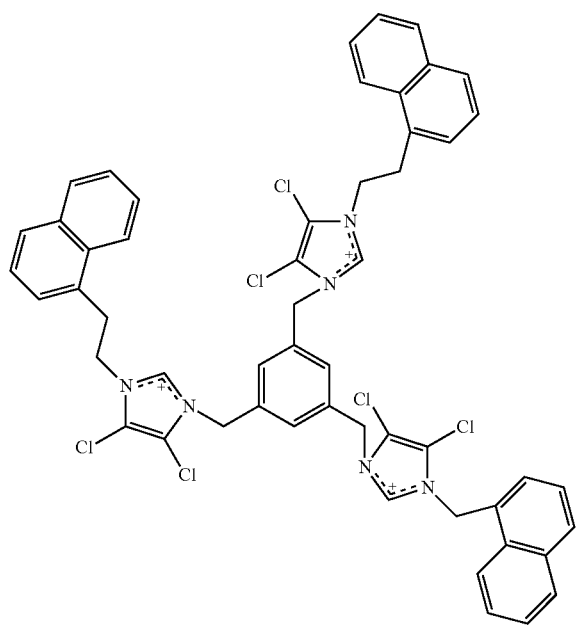

48
-continued

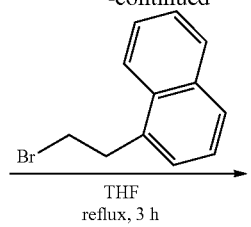
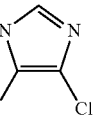
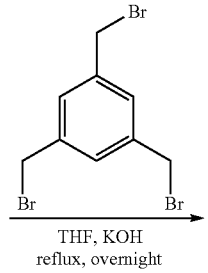
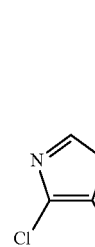
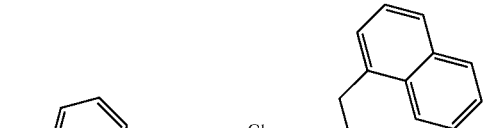

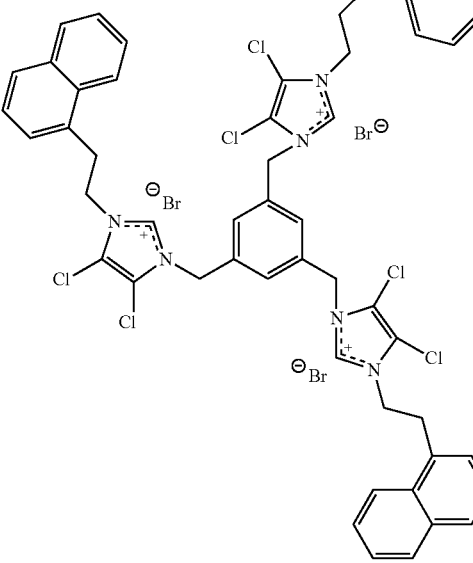

Synthesis of 3,3',3"-(5-((4,5-dichloro-1-(naphthalen-1-ylmethyl)-1H-imidazol-3-ium-3-yl)methyl)-1,3-phenylene)bis(methylene)bis(4,5-dichloro-1-(2-(naphthalen-1-yl)ethyl)-1H-imidazol-3-ium) bromide)

4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1-(bromoethyl)naphthalene (5.15 g, 21.90 mmol) was added to the solution and refluxed for 3 h. Solution was filtered while hot to remove the KBr precipitate and the filtrate was returned to reflux. 1,3,5-tris(bromomethyl)benzene (2.61, 7.30 mmol) was added to the solution and refluxed overnight. The volatiles were removed in vacuo and the resulting waxy yellow solid was washed in ethyl ether. A white precipitate was collected and analyzed. ¹H NMR (300 MHz, DMSO-d₆): δ 3.60, 4.66, 5.49, 7.22, 7.45, 7.77, 7.98, 8.13, 10.11.

Prophetic Examples are as follows:

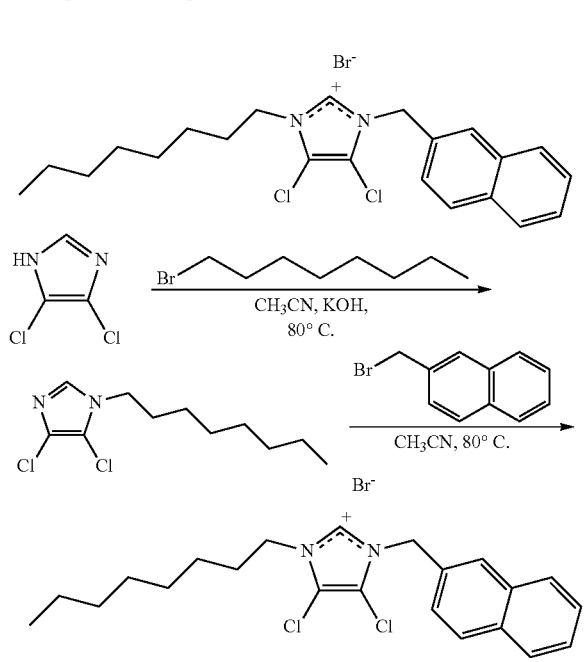

Synthesis of
1-octyl-3-methylnaphthyl-4,5-dichloroimidazolium
bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromooctane (1.55 mL, 9 mmol) will be added and the solution will be allowed to reflux overnight. The solution will be filtered hot to remove a white precipitate (presumed to be KBr) and 2-bromomethylnaphthalene (1.98 g, 9 mmol) will be added and the mixture will be returned to reflux overnight. The mixture will be allowed to cool to room temperature, resulting in a yellow/white precipitate.

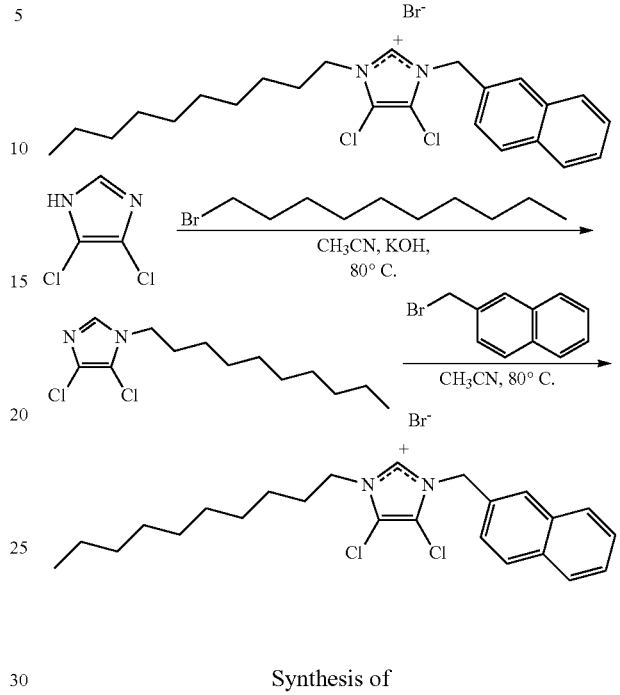

Synthesis of
1-decyl-3-methylnaphthyl-4,5-dichloroimidazolium
bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromodecane (9 mmol) will be added and the solution will be allowed to reflux overnight. The solution will be filtered hot to remove a white precipitate (presumed to be KBr) and 2-bromomethylnaphthalene (1.98 g, 9 mmol) will be added and the mixture will be returned to reflux overnight. The mixture will be allowed to cool to room temperature, resulting in a yellow/white precipitate.

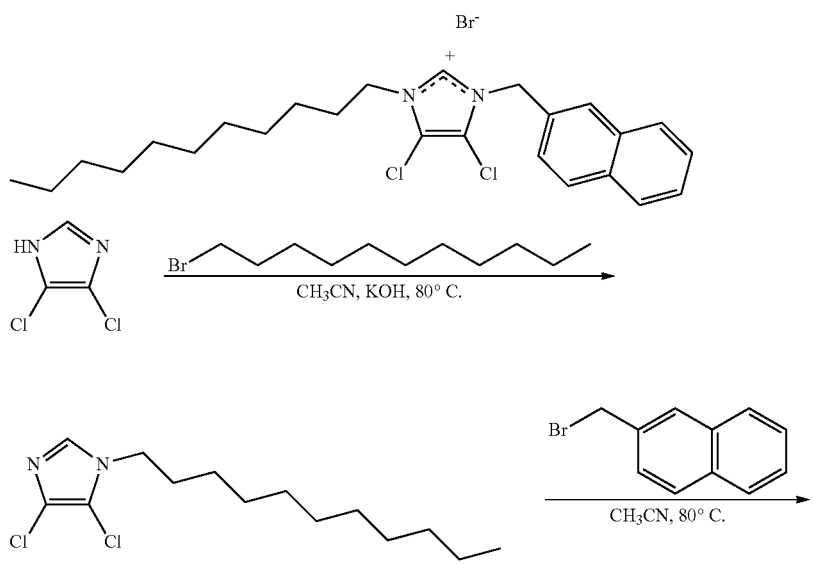

-continued

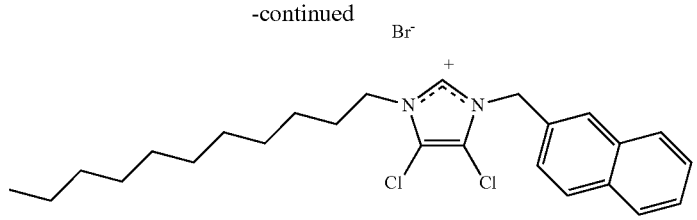

Synthesis of 1-undecyl-3-methylnaphthyl-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromoundecane (9 mmol) will be added and the solution will be allowed to reflux overnight. The solution will be filtered hot to remove a white precipitate (presumed to be KBr) and 2-bromomethylnaphthalene (1.98 g, 9 mmol) will be added and the mixture will be returned to reflux overnight. The mixture will be allowed to cool to room temperature, resulting in a yellow/white precipitate.

The mixture will be allowed to cool to room temperature, resulting in a yellow/white precipitate.

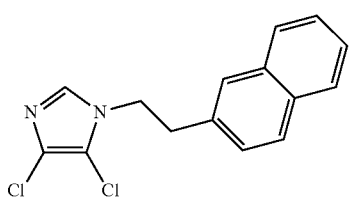

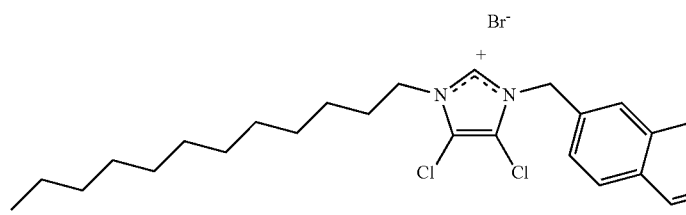

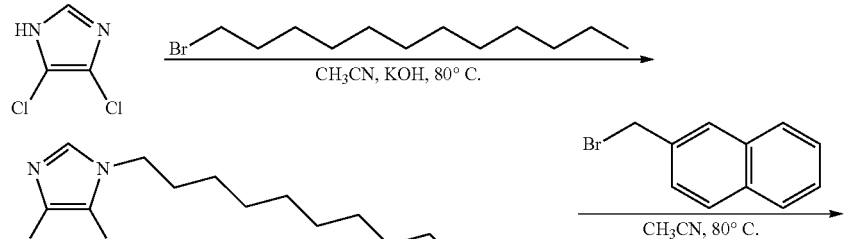

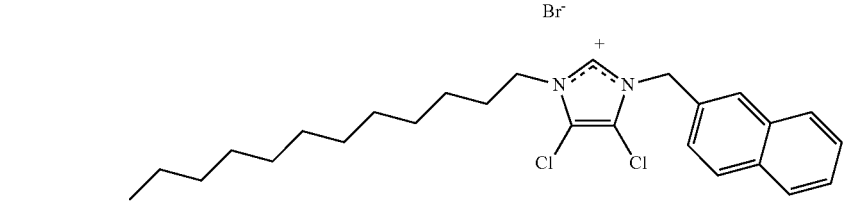

Synthesis of 1-undecyl-3-methylnaphthyl-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromododecane (9 mmol) will be added and the solution will be allowed to reflux overnight. The solution will be filtered hot to remove a white precipitate (presumed to be KBr) and 2-bromomethylnaphthalene (1.98 g, 9 mmol) will be added and the mixture will be returned to reflux overnight.

-continued

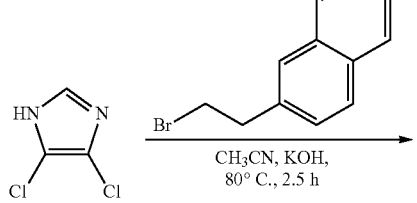

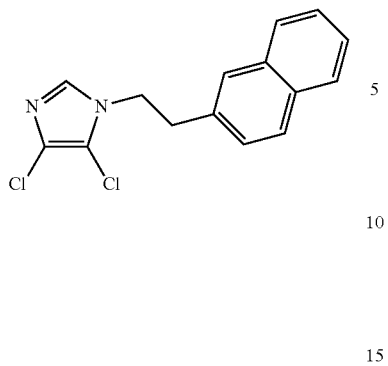

Synthesis of 1-(2-ethylnaphthyl)-4,5-dichloroimidazole 4,5-Dichloroimidazole (1 mmol) will be dissolved into 1 mL of acetonitrile. Potassium hydroxide (0.061 g, 1.1 mmol) will be added and the mixture will be allowed to stir for 0.5 h. 2-bromoethylnaphthalene (1 mmol) will be added and the solution will be allowed to reflux overnight. The solution will be filtered hot to remove a white precipitate (presumed to be KBr) and the solution will be allowed to cool to room temperature. The volatiles will be removed en vacuo resulting in the product.

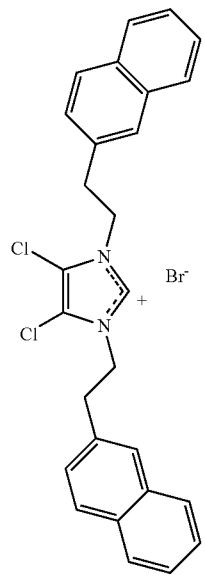

Synthesis of 1,3-bis(2-ethyl-2-naphthyl)-4,5-dichloroimidazolium bromide 4,5-Dichloroimidazole (9 mmol) will be dissolved into acetonitrile. Potassium hydroxide (0.61 g, 9.9 mmol) will be added and the mixture will be allowed to stir for 0.5 h. 2-bromoethylnaphthalene (9 mmol) will be added and the solution will be allowed to reflux overnight. The solution will be filtered hot to remove a white precipitate (presumed to be KBr), the solution will be concentrated down to 20 mL and will be transferred to a pressure tube. A second equivalent of 2-bromoethylnaphthalene (9 mmol) will be added; the pressure tube will be sealed, and will be heated overnight. The solution will be allowed to cool to room temperature. The volatiles will be removed en vacuo resulting in the product.

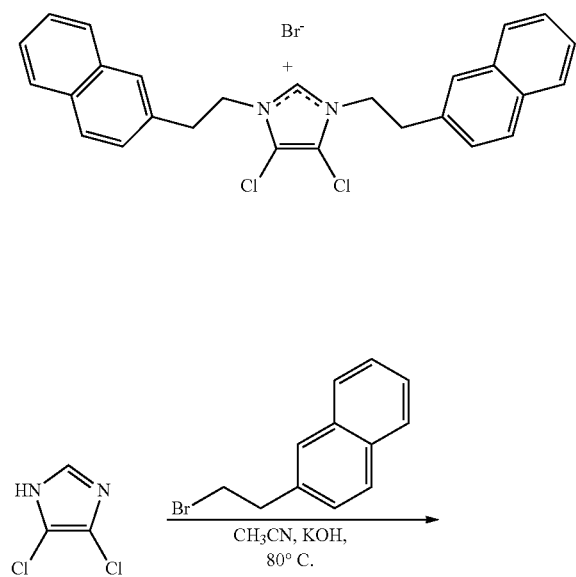

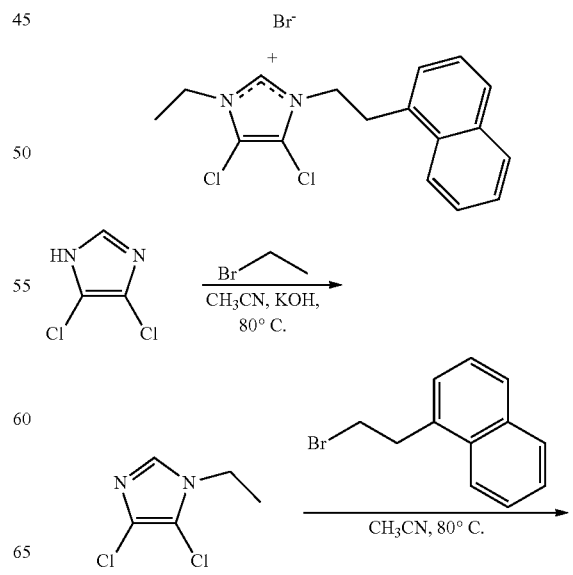

-continued

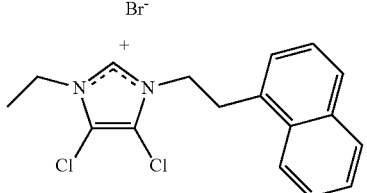

Synthesis of 1-ethyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromoethane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

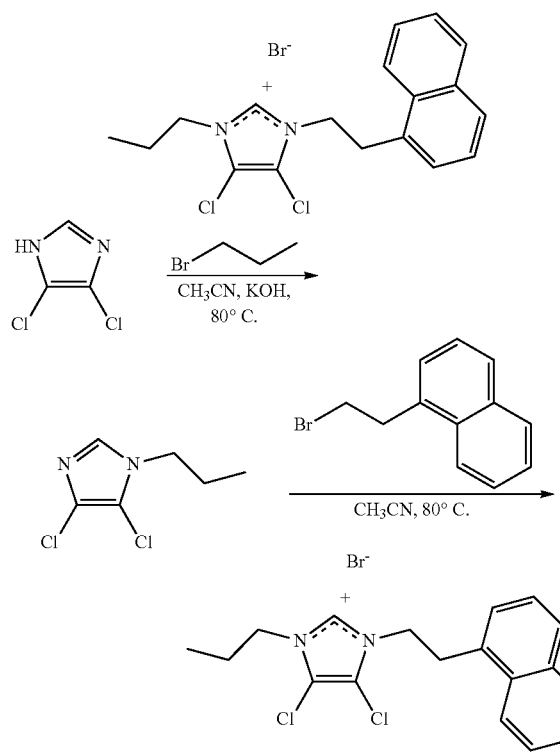

Synthesis of 1-propyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromopropane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

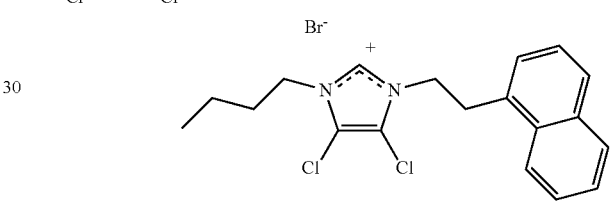

Synthesis of 1-butyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromobutane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

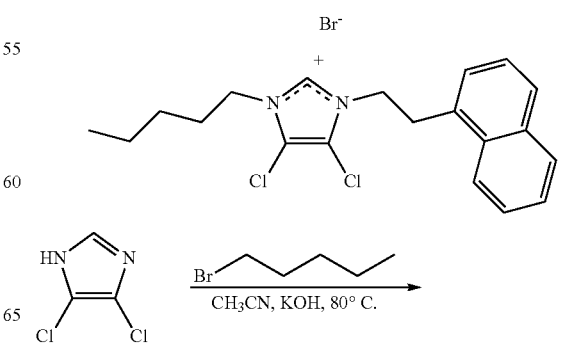

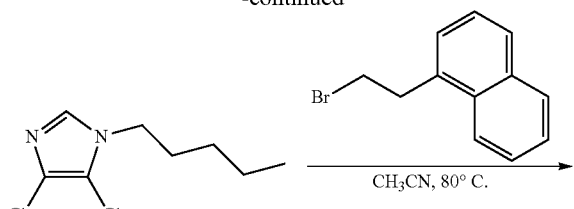

Synthesis of 1-pentyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

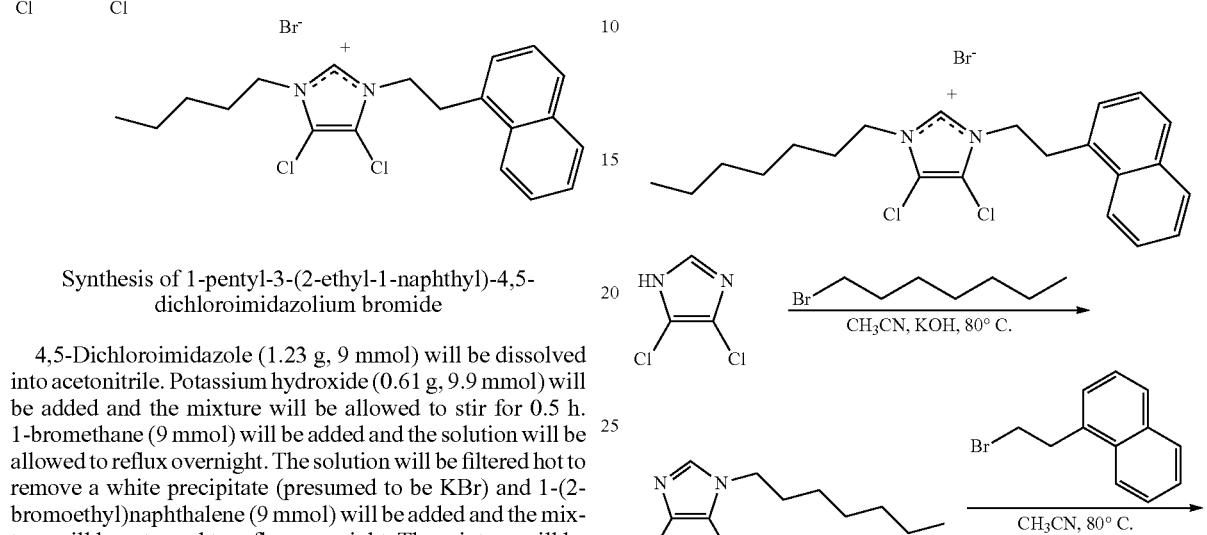

Synthesis of 1-hexyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

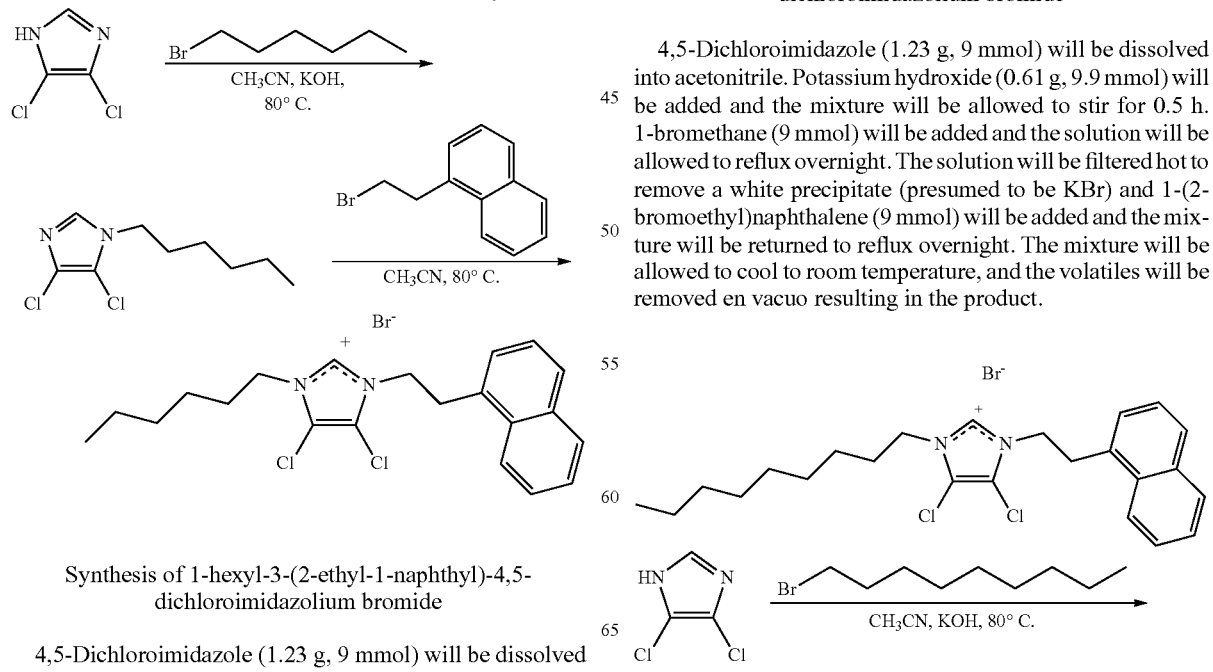

Synthesis of 1-heptyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

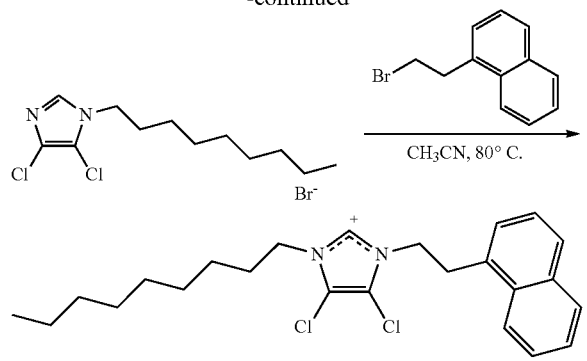

Synthesis of 1-octyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

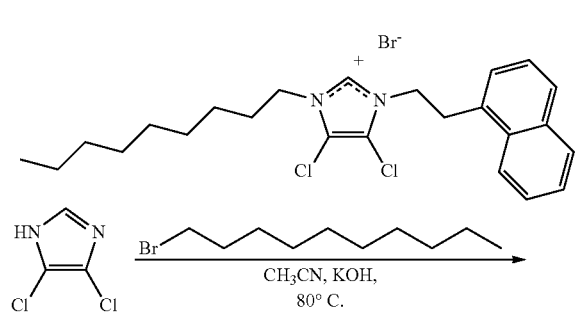

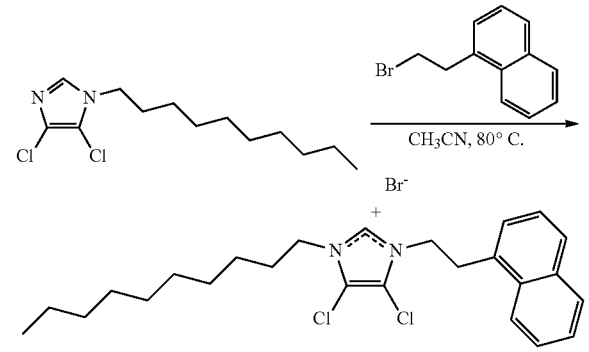

Synthesis of 1-nonyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

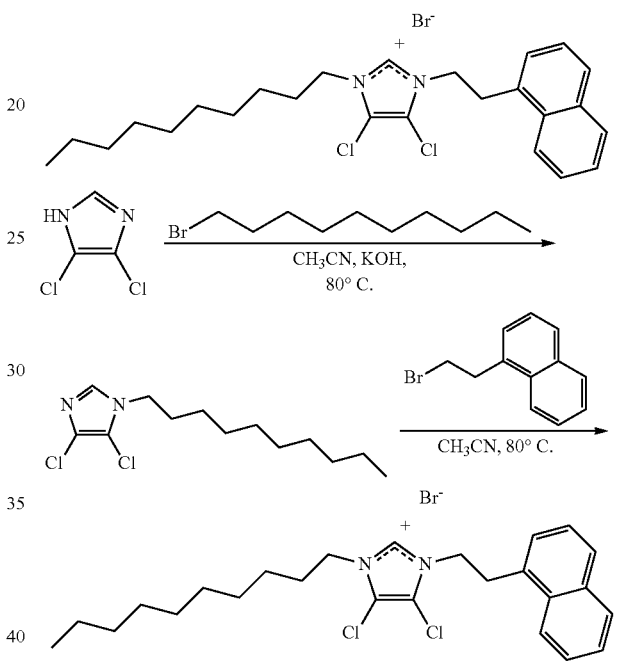

Synthesis of 1-decyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

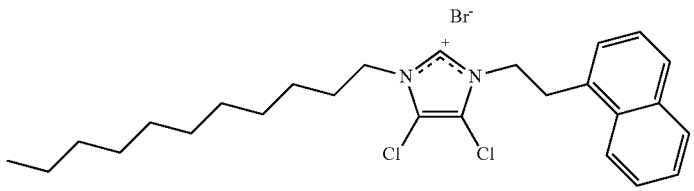

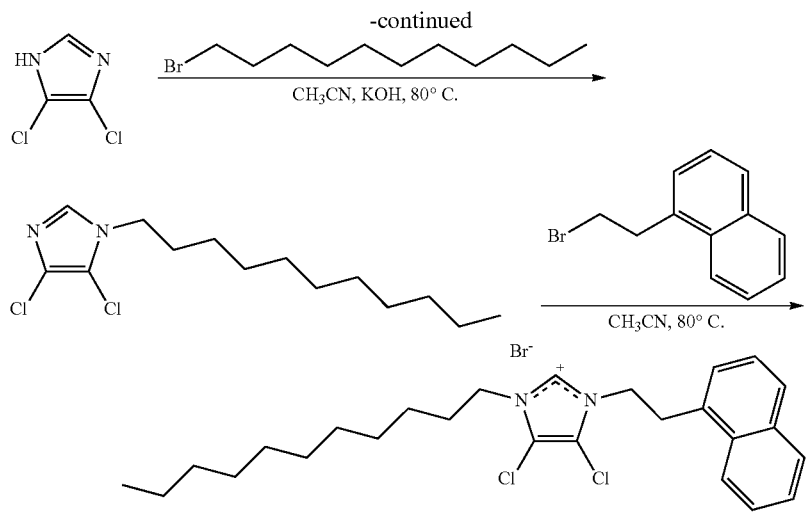

Synthesis of 1-undecyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

Synthesis of 1-dodecyl-3-(2-ethyl-1-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

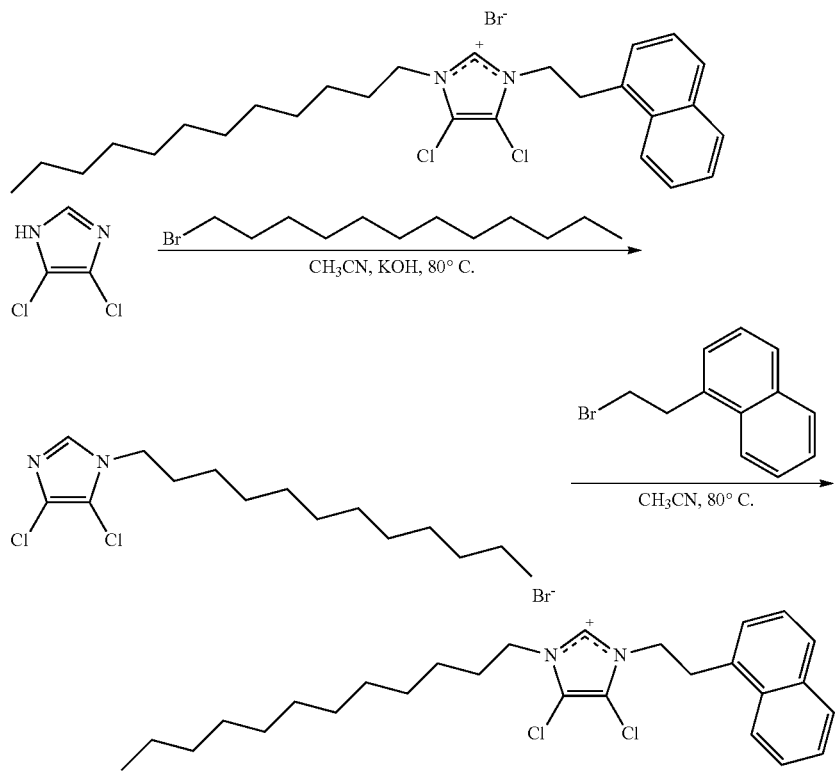

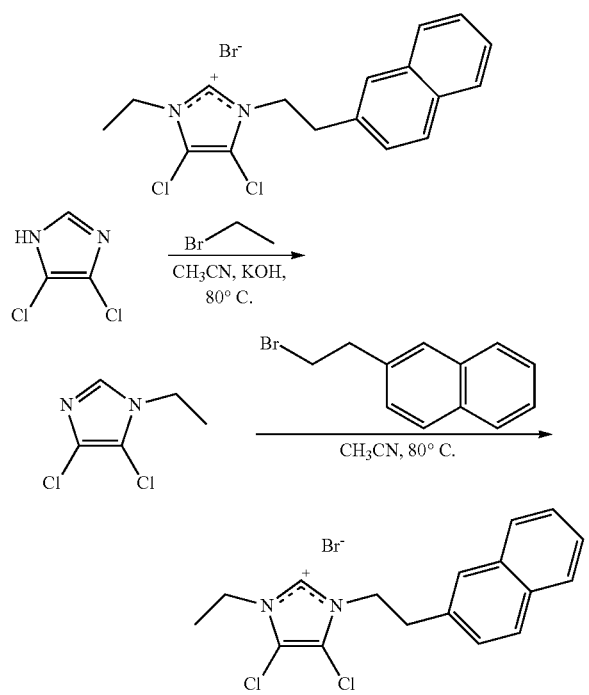

Synthesis of 1-ethyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromoethane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

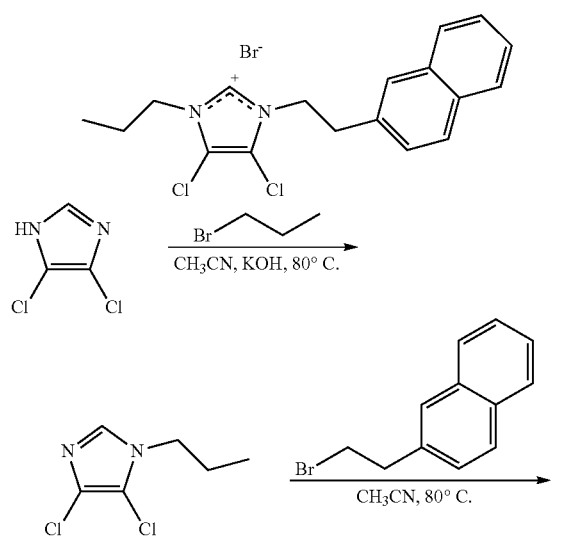

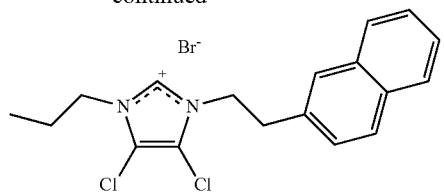

Synthesis of 1-propyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromopropane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

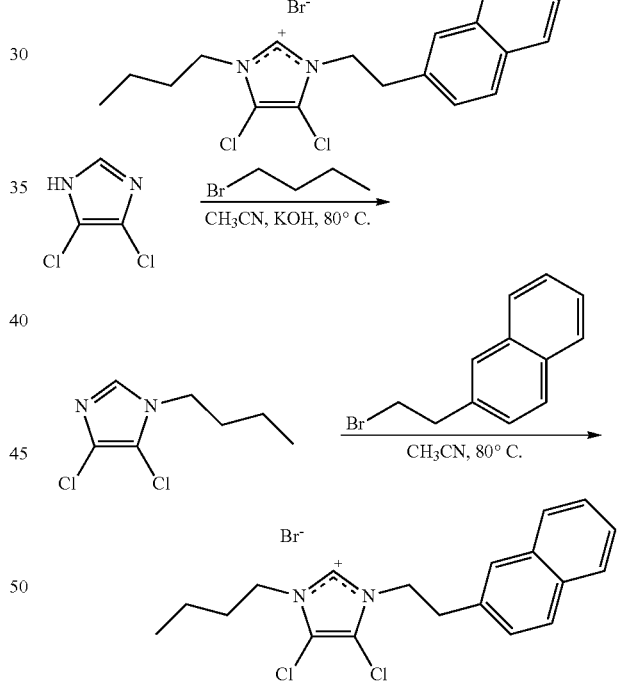

Synthesis of 1-butyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromobutane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

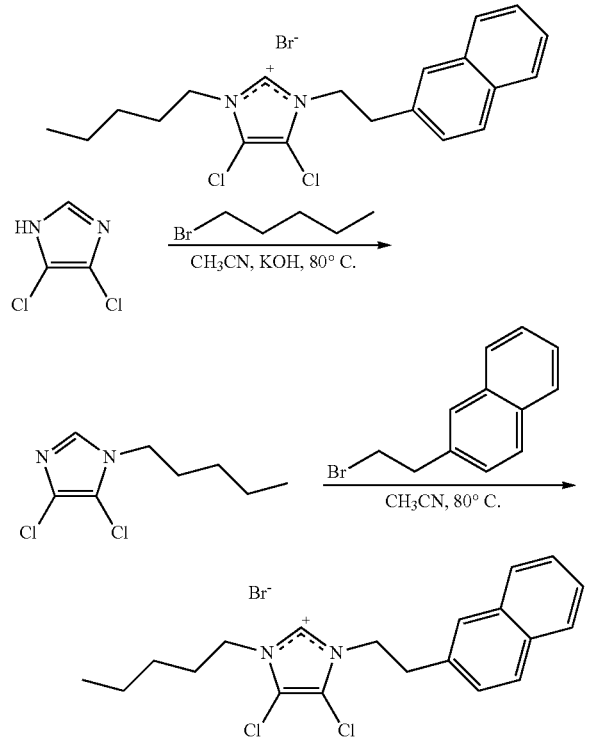

Synthesis of 1-pentyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

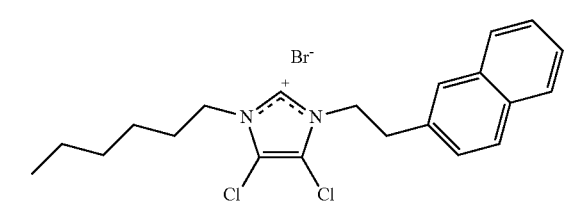

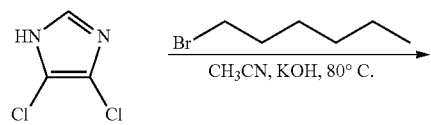

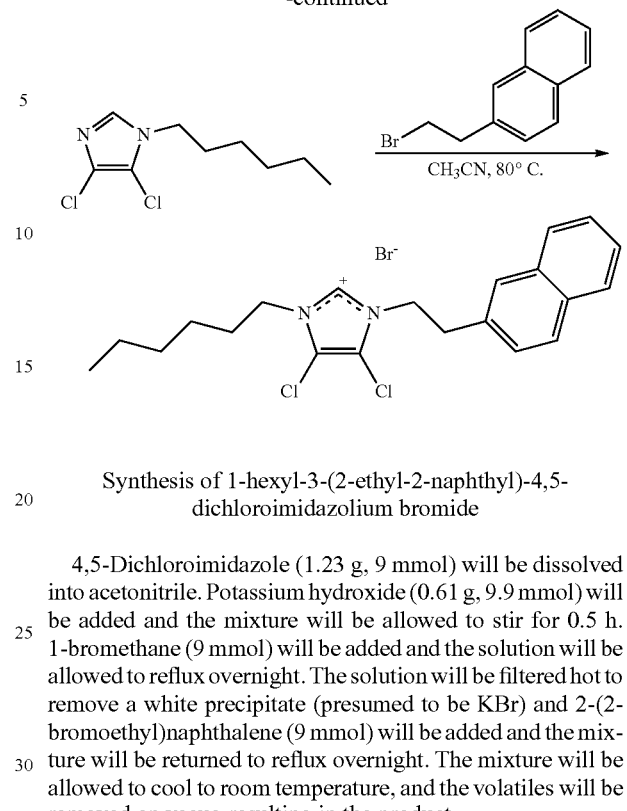

Synthesis of 1-hexyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

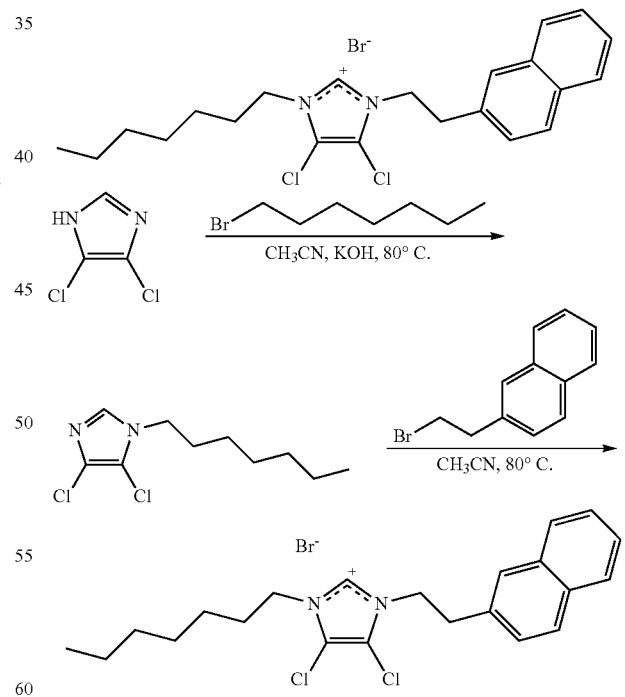

Synthesis of 1-heptyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

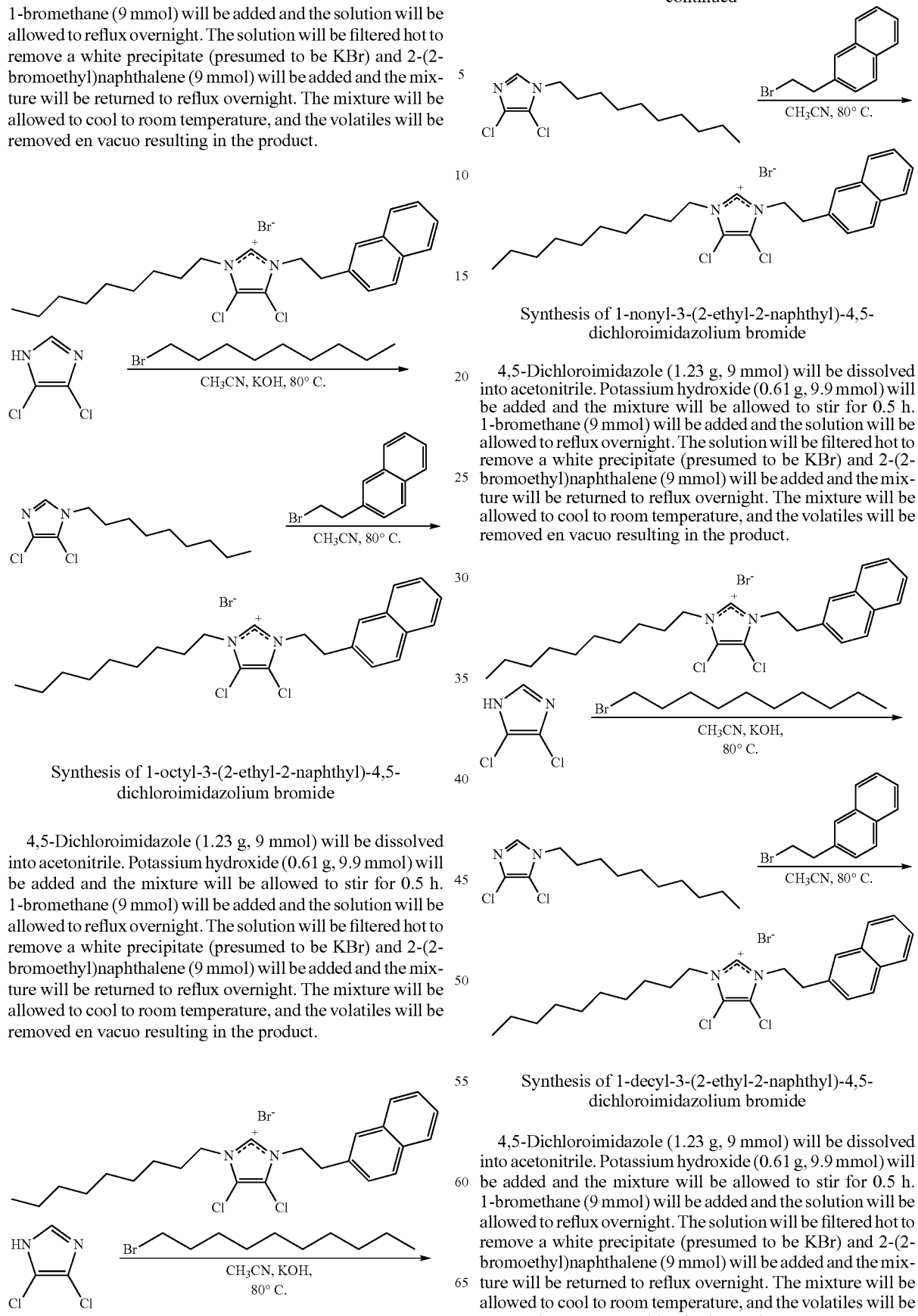

Synthesis of 1-octyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

Synthesis of 1-nonyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

Synthesis of 1-decyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

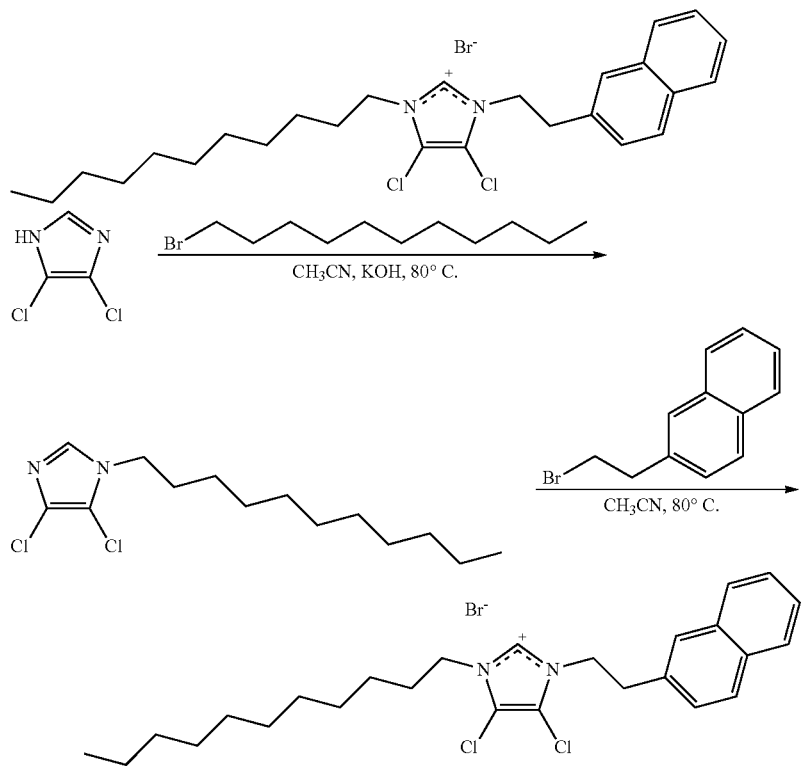

Synthesis of 1-undecyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

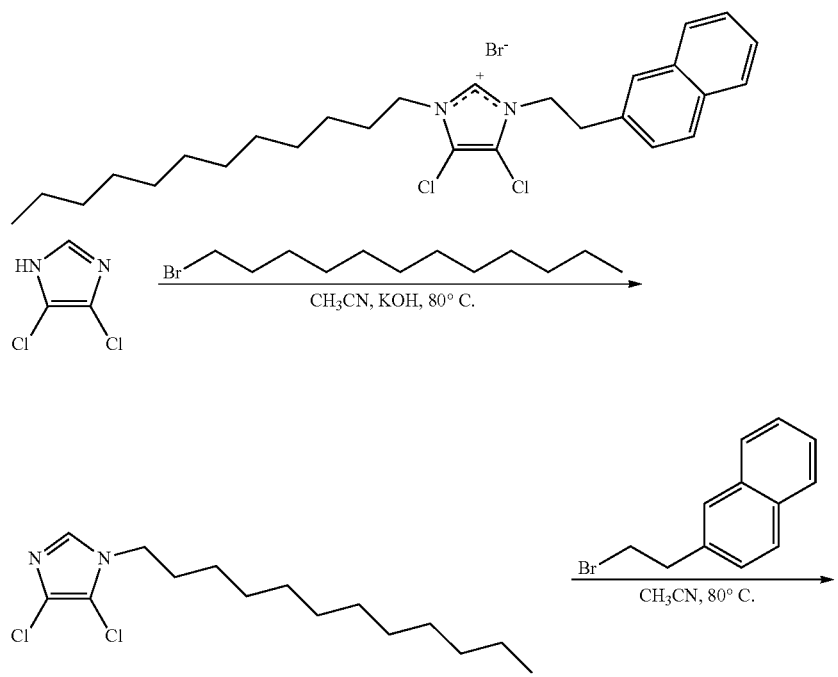

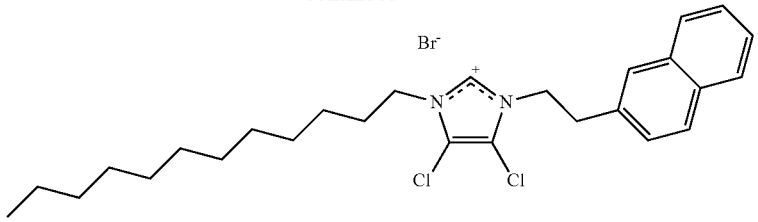

Synthesis of 1-dodecyl-3-(2-ethyl-2-naphthyl)-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromethane (9 mmol) will be added and the solution will be allowed to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

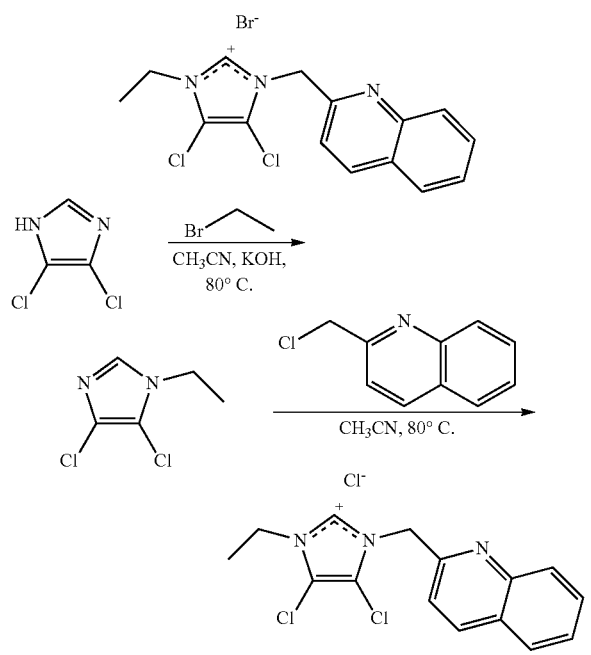

Synthesis of 1-ethyl-3-methylquinoline-4,5-dichloroimidazolium chloride 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromoethane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be returned to reflux overnight. The mixture will be allowed to cool to room temperature, resulting in a yellow/white precipitate.

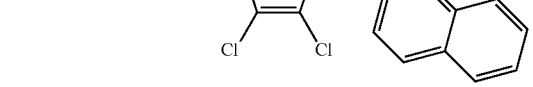

Synthesis of 1-propyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromopropane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture will be returned to reflux overnight. The mixture will be allowed to cool to room temperature, resulting in a yellow/white precipitate.

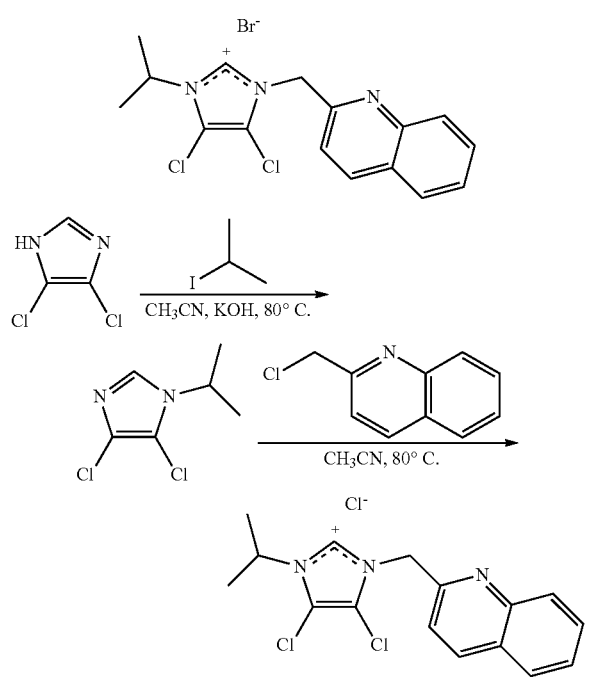

Synthesis of 2-propyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 2-iodopropane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be returned to reflux overnight. The mixture will be allowed to cool to room temperature, resulting in a yellow/white precipitate.

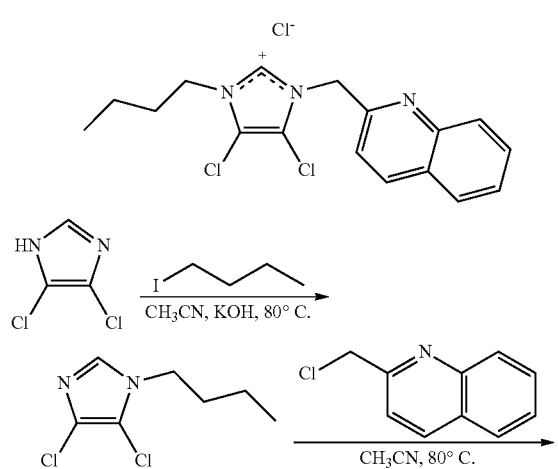

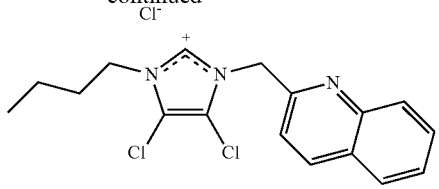

Synthesis of 1-butyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-iodobutane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be returned to reflux overnight. The mixture will be allowed to cool to room temperature, resulting in a yellow/white precipitate.

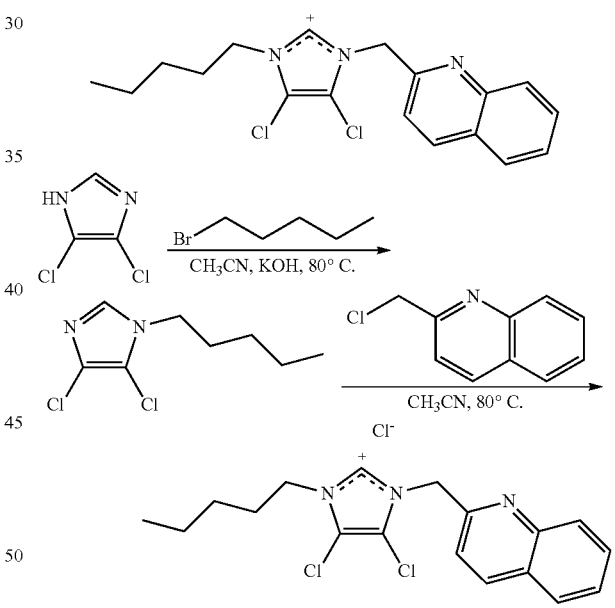

Synthesis of 1-pentyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromopentane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be returned to reflux overnight. The mixture will be allowed to cool to room temperature, resulting in a yellow/white precipitate.

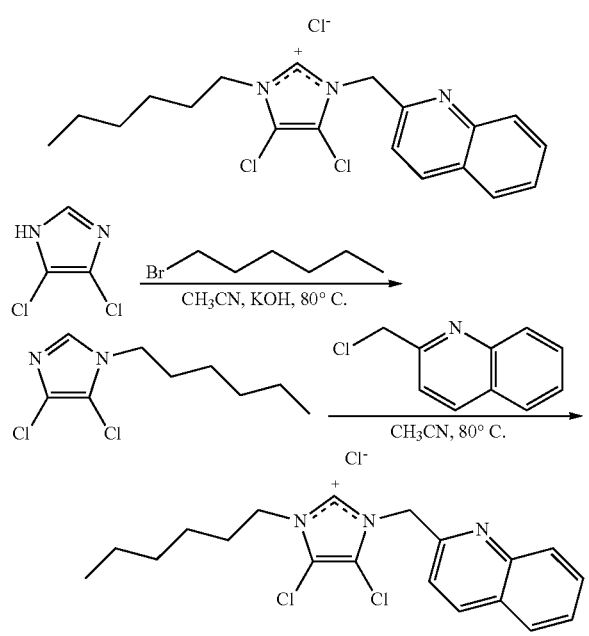

Synthesis of 1-hexyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromohexane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be returned to reflux overnight. The mixture will be allowed to cool to room temperature, resulting in a yellow/white precipitate.

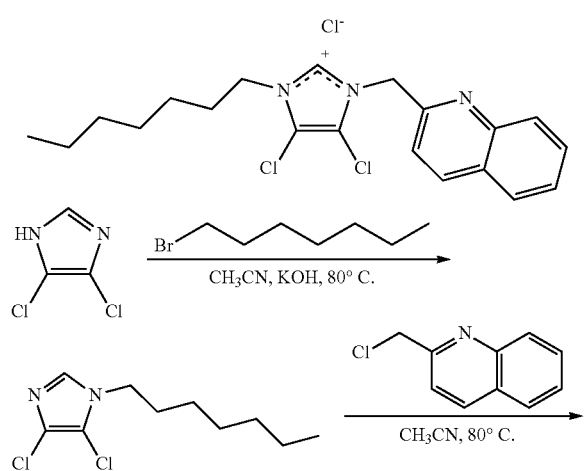

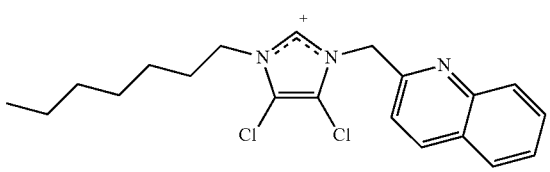

Synthesis of 1-heptyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromoheptane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be returned to reflux overnight. The mixture will be allowed to cool to room temperature, resulting in a yellow/white precipitate.

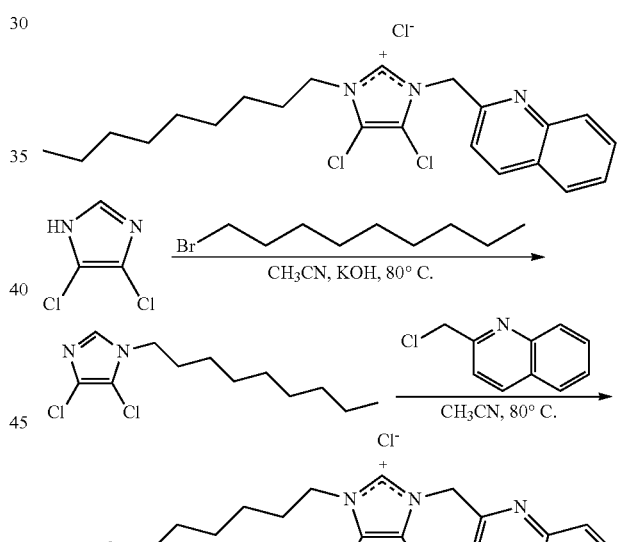

Synthesis of 1-octyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromooctane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be

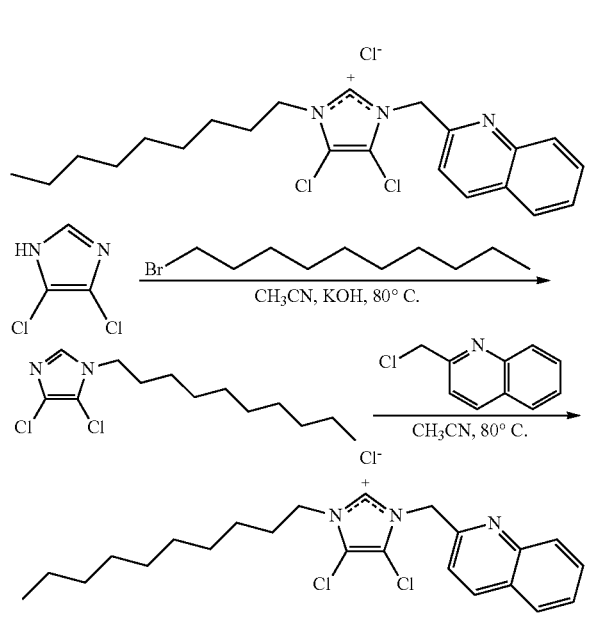

Synthesis of 1-nonyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromononane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be returned to reflux overnight. The mixture will be allowed to cool to room temperature, resulting in a yellow/white precipitate.

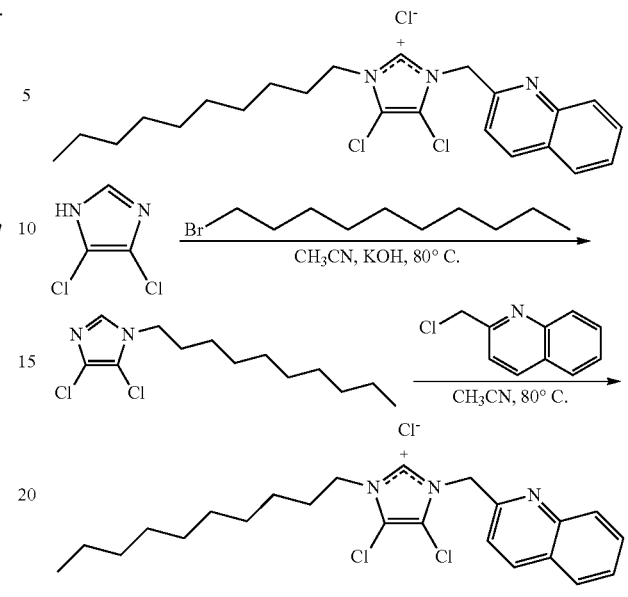

Synthesis of 1-decyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromodecane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be returned to reflux overnight. The mixture will be allowed to cool to room temperature, resulting in a yellow/white precipitate.

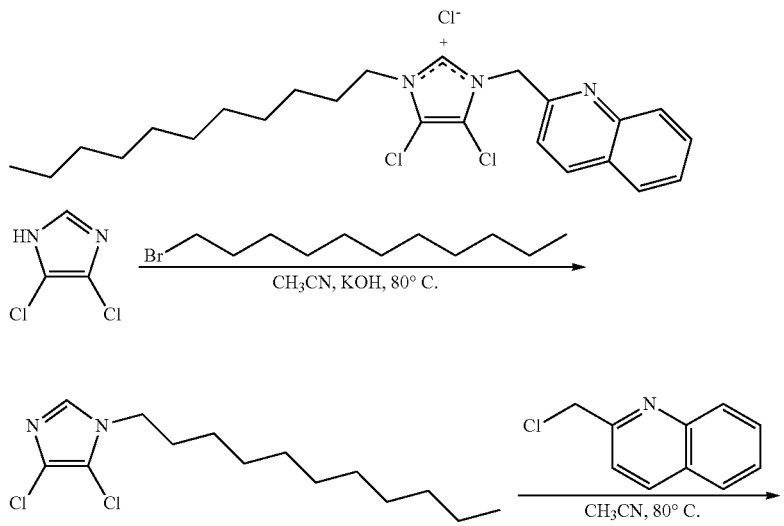

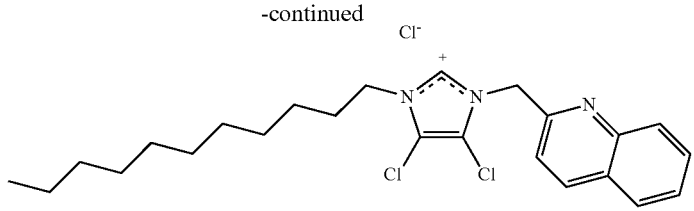

Synthesis of 1-undecyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromoundecane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be returned to reflux overnight. The mixture will be allowed to cool to room temperature, resulting in a yellow/white precipitate.

Synthesis of 1-dodecyl-3-methylquinoline-4,5-dichloroimidazolium bromide 4,5-Dichloroimidazole (1.23 g, 9 mmol) will be dissolved into acetonitrile. Potassium hydroxide (0.61 g, 9.9 mmol) will be added and the mixture will be allowed to stir for 0.5 h. 1-bromododecane (9 mmol) will be added and the solution will be allowed to reflux overnight. The solution will be filtered hot to remove a white precipitate (presumed to be KBr). 2-chloromethylquinoline hydrochloride (9 mmol) will be dissolved into acetonitrile along with an equivalent of base. This mixture will be added to the previous mixture and will be returned to reflux overnight. The mixture will be allowed to cool to room temperature, resulting in a yellow/white precipitate.

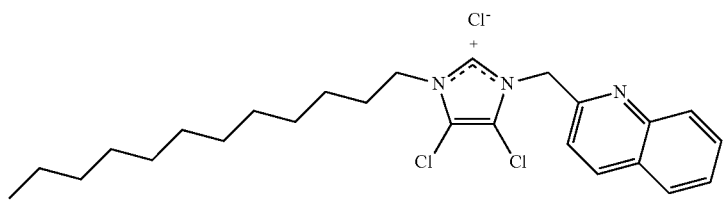

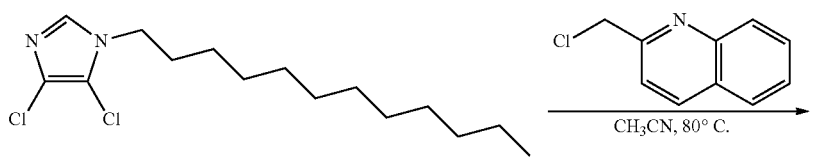

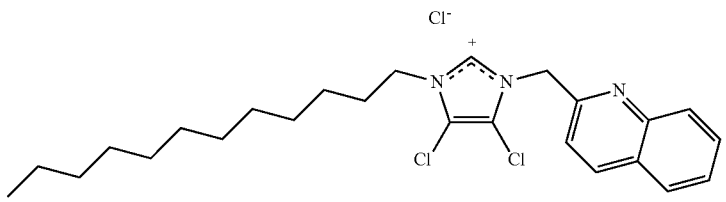

81

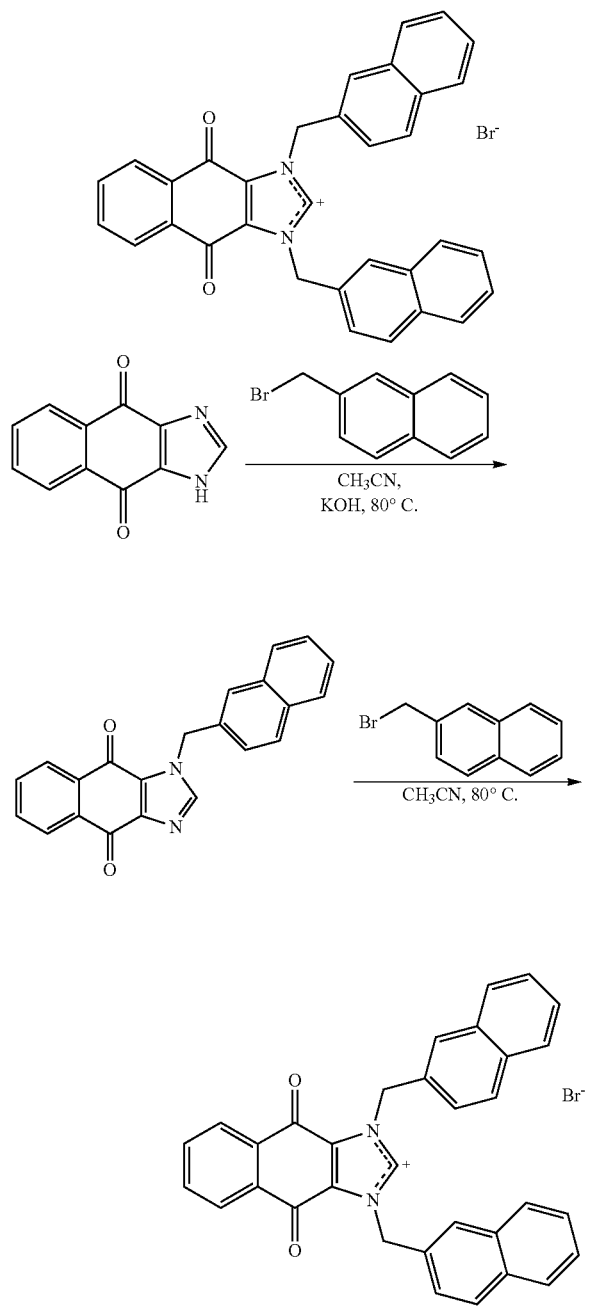

Synthesis of 1,3-bis(2-methylnaphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 2-bromomethylnaphthalene (9 mmol) will be added and the mixture will be returned to reflux overnight. The solution will be filtered hot to remove a white precipitate (presumed to be KBr) and 2-bromomethylnaphthalene (9 mmol) will be added and the mixture will be returned to reflux overnight. The mixture will be allowed to cool to room temperature, and the volatiles will be removed en vacuo resulting in the product.

82

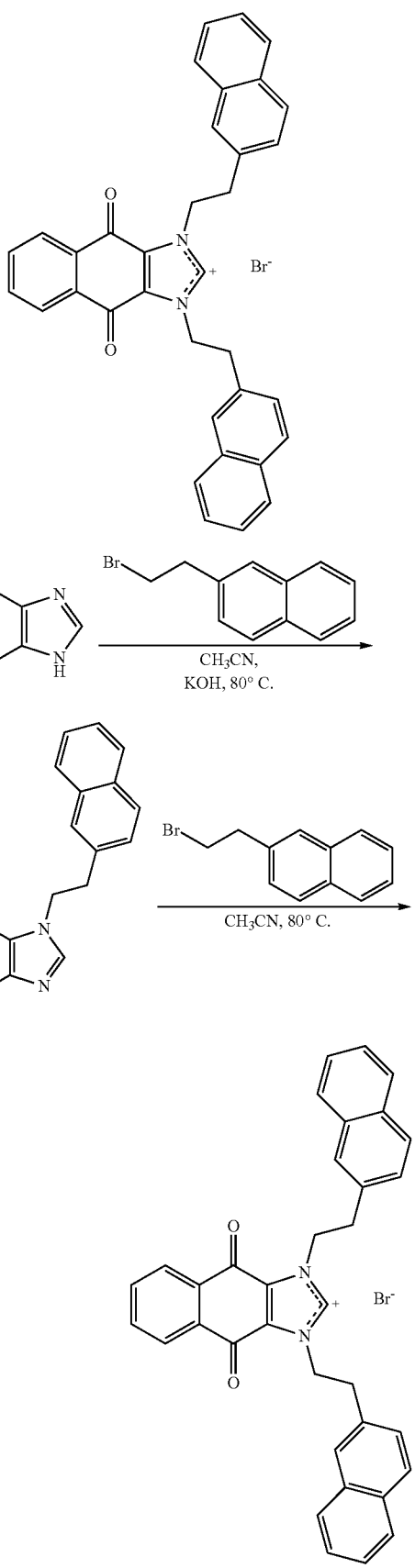

Synthesis of 1,3-bis(2-ethylnaphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 2-bromoethylnaphthalene (9 mmol) will be added and the mixture will be returned to reflux overnight. The solution will be filtered hot to remove a white precipitate (presumed to be KBr) and 2-bromoethylnaphthalene (9 mmol) will be added and the mixture will be returned to reflux overnight. The mixture will be allowed to cool to room temperature, and the volatiles will be removed en vacuo resulting in the product.

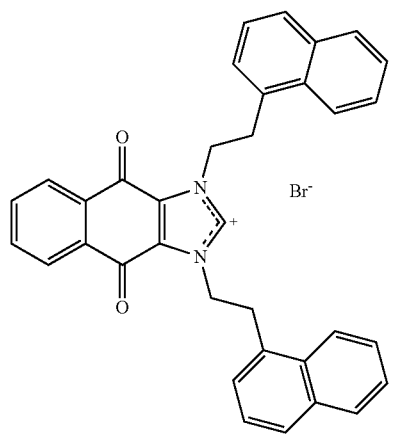

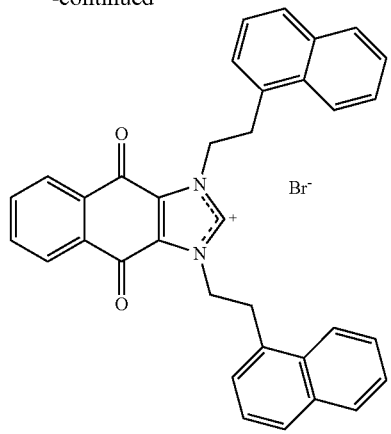

Synthesis of 1,3-bis(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-(2-bromoethyl)naphthalene (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

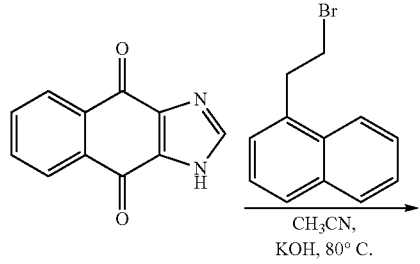

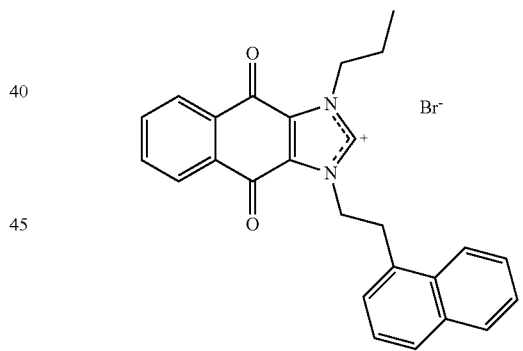

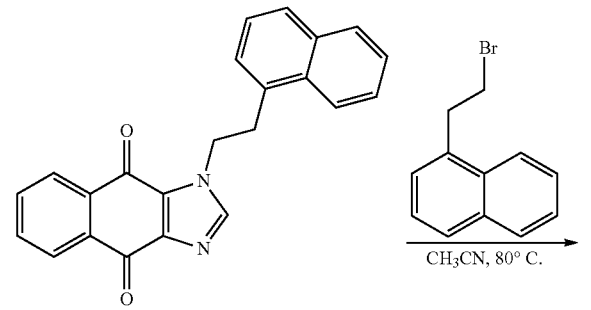

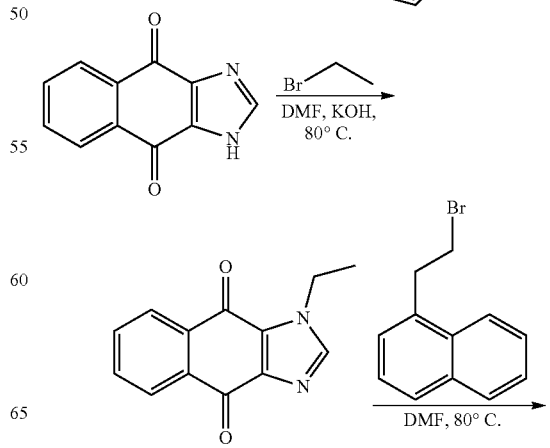

85

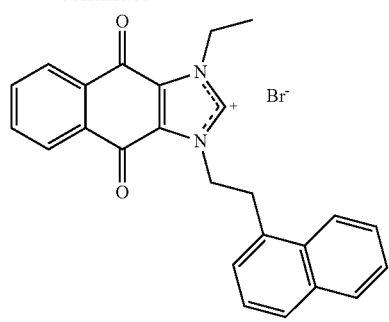

Synthesis of 1-ethyl-3-(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromoethane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

86

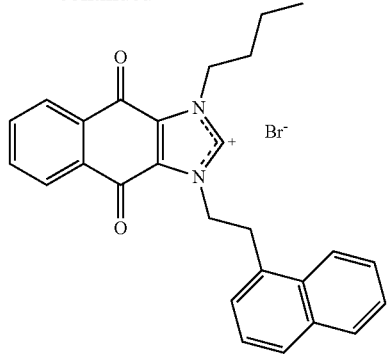

Synthesis of 1-propyl-3-(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromopropane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

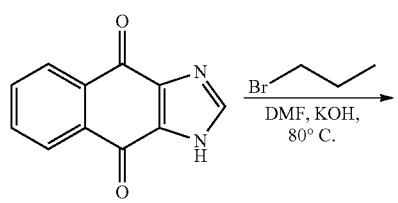

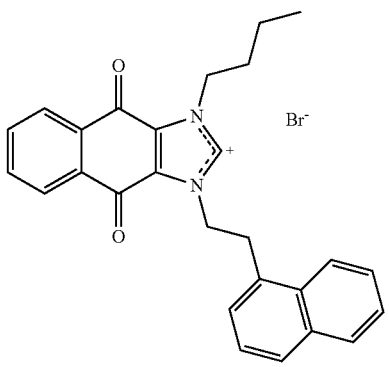

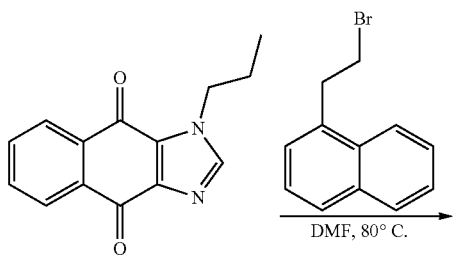

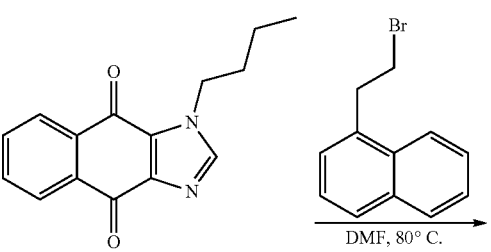

Synthesis of 1-butyl-3-(2-ethyl-1-naphthal)naphtho[2,3-d]-4,9-dione-imidazolium bromide

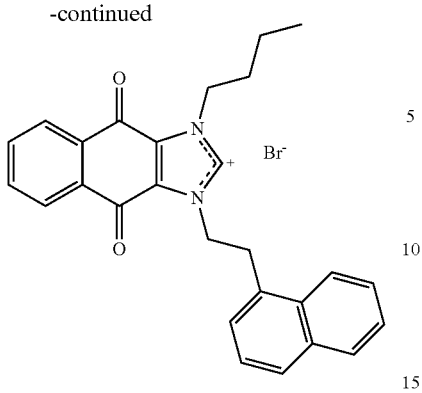

1H-naphtho[2,3-d]imidazole-4,9-dione (9 mmol) will be dissolved into DMF. Potassium carbonate (9.9 mmol) will be added and the mixture will be allowed to stir for 0.5 h and 1-bromobutane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

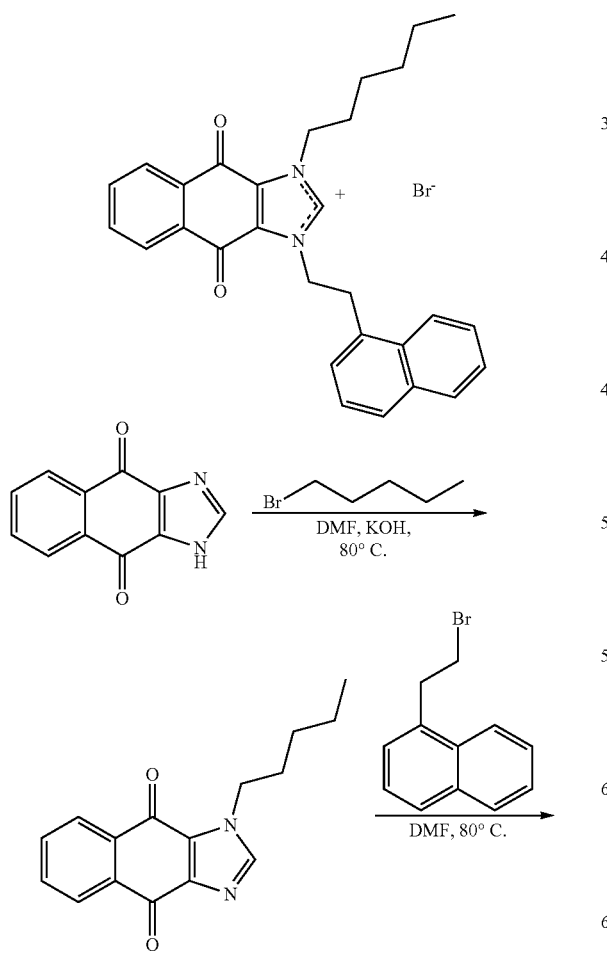

Synthesis of 1-pentyl-3-(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromopentane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

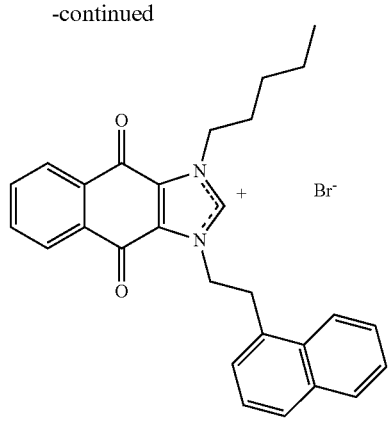

Synthesis of 1-hexyl-3-(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromohexane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

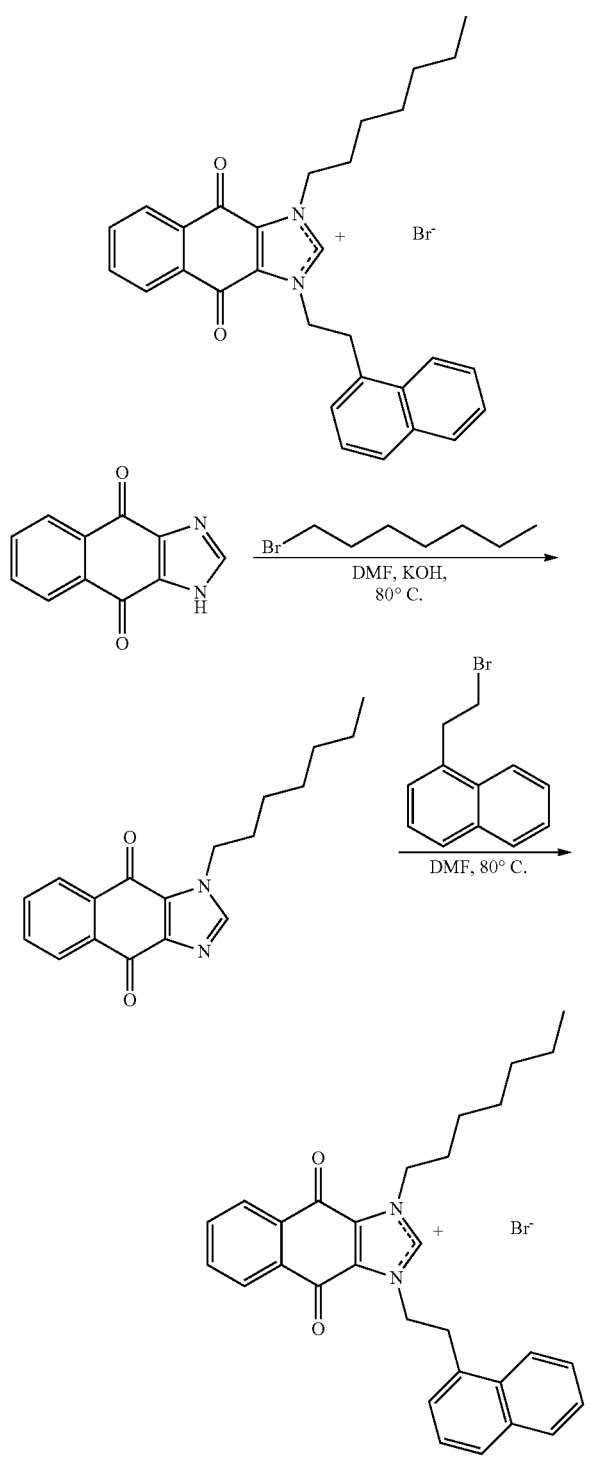

Synthesis of 1-heptyl-3-(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromoheptane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

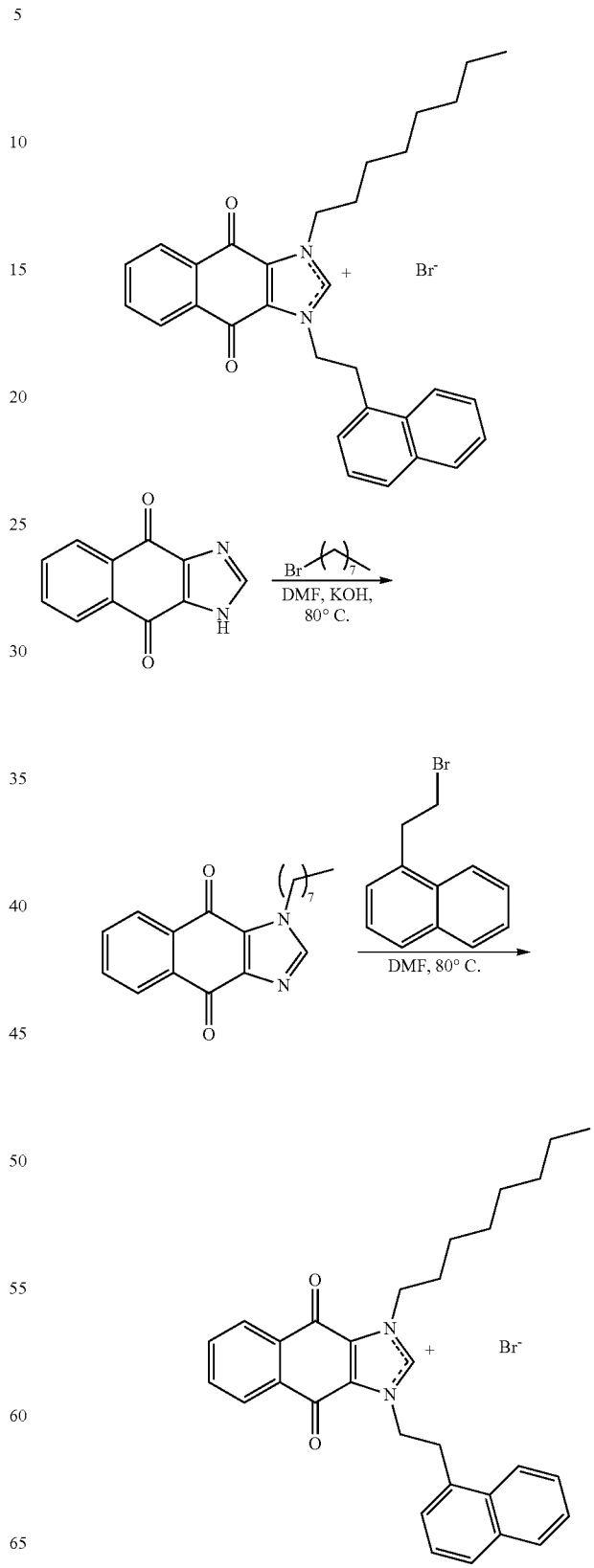

Synthesis of 1-octyl-3-(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromooctane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

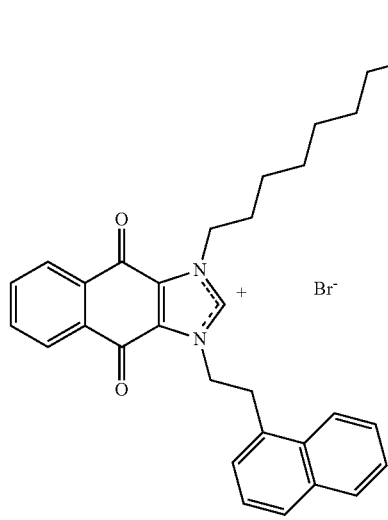

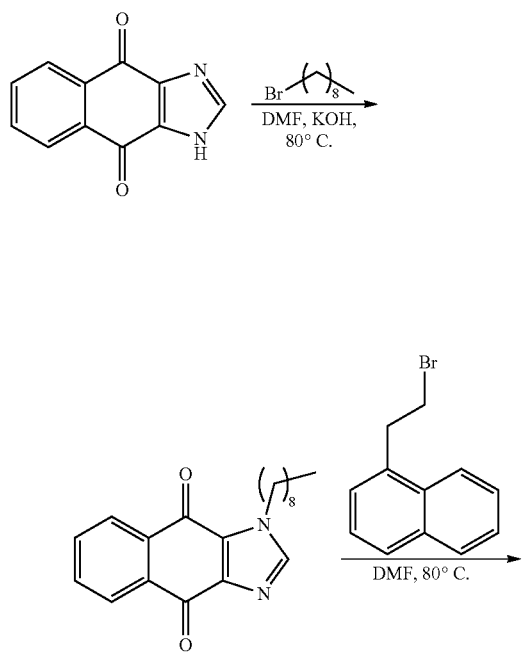

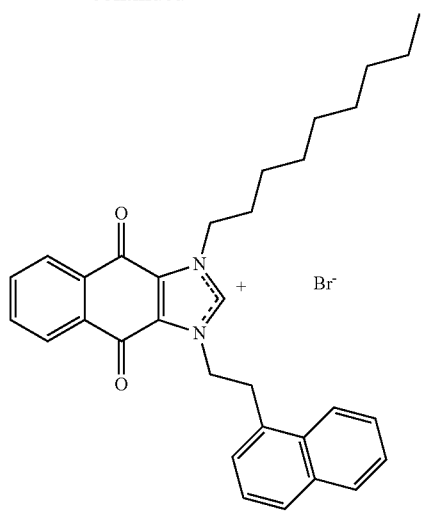

Synthesis of 1-nonyl-3-(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromononane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

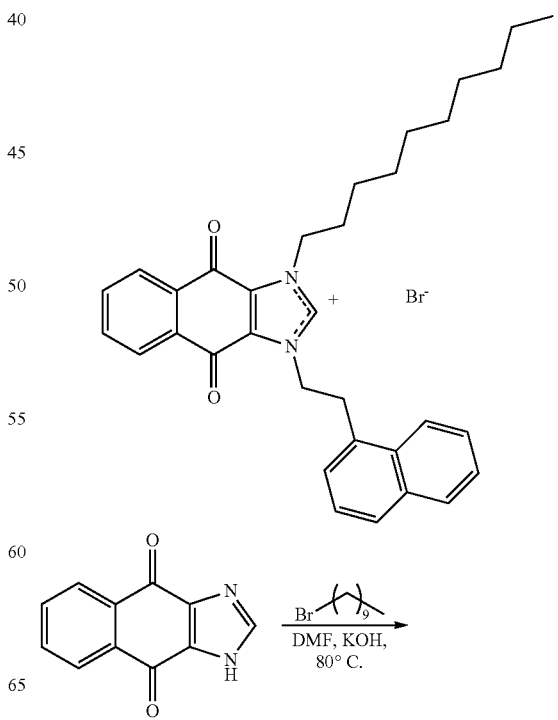

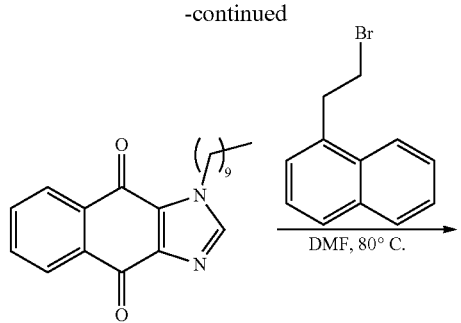
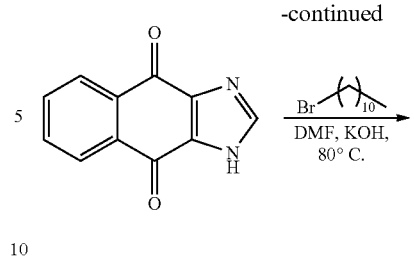

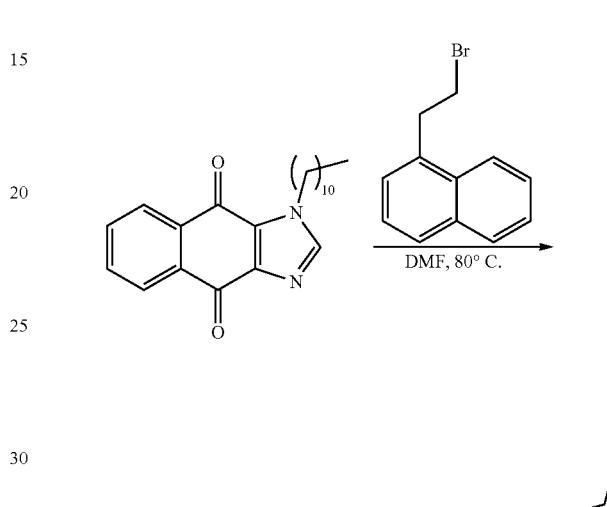

Synthesis of 1-decyl-3-(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromodecane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

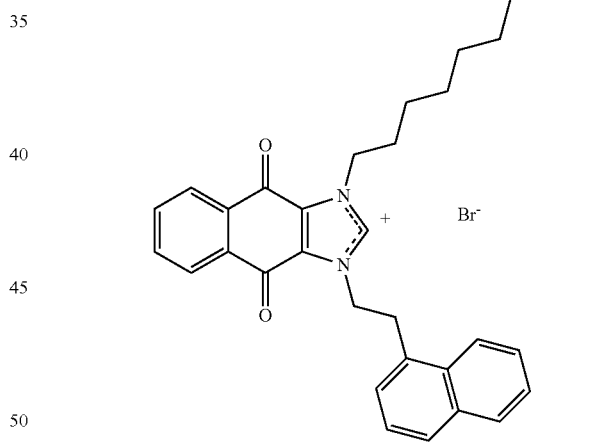

Synthesis of 1-undecyl-3-(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromoundecane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

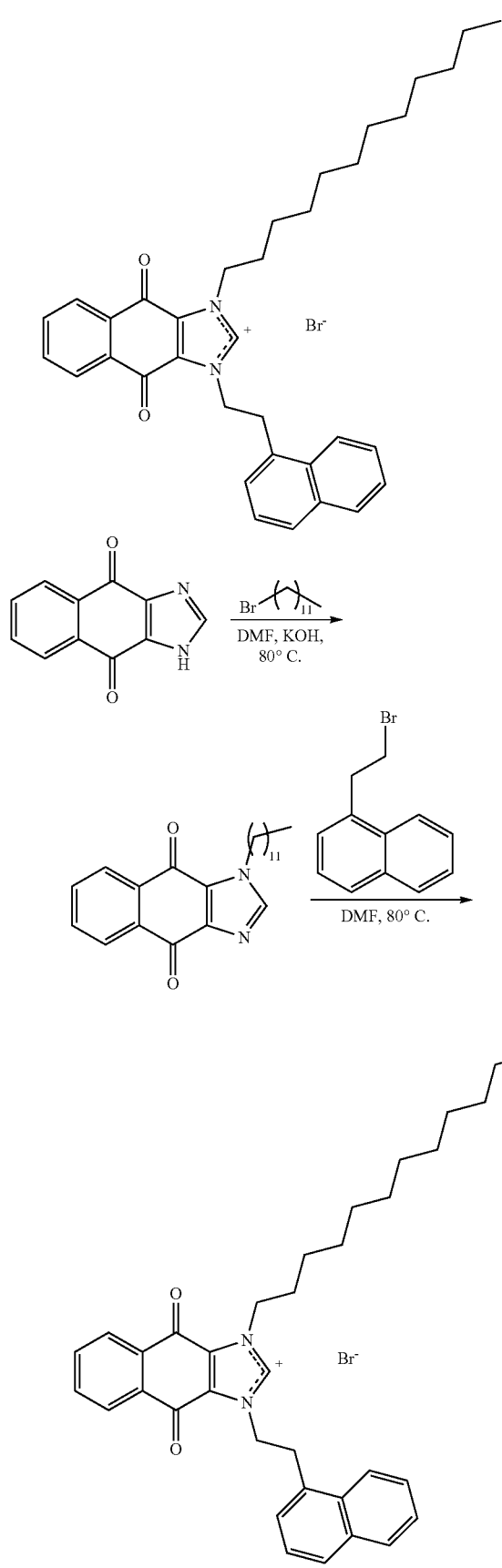

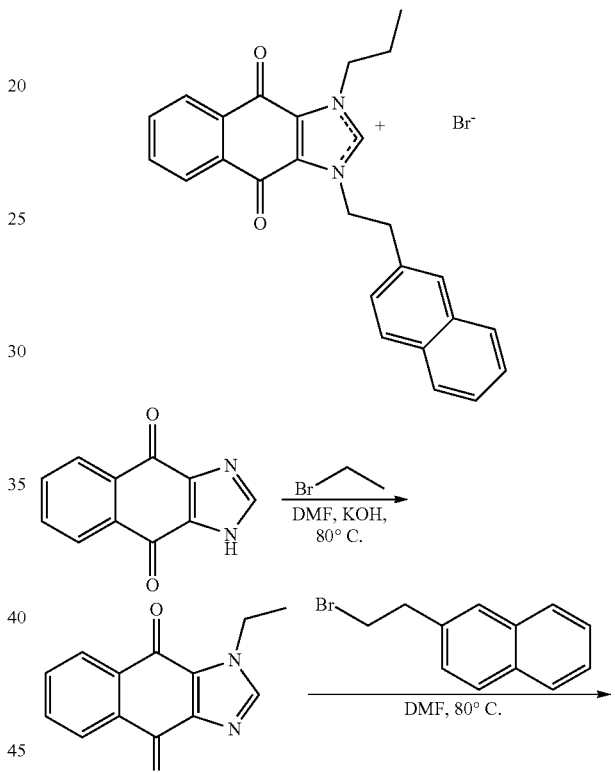

Synthesis of 1-dodecyl-3-(2-ethyl-1-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromododecane (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

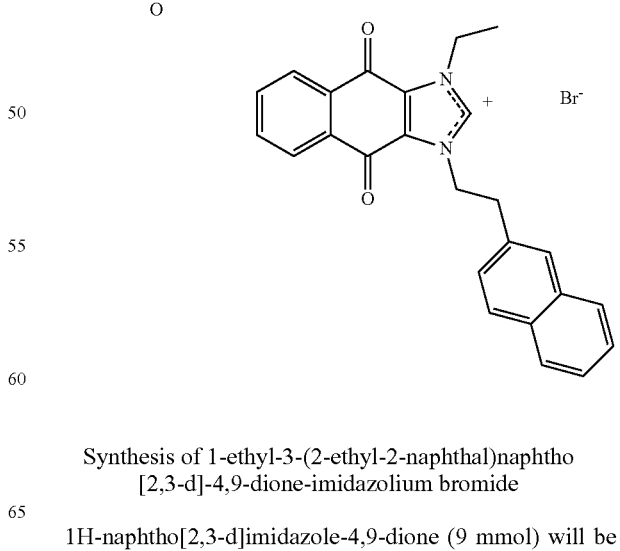

Synthesis of 1-ethyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromoethane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

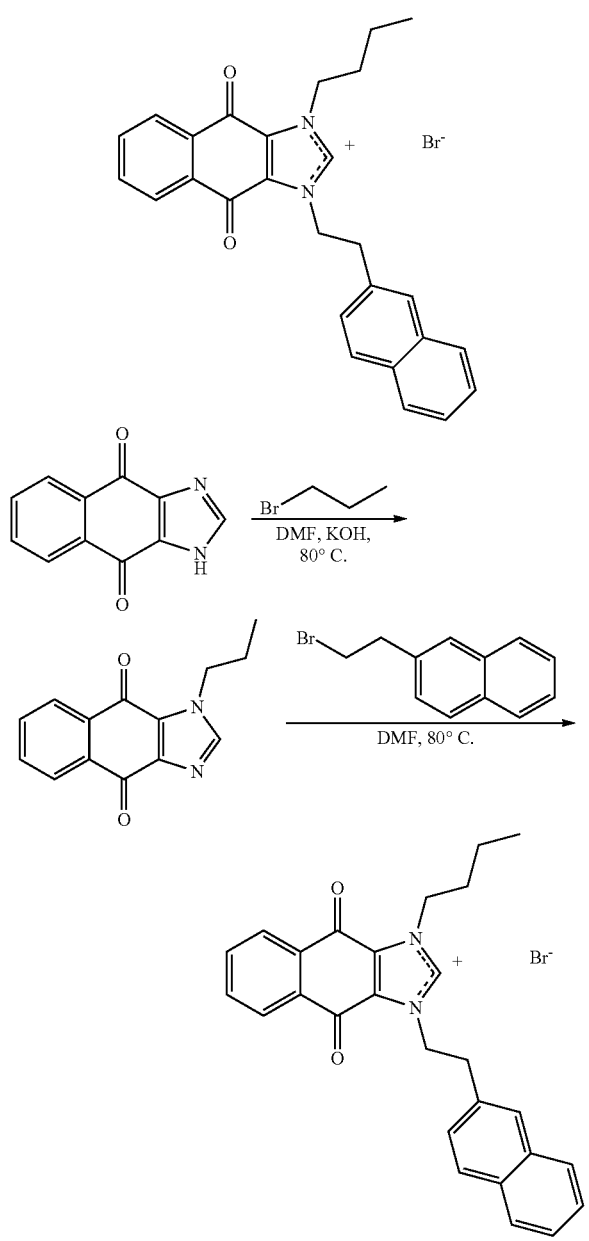

Synthesis of 1-propyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromopropane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

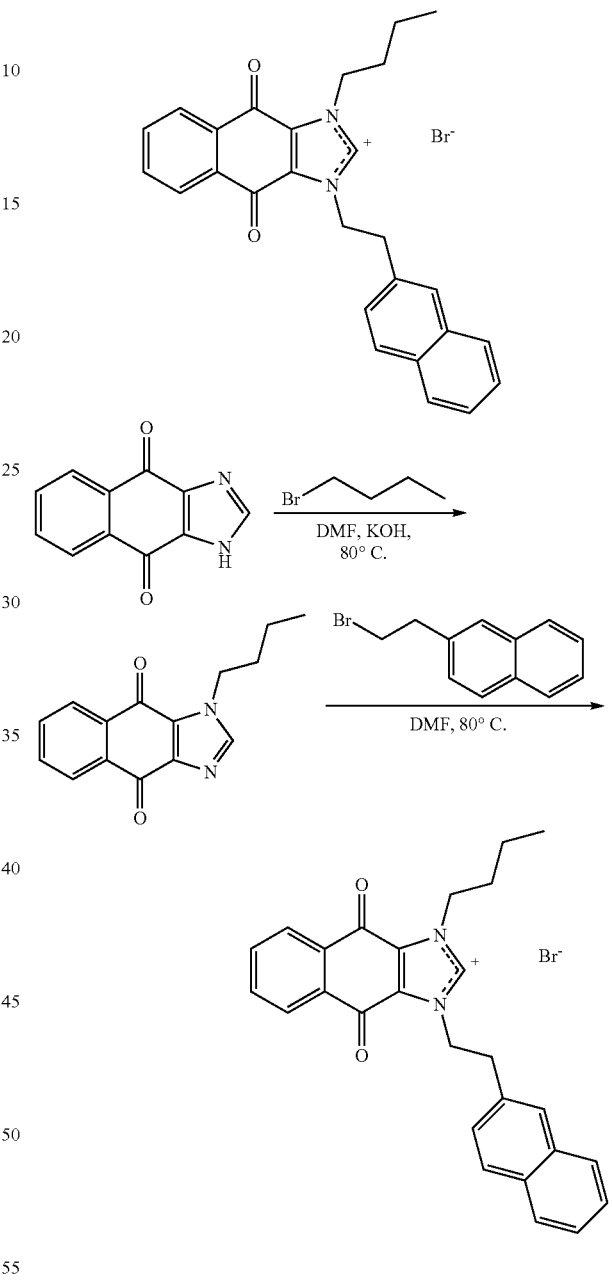

Synthesis of 1-butyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromobutane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

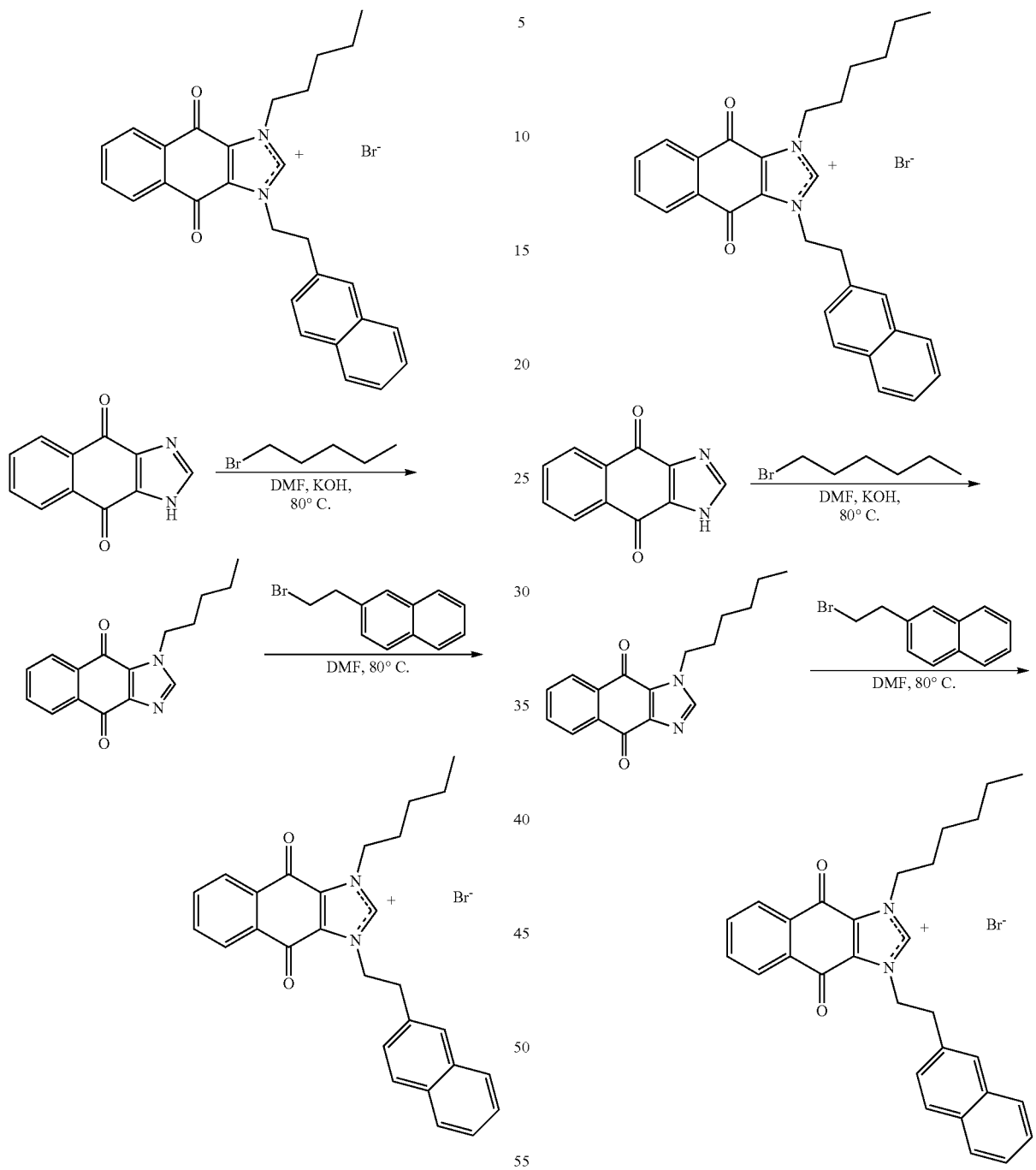

Synthesis of 1-pentyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromopentane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

Synthesis of 1-hexyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromohexane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

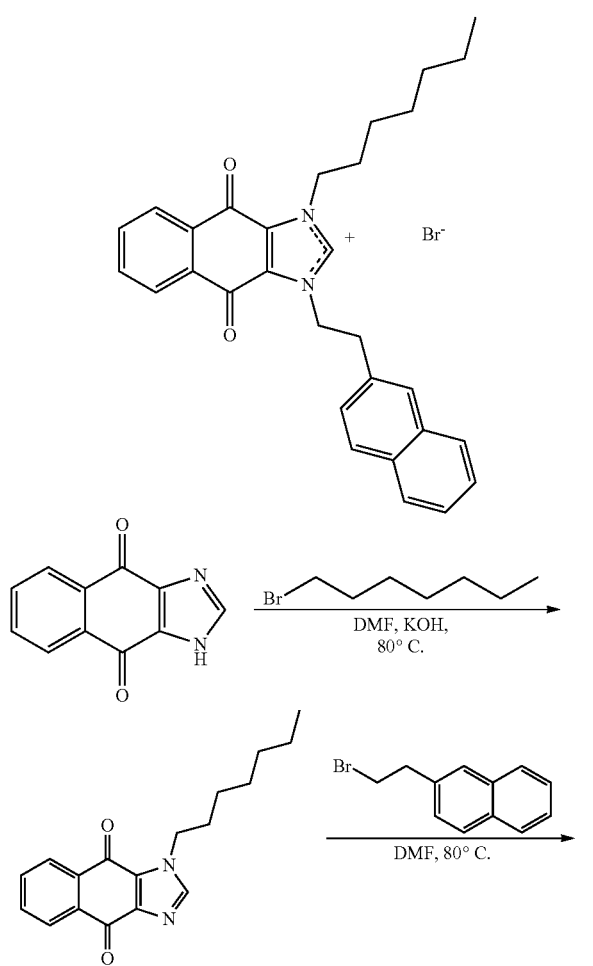

Synthesis of 1-heptyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromoheptane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

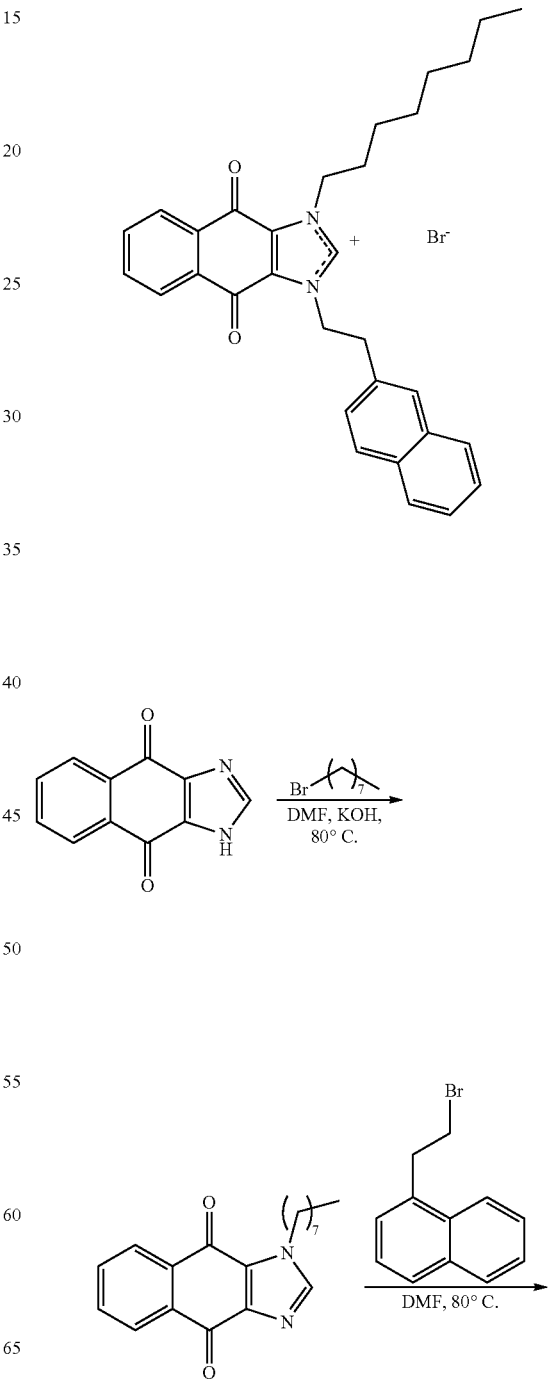

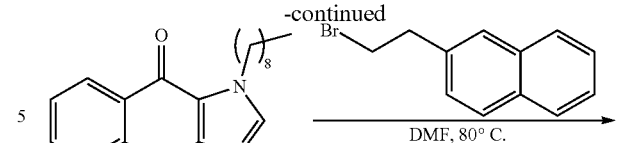

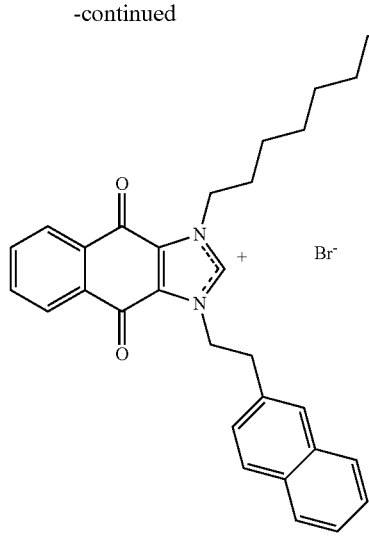

Synthesis of 1-octyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromooctane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

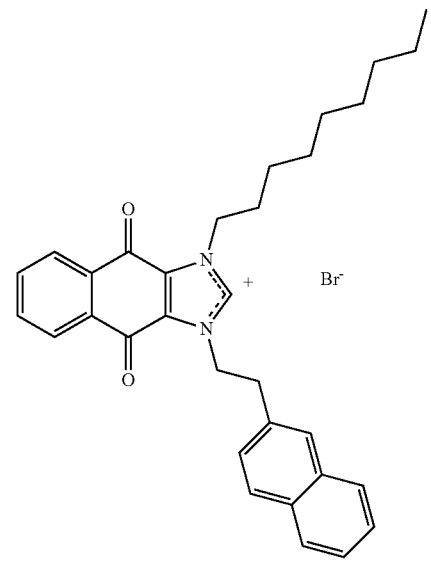

Synthesis of 1-nonyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromononane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

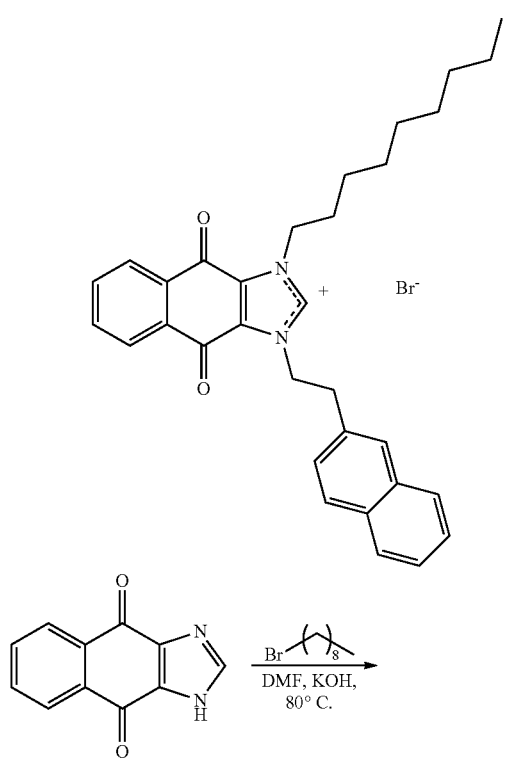

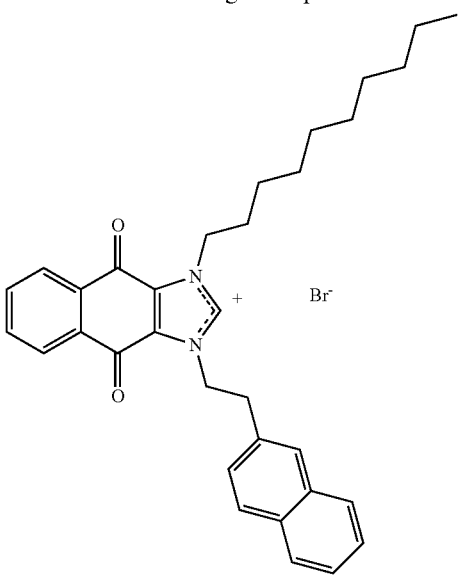

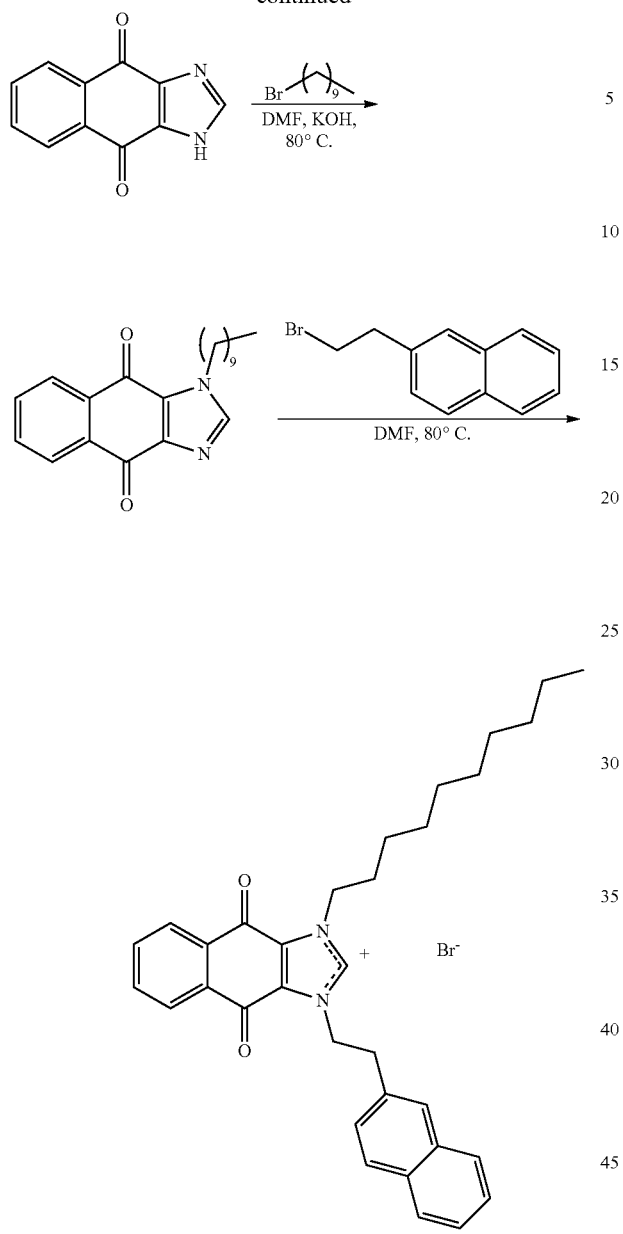
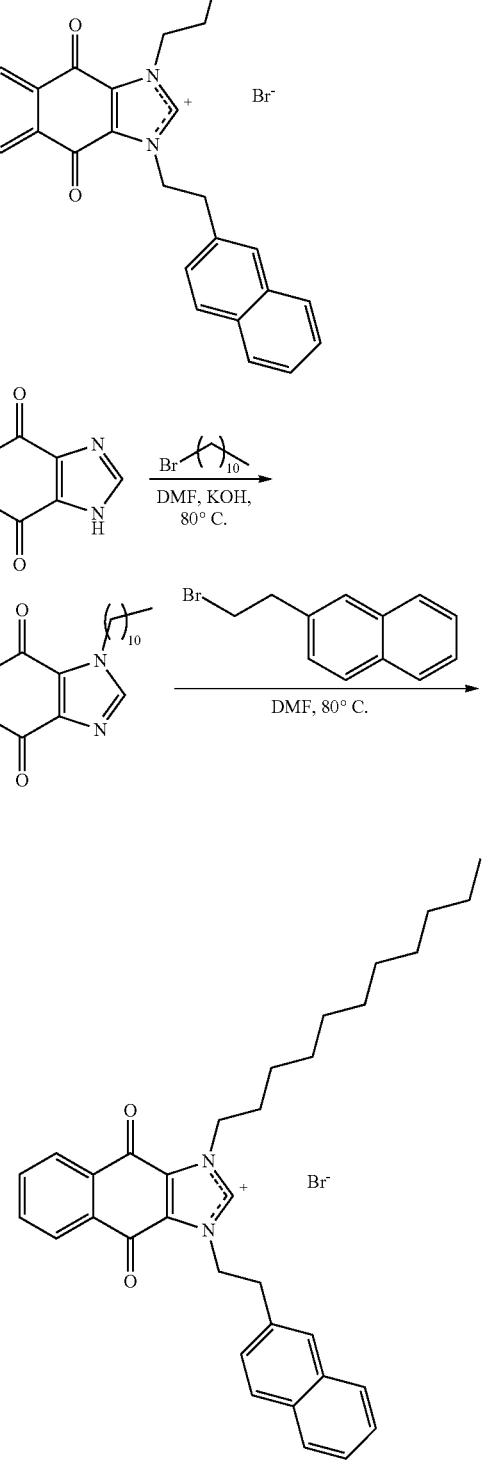

Synthesis of 1-decyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromodecane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

Synthesis of 1-undecyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromoundecane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

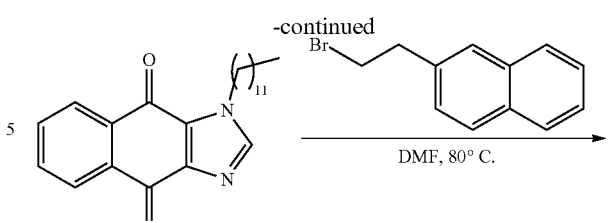

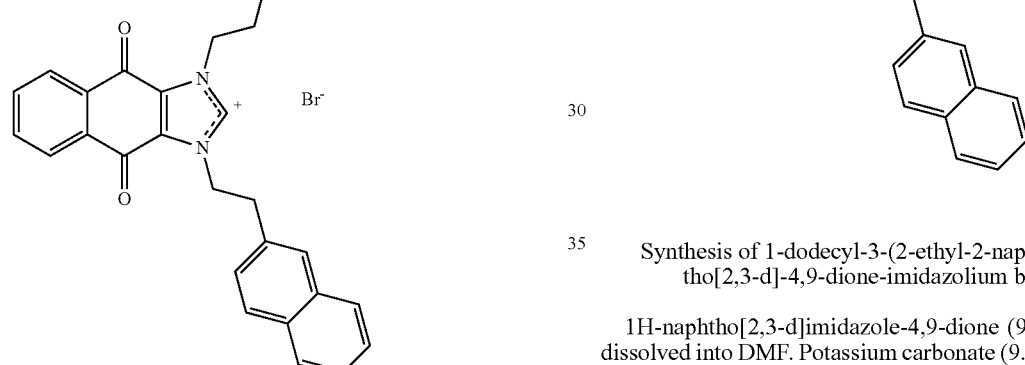

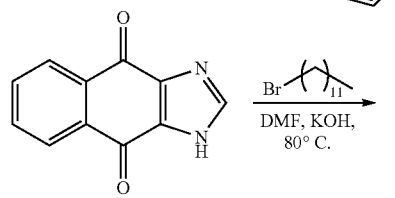

Synthesis of 1-dodecyl-3-(2-ethyl-2-naphthal)naphtho[2,3-d]-4,9-dione-imidazolium bromide 1H-naphtho[2,3-d]imidazole-4,9-dione (9 mmol) will be dissolved into DMF. Potassium carbonate (9.9 mmol) will be added and the mixture will be allowed to stir for 0.5 h and 1-bromododecane (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

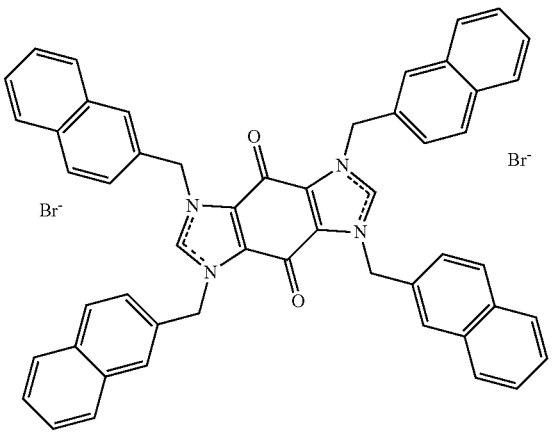

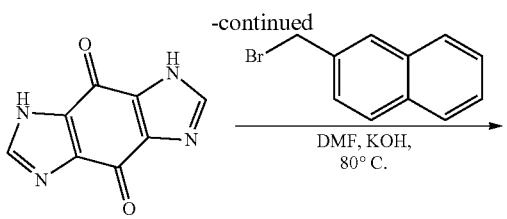

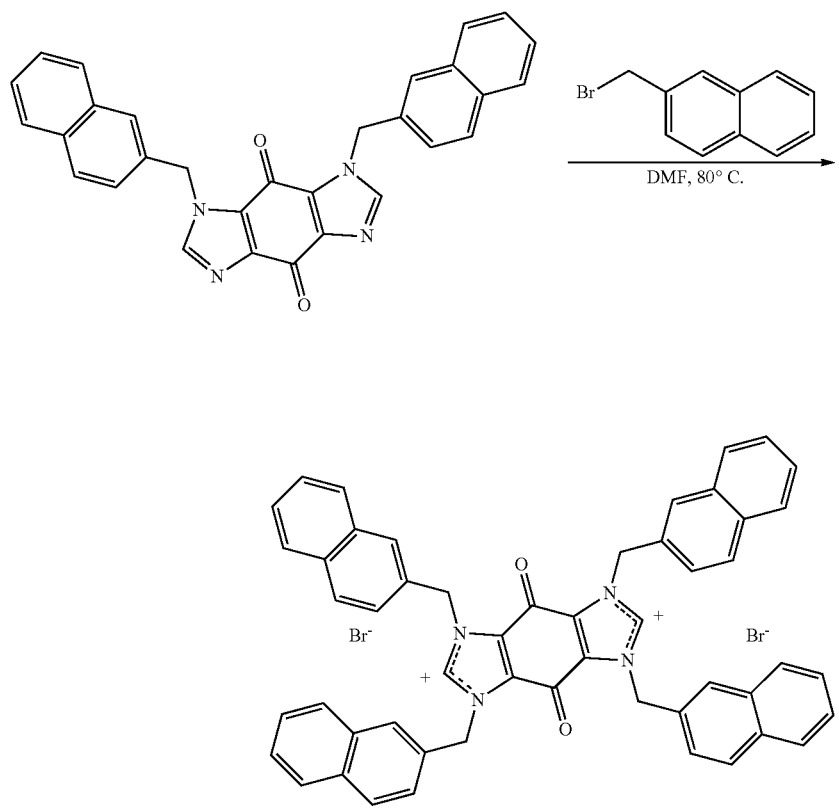

Synthesis of 1,3,5,7-tetrakis(2-methylnaphthal)-4,8-dioxo-3,4,7,8-tetrahydrobenzo[1,2-d:4,5-d']diimidazolium bromide Benzo[1,2-d:4,5-d']diimidazole-4,8-dione will be dissolved into DMF. Potassium carbonate (9.9 mmol) will be added and the mixture will be allowed to stir for 0.5 h and 2-bromomethyl naphthalene (9 mmol) will be added and the mixture will be returned to reflux overnight. The solution will be filtered hot to remove a white precipitate (presumed to be KBr) and 2-bromomethyl naphthalene (9 mmol) will be added and the mixture will be returned to reflux overnight. The mixture will be allowed to cool to room temperature, and the volatiles will be removed en vacuo resulting in the product.

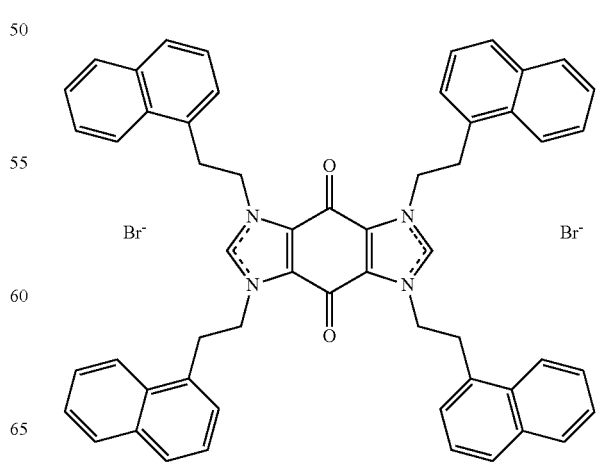

111
-continued

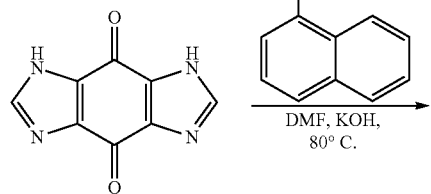

DMF, KOH,
80° C.

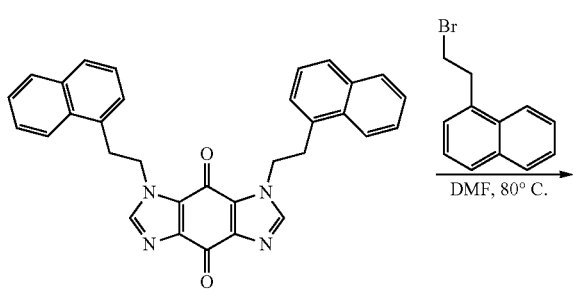

DMF, 80° C.

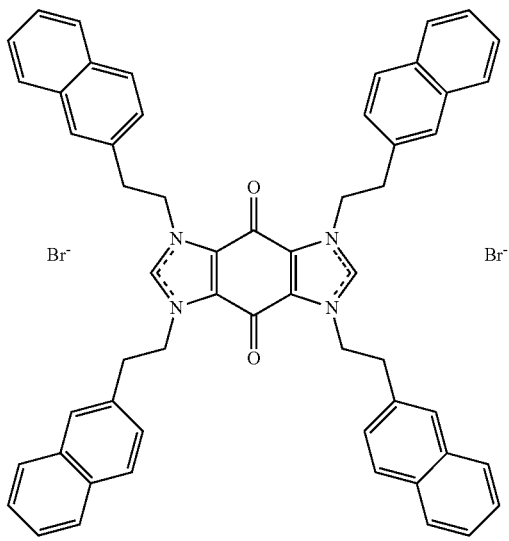

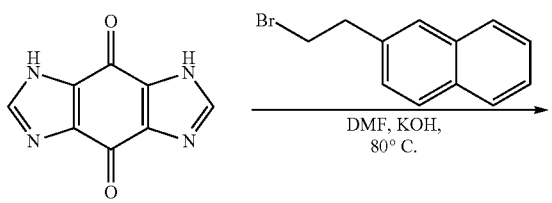

DMF, KOH,
80° C.

112
-continued

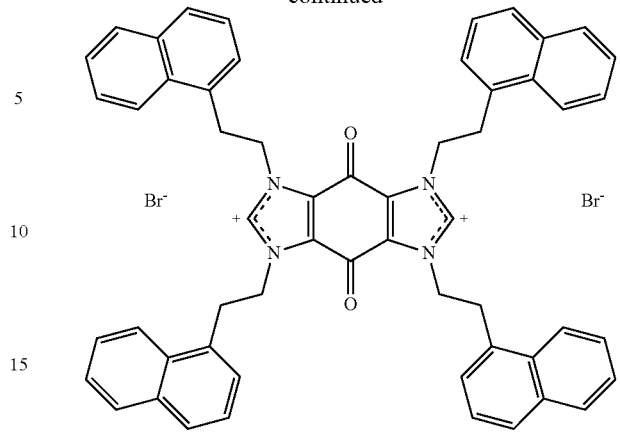

Synthesis of 1,3,5,7-tetrakis(2-ethyl-1-naphthal)-4,8-dioxo-3,4,7,8-tetrahydrobenzo[1,2-d:4,5-d']diimidazolium bromide Benzo[1,2-d:4,5-d']diimidazole-4,8-dione will be dissolved into DMF. Potassium carbonate (9.9 mmol) will be added and the mixture will be allowed to stir for 0.5 h and 1-(2-bromoethyl)naphthalene (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

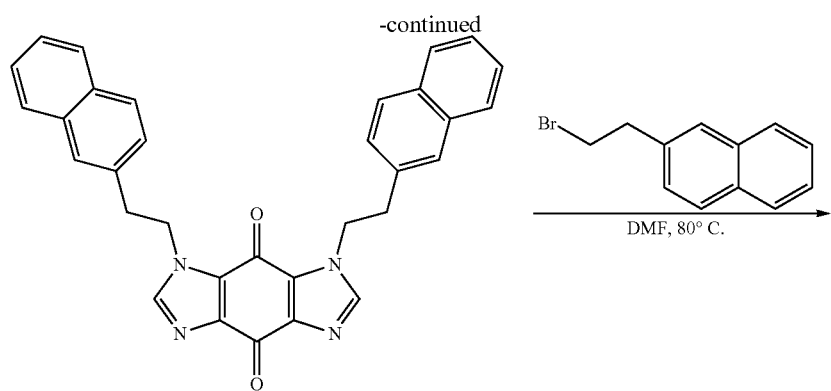

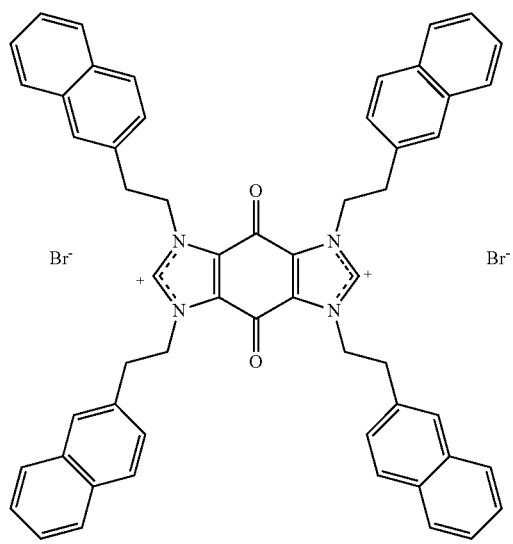

Synthesis of 1,3,5,7-tetrakis(2-ethyl-2-naphthal)-4,8-dioxo-3,4,7,8-tetrahydrobenzo[1,2-d:4,5-d']diimidazolium bromide Benzo[1,2-d:4,5-d']diimidazole-4,8-dione will be dissolved into DMF. Potassium carbonate (9.9 mmol) will be added and the mixture will be allowed to stir for 0.5 h and 2-(2-bromoethyl)naphthalene (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

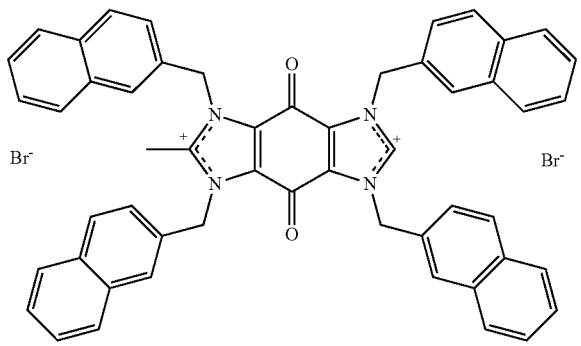

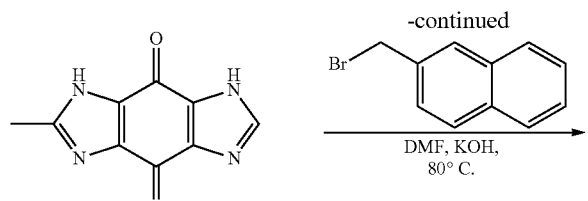

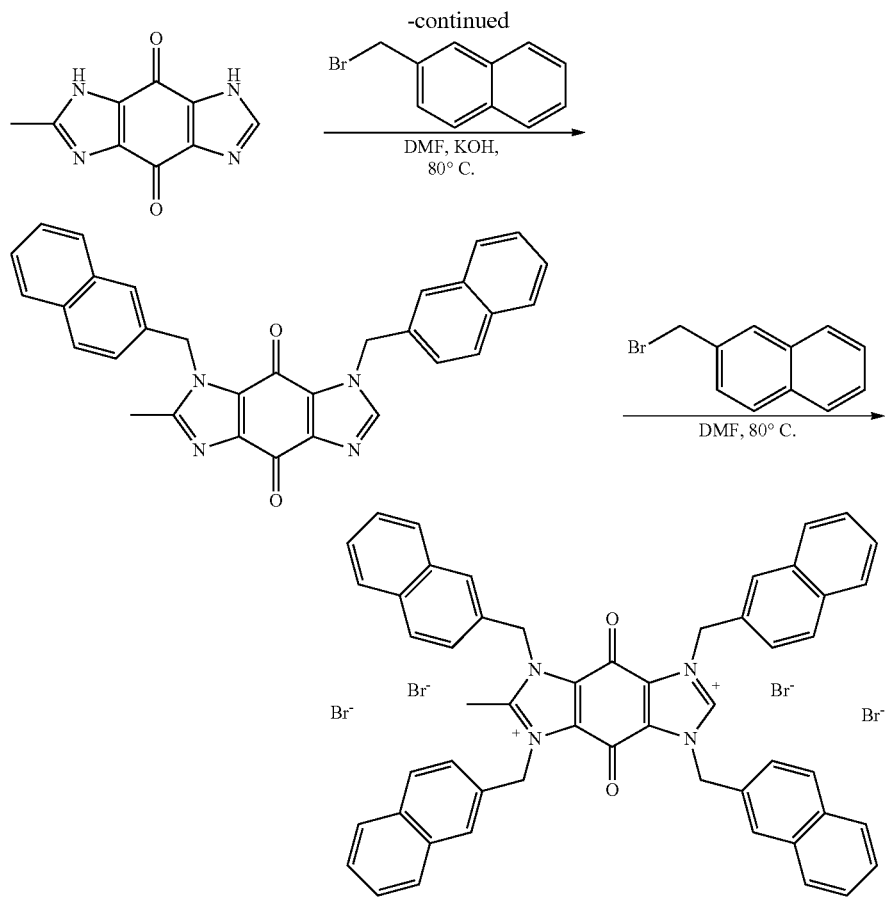

Synthesis of 2-methyl-1,3,5,7-tetrakis(2-methyl-naphthal)-4,8-dioxo-3,4,7,8-tetrahydrobenzo[1,2-d:4,5-d']diimidazolium bromide 2-methylbenzo[1,2-d:4,5-d']diimidazole-4,8-dione will be dissolved into DMF. Potassium carbonate (9.9 mmol) will be added and the mixture will be allowed to stir for 0.5 h and 2-bromomethyl naphthalene (9 mmol) will be added and the mixture will be returned to reflux overnight. The solution will be filtered hot to remove a white precipitate (presumed to be KBr) and 2-bromomethyl naphthalene (9 mmol) will be added and the mixture will be returned to reflux overnight. The mixture will be allowed to cool to room temperature, and the volatiles will be removed en vacuo resulting in the product.

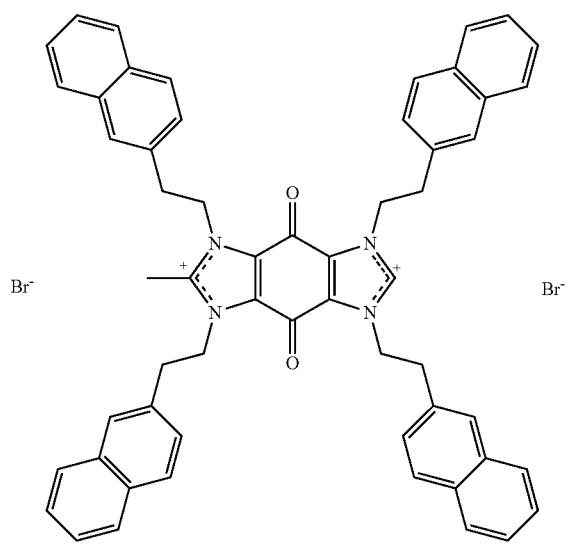

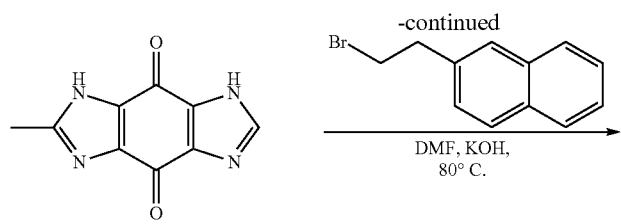

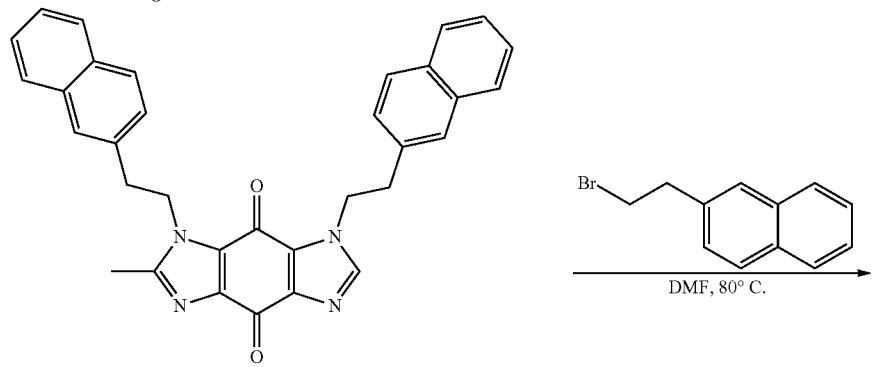

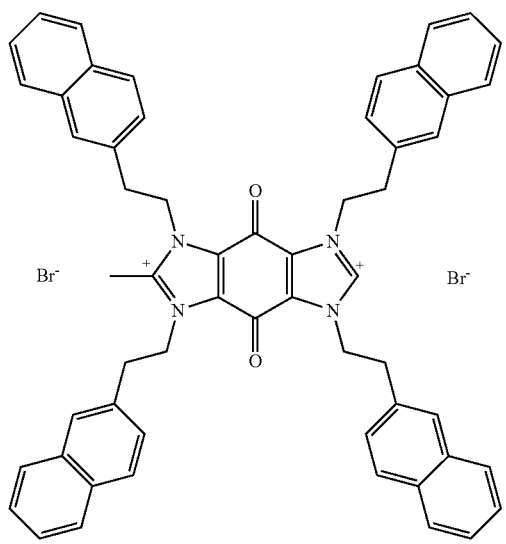

Synthesis of 2-methyl-1,3,5,7-tetrakis(2-ethyl-2-naphthal)-4,8-dioxo-3,4,7,8-tetrahydrobenzo[1,2-d:4,5-d']diimidazolium bromide 2-methylbenzo[1,2-d:4,5-d']diimidazole-4,8-dione will be dissolved into DMF. Potassium carbonate (9.9 mmol) will be added and the mixture will be allowed to stir for 0.5 h and 2-(2-bromoethyl)naphthalene (9 mmol) will be added and the mixture will be returned to reflux overnight. The solution will be filtered hot to remove a white precipitate (presumed to be KBr) and 2-(2-bromoethyl)naphthalene (9 mmol) will be added and the mixture will be returned to reflux overnight. The mixture will be allowed to cool to room temperature, and the volatiles will be removed en vacuo resulting in the product.

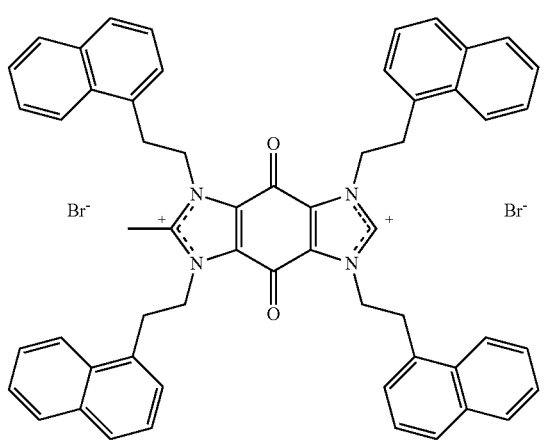

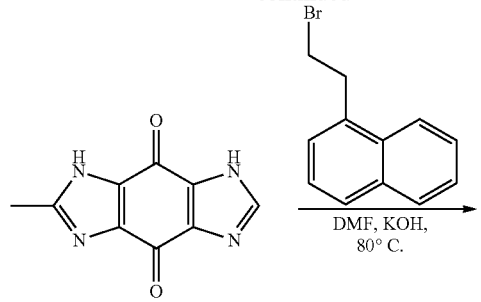
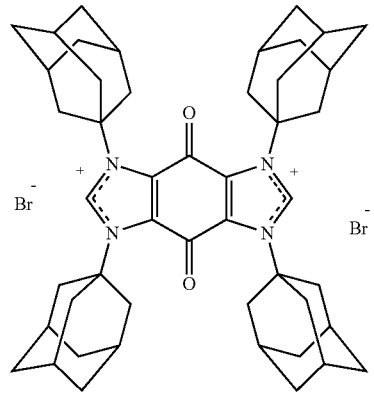
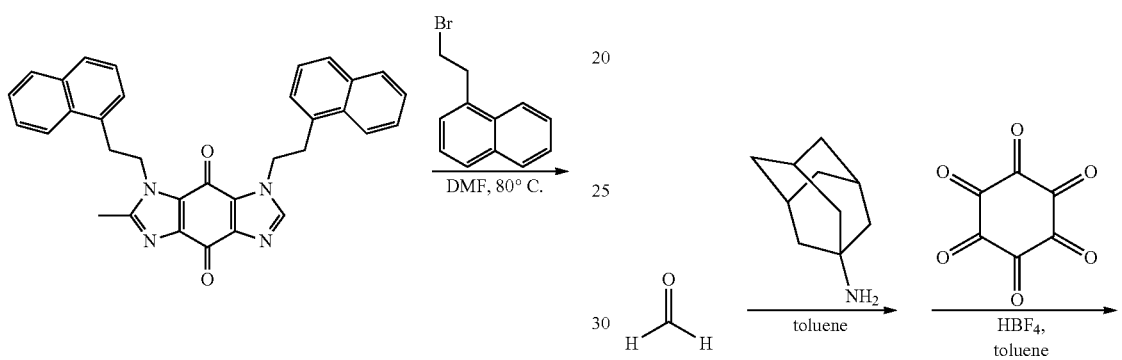
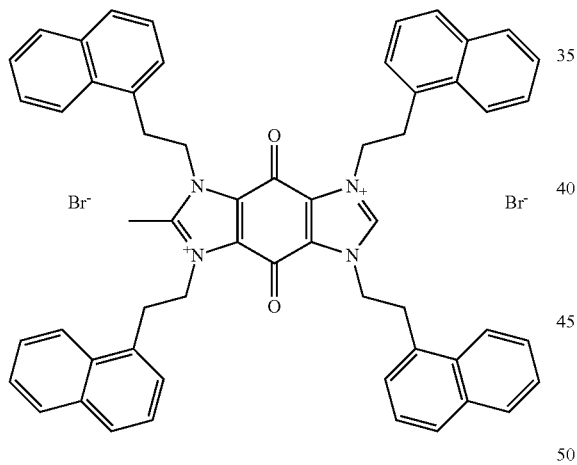
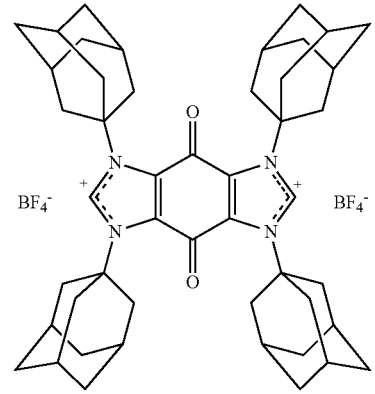

Synthesis of 2-methyl-1,3,5,7-tetrakis(2-ethyl-1-naphthal)-4,8-dioxo-3,4,7,8-tetrahydrobenzo[1,2-d:4,5-d']diimidazolium bromide 2-methylbenzo[1,2-d:4,5-d']diimidazole-4,8-dione will be dissolved into DMF. Potassium carbonate (9.9 mmol) will be added and the mixture will be allowed to stir for 0.5 h and 1-(2-bromoethyl)naphthalene (9 mmol) will be added and the mixture will be returned to reflux overnight. The solution will be filtered hot to remove a white precipitate (presumed to be KBr) and 1-(2-bromoethyl)naphthalene (9 mmol) will be added and the mixture will be returned to reflux overnight. The mixture will be allowed to cool to room temperature, and the volatiles will be removed en vacuo resulting in the product.

Synthesis of 1,3,5,7-tetrakis(adamantyl)-4,8-dioxo-3,4,7,8-tetrahydrobenzo[1,2-d:4,5-d']diimidazolium bromide Paraformaldehyde (0.32 mmol) will be dissolved into toluene. Adamantyl amine (0.66 mmol) will be added slowly and the mixture will be heated stirred at room temperature for 1 h. The mixture will be cooled to 0° C. and another equivalent of adamantly amine (0.66 mmol) will be added. A 3N solution of $HBF_4$(aq) will be added dropwise and upon returning to room temperature 1,2,3,4,5,6-cyclohexanehexone will be added. The mixture will be stirred at 60° C. for 36 h, after which the solvent will be removed en vacuo to obtain the product.

121

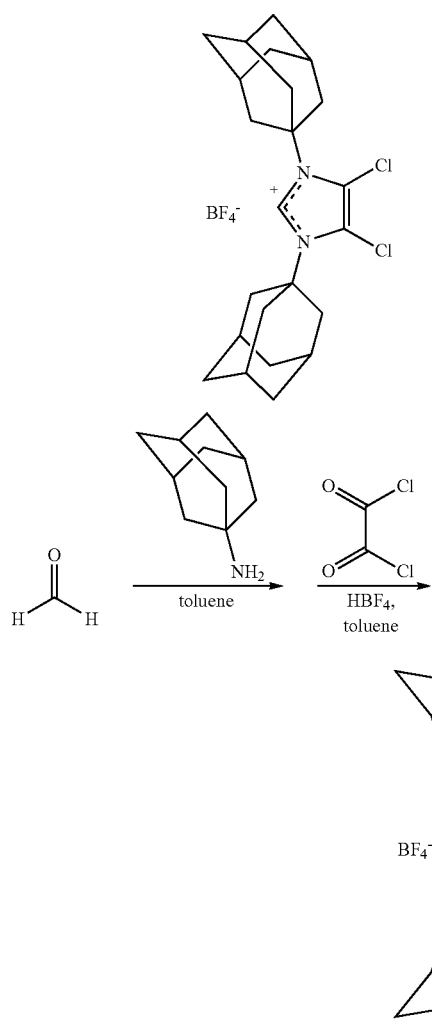

Synthesis of 1,3-bisadamantyl-4,5-dichloroimidazolium tetrafluoroborate

Paraformaldehyde (0.32 mmol) will be dissolved into toluene. Adamantyl amine (0.33 mmol) will be added slowly and the mixture will be heated stirred at room temperature for 1 h. The mixture will be cooled to 0° C. and another equivalent of adamantly amine (0.33 mmol) will be added. A 3N solution of $HBF_4$(aq) will be added dropwise and upon returning to room temperature oxalyl dichloride (0.33 mmol) will be added. The mixture will be stirred at 60° C. for 36 h, after which the solvent will be removed en vacuo to obtain the product.

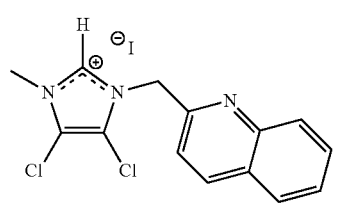

122

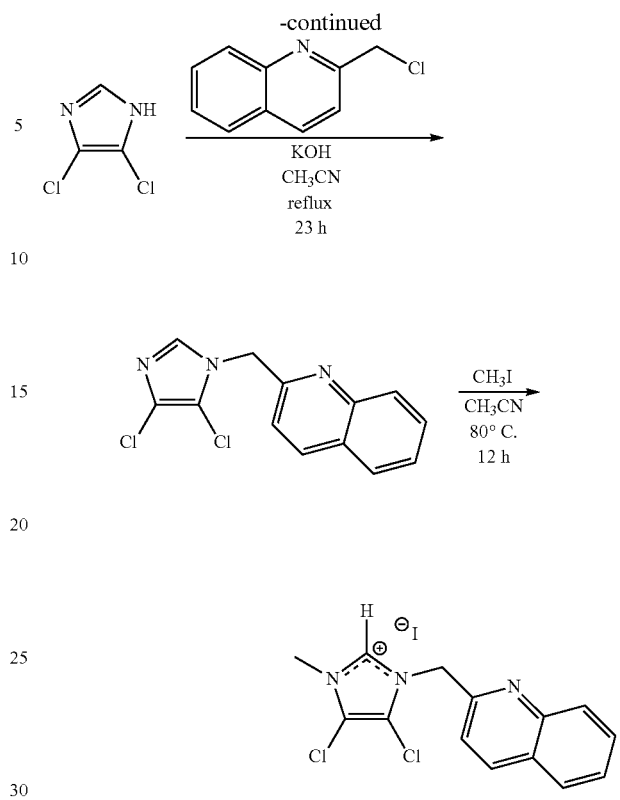

Synthesis of 3-methyl-1-(quinolin-2-ylmethyl)-4,5-dichloroimidazolium iodide 4,5-Dichloroimidazole (2.00 g, 14.6 mmol) was dissolved in 15 mL acetonitrile in a round bottom flask. Potassium hydroxide (0.90 g, 16.0 mmol) was added and the mixture was refluxed for 15 min. Concurrently, 2-chloromethylquinoline hydrochloride (3.13 g, 14.6 mmol) and potassium hydroxide (0.82 g, 14.6 mmol) were added to a second round bottom flask and stirred in 60 mL acetonitrile at reflux for 10 min. The contents of the second flask were added to the first, and the combined mixture was refluxed overnight, during which time a white precipitate formed. The reaction mixture was filtered hot, yielding a clear, tan filtrate. Slow evaporation and cooling of the filtrate yielded tan crystals of 1-(quinolin-2-ylmethyl)-4,5-dichloroimidazole, which were collected by a second filtration. The crystals (0.278 g, 1.0 mmol) will be dissolved in a minimum volume of DMF. Iodomethane (0.62 mL, 10.0 mmol) will be added and the mixture will be heated at 80° C. for 12 h. Removal of the volatile components under reduced pressure will yield the product.

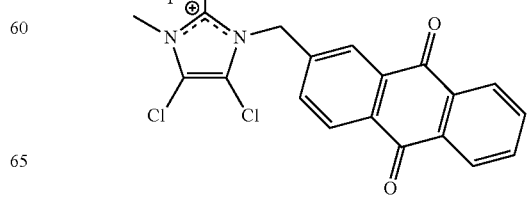

123
-continued

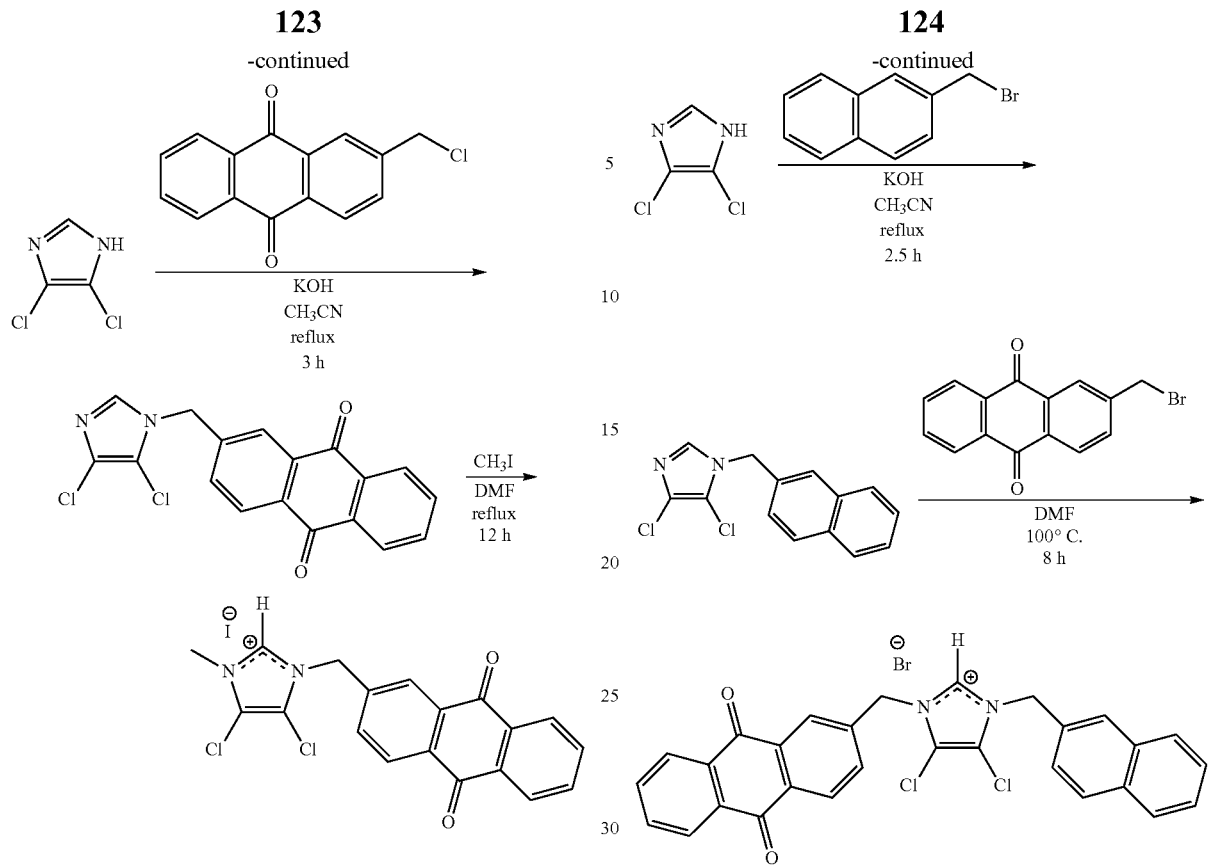

Synthesis of 3-methyl-1-(2-methylanthraquinonyl)-4,5-dichloroimidazolium iodide 4,5-Dichloroimidazole (0.18 g, 1.33 mmol) and potassium hydroxide (0.08 g, 1.46 mmol) were combined in a round bottom flask. Acetonitrile (2 mL) was added and the mixture was stirred at reflux for 30 min, dissolving the remaining solid. Concurrently, 2-(Bromomethyl)anthraquinone (0.40 g, 1.33 mmol) was added to 30 mL acetonitrile and stirred at reflux for 30 min, partially dissolving the solid. The solution in the initial flask was added to the 2-(bromomethyl)anthraquinone mixture, and the solution was returned to reflux for 3 h. The mixture was filtered hot, and a precipitate quickly formed in the tan filtrate. The precipitate was collected by a second filtration and washed with cold acetonitrile to yield a yellow powder. This solid (0.50 g, 1.0 mmol) will be dissolved in DMF and heated at 80° C. Iodomethane (0.62 mL, 10.0 mmol) will be added slowly and the reaction mixture will be heated for 12 h. Removal of the volatile components under reduced pressure will yield the product.

124
-continued

Synthesis of 1-(naphthalen-2-ylmethyl)-3-(2-methylanthraquinonyl)-4,5-dichloroimidazolium bromide 4,5-Dichloroimidazole (1.37 g, 10.0 mmol) and potassium hydroxide (0.61 g, 11.0 mmol) were placed in a round bottom flask and 10 mL acetonitrile was added. The mixture was refluxed for 30 min. The flask was removed from the head and 2-(bromomethyl)naphthalene (2.21, 10.0 mmol) was added. The mixture was returned to heat and refluxed for 2.5 h, during which time a white precipitate formed. The mixture was filtered hot, and upon cooling a precipitate formed in the filtrate. The solid, the mono-substituted imidazole, was collected by a second filtration. This solid (0.28 g, 1.0 mmol) and 2-(bromomethyl)anthraquinone (0.90 g, 3.0 mmol) will be placed in a high-pressure vessel and dissolved in the minimum volume of DMF. The solution will be heated to 100° C. for 8 h. Removal of the volatile components under reduced pressure will yield the product.

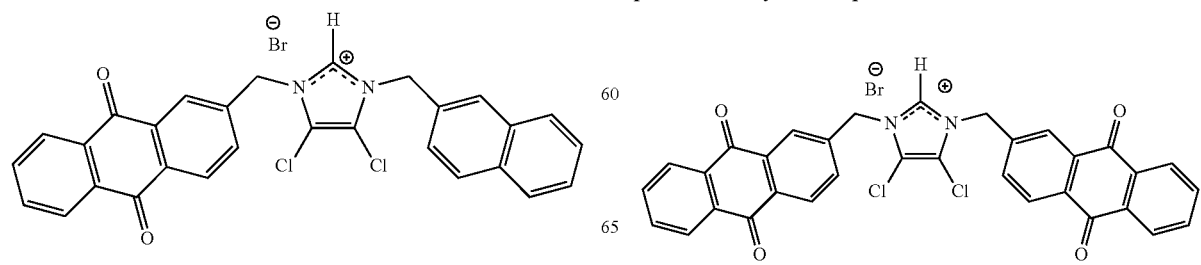

-continued

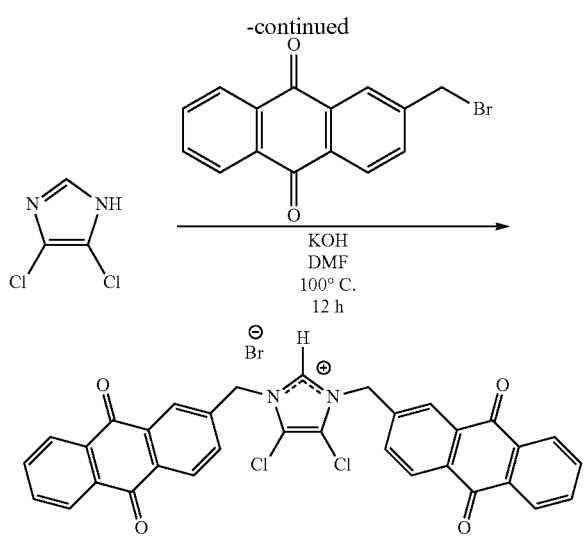

Synthesis of 1,3-bis(2-methylanthraquinonyl)-4,5-dichloroimidazolium bromide 4,5-Dichloroimidazole (0.14 g, 1.0 mmol) and potassium hydroxide (0.06 g, 1.1 mmol) will be dissolved in the minimum volume of DMF in a high-pressure vessel. The solution will be heated at 80° C. for 30 min. The vessel will be removed from heat and 2-(bromomethyl)anthraquinone (1.20 g, 4.0 mmol) will be added. If not all solid dissolves, DMF will be added until all reactants are in solution. The vessel will be sealed and heated at 100° C. for 12 h. The volatile components will be removed under reduced pressure, and the remaining mixture washed with water to remove potassium bromide. The remaining solid will be collected and should be the product.

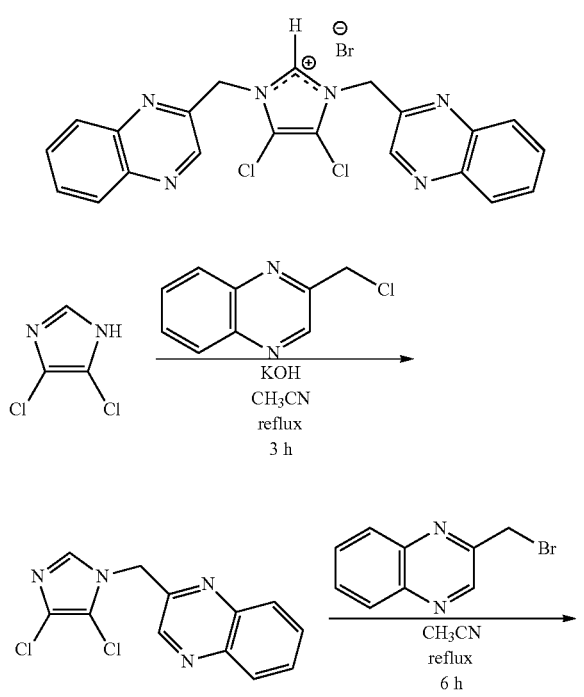

-continued

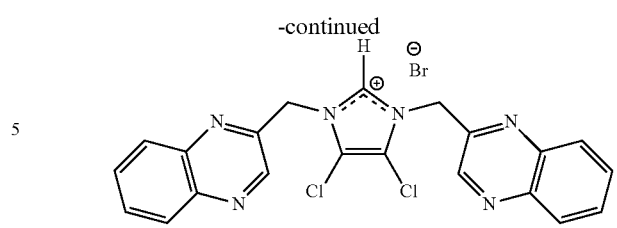

Synthesis of 1,3-bis(quinoxalin-2-ylmethyl)-4,5-dichloroimidazolium bromide 4,5-dichloroimidazole (1.37 g, 10 mmol) will be dissolved in a minimum amount of acetonitrile and potassium hydroxide (0.62 g, 11 mmol) will be added. The mixture will be stirred at reflux until the potassium hydroxide is consumed, approximately 30 min. 2-(Bromomethyl)quinoxaline (2.23 g, 10.0 mmol) will be added and the mixture will be returned to reflux for 3 h. The mixture will be filtered hot to remove the potassium bromide generated. A second addition of 2-(bromomethyl)quinoxaline (2.23 g, 10.0 mmol) will be made to the reaction solution, which will be returned to reflux for 6 h. Removal of the volatile components under reduced pressure should yield the product.

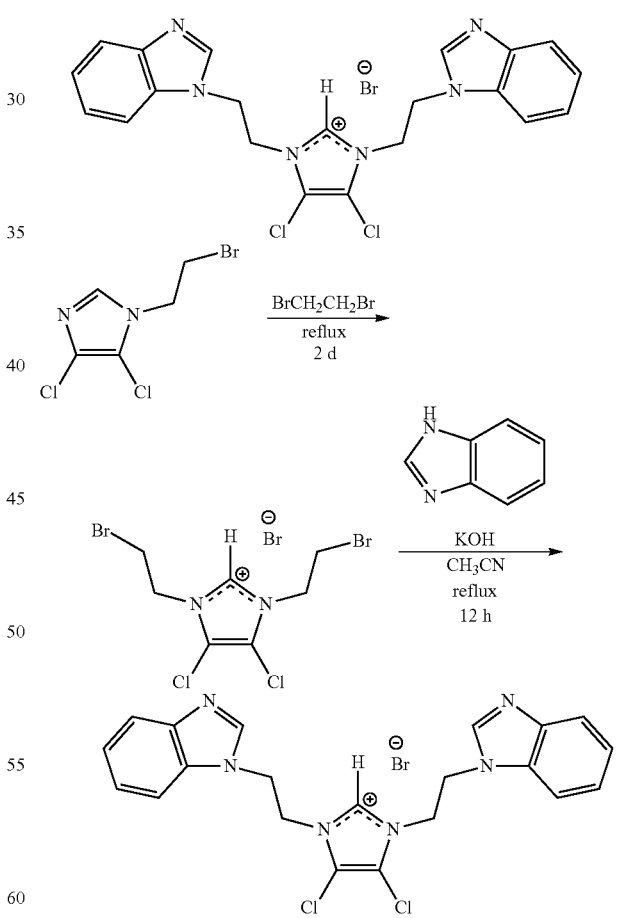

Synthesis of 1,3-bis(2-(benzimidazol-1-yl)ethyl)-4,5-dichloroimidazolium bromide 1-(2-Bromoethyl)-4,5-dichloroimidazole was synthesized from a literature procedure. To this solid (1.1 g, 4.5 mmol)

was added 1,2-dibromoethane (1.5 mL, 18 mmol). The mixture was refluxed for 2 d, during which time a precipitate formed. The solid was collected by filtration and determined to be the desired product, 1,3-(2-bromoethyl)-4,5-dichloroimidazole. This solid (4.31 g, 10 mmol) will be added to a refluxing mixture of benzimidazole (1.18 g, 10.0 mmol) and KOH (0.56 g, 10 mmol) in acetonitrile and stirred for 12 hours. The mixture will be filtered to remove the potassium bromide generated, and the volatile components of the filtrate will be removed under reduced pressure to yield the desired product.

added to the filtrate, which will be returned to 80° C. for 12 h. The mixture will again be filtered hot to remove KCl and excess base from the neutralization reaction, and the volatile components of the filtrate will be removed under reduced pressure to yield the product.

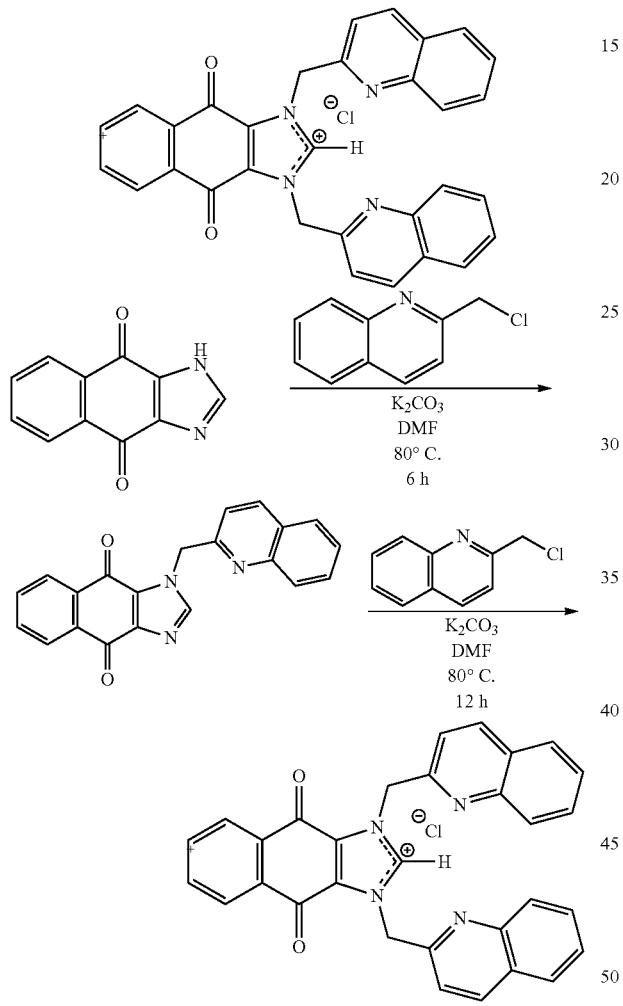
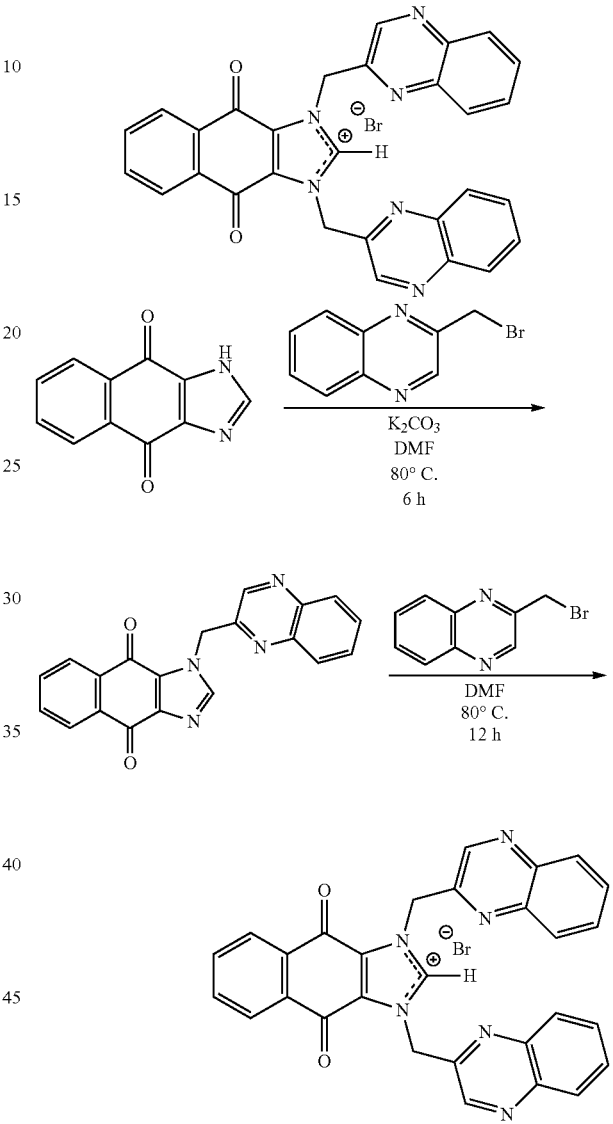

Synthesis of 1,3-bis(quinolin-2-ylmethyl)naphtho[2,3-d]-4,9-dione-imidazolium bromide Naphtho[2,3-d]imidazole-4,9-dione (1.98 g, 10.0 mmol) and potassium carbonate (2.07 g, 15.0 mmol) will be dissolved in a minimum volume of DMF and heated at 80° C. for 1 h. A solution of 2-(chloromethyl)quinoline will be prepared by combining 2-(chloromethyl)quinolone hydrochloride (2.14 g, 10 mmol) and potassium carbonate (2.07 g, 15.0 mmol) in DMF and heating at 80° C. for 30 min, and this solution will be added to the reaction mixture. The mixture will be heated at 80° C. for 6 h. The mixture will be filtered hot to remove any excess base and KCl generated. A second equivalent of neutralized 2-chloromethylquinoline will be Synthesis of 1,3-bis(quinoxalin-2-ylmethyl)naphtho[2,3-d]-4,9-dione-imidazolium bromide Naphtho[2,3-d]imidazole-4,9-dione (1.98 g, 10.0 mmol) and potassium carbonate (2.07 g, 15.0 mmol) will be dissolved in a minimum volume of DMF and heated at 80° C. for 1 h. 2-(Bromomethyl)quinoxaline (2.23 g, 10.0 mmol) will be added and the mixture will be heated at 80° C. for 6 h. The mixture will be filtered hot to remove any excess base and KCl generated. A second equivalent of 2-(Bromomethyl)quinoxaline will be added to the filtrate, which will be returned to 80° C. for 12 h. The volatile components of the reaction mixture will be removed under reduced pressure to yield the product.

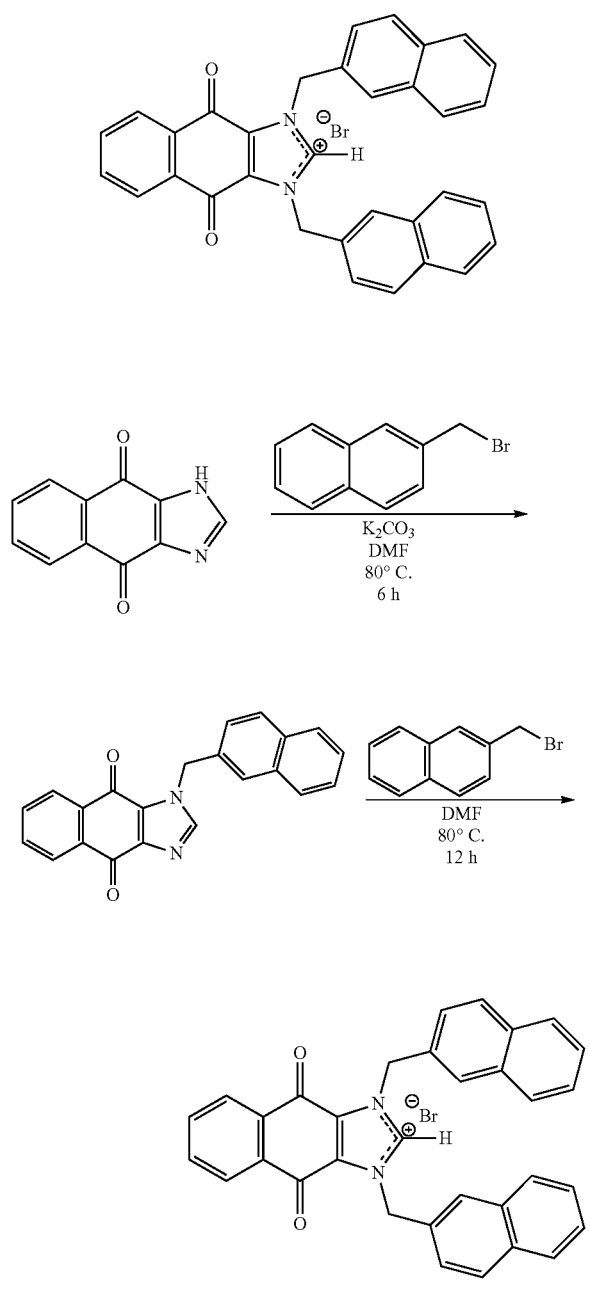

Synthesis of 1,3-bis(naphthalen-2-ylmethyl)naphtho[2,3-d]-4,9-dione-imidazolium bromide Naphtho[2,3-d]imidazole-4,9-dione (1.98 g, 10.0 mmol) and potassium carbonate (2.07 g, 15.0 mmol) will be dissolved in a minimum volume of DMF and heated at 80° C. for 1 h. 2-(Bromomethyl)naphthalene (2.23 g, 10.0 mmol) will be added and the mixture will be heated at 80° C. for 6 h. The mixture will be filtered hot to remove any excess base and KCl generated. A second equivalent of 2-(Bromomethyl)naphthalene will be added to the filtrate, which will be returned to 80° C. for 12 h. The volatile components of the reaction mixture will be removed under reduced pressure to yield the product.

Synthesis of 4,11-dihydroxy-1,3-bis(quinolin-2-ylmethyl)anthra[2,3-d]-5,10-dione-imidazolium chloride 4,11-Dihydroxy-anthra[2,3-d]imidazole-5,10-dione (2.80 g, 10.0 mmol) and potassium carbonate (2.07 g, 15.0 mmol) will be dissolved in a minimum volume of DMF and heated at 80° C. for 1 h. A solution of 2-(chloromethyl)quinoline will be prepared by combining 2-(chloromethyl)quinolone hydrochloride (2.14 g, 10 mmol) and potassium carbonate (2.07 g, 15.0 mmol) in DMF and heating at 80° C. for 30 min, and this solution will be added to the reaction mixture. The mixture will be heated at 80° C. for 6 h. The mixture will be filtered hot to remove any excess base and KCl generated. A second equivalent of neutralized 2-chloromethylquinoline will be added to the filtrate, which will be returned to 80° C. for 12 h. The mixture will again be filtered hot to remove KCl and excess base from the neutralization reaction, and the volatile components of the filtrate will be removed under reduced pressure to yield the product.

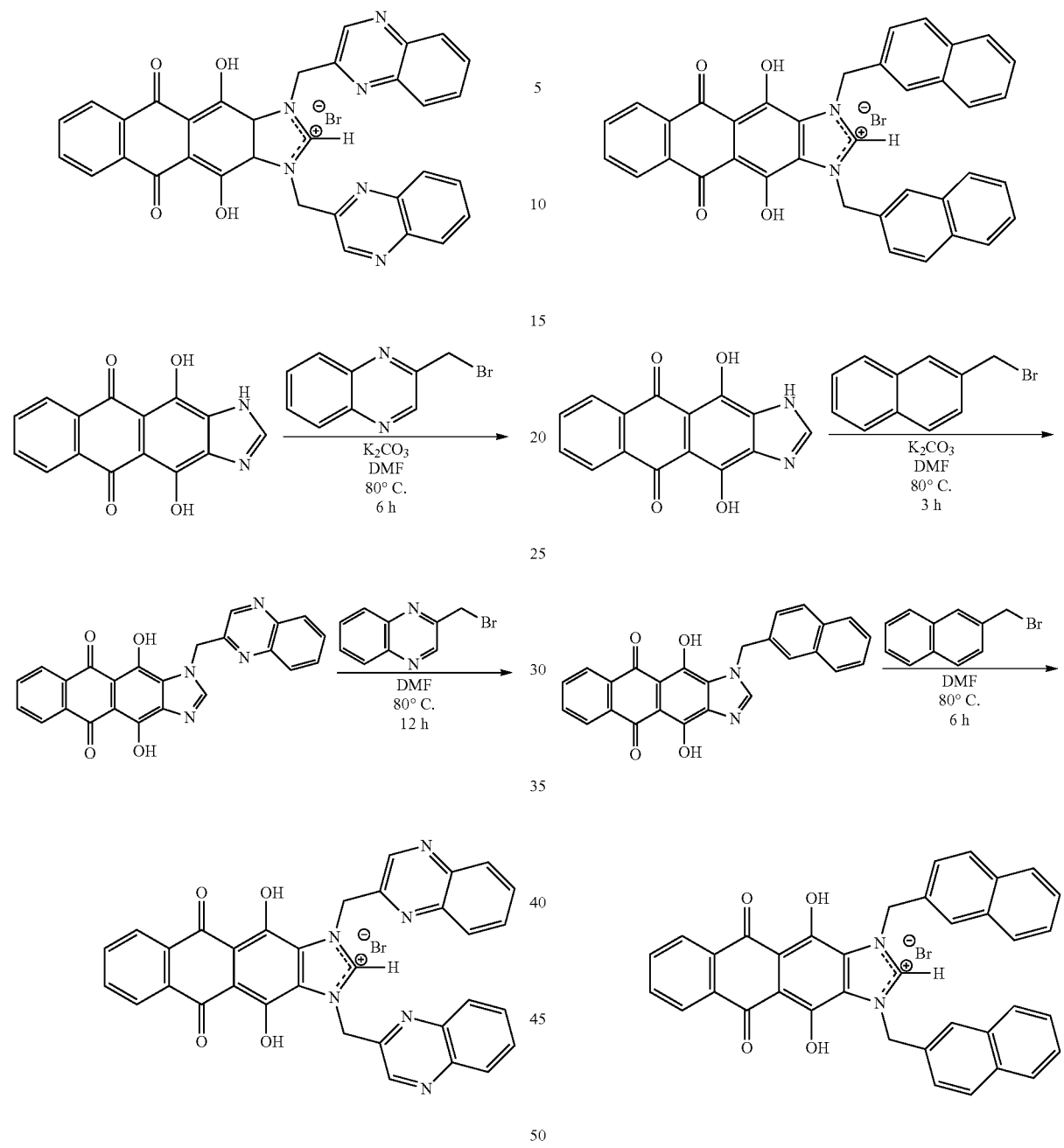

Synthesis of 4,11-dihydroxy-1,3-bis(quinoxalin-2-ylmethyl)anthra[2,3-d]-5,10-dione-imidazolium bromide Synthesis of 4,11-dihydroxy-1,3-bis(naphthalen-2-ylmethyl)anthra[2,3-d]-5,10-dione-imidazolium bromide 4,11-dihydroxy-anthra[2,3-d]imidazole-5,10-dione (2.80 g, 10.0 mmol) and potassium carbonate (2.07 g, 15.0 mmol) will be dissolved in a minimum volume of DMF and heated at 80° C. for 1 h. 2-(Bromomethyl)quinoxaline (2.23 g, 10.0 mmol) will be added and the mixture will be heated at 80° C. for 6 h. The mixture will be filtered hot to remove any excess base and KCl generated. A second equivalent of 2-(Bromomethyl)quinoxaline will be added to the filtrate, which will be returned to 80° C. for 12 h. The volatile components of the reaction mixture will be removed under reduced pressure to yield the product.

4,11-dihydroxy-anthra[2,3-d]imidazole-5,10-dione (2.80 g, 10.0 mmol) and potassium carbonate (2.07 g, 15.0 mmol) will be dissolved in a minimum volume of DMF and heated at 80° C. for 1 h. 2-(Bromomethyl)naphthalene (2.21 g, 10.0 mmol) will be added and the mixture will be heated at 80° C. for 3 h. The mixture will be filtered hot to remove any excess base and KBr generated. A second equivalent of 2-(Bromomethyl)naphthalene will be added to the filtrate, which will be returned to 80° C. for 6 h. The volatile components of the reaction mixture will be removed under reduced pressure to yield the product.

133  134

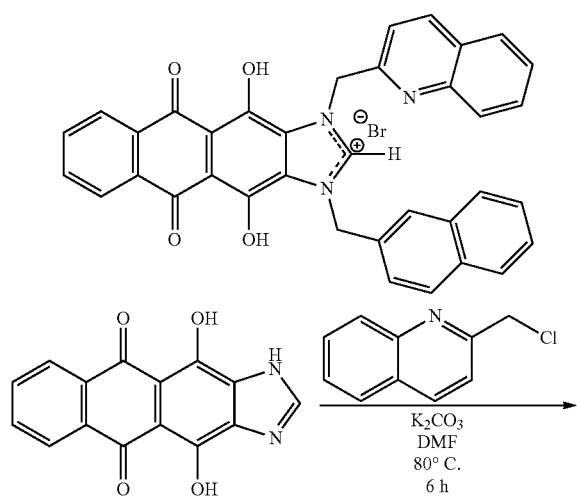
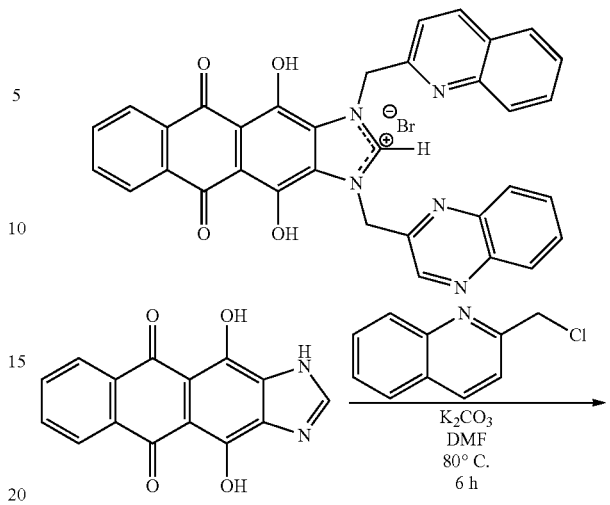

Synthesis of 4,11-dihydroxy-1-(quinolin-2-ylmethyl)-3-(naphthalen-2-ylmethyl)anthra[2,3-d]-5,10-dione-imidazolium bromide 4,11-dihydroxy-anthra[2,3-d]imidazole-5,10-dione (2.80 g, 10.0 mmol) and potassium carbonate (2.07 g, 15.0 mmol) will be dissolved in a minimum volume of DMF and heated at 80° C. for 1 h. A solution of 2-(chloromethyl)quinoline will be prepared by combining 2-(chloromethyl)quinolone hydrochloride (2.14 g, 10 mmol) and potassium carbonate (2.07 g, 15.0 mmol) in DMF and heating at 80° C. for 30 min, and this solution will be added to the reaction mixture. The mixture will be heated at 80° C. for 6 h. The mixture will be filtered hot to remove any excess base and KCl generated. 2-(Bromomethyl)naphthalene (2.21 g, 10.0 mmol) will be added to the filtrate, which will be returned to 80° C. for 12 h. The volatile components will be removed under reduced pressure to yield the product.

Synthesis of 4,11-dihydroxy-1-(quinolin-2-ylmethyl)-3-(quinoxalin-2-ylmethyl)anthra[2,3-d]-5,10-dione-imidazolium bromide 4,11-dihydroxy-anthra[2,3-d]imidazole-5,10-dione (2.80 g, 10.0 mmol) and potassium carbonate (2.07 g, 15.0 mmol) will be dissolved in a minimum volume of DMF and heated at 80° C. for 1 h. A solution of 2-(chloromethyl)quinoline will be prepared by combining 2-(chloromethyl)quinolone hydrochloride (2.14 g, 10 mmol) and potassium carbonate (2.07 g, 15.0 mmol) in DMF and heating at 80° C. for 30 min, and this solution will be added to the reaction mixture. The mixture will be heated at 80° C. for 6 h. The mixture will be filtered hot to remove any excess base and KCl generated. 2-(Bromomethyl)quinoxaline (2.23 g, 10.0 mmol) will be added to the filtrate, which will be returned to 80° C. for 12 h. The volatile components will be removed under reduced pressure to yield the product.

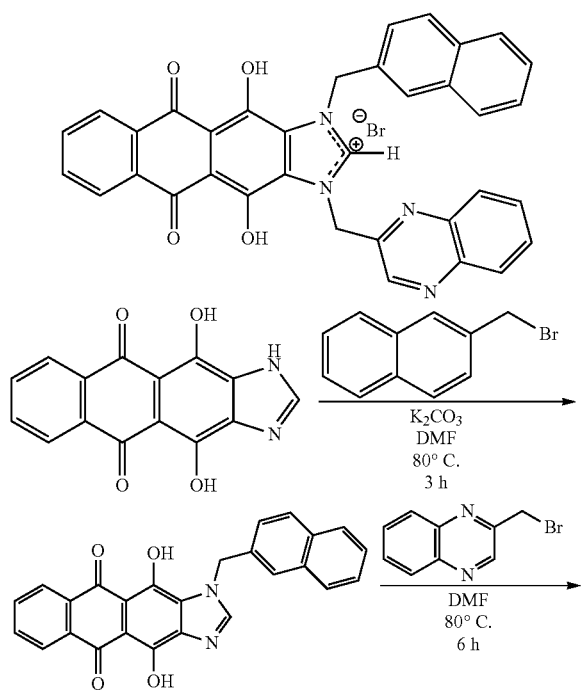

Synthesis of 4,11-dihydroxy-1-(naphthalen-2-ylmethyl)-3-(quinoxalin-2-ylmethyl)anthra[2,3-d]-5,10-dione-imidazolium bromide 4,11-dihydroxy-anthra[2,3-d]imidazole-5,10-dione (2.80 g, 10.0 mmol) and potassium carbonate (2.07 g, 15.0 mmol) will be dissolved in a minimum volume of DMF and heated at 80° C. for 1 h. 2-(Bromomethyl)naphthalene (2.21 g, 10.0 mmol) will be added and the mixture will be heated at 80° C. for 3 h. The mixture will be filtered hot to remove any excess base and KBr generated. 2-(Bromomethyl)quinoxaline will be added to the filtrate, which will be returned to 80° C. for 6 h. The volatile components of the reaction mixture will be removed under reduced pressure to yield the product.

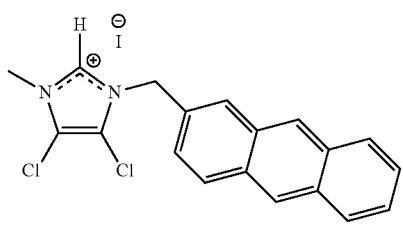

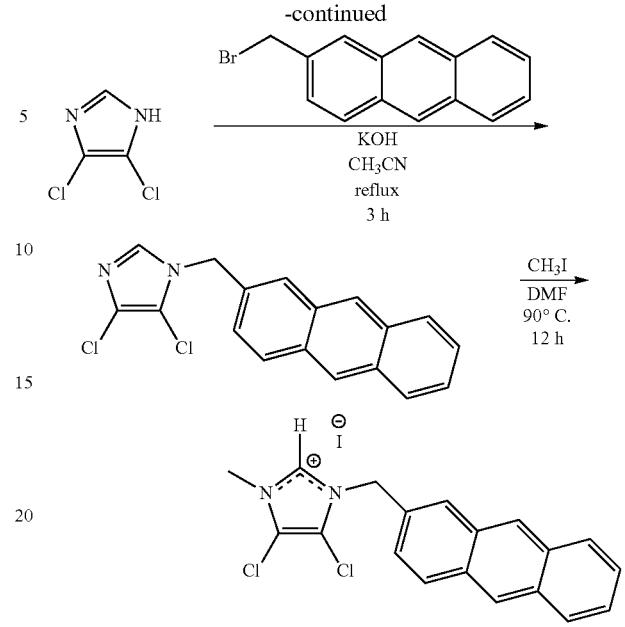

Synthesis of 1-(anthracen-2-ylmethyl)-3-methyl-4,5-dichloroimidazolium iodide 4,5-Dichloroimidazole (0.18 g, 1.33 mmol) and potassium hydroxide (0.08 g, 1.46 mmol) will be dissolved in a minimum volume of acetonitrile and stirred at reflux for 30 min. 2-(Bromomethyl)anthracene (2.71 g, 10.0 mmol) will be added and the mixture will be returned to reflux for 3 h. The mixture will be filtered hot to remove the KBr generated. The volatile components will be removed under reduced pressure to yield the mono-substituted imidazole. A minimum amount of DMF will be added to the remaining residue to dissolve it, and iodomethane (6.2 mL, 100 mmol) will be added. The reaction mixture will be refluxed for 12 hours. The volatile components will be removed under reduced pressure to yield the product.

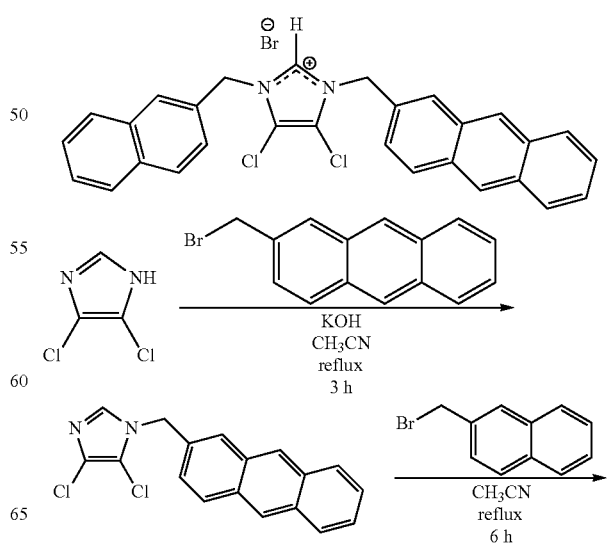

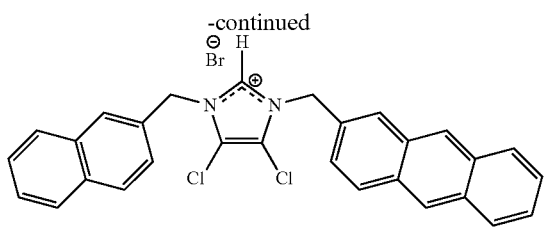

Synthesis of 1-(anthracen-2-ylmethyl)-3-(napthalen-2-ylmethyl)-4,5-dichloroimidazolium bromide 4,5-Dichloroimidazole (0.18 g, 1.33 mmol) and potassium hydroxide (0.08 g, 1.46 mmol) will be dissolved in a minimum volume of acetonitrile and stirred at reflux for 30 min. 2-(Bromomethyl)anthracene (2.71 g, 10.0 mmol) will be added and the mixture will be returned to reflux for 3 h. The mixture will be filtered hot to remove the KBr generated. 2-(Bromomethyl)naphthalene (2.21 g, 10.0 mmol) will be added to the filtrate and the mixture will be returned to reflux for 6 h. The volatile components will be removed under reduced pressure to yield the product.

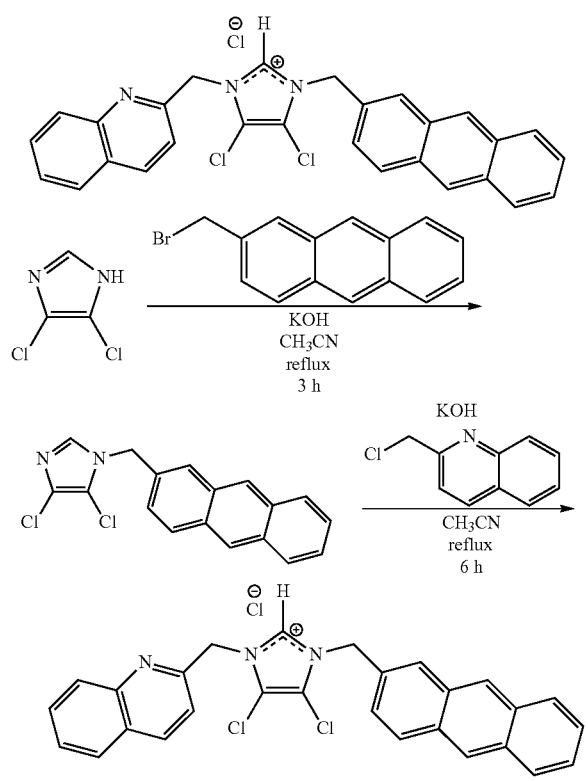

Synthesis of 1-(anthracen-2-ylmethyl)-3-(quinolin-2-ylmethyl)-4,5-dichloroimidazolium chloride 4,5-Dichloroimidazole (0.18 g, 1.33 mmol) and potassium hydroxide (0.08 g, 1.46 mmol) will be dissolved in a minimum volume of acetonitrile and stirred at reflux for 30 min. 2-(Bromomethyl)anthracene (2.71 g, 10.0 mmol) will be added and the mixture will be returned to reflux for 3 h. The mixture will be filtered hot to remove the KBr generated. A solution of 2-(chloromethyl)quinoline will be prepared by combining 2-(chloromethyl)quinolone hydrochloride (2.14 g, 10 mmol) and potassium hydroxide (0.56 g, 10.0 mmol) in acetonitrile and refluxing the mixture for 30 min, and this solution will be added to the filtrate. The combined mixture will be returned to reflux for 6 h. The volatile components will be removed under reduced pressure, and the resulting solid will be washed with water to remove the KCl generated in the neutralization of the quinoline. The remaining solid will be dried and will be the product.

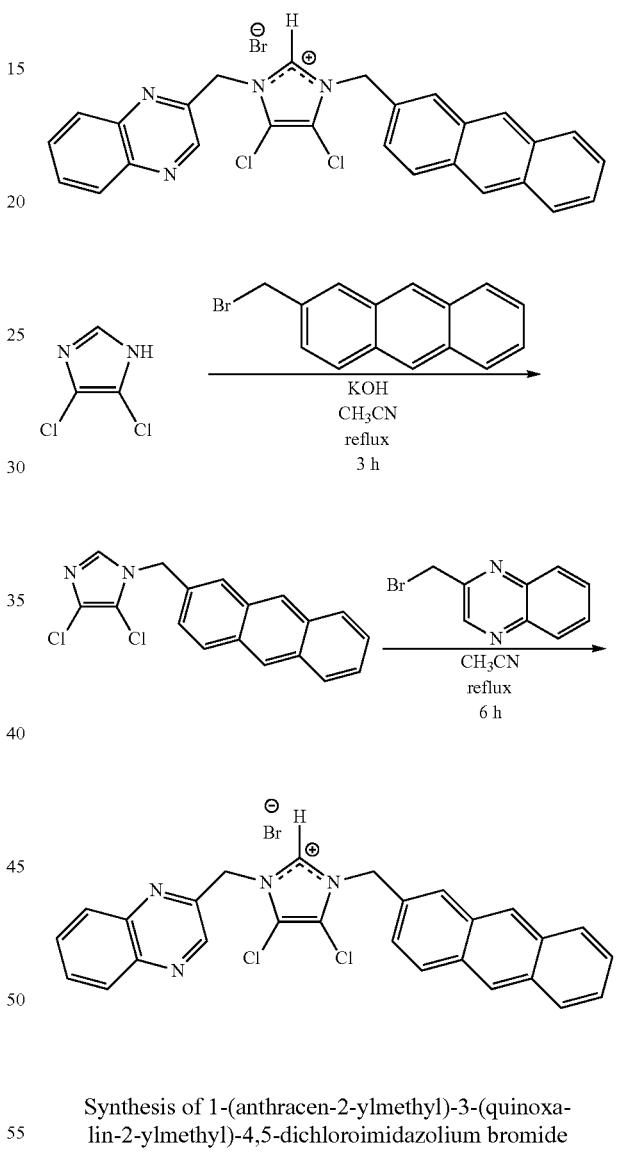

Synthesis of 1-(anthracen-2-ylmethyl)-3-(quinoxalin-2-ylmethyl)-4,5-dichloroimidazolium bromide 4,5-Dichloroimidazole (0.18 g, 1.33 mmol) and potassium hydroxide (0.08 g, 1.46 mmol) will be dissolved in a minimum volume of acetonitrile and stirred at reflux for 30 min. 2-(Bromomethyl)anthracene (2.71 g, 10.0 mmol) will be added and the mixture will be returned to reflux for 3 h. The mixture will be filtered hot to remove the KBr generated. 2-(Bromomethyl)quinoxaline (2.23 g, 10.0 mmol) will be added to the filtrate and the mixture will be returned to reflux for 6 h. The volatile components will be removed under reduced pressure to yield the product.

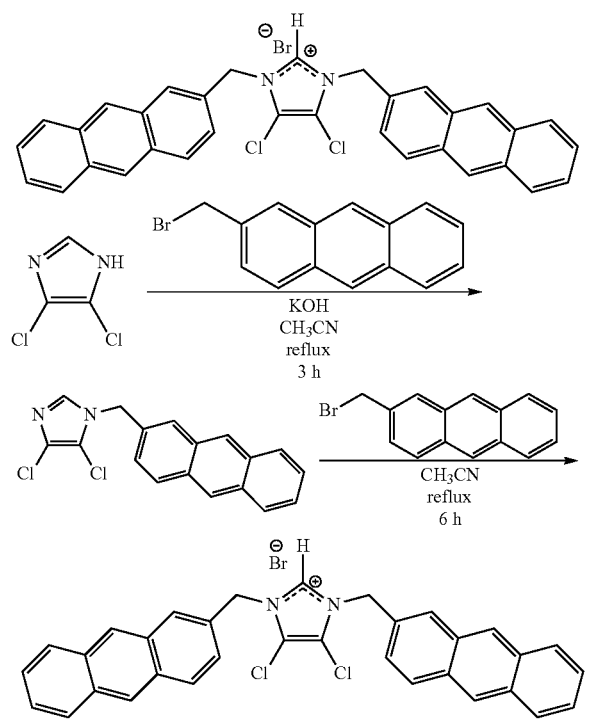

Synthesis of 1,3-bis(anthracen-2-ylmethyl)-4,5-dichloroimidazolium bromide 4,5-Dichloroimidazole (0.18 g, 1.33 mmol) and potassium hydroxide (0.08 g, 1.46 mmol) will be dissolved in a minimum volume of acetonitrile and stirred at reflux for 30 min. 2-(Bromomethyl)anthracene (2.71 g, 10.0 mmol) will be added and the mixture will be returned to reflux for 3 h. The mixture will be filtered hot to remove the KBr generated. A second equivalent of 2-(bromomethyl)anthracene will be added to the filtrate and the mixture will be returned to reflux for 6 h. The volatile components will be removed under reduced pressure to yield the product.

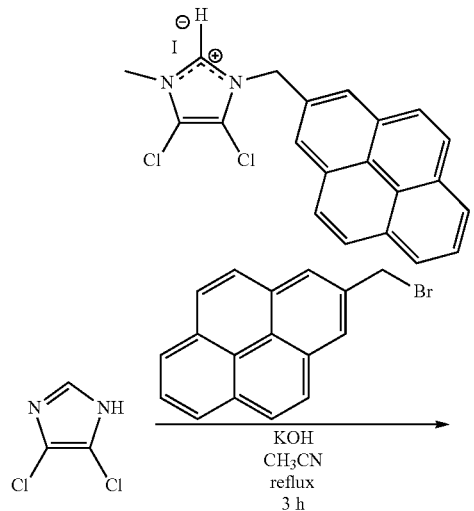

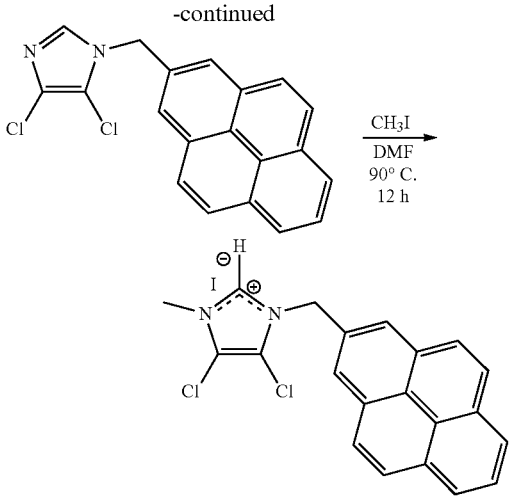

Synthesis of 3-methyl-1-(pyren-2-ylmethyl)-4,5-dichloroimidazolium iodide 4,5-Dichloroimidazole (0.18 g, 1.33 mmol) and potassium hydroxide (0.08 g, 1.46 mmol) will be dissolved in a minimum volume of acetonitrile and stirred at reflux for 30 min. 2-(Bromomethyl)pyrene (2.95 g, 10.0 mmol) will be added and the mixture will be returned to reflux for 3 h. The mixture will be filtered hot to remove the KBr generated. The volatile components will be removed under reduced pressure to yield the mono-substituted imidazole. A minimum amount of DMF will be added to the remaining residue to dissolve it, and iodomethane (6.2 mL, 100 mmol) will be added. The reaction mixture will be refluxed for 12 hours. The volatile components will be removed under reduced pressure to yield the product.

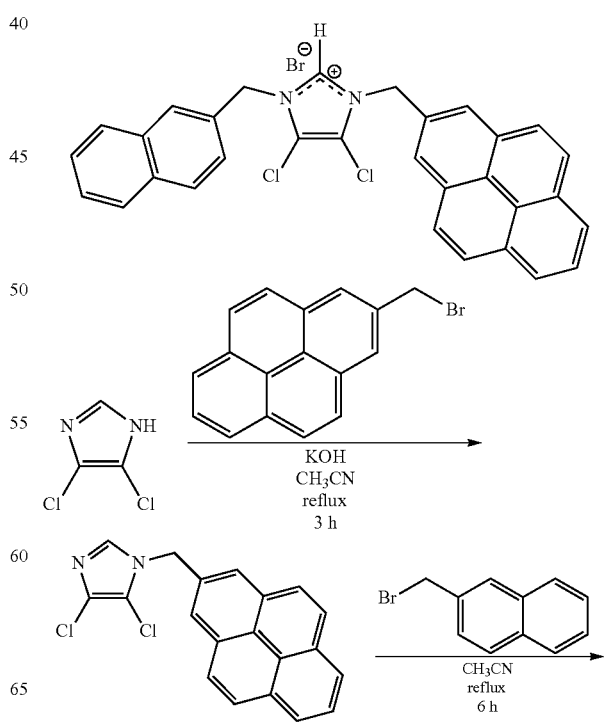

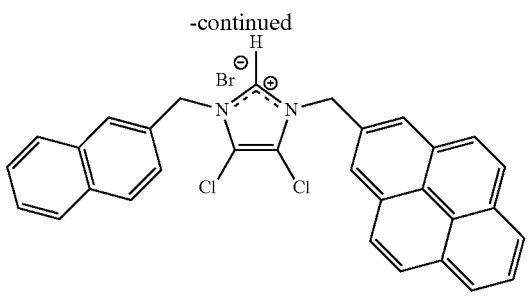

Synthesis of 1-(napthalen-2-ylmethyl)-3-(pyren-2-ylmethyl)-4,5-dichloroimidazolium bromide 4,5-Dichloroimidazole (0.18 g, 1.33 mmol) and potassium hydroxide (0.08 g, 1.46 mmol) will be dissolved in a minimum volume of acetonitrile and stirred at reflux for 30 min. 2-(Bromomethyl)pyrene (2.95 g, 10.0 mmol) will be added and the mixture will be returned to reflux for 3 h. The mixture will be filtered hot to remove the KBr generated. 2-(Bromomethyl)naphthalene (2.21 g, 10.0 mmol) will be added to the filtrate and the mixture will be returned to reflux for 6 h. The volatile components will be removed under reduced pressure to yield the product.

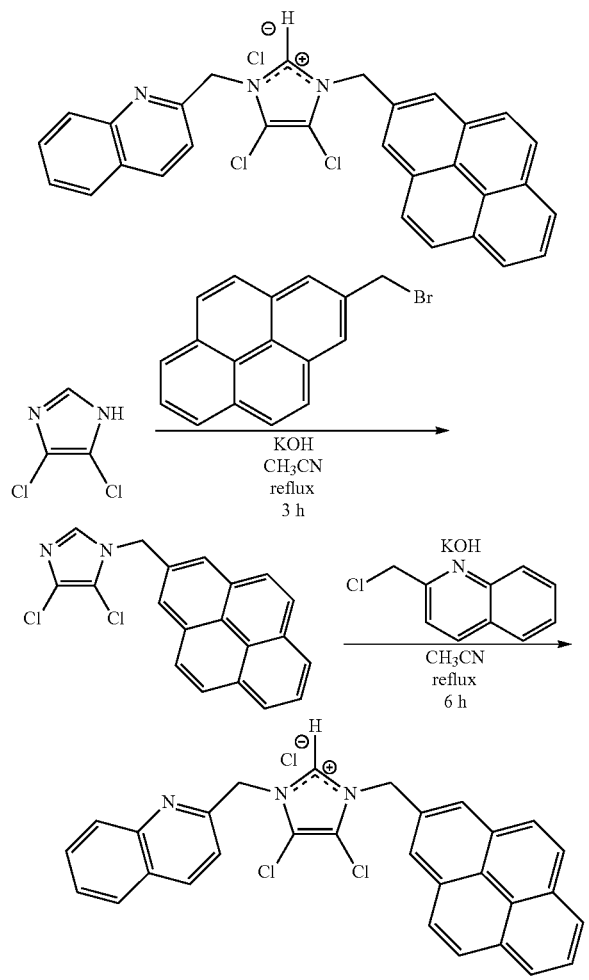

Synthesis of 1-(pyren-2-ylmethyl)-3-(quinolin-2-ylmethyl)-4,5-dichloroimidazolium chloride 4,5-Dichloroimidazole (0.18 g, 1.33 mmol) and potassium hydroxide (0.08 g, 1.46 mmol) will be dissolved in a minimum volume of acetonitrile and stirred at reflux for 30 min. 2-(Bromomethyl)pyrene (2.95 g, 10.0 mmol) will be added and the mixture will be returned to reflux for 3 h. The mixture will be filtered hot to remove the KBr generated. A solution of 2-(chloromethyl)quinoline will be prepared by combining 2-(chloromethyl)quinolone hydrochloride (2.14 g, 10 mmol) and potassium hydroxide (0.56 g, 10.0 mmol) in acetonitrile and refluxing the mixture for 30 min, and this solution will be added to the filtrate. The combined mixture will be returned to reflux for 6 h. The volatile components will be removed under reduced pressure, and the resulting solid will be washed with water to remove the KCl generated in the neutralization of the quinoline. The remaining solid will be dried and will be the product.

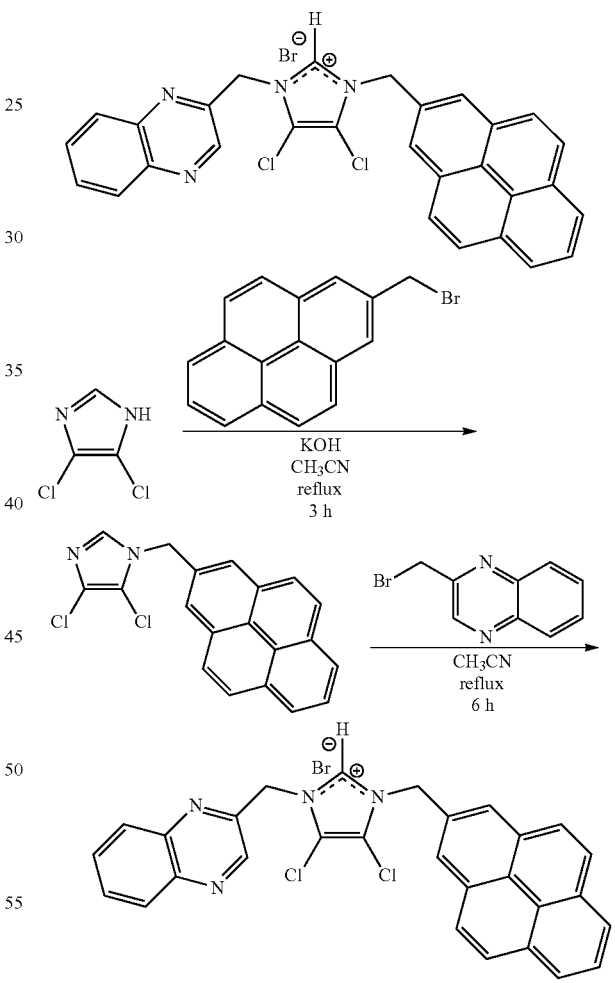

Synthesis of 1-(pyren-2-ylmethyl)-3-(quinoxalin-2-ylmethyl)-4,5-dichloroimidazolium bromide 4,5-Dichloroimidazole (0.18 g, 1.33 mmol) and potassium hydroxide (0.08 g, 1.46 mmol) will be dissolved in a minimum volume of acetonitrile and stirred at reflux for 30 min. 2-(Bromomethyl)pyrene (2.95 g, 10.0 mmol) will be added and the mixture will be returned to reflux for 3 h. The mixture will be filtered hot to remove the KBr generated. 2-(Bromomethyl)quinoxaline (2.23 g, 10.0 mmol) will be added to the filtrate and the mixture will be returned to reflux for 6 h. The volatile components will be removed under reduced pressure to yield the product

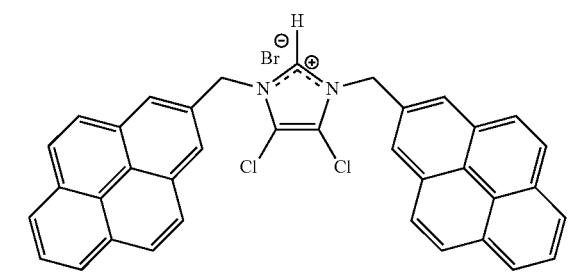

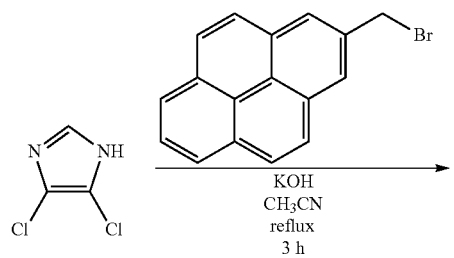

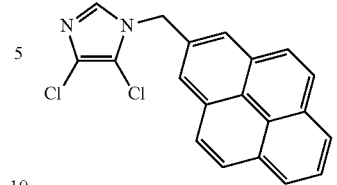

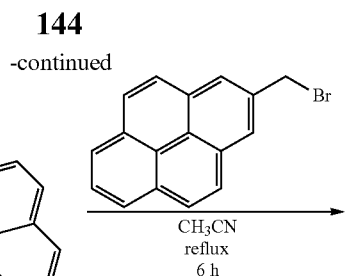

Synthesis of 1,3-bis(pyren-2-ylmethyl)-4,5-dichloroimidazolium bromide 4,5-Dichloroimidazole (0.18 g, 1.33 mmol) and potassium hydroxide (0.08 g, 1.46 mmol) will be dissolved in a minimum volume of acetonitrile and stirred at reflux for 30 min. 2-(Bromomethyl)pyrene (2.95 g, 10.0 mmol) will be added and the mixture will be returned to reflux for 3 h. The mixture will be filtered hot to remove the KBr generated. A second equivalent of 2-(bromomethyl)pyrene will be added to the filtrate and the mixture will be returned to reflux for 6 h. The volatile components will be removed under reduced pressure to yield the product.

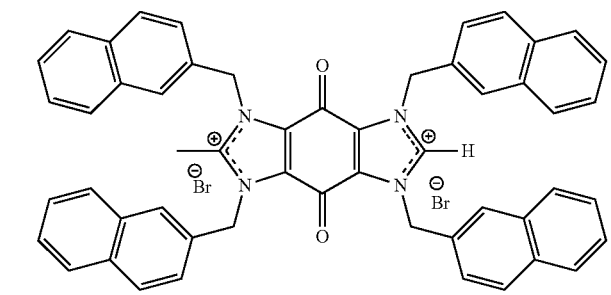

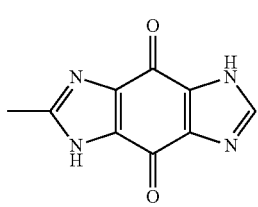

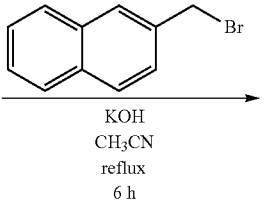

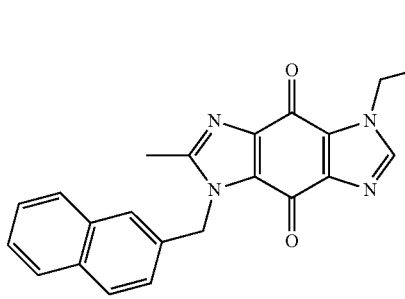

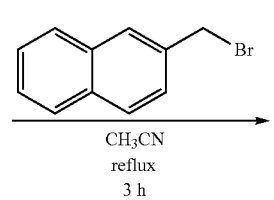

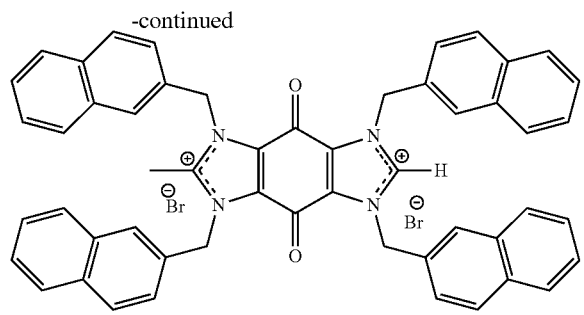

Synthesis of 2-methyl-1,3,5,7-tetrakis(naphthalen-2-ylmethyl)-4,8-dione-benzo[1,2-d:4,5-d']diimidazolium dibromide 2-Methylbenzo(1,2-d:4,5-d')diimidazole-4,8-dione (2.02 g, 10 mmol) will be dissolved in a minimum volume of acetonitrile. Potassium hydroxide (0.62 g, 11.0 mmol) will be added and the mixture will be refluxed until the base is consumed. 2-(Bromomethyl)naphthalene (2.21 g, 10 mmol) will be added and the mixture will be refluxed for 3 h. The mixture will be filtered hot to remove the KBr generated, and a second equivalent of 2-(Bromomethyl)naphthalene will be added to the filtrate. The mixture will be returned to reflux for 3 h. The volatile components of the reaction mixture will be removed under reduced pressure, yielding the product.

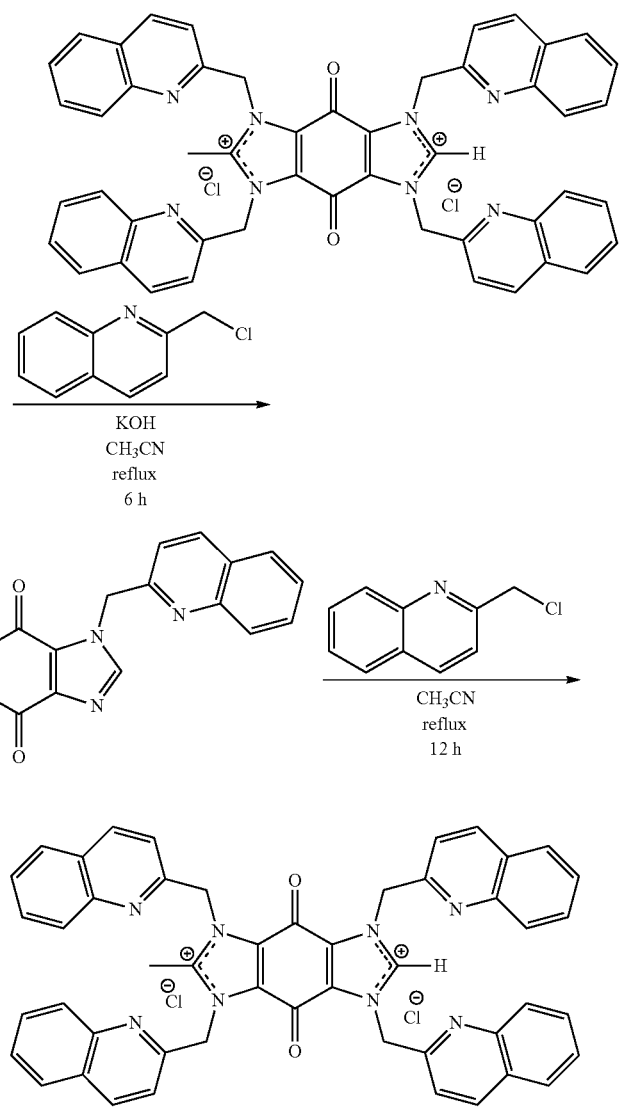

147

Synthesis of 2-methyl-1,3,5,7-tetrakis(quinolin-2-ylmethyl)-4,8-dione-benzo[1,2-d:4,5-d']diimidazolium dichloride 2-Methylbenzo(1,2-d:4,5-d']diimidazole-4,8-dione (2.02 g, 10 mmol) will be dissolved in a minimum volume of acetonitrile. Potassium hydroxide (0.62 g, 11.0 mmol) will be added and the mixture will be refluxed until the base is consumed. A solution of 2-(chloromethyl)quinoline will be prepared by combining 2-(chloromethyl)quinolone hydrochloride (2.14 g, 10 mmol) and potassium hydroxide (0.56 g, 10.0 mmol) in acetonitrile and refluxing the mixture for 30 min, and this solution will be added to the reaction mixture. The combined reaction mixture will be refluxed for 6 h. The mixture will be filtered hot to remove any KCl generated. A second equivalent of neutralized 2-chloromethylquinoline will be added to the filtrate, which will be returned to reflux for 12 h. The mixture will again be filtered hot to remove KCl from the neutralization reaction, and the volatile components of the filtrate will be removed under reduced pressure to yield the product.

148

Synthesis of 2-methyl-1,3,5,7-tetrakis(quinoxalin-2-ylmethyl)-4,8-dione-benzo[1,2-d:4,5-d']diimidazolium dibromide 2-Methylbenzo(1,2-d:4,5-d']diimidazole-4,8-dione (2.02 g, 10 mmol) will be dissolved in a minimum volume of acetonitrile. Potassium hydroxide (0.62 g, 11.0 mmol) will be added and the mixture will be refluxed until the base is consumed. 2-(Bromomethyl)quinoxaline (2.23 g, 10 mmol) will be added and the mixture will be refluxed for 6 h. The mixture will be filtered hot to remove the KBr generated, and a second equivalent of 2-(Bromomethyl)quinoxaline will be added to the filtrate. The mixture will be returned to reflux for 12 h. The volatile components of the reaction mixture will be removed under reduced pressure to yield the product.

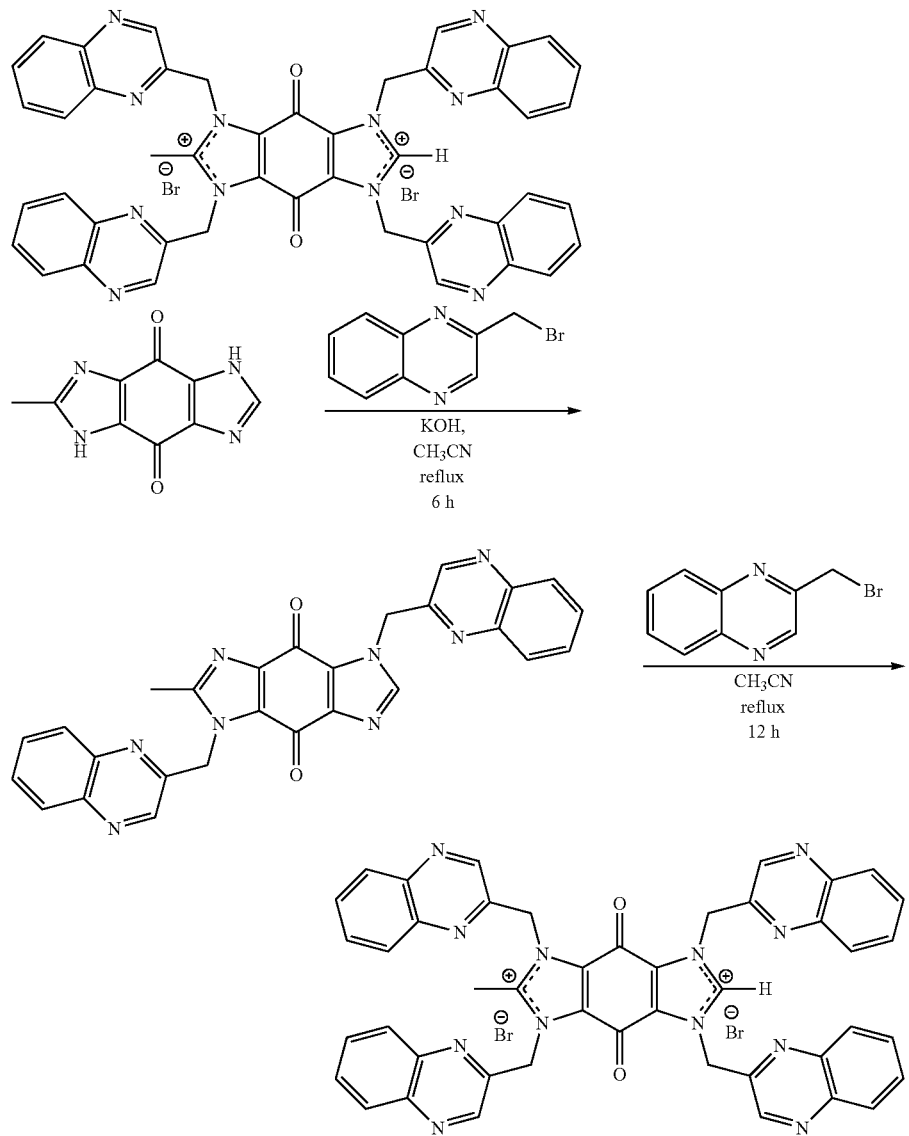

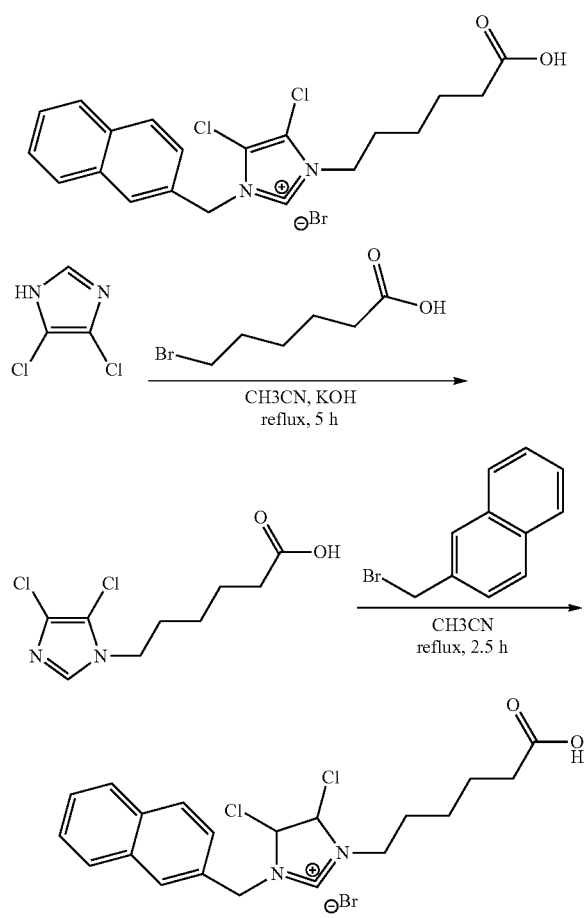

Synthesis of 1-(5-carboxypentyl)-4,5-dichloro-3-(naphthalen-2-ylmethyl)-1 H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 6-bromohexanoic acid (1.44 g, 7.36 mmol) was added to the solution and refluxed for 5 h. Solution was filtered to remove the KBr precipitate and placed back onto reflux. An equivalent of 2-(bromomethyl)naphthalene (1.63 g, 7.36 mmol) was added to solution and refluxed for 2.5 h. The solution was neutralized with 6M HBr, volatiles removed in vacuo, and the resulting product will be collected and analyzed.

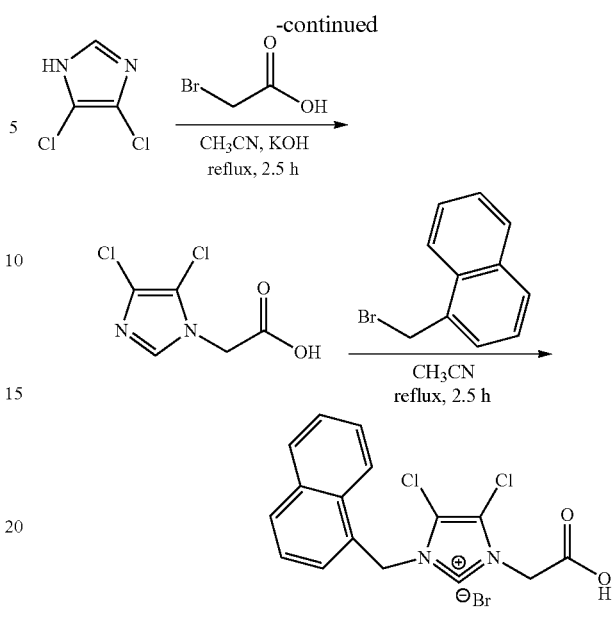

Synthesis of 1-(carboxymethyl)-4,5-dichloro-3-(naphthalen-1-ylmethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 2-bromoacetic acid (2.15 g, 15.46 mmol) was added to the solution and refluxed for 2.5 h. Solution was filtered to remove the KBr precipitate and placed back onto reflux. An equivalent of 1-(bromomethyl)naphthalene (1.63 g, 7.36 mmol) was added to solution and refluxed for 2.5 h. The solution was neutralized with 6M HBr, volatiles removed in vacuo, and the resulting product will be collected and analyzed.

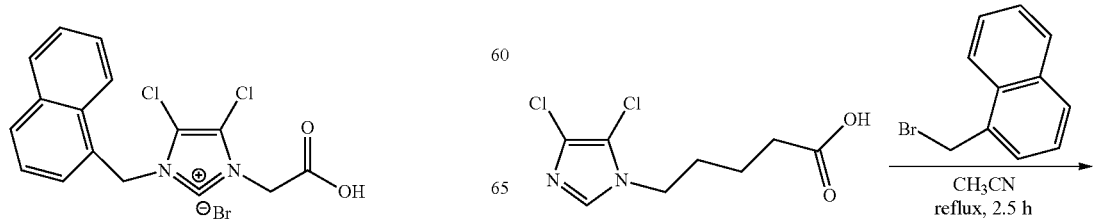

-continued

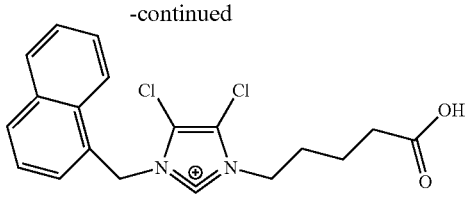

Synthesis of 1-(4-carboxybutyl)-4,5-dichloro-3-(naphthalen-1-ylmethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 5-bromopentanoic acid (1.33 g, 7.36 mmol) was added to the solution and refluxed for 5 h. Solution was filtered to remove the KBr precipitate and placed back onto reflux. An equivalent of 1-(bromomethyl)naphthalene (1.63 g, 7.36 mmol) was added to solution and refluxed for 2.5 h. The solution was neutralized with 6M HBr, volatiles removed in vacuo, and the resulting product will be collected and analyzed.

Synthesis of 1-(5-carboxypentyl)-4,5-dichloro-3-(naphthalen-1-ylmethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 6-bromohexanoic acid (1.44 g, 7.36 mmol) was added to the solution and refluxed for 5 h. Solution was filtered to remove the KBr precipitate and placed back onto reflux. An equivalent of 1-(bromomethyl)naphthalene (1.63 g, 7.36 mmol) was added to solution and refluxed for 2.5 h. The solution was neutralized with 6M HBr, volatiles removed in vacuo, and the resulting product will be collected and analyzed.

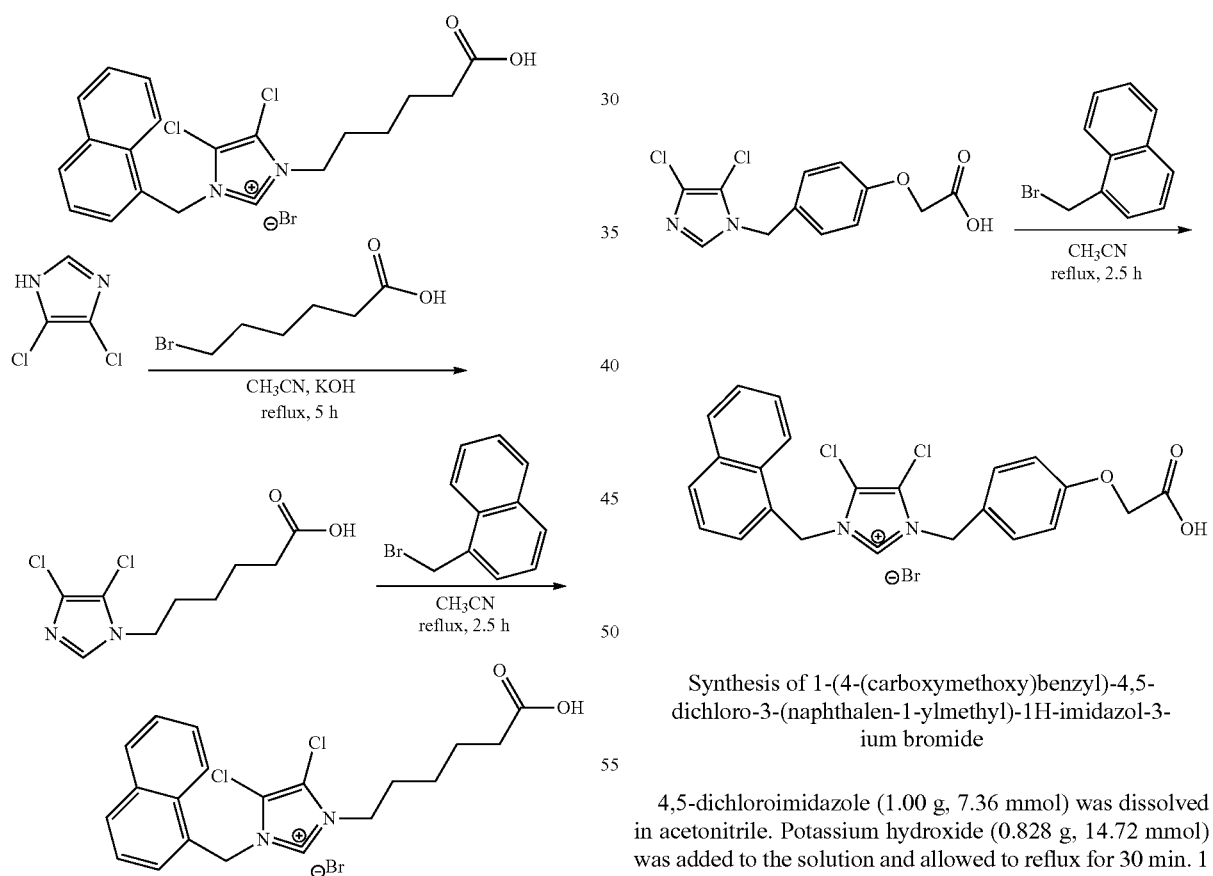

Synthesis of 1-(4-(carboxymethoxy)benzyl)-4,5-dichloro-3-(naphthalen-1-ylmethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 2-(4-(bromomethyl)phenoxy)acetic acid (1.80 g, 7.36 mmol) was added to the solution and refluxed for 5 h. Solution was filtered to remove the KBr precipitate and placed back onto reflux. An equivalent of 1-(bromomethyl)naphthalene (1.63 g, 7.36 mmol) was added to solution and refluxed for 2.5 h. The solution was neutralized with 6M HBr, volatiles removed in vacuo, and the resulting product will be collected and analyzed.

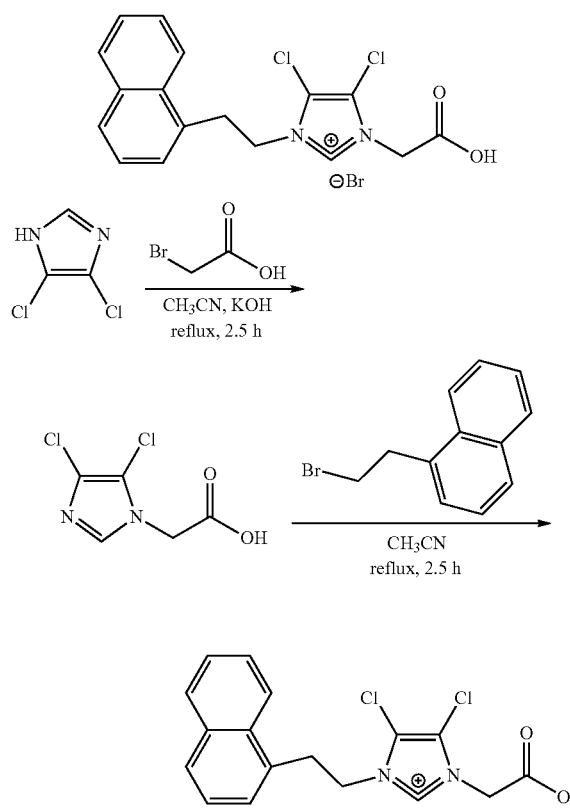

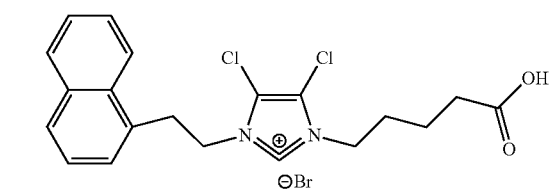

Synthesis of 1-(carboxymethyl)-4,5-dichloro-3-(2-(naphthalen-1-yl)ethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 2-bromoacetic acid (2.15 g, 15.46 mmol) was added to the solution and refluxed for 2.5 h. Solution was filtered to remove the KBr precipitate and placed back onto reflux. An equivalent of 1-(2-bromoethyl)naphthalene (1.73 g, 7.36 mmol) was added to solution and refluxed for 2.5 h. The solution was neutralized with 6M HBr, volatiles removed in vacuo, and the resulting product will be collected and analyzed.

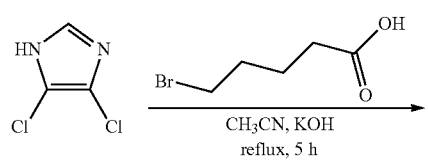

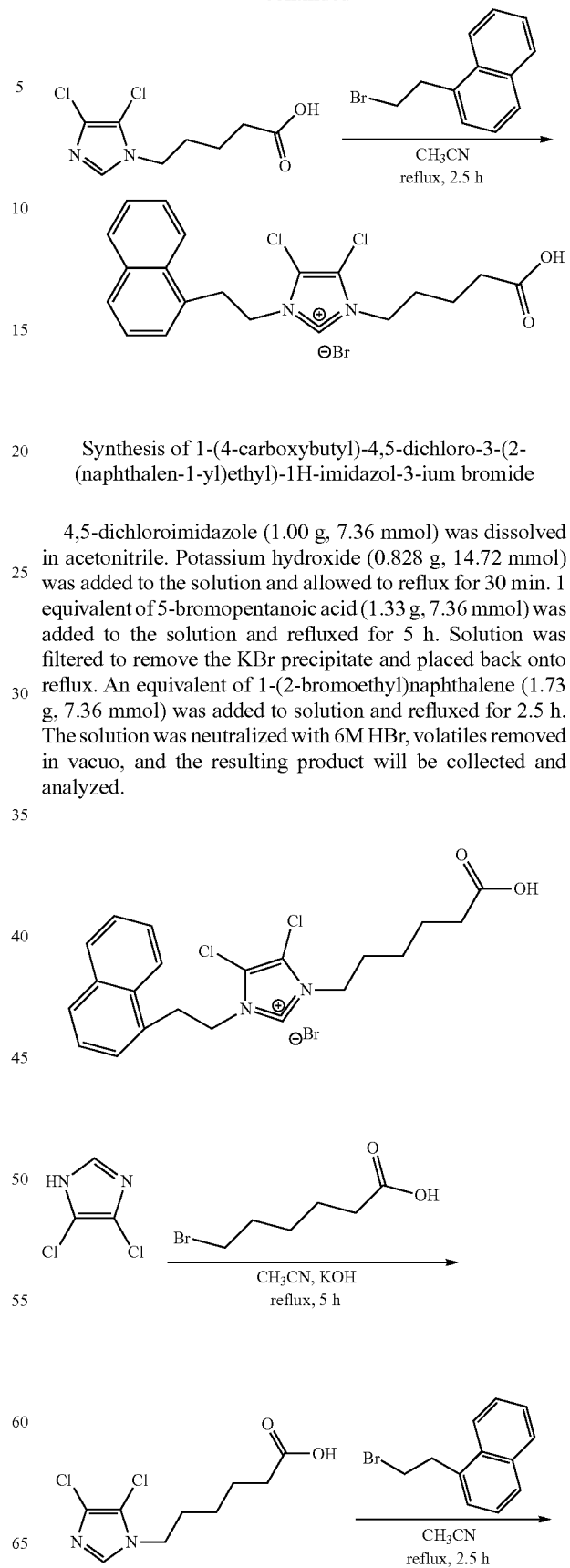

Synthesis of 1-(4-carboxybutyl)-4,5-dichloro-3-(2-(naphthalen-1-yl)ethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 5-bromopentanoic acid (1.33 g, 7.36 mmol) was added to the solution and refluxed for 5 h. Solution was filtered to remove the KBr precipitate and placed back onto reflux. An equivalent of 1-(2-bromoethyl)naphthalene (1.73 g, 7.36 mmol) was added to solution and refluxed for 2.5 h. The solution was neutralized with 6M HBr, volatiles removed in vacuo, and the resulting product will be collected and analyzed.

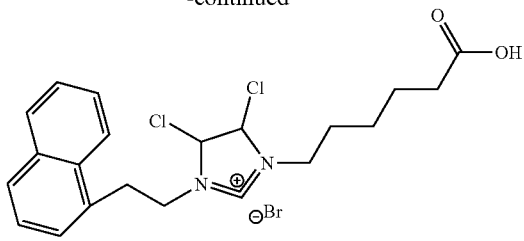

Synthesis of 1-(5-carboxypentyl)-4,5-dichloro-3-(2-(naphthalen-1-yl)ethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 6-bromohexanoic acid (1.44 g, 7.36 mmol) was added to the solution and refluxed for 5 h. Solution was filtered to remove the KBr precipitate and placed back onto reflux. An equivalent of 1-(2-bromoethyl)naphthalene (1.73 g, 7.36 mmol) was added to solution and refluxed for 2.5 h. The solution was neutralized with 6M HBr, volatiles removed in vacuo, and the resulting product will be collected and analyzed.

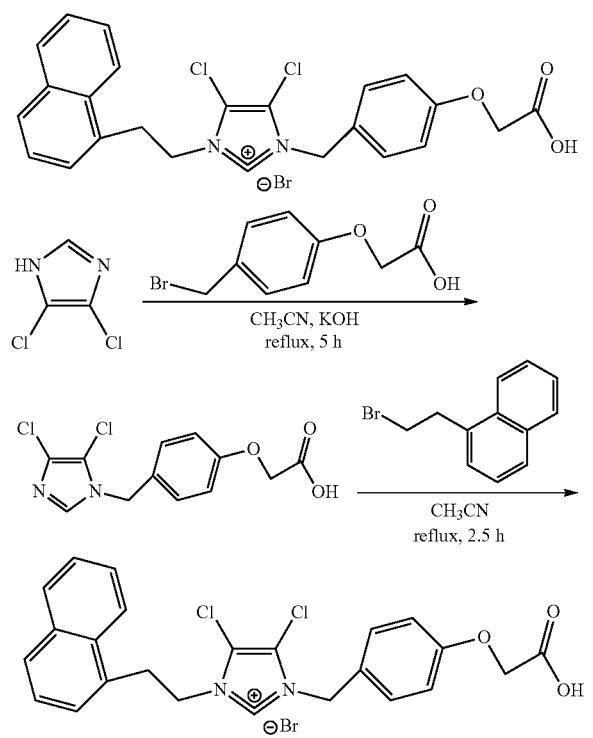

Synthesis of 1-(4-(carboxymethoxy)benzyl)-4,5-dichloro-3-(2-(naphthalen-1-yl)ethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 2-(4-(bromomethyl)phenoxy)acetic acid (1.80 g, 7.36 mmol) was added to the solution and refluxed for 5 h. Solution was filtered to remove the KBr precipitate and placed back onto reflux. An equivalent of 1-(2-bromoethyl)naphthalene (1.73 g, 7.36 mmol) was added to solution and refluxed for 2.5 h. The solution was neutralized with 6M HBr, volatiles removed in vacuo, and the resulting product will be collected and analyzed.

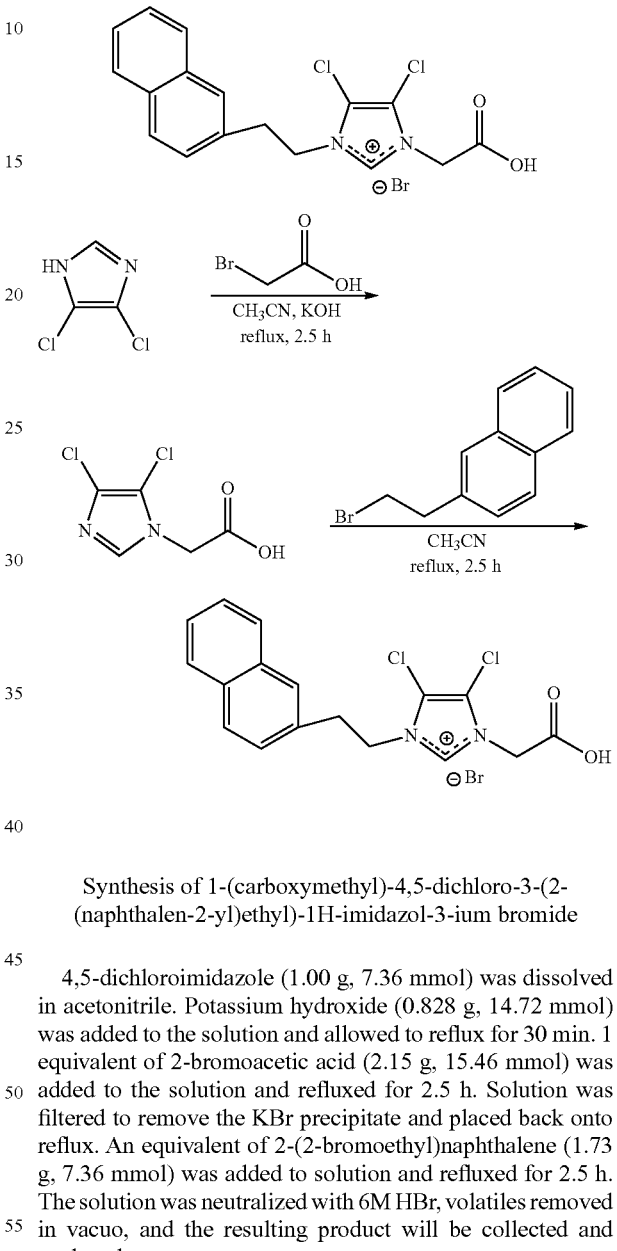

Synthesis of 1-(carboxymethyl)-4,5-dichloro-3-(2-(naphthalen-2-yl)ethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 2-bromoacetic acid (2.15 g, 15.46 mmol) was added to the solution and refluxed for 2.5 h. Solution was filtered to remove the KBr precipitate and placed back onto reflux. An equivalent of 2-(2-bromoethyl)naphthalene (1.73 g, 7.36 mmol) was added to solution and refluxed for 2.5 h. The solution was neutralized with 6M HBr, volatiles removed in vacuo, and the resulting product will be collected and analyzed.

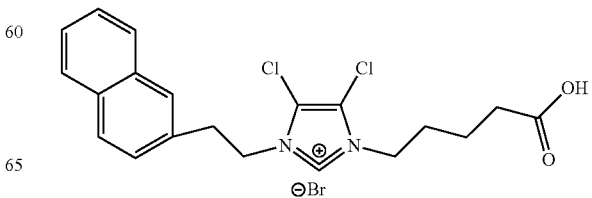

-continued

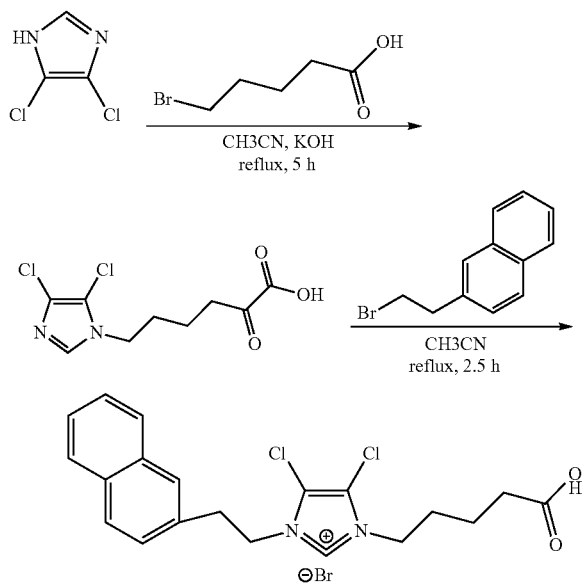

Synthesis of 1-(4-carboxybutyl)-4,5-dichloro-3-(2-(naphthalen-2-yl)ethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 5-bromopentanoic acid (1.33 g, 7.36 mmol) was added to the solution and refluxed for 5 h. Solution was filtered to remove the KBr precipitate and placed back onto reflux. An equivalent of 2-(2-bromoethyl)naphthalene (1.73 g, 7.36 mmol) was added to solution and refluxed for 2.5 h. The solution was neutralized with 6M HBr, volatiles removed in vacuo, and the resulting product will be collected and analyzed.

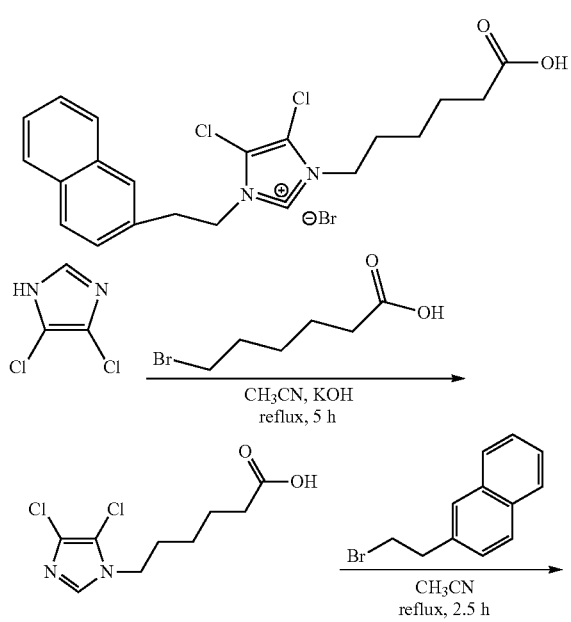

-continued

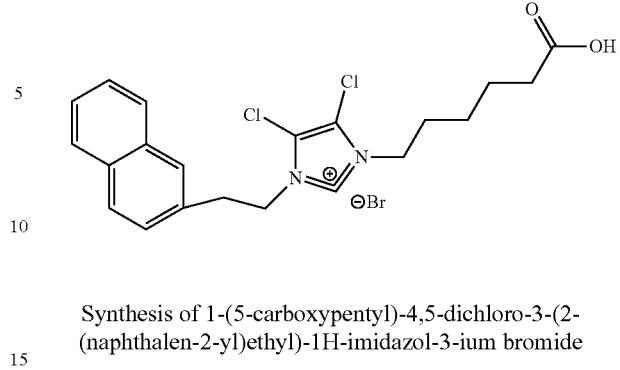

Synthesis of 1-(5-carboxypentyl)-4,5-dichloro-3-(2-(naphthalen-2-yl)ethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 5-bromohexanoic acid (1.44 g, 7.36 mmol) was added to the solution and refluxed for 5 h. Solution was filtered to remove the KBr precipitate and placed back onto reflux. An equivalent of 2-(2-bromoethyl)naphthalene (1.73 g, 7.36 mmol) was added to solution and refluxed for 2.5 h. The solution was neutralized with 6M HBr, volatiles removed in vacuo, and the resulting product will be collected and analyzed.

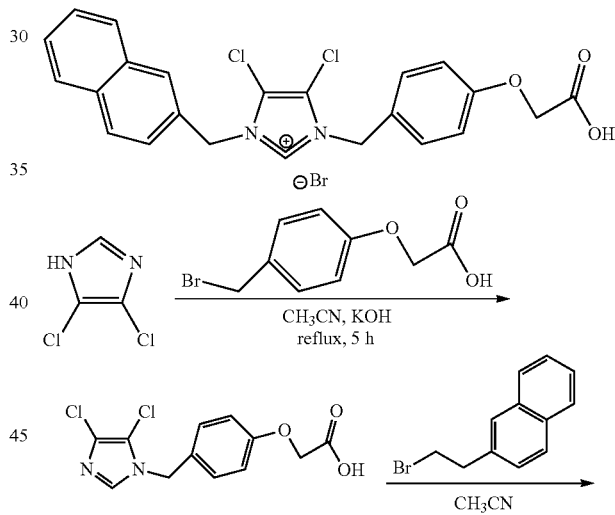

Synthesis of 1-(4-(carboxymethoxy)benzyl)-4,5-dichloro-3-(2-(naphthalen-2-yl)ethyl)-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 1 equivalent of 2-(4-(bromomethyl)phenoxy)acetic acid (1.80 g, 7.36 mmol) was added to the solution and refluxed for 5 h.

Solution was filtered to remove the KBr precipitate and placed back onto reflux. An equivalent of 2-(2-bromoethyl-naphthalene (1.73 g, 7.36 mmol) was added to solution and refluxed for 2.5 h. The solution was neutralized with 6M HBr, volatiles removed in vacuo, and the resulting product will be collected and analyzed.

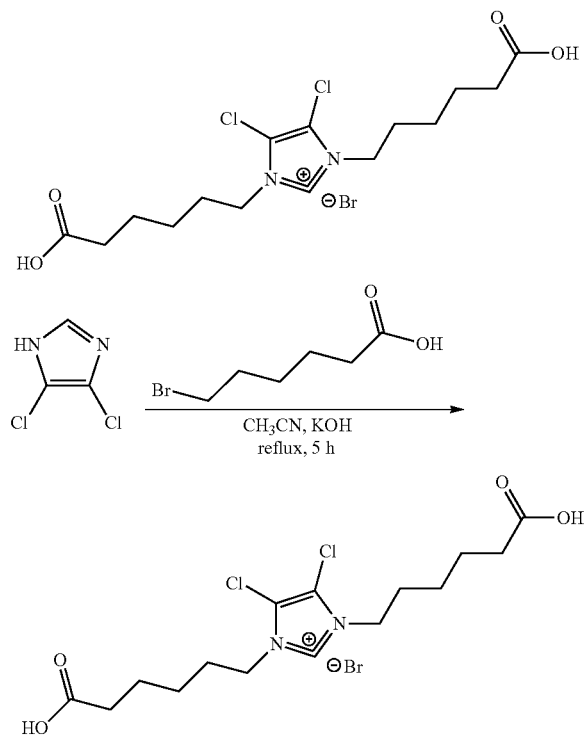

Synthesis of 1,3-bis(5-carboxypentyl)-4,5-dichloro-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 2 equivalents of 6-bromohexanoic acid (2.87 g, 14.72 mmol) was added to the solution and refluxed for 5 h. Solution was filtered to remove the KBr precipitate and neutralized with 6M HBr. Volatiles were removed in vacuo and the resulting product will be collected and analyzed.

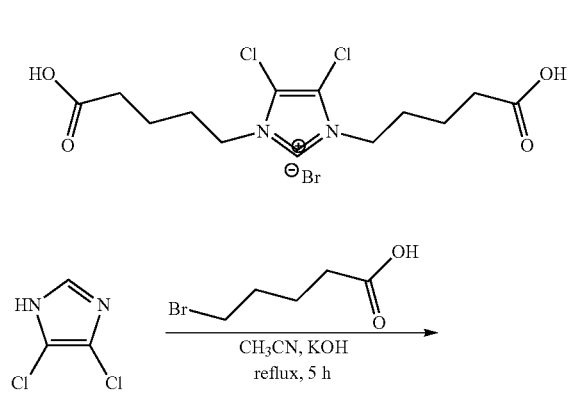

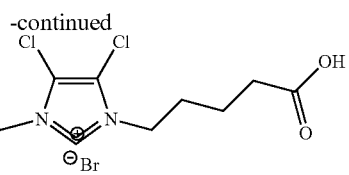

Synthesis of 1,3-bis(4-carboxybutyl)-4,5-dichloro-1H-imidazol-3-ium bromide 4,5-dichloroimidazole (1.00 g, 7.36 mmol) was dissolved in acetonitrile. Potassium hydroxide (0.828 g, 14.72 mmol) was added to the solution and allowed to reflux for 30 min. 2 equivalents of 2-bromopentanoic acid (2.66 g, 14.72 mmol) was added to the solution and refluxed for 5 h. Solution was filtered to remove the KBr precipitate and neutralized with 6M HBr. Volatiles were removed in vacuo and the resulting product will be collected and analyzed.

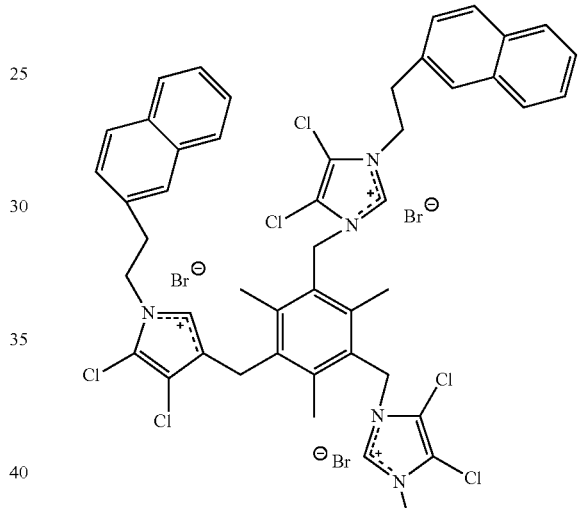

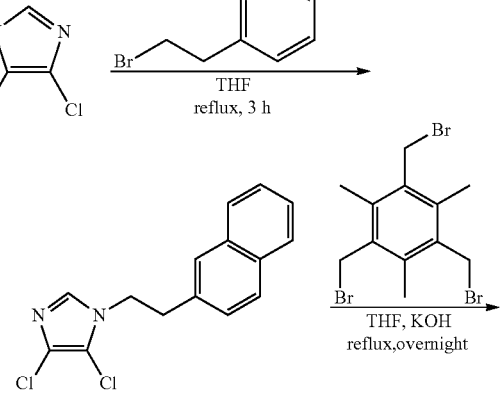

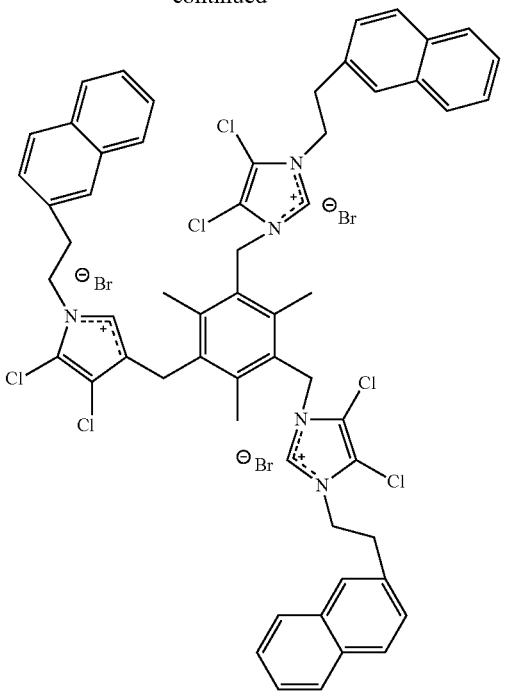

Synthesis of 3,3',3"-(2,4,6-trimethylbenzene-1,3,5-triyl)tris(methylene)tris(4,5-dichloro-1-(2-(naphthalen-2-yl)ethyl)-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 2-(bromoethyl)naphthalene (5.15 g, 21.90 mmol) was added to the solution and refluxed for 3 h. Solution was filtered while hot to remove the KBr precipitate and the filtrate was returned to reflux. 1,3,5-tris(bromomethyl)-2,4,6-trimethylbenzene (2.91 g, 7.30 mmol) was added to the solution and refluxed overnight. The volatiles were removed in vacuo and the resulting waxy yellow solid was washed in ethyl ether. A resulting product will be collected and analyzed.

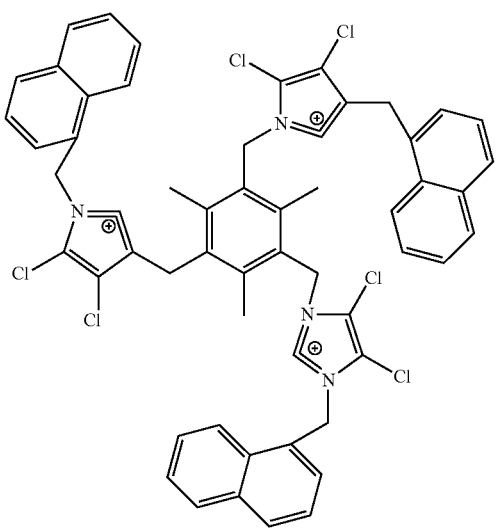

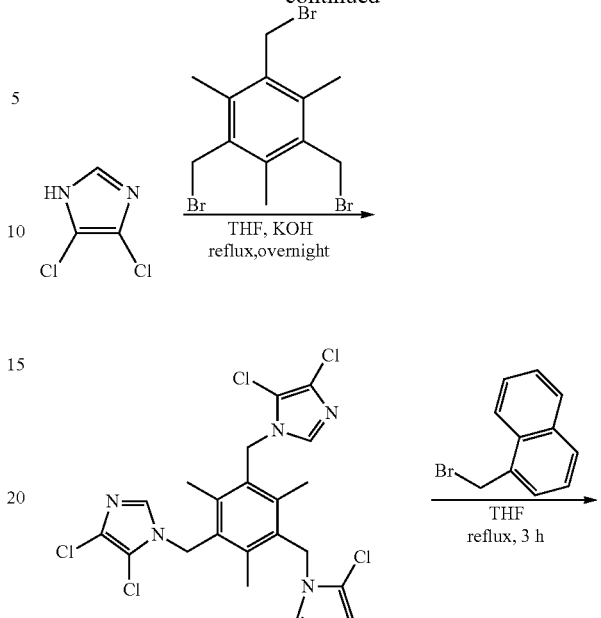

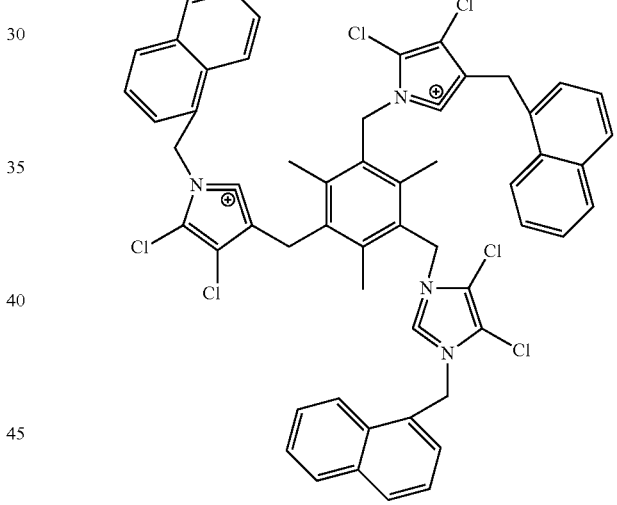

Synthesis of 3,3',3"-(2,4,6-trimethylbenzene-1,3,5-triyl)tris(methylene)tris(4,5-dichloro-1-(naphthalen-1-ylmethyl)-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)-2,4,6-trimethylbenzene (2.91 g, 7.30 mmol) was added to the solution and refluxed overnight. Solution was filtered while hot to remove the KBr precipitate and the filtrate returned to reflux. 1-(bromomethyl)naphthalene (4.84 g, 21.90 mmol) was added to the solution and refluxed for 3 h. The volatiles were removed in vacuo and the resulting waxy yellow solid was washed in ethyl ether. A resulting product will be collected and analyzed.

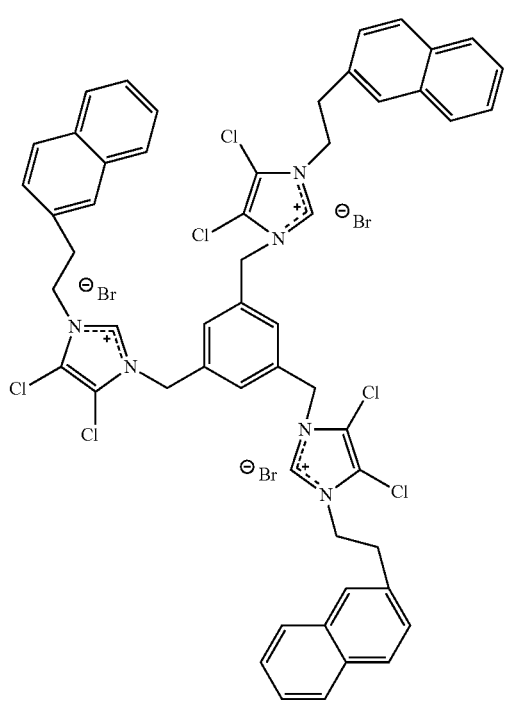

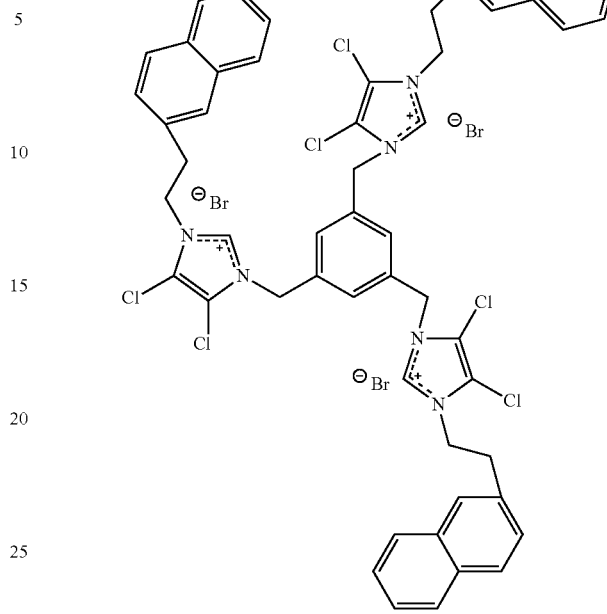

Synthesis of 3,3',3"-(benzene-1,3,5-triyltris(methylene))tris(4,5-dichloro-1-(2-(naphthalen-2-yl)ethyl)-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 2-(bromoethyl)naphthalene (5.15 g, 21.90 mmol) was added to the solution and refluxed for 3 h. Solution was filtered while hot to remove the KBr precipitate and the filtrate was returned to reflux. 1,3,5-tris(bromomethyl)benzene (2.61, 7.30 mmol) was added to the solution and refluxed overnight. The volatiles were removed in vacuo and the resulting waxy yellow solid was washed in ethyl ether. A resulting product will be collected and analyzed.

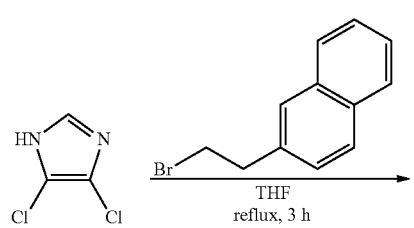

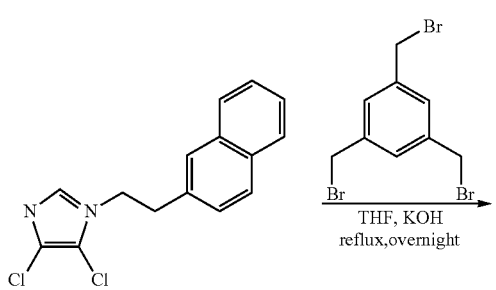

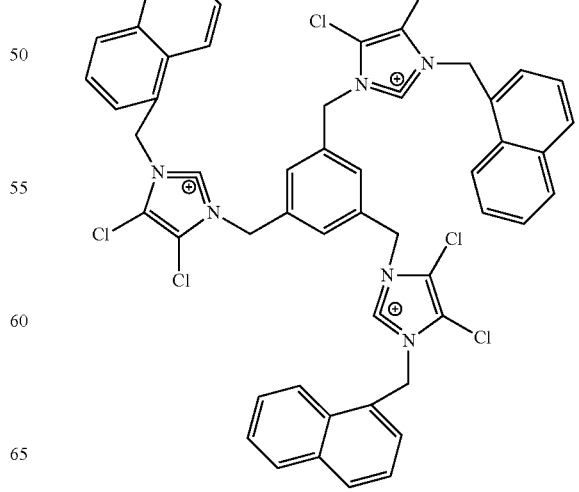

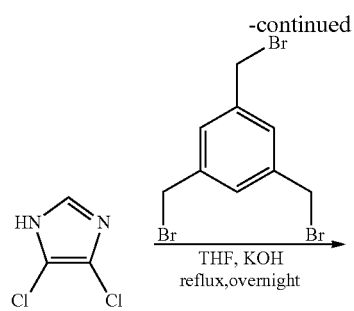

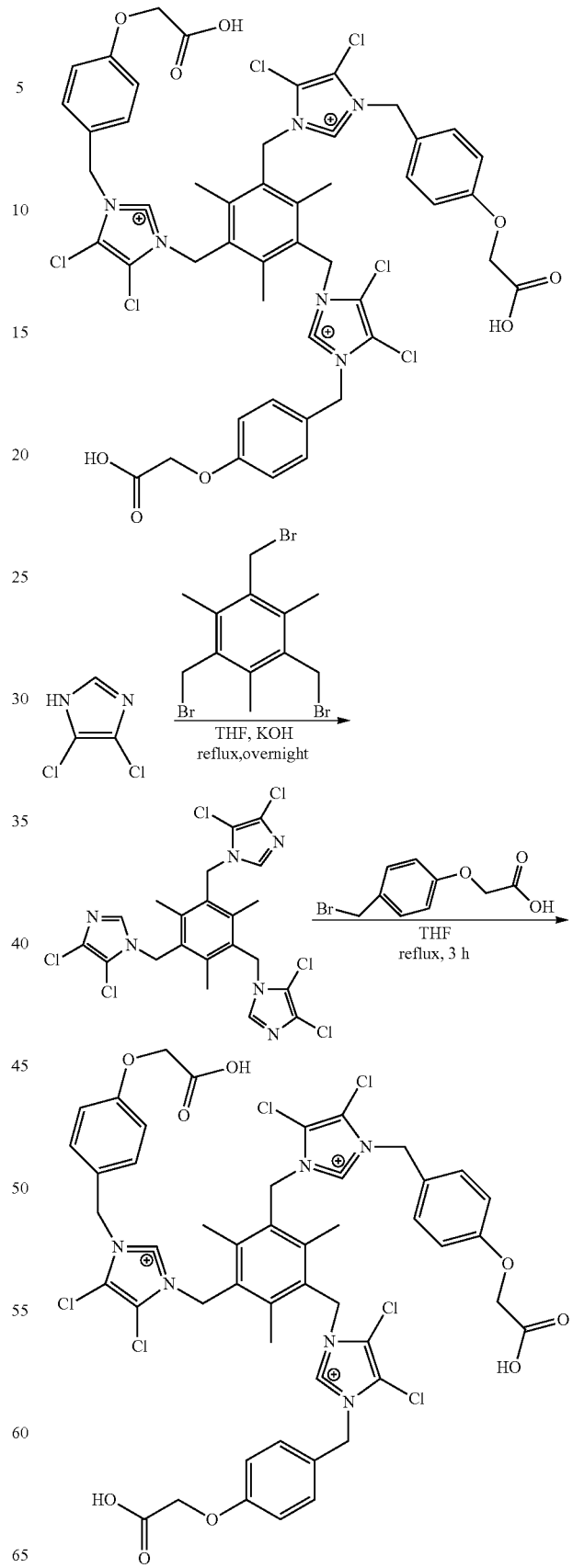

Synthesis of 3,3',3''-(benzene-1,3,5-triyltris(methylene))tris(4,5-dichloro-1-(naphthalen-1-ylmethyl)-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)benzene (2.61, 7.30 mmol) was added to the solution and refluxed overnight. Solution was filtered while hot to remove the KBr precipitate and the filtrate returned to reflux. 1-(bromomethyl)naphthalene (4.84 g, 21.90 mmol) was added to the solution and refluxed for 3 h. The volatiles were removed in vacuo and the resulting waxy yellow solid was washed in ethyl ether. A resulting product will be collected and analyzed.

Synthesis of 3,3',3''-(2,4,6-trimethylbenzene-1,3,5-triyl)tris(methylene)tris(1-(4-(carboxymethoxy)benzyl)-4,5-dichloro-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)-2,4,6-trimethylbenzene (2.91 g, 7.30 mmol) was added to the solution and refluxed overnight. Solution was filtered while hot to remove the KBr precipitate and the filtrate returned to reflux. 2-(4-(bromomethyl)phenoxy)acetic acid (5.37 g, 21.90 mmol) was added to the solution and refluxed for 3 h. Solution was filtered to remove the KBr precipitate. The solution was neutralized with 6M HBr, volatiles removed in vacuo, and the resulting waxy yellow solid was washed in ethyl ether. A resulting product will be collected and analyzed.

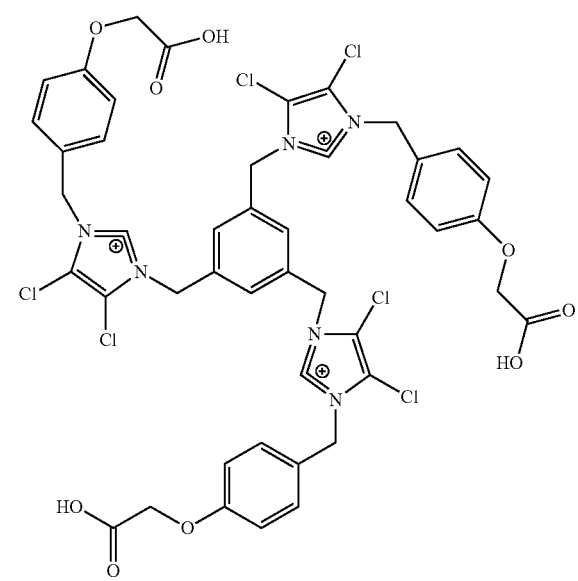

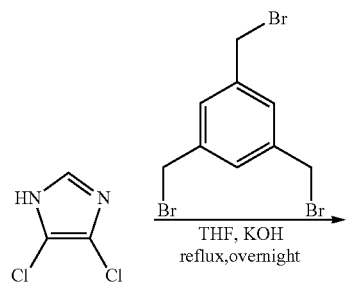

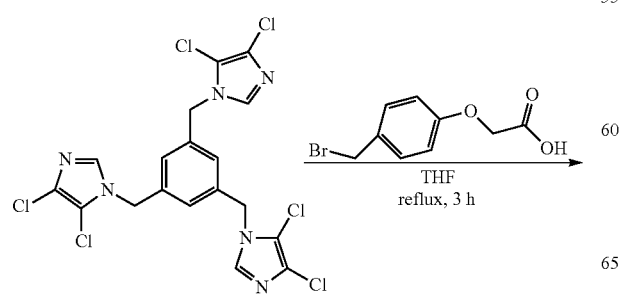

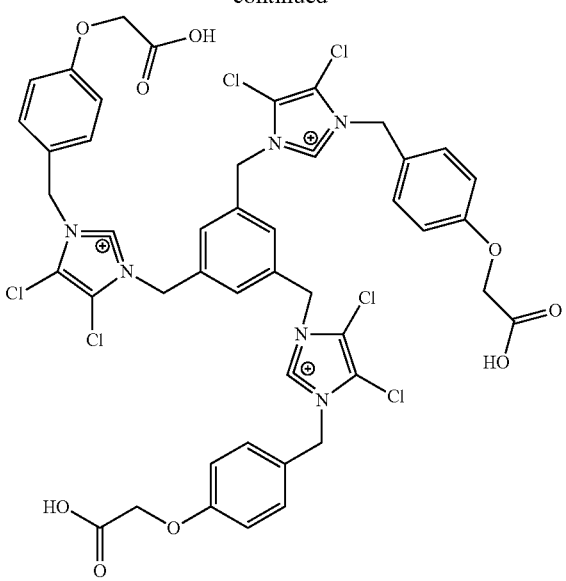

Synthesis of 3,3',3''-(benzene-1,3,5-triyltris(methylene))tris(1-(4-(carboxymethoxy)benzyl)-4,5-dichloro-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)benzene (2.61, 7.30 mmol) was added to the solution and refluxed overnight. Solution was filtered while hot to remove the KBr precipitate and the filtrate returned to reflux. 2-(4-(bromomethyl)phenoxy)acetic acid (5.37 g, 21.90 mmol) was added to the solution and refluxed for 3 h. Solution was filtered to remove the KBr precipitate. The solution was neutralized with 6M HBr, volatiles removed in vacuo, and the resulting waxy yellow solid was washed in ethyl ether. A resulting product will be collected and analyzed.

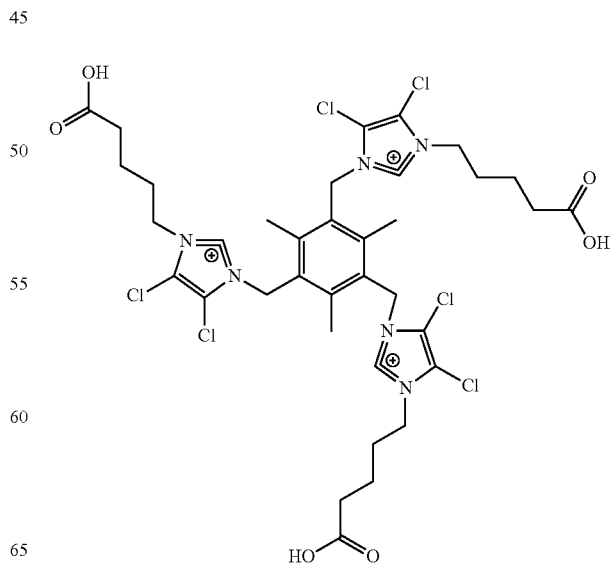

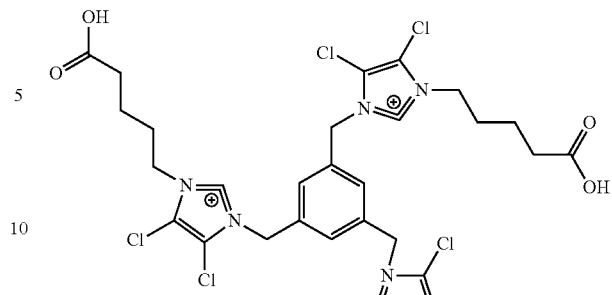

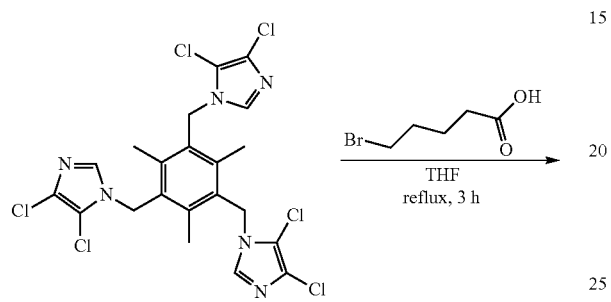

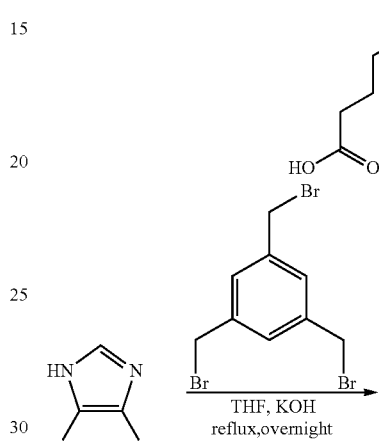

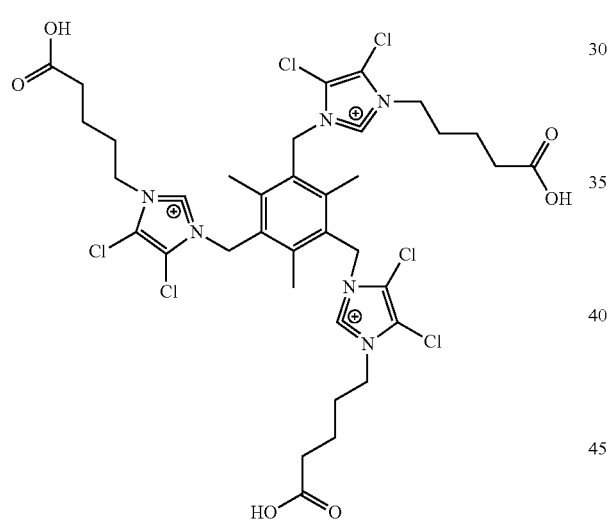

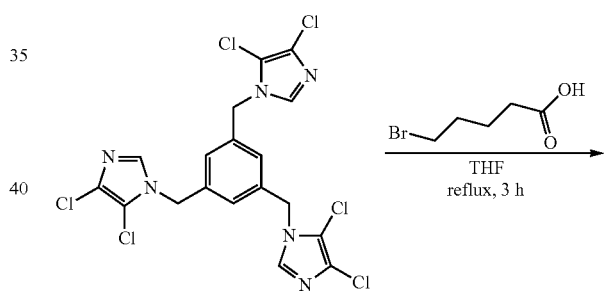

Synthesis of 3,3',3"-(2,4,6-trimethylbenzene-1,3,5-triyl)tris(methylene)tris(1-(4-carboxybutyl)-4,5-dichloro-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)-2,4,6-trimethylbenzene (2.91 g, 7.30 mmol) was added to the solution and refluxed overnight. Solution was filtered while hot to remove the KBr precipitate and the filtrate returned to reflux. 5-bromopentanoic acid (3.96 g, 21.90 mmol) was added to the solution and refluxed for 3 h. Solution was filtered to remove the KBr precipitate. The solution was neutralized with 6M HBr, volatiles removed in vacuo, and the resulting waxy yellow solid was washed in ethyl ether. A resulting product will be collected and analyzed.

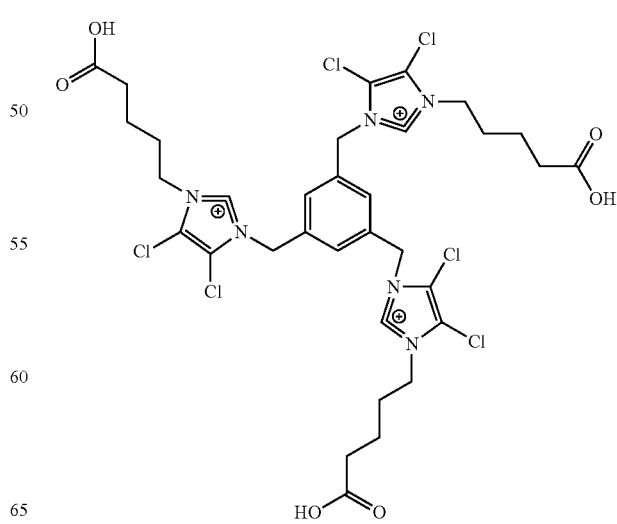

Synthesis of 3,3',3"-(benzene-1,3,5-triyltris(methylene))tris(1-(4-carboxybutyl)-4,5-dichloro-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)benzene (2.61, 7.30 mmol) was added to the solution and refluxed overnight. Solution was filtered while hot to remove the KBr precipitate and the filtrate returned to reflux. 5-bromopentanoic acid (3.96 g, 21.90 mmol) was added to the solution and refluxed for 3 h. Solution was filtered to remove the KBr precipitate. The solution was neutralized with 6M HBr, volatiles removed in vacuo, and the resulting waxy yellow solid was washed in ethyl ether. A resulting product will be collected and analyzed.

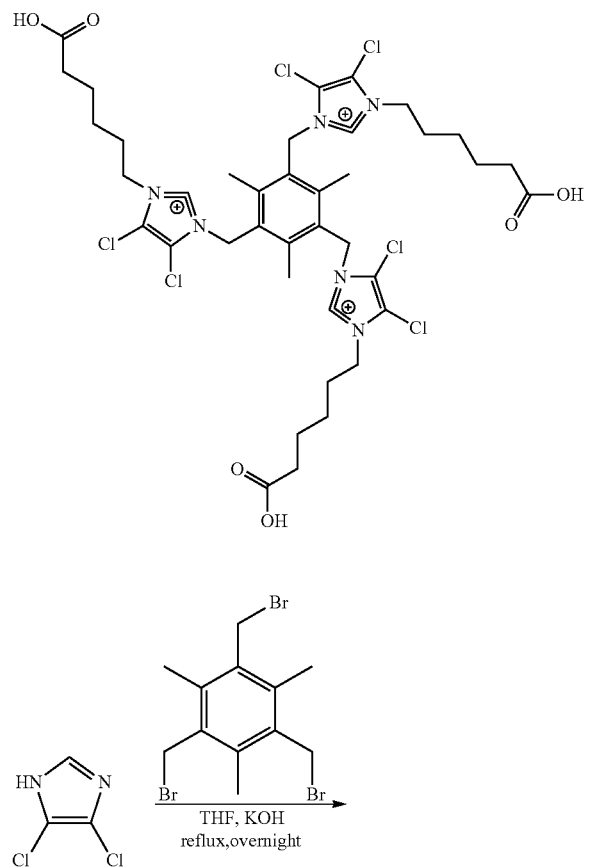

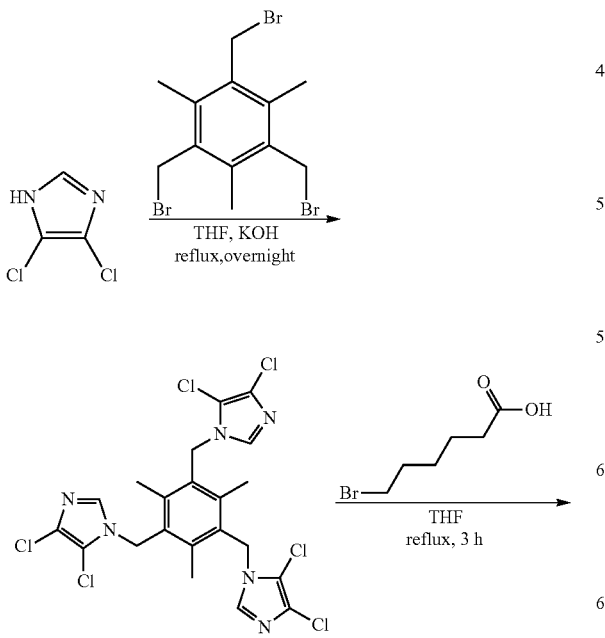

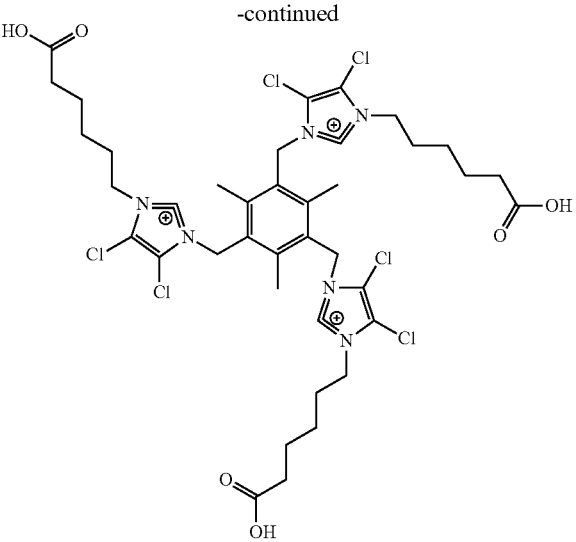

Synthesis of 3,3',3"-(2,4,6-trimethylbenzene-1,3,5-triyl)tris(methylene)tris(1-(5-carboxypentyl)-4,5-dichloro-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)-2,4,6-trimethylbenzene (2.91 g, 7.30 mmol) was added to the solution and refluxed overnight. Solution was filtered while hot to remove the KBr precipitate and the filtrate returned to reflux. 6-bromohexanoic acid (4.27 g, 21.90 mmol) was added to the solution and refluxed for 3 h. Solution was filtered to remove the KBr precipitate. The solution was neutralized with 6M HBr, volatiles removed in vacuo, and the resulting waxy yellow solid was washed in ethyl ether. A resulting product will be collected and analyzed.

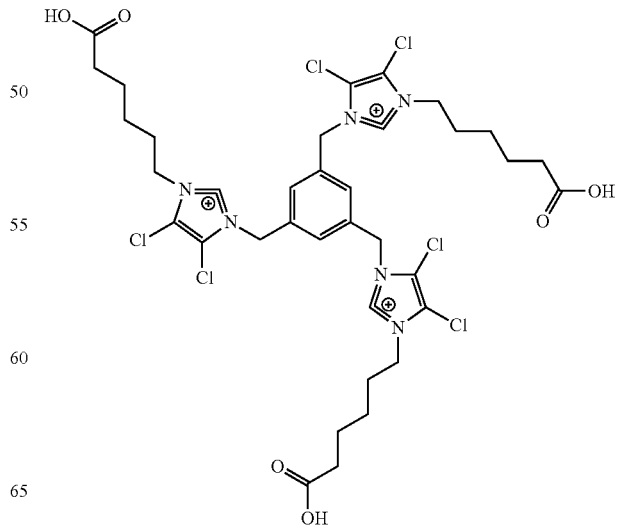

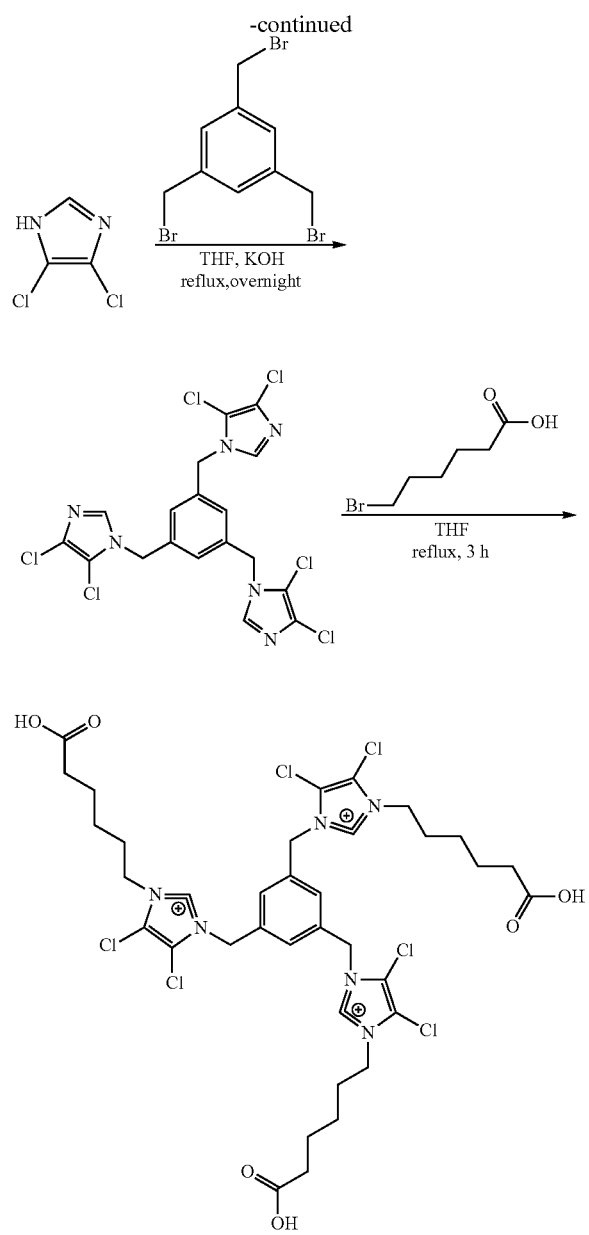
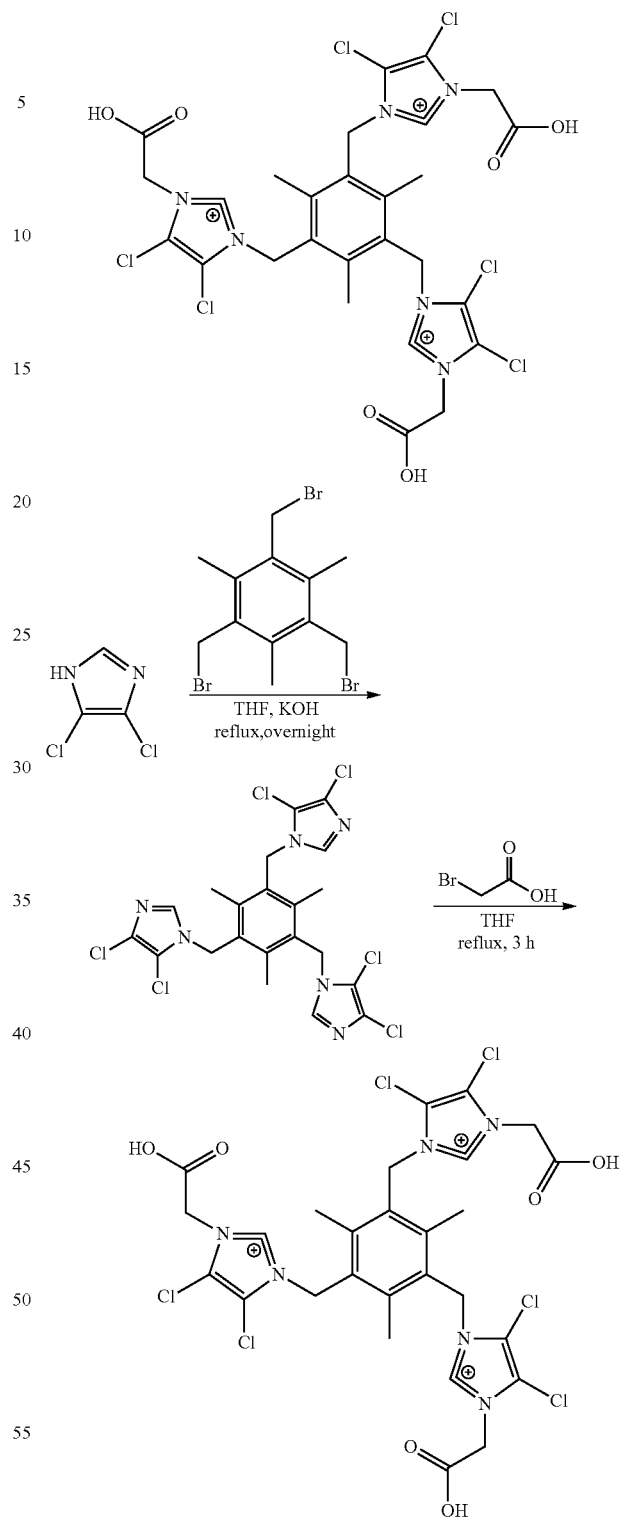

Synthesis of 3,3',3''-(benzene-1,3,5-triyltris(methylene))tris(1-(5-carboxypentyl)-4,5-dichloro-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)benzene (2.61, 7.30 mmol) was added to the solution and refluxed overnight. Solution was filtered while hot to remove the KBr precipitate and the filtrate returned to reflux. 6-bromohexanoic acid (4.27 g, 21.90 mmol) was added to the solution and refluxed for 3 h. Solution was filtered to remove the KBr precipitate. The solution was neutralized with 6M HBr, volatiles removed in vacuo, and the resulting waxy yellow solid was washed in ethyl ether. A resulting product will be collected and analyzed.

Synthesis of 3,3',3''-(2,4,6-trimethylbenzene-1,3,5-triyl)tris(methylene)tris(1-(carboxymethyl)-4,5-dichloro-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)-2,4,6-trimethylbenzene (2.91 g, 7.30 mmol) was added to the solution and refluxed overnight. Solution was filtered while hot to remove the KBr precipitate and the filtrate returned to reflux. 2-bromoacetic acid (3.04 g, 21.90 mmol) was added to the solution and refluxed for 3 h. Solution was filtered to remove the KBr precipitate, neutralized with 6M HBr, volatiles removed in vacuo, and the resulting waxy yellow solid was washed in ethyl ether. A resulting product will be collected and analyzed.

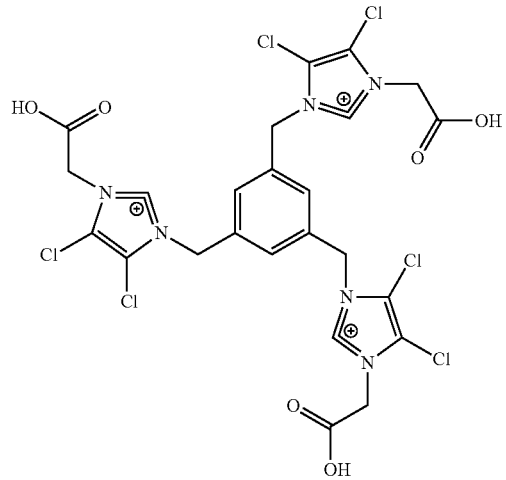

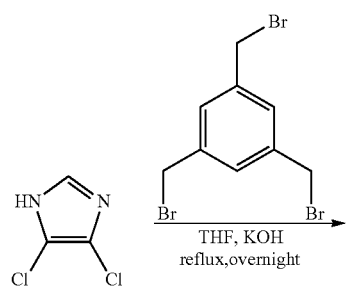

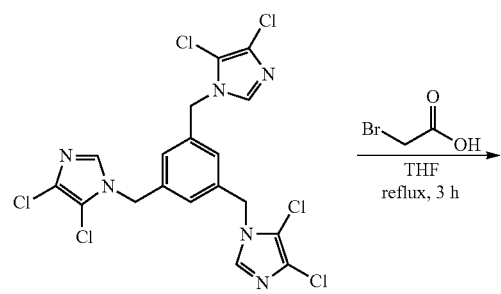

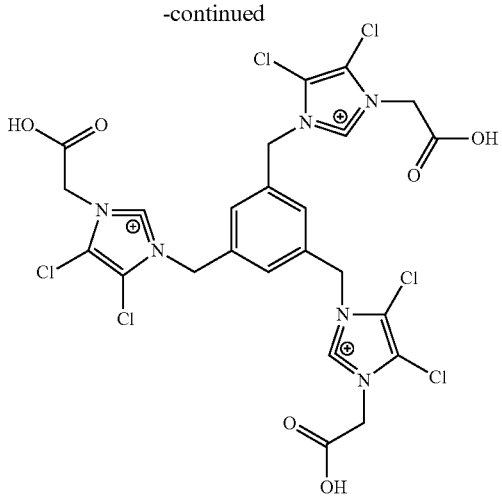

Synthesis of 3,3',3''-(benzene-1,3,5-triyltris(methylene))tris(1-(carboxymethyl)-4,5-dichloro-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)benzene (2.61, 7.30 mmol) was added to the solution and refluxed overnight. Solution was filtered while hot to remove the KBr precipitate and the filtrate returned to reflux. 2-bromoacetic acid (3.04 g, 21.90 mmol) was added to the solution and refluxed for 3 h. Solution was filtered to remove the KBr precipitate, neutralized with 6M HBr, volatiles removed in vacuo, and the resulting waxy yellow solid was washed in ethyl ether. A resulting product will be collected and analyzed.

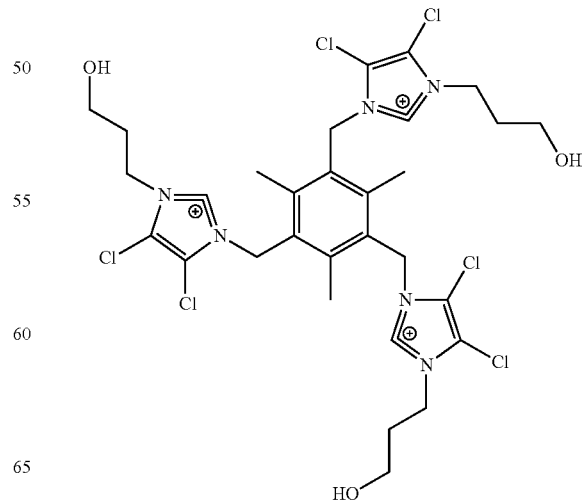

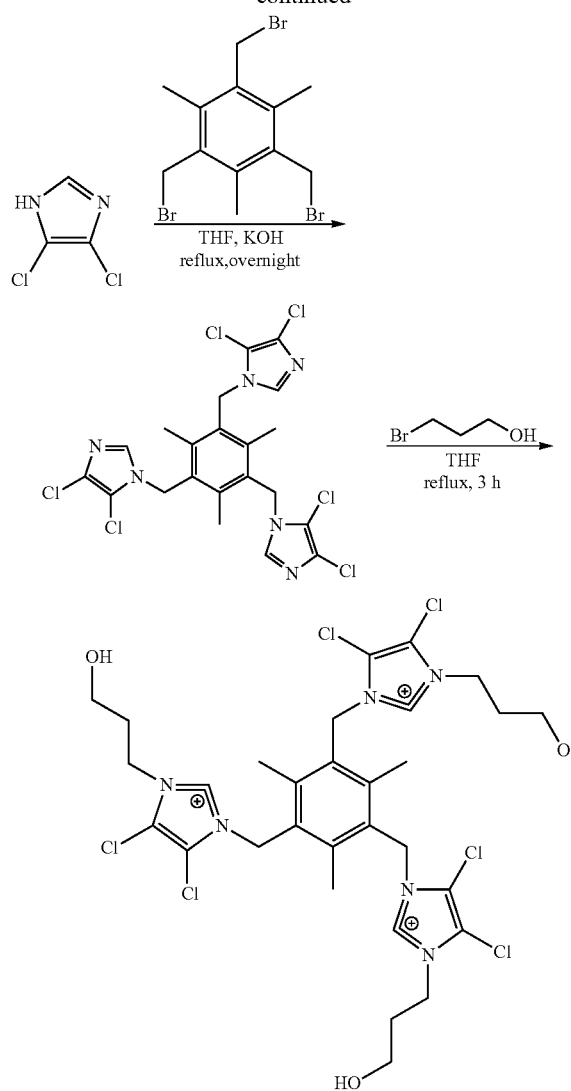

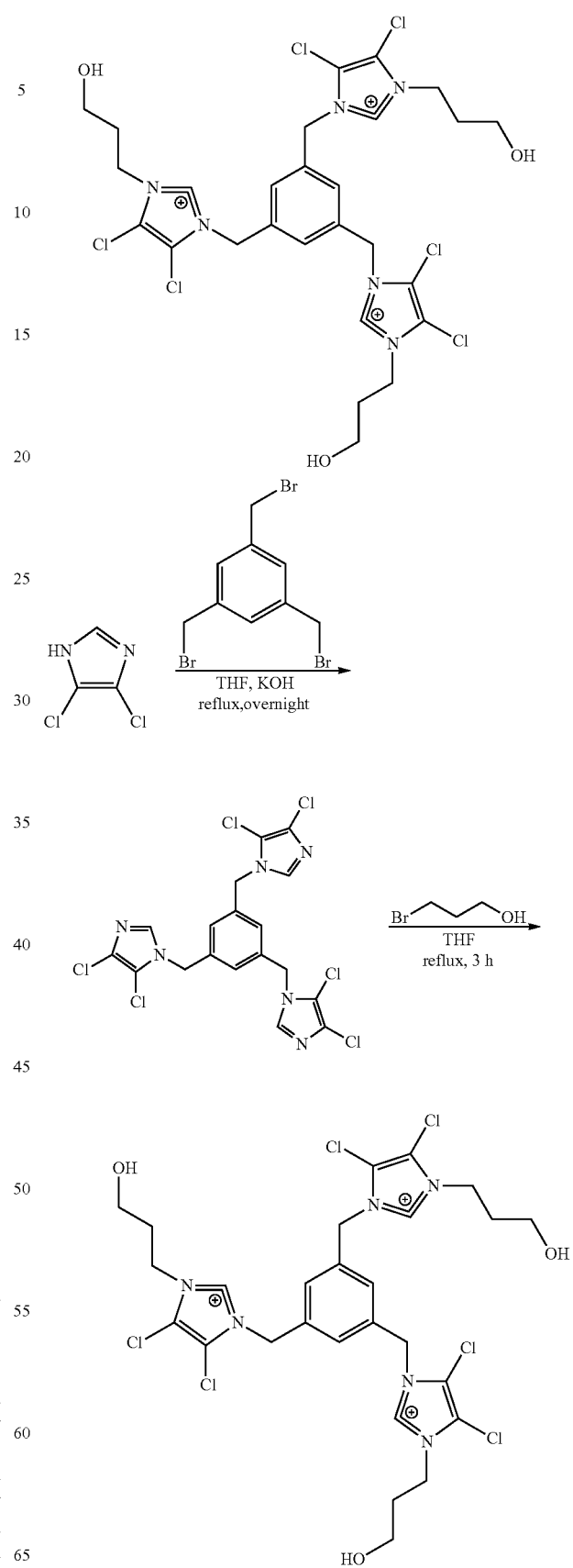

Synthesis of 3,3',3''-(2,4,6-trimethylbenzene-1,3,5-triyl)tris(methylene)tris(4,5-dichloro-1-(3-hydroxypropyl)-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)-2,4,6-trimethylbenzene (2.91 g, 7.30 mmol) was added to the solution and refluxed overnight. Solution was filtered while hot to remove the KBr precipitate and the filtrate returned to reflux. 3-bromopropanol (3.04 g, 21.90 mmol) was added to the solution and refluxed for 3 h. Solution was filtered to remove the KBr precipitate, neutralized with 6M HBr, volatiles removed in vacuo, and the resulting waxy yellow solid was washed in ethyl ether. A resulting product will be collected and analyzed.

Synthesis of 3,3',3"-(benzene-1,3,5-triyltris(methylene))tris(4,5-dichloro-1-(3-hydroxypropyl)-1H-imidazol-3-ium) bromide 4,5-dichloroimidazole (3.00 g, 21.90 mmol) was dissolved in THF and brought to reflux. Potassium hydroxide (2.46 g, 43.80 mmol) was added to the solution and allowed to reflux for 30 min. 1,3,5-tris(bromomethyl)benzene (2.61, 7.30 mmol) was added to the solution and refluxed overnight. Solution was filtered while hot to remove the KBr precipitate and the filtrate returned to reflux. 3-bromopropanol (3.04 g, 21.90 mmol) was added to the solution and refluxed for 3 h. Solution was filtered to remove the KBr precipitate, neutralized with 6M HBr, volatiles removed in vacuo, and the resulting waxy yellow solid was washed in ethyl ether. A resulting product will be collected and analyzed.

Methodology of the In Vitro Cancer Screen

The MTT assay was carried out on NCI-H460 and MB-157 cancer cells to determine the in vitro efficacy of the compounds. The cell lines were plated in 96 well microtiter plates at 5000 cells per well and incubated at 37° C., 5% $CO_2$, 95% air and 100% relative humidity for 12-18 hours prior to addition of experimental drugs. All compounds including cisplatin were dissolved using a 1% DMSO/Water solution and then diluted into the appropriate concentration and media. Following drug addition, the plates are incubated for an additional 72 hours test period at 37° C., 5% $CO_2$, 95% air and 100% relative humidity. After the test period 10 μL of MTT stock solution was added to each well and incubated for 4 hours. Test compounds were carefully removed and 100 μL of DMSO was added per well and incubated for 30 minutes. The optical density was read at 540 nm and wells were averaged according to concentrations.

In light of the foregoing, it should now be evident.

Although the present invention has been described in considerable detail with reference to certain embodiments, other embodiments are possible. Therefore, the spirit and scope of the appended claims should not be limited to the description of the embodiments contained herein.

What is claimed is:

1. An azolium or purinium salt composition having one of the formulas (I) to (VIII):

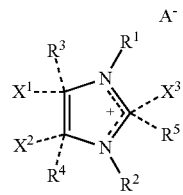

(I)

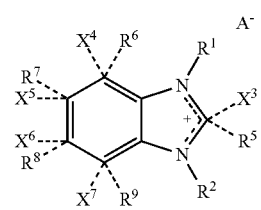

(II)

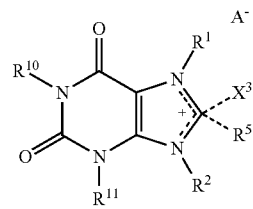

(III)

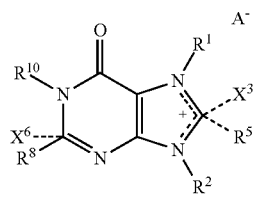

(IV)

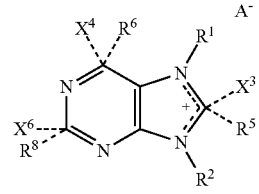

(V)

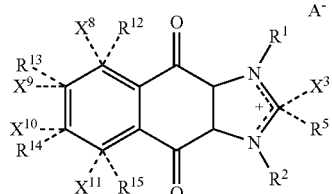

(VI)

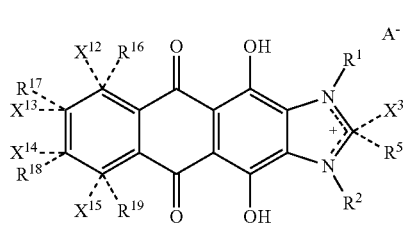

(VII)

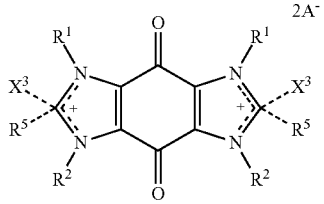

(VIII)

wherein dashed lines in formulas (I) to (VIII) represent a variable attachment of either R or X to a corresponding ring atom;

wherein each $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ when present, may be the same or different, and is a halogen;

wherein $R^1$ is selected from $C_1$ to $C_{20}$ alkyl, $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, fluoroquinolone compounds, penicillin compounds, aminoglycoside compounds; cephalosporin compounds, glycopeptides, sulfonamides, tetracycline, anti-microbial compounds, steroids, anti-inflammatory compounds, anti-fungal compounds, anti-bacterial compounds, antagonist compounds, chemotherapy compounds; and tumor suppressor compounds;

wherein $R^2$ is selected from $C_1$ to $C_{20}$ substituted allkyl, $C_1$ to $C_{20}$ alkyl heteroatom groups where heteroatom is selected from S, O, or N, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_6$ to $C_{12}$ substituted aryl, polycyclic aromatics, substituted polycyclic aromatics, $C_6$ to $C_{12}$ alkoxy, $C_1$ to $C_{12}$ alcohols, $C_1$ to $C_{12}$ carboxy; biphenyl, $C_1$ to $C_6$ alkyl heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, fluoroquinolone compounds, penicillin compounds, aminoglycoside compounds; cephalosporin compounds, glycopeptides, sulfonamides, tetracycline, anti-microbial compounds, steroids, anti-inflammatory compounds, anti-fungal compounds, anti-bacterial compounds, antagonist compounds, chemotherapy compounds, and tumor suppressor compounds;

wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$, when present, are each independently selected from hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N; $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, hydroxyl, carbonyl, amino, acetyl, acetoxy, oxo, nitro, cyano, isocyano, cyanato, isocyanato, fluoroquinolone compound, penicillin compounds, aminoglycoside compounds; cephalosporin compounds, glycopeptides, sulfonamides, tetracycline, anti-microbial compounds, steroids, anti-inflammatory compounds, anti-fungal compounds anti-bacterial compounds, antagonist compounds, chemotherapy compounds; and tumor suppressor compounds;

wherein at least one X is always present in each of the formulas (I) to (VIII); and wherein A is defined as an anion independently selected as a halide, hydroxide, alkoxide, aryloxide, carboxylate, sulfate, phosphate, triflate, tosylate or borate.

2. A multicationic azolium or purinium salt composition having one of the formulas (IX) to (XI):

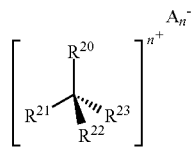
(IX)

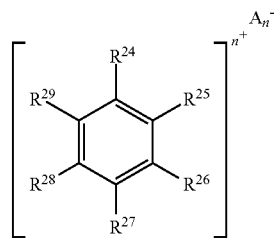
(X)

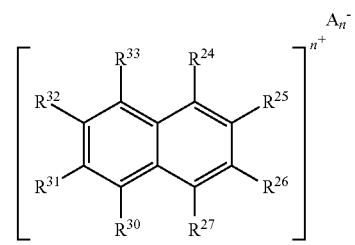
(XI)

wherein at least two of the R groups present in formulas (IX) to (XI) are independently selected from one of the cationic structural portions defined in formulas (I) to (VIII)

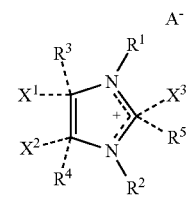
(I)

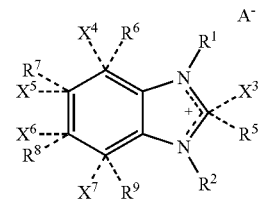
(II)

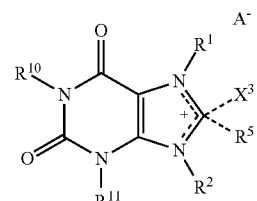
(III)

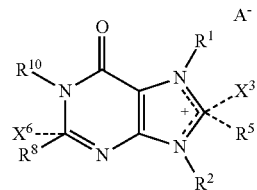
(IV)

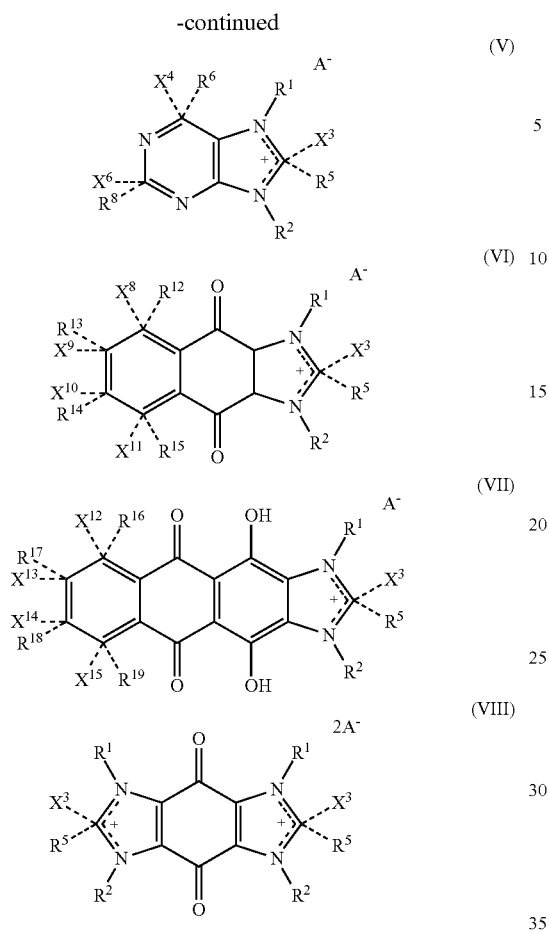

wherein dashed lines in formulas (I) to (VIII) represent a variable attachment of either R or X to a corresponding ring atom;

wherein at least one X is always present, wherein each $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ may be the same or different, and is a halogen;

wherein $R^1$ is selected from $C_1$ to $C_{20}$ alkyl, $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, fluoroquinolone compounds, penicillin compounds, aminoglycoside compounds; cephalosporin compounds, glycopeptides, sulfonamides, tetracycline, anti-microbial compounds, steroids, anti-inflammatory compounds, anti-fungal compounds, anti-bacterial compounds, antagonist compounds, chemotherapy compounds; and tumor suppressor compounds;

wherein $R^2$ is selected from $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkynyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, fluoroquinolone compounds, penicillin compounds, aminoglycoside compounds; cephalosporin compounds, glycopeptides, sulfonamides, tetracycline, anti-microbial compounds, steroids, anti-inflammatory compounds, anti-fungal compounds, anti-bacterial compounds, antagonist compounds, chemotherapy compounds; and tumor suppressor compound;

wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$, are each independently selected from any of the cationic structural portions of formulas (I) to (VIII) above, hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy; biphenyl, $C_1$ to $C_6$ alkyl biphenyl, $C_2$ to $C_6$ alkenyl biphenyl, $C_2$ to $C_6$ alkynyl biphenyl, hydroxyl, carbonyl, amino, acetyl, acetoxy, oxo, nitro, cyano, isocyano, cyanato, isocyanato, fluoroquinolone compounds, penicillin compounds, aminoglycoside compounds; cephalosporin compounds, glycopeptides, sulfonamides, tetracycline, anti-microbial compounds, steroids, anti-inflammatory compounds, anti-fungal compounds, anti-bacterial compounds, antagonist compounds chemotherapy compounds; and tumor suppressor compounds; and wherein $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$ and $R^{33}$ are each independently selected from hydrogen, $C_1$ to $C_{20}$ alkyl, $C_1$ to $C_{20}$ substituted alkyl, $C_1$ to $C_{20}$ alkyl heteroatom groups where the heteroatom is selected from S, O, or N, $C_3$ to $C_{12}$ cycloalkyl, $C_3$ to $C_{12}$ substituted cycloalkyl, $C_2$ to $C_{12}$ alkenyl, $C_3$ to $C_{12}$ cycloalkenyl, $C_3$ to $C_{12}$ substituted cycloalkenyl, $C_2$ to $C_{12}$ alkynyl, $C_6$ to $C_{12}$ aryl, $C_5$ to $C_{12}$ substituted aryl, polycyclic aromatics, substituted polycyclic aromatics, $C_6$ to $C_{12}$ arylalkyl, $C_6$ to $C_{12}$ alkylaryl, $C_3$ to $C_{12}$ heterocyclic, $C_3$ to $C_{12}$ substituted heterocyclic, $C_1$ to $C_{12}$ alkoxy, $C_1$ to $C_{12}$ alcohols, $C_1$ to $C_{12}$ carboxy, biphenyl, $C_1$ to $C_6$ alkyl biphenyl, $C_2$ to $C_6$ alkenyl biphenyl, $C_2$ to $C_6$ alkynyl biphenyl, halogen, hydroxyl, carbonyl, amino, acetyl, acetoxy, oxo, nitro, cyano, isocyano, cyanato, isocyanato, fluoroquinolone compounds, penicillin compounds, aminoglycoside compounds; cephalosporin compounds, glycopeptides, sulfonamide tetracycline, anti-microbial compounds, steroids, anti-inflammatory compounds anti-fungal compounds, anti-bacterial compounds, antagonist compounds, chemotherapy compounds; tumor suppressor compounds;

wherein for each formula (IX) to (XI), each n is a integer from 1 to 8 based upon the number of R groups in the formula, and is the same integer; and wherein A is defined as an anion independently selected as a halide, hydroxide, alkoxide, aryloxide, carboxylate, sulfate, phosphate, triflate, tosylate or borate.

* * * * *